(12) United States Patent
Hensel et al.

(10) Patent No.: US 7,700,104 B2
(45) Date of Patent: Apr. 20, 2010

(54) **ATTENUATED *SALMONELLA* SP12 MUTANTS AS ANTIGEN CARRIERS**

(75) Inventors: Michael Hensel, Erlangen (DE); David William Holden, London (GB); Jacqueline Elizabeth Shea, High Wycombe (GB)

(73) Assignee: Emergent Product Development UK Limited, Berkshire (GB)

( * ) Notice: Subject to any disclaimer, the term of this patent is extended or adjusted under 35 U.S.C. 154(b) by 1246 days.

(21) Appl. No.: 10/763,883

(22) Filed: Jan. 23, 2004

(65) Prior Publication Data

US 2004/0203039 A1    Oct. 14, 2004

Related U.S. Application Data

(62) Division of application No. 09/763,620, filed as application No. PCT/EP99/06514 on Sep. 3, 1999, now Pat. No. 6,936,425.

(30) Foreign Application Priority Data

Sep. 4, 1998    (EP) ................... 98116827

(51) Int. Cl.
*A61K 39/00* (2006.01)
*G01N 33/53* (2006.01)
*G01N 33/569* (2006.01)

(52) U.S. Cl. .................... 424/184.1; 435/7.2; 435/7.35

(58) Field of Classification Search .............. 424/184.1; 435/7.1; 536/23.1
See application file for complete search history.

(56) References Cited

U.S. PATENT DOCUMENTS

| | | | |
|---|---|---|---|
| 4,440,859 A | 4/1984 | Rutter | |
| 4,530,901 A | 7/1985 | Weissmann | |
| 4,550,081 A | 10/1985 | Stocker | |
| 4,582,800 A | 4/1986 | Crowl | |
| 4,677,063 A | 6/1987 | Mark | |
| 4,704,362 A | 11/1987 | Itakura | |
| 4,710,463 A | 12/1987 | Murray | |
| 4,757,006 A | 7/1988 | Toole | |
| 4,766,075 A | 8/1988 | Goeddel | |
| 4,810,648 A | 3/1989 | Stalker | |
| 4,837,151 A | 6/1989 | Stocker | |
| 5,210,035 A | 5/1993 | Stocker | |
| 5,356,797 A | 10/1994 | Niesel | |
| 5,397,697 A | 3/1995 | Lam et al. | |
| 5,527,674 A | 6/1996 | Guerra et al. | |
| 5,618,666 A | 4/1997 | Popoff et al. | |
| 5,643,579 A | 7/1997 | Hung | |
| 5,700,683 A | 12/1997 | Stover et al. | |
| 5,700,928 A | 12/1997 | Hodgson et al. | |
| 5,876,931 A | 3/1999 | Holden | |
| 6,015,669 A | 1/2000 | Holden | |
| 6,251,406 B1 | 6/2001 | Haefliger | |
| 6,342,215 B1 | 1/2002 | Holden et al. | |
| 6,458,368 B1 | 10/2002 | Haefliger | |
| 6,585,975 B1 | 7/2003 | Kleanthous | |
| 6,756,042 B1 | 6/2004 | Feldman | |
| 6,846,667 B1 | 1/2005 | Crooke | |
| 6,936,425 B1 | 8/2005 | Hensel | |
| 6,951,732 B2 | 10/2005 | Clarke | |
| 6,984,490 B1 | 1/2006 | Holden | |
| 7,211,264 B2 | 5/2007 | Feldman | |
| 7,449,178 B2 | 11/2008 | Crooke | |
| 2004/0203039 A1 | 10/2004 | Hensel | |
| 2006/0216309 A1 | 9/2006 | Holden | |
| 2008/0075739 A1 | 3/2008 | Hensel et al. | |
| 2008/0175866 A1 | 7/2008 | Holden | |

FOREIGN PATENT DOCUMENTS

| | | |
|---|---|---|
| EP | 0889120 | 1/1999 |
| WO | WO 92/01056 | 1/1992 |
| WO | WO 9220805 | 11/1992 |
| WO | WO 93/04202 | 3/1993 |
| WO | WO 9310246 | 5/1993 |
| WO | WO 9411024 | 5/1994 |
| WO | WO 94/26933 | 11/1994 |
| WO | WO 9611708 | 4/1996 |
| WO | WO 96/17951 | 6/1996 |
| WO | WO 9718225 | 5/1997 |

(Continued)

OTHER PUBLICATIONS

Deiwick et al. (Journal of Bacteriology, vol. 180, No. 18, pp. 4775-4780, Sep. 1, 1998).*
Tsolis et al. ( Infection and Immunity vol. 63, No. 5, pp. 1739-1744, May 1995).*
Burgess et al. (J of Cell Biology, 1990 vol. 111, pp. 2129 2138).*
Lazar et al (Molecular and Cellular Biology, 1988, vol. 8, pp. 1247 1252).*
Bergman et al, "The IcrB (yscN/U) gene cluster of *Yersinia pseudotuberculosis* is involved in Yop secretion and shows high homology to the spa gene clusters of *Shigelle flexneri* and *Salmonella typhimurium*", *J. Bacteriol*, 176(9):2619-26 (1994).
Buchmeier et al, "Recombination-deficient mutants of *Salmonella typhimurium* are avirulent and sensitive to the oxidative burst of macrophages", *Mol. Microbiol.*, 7(6):933-6 (1993).

(Continued)

*Primary Examiner*—Robert B. Mondesi
*Assistant Examiner*—Khatol Shahnan-Shah
(74) *Attorney, Agent, or Firm*—Cooley Godward Kronish LLP

(57) ABSTRACT

The present invention relates to vaccines, in particular, to an attenuated gram-negative cell comprising the SPI2 gene locus, wherein at least one gene of the SPI2 locus is inactivated, wherein said inactivation results in an attenuation/reduction of virulence compared to the wild type of said cell, and to a carrier for the presentation of an antigen to a host, which carrier is said attenuated gram-negative cell, wherein said cell comprises at least one heterologous nucleic acid molecule comprising a nucleic acid sequence coding for said antigen, wherein said cell is capable of expressing said nucleic acid molecule or capable of causing the expression of said nucleic acid molecule in a target cell.

16 Claims, 31 Drawing Sheets

FOREIGN PATENT DOCUMENTS

| | | |
|---|---|---|
| WO | WO 9806428 | 2/1998 |
| WO | WO 9835562 | 8/1998 |
| WO | WO 9901473 | 1/1999 |
| WO | WO 9945120 | 9/1999 |
| WO | WO 0014240 | 3/2000 |
| WO | WO 0132697 | 5/2001 |
| WO | WO 0185772 | 11/2001 |
| WO | WO 03044047 | 5/2003 |

OTHER PUBLICATIONS

Galan and Curtiss, "Cloning and molecular characterization of genes whose products allow *Salmonella typhimurium* to penetrate tissue culture cells", *Proc. Natl. Acad. Sci. USA*, 86(16):6383-7 (1989).

Galan and Curtiss, "Virulence and vaccine potential of phoP mutants of *Salmonella typhimurium*", *Microb. Pathog.*, 6(6):433-43 (1989).

Groisman and Ochman, "Cognate gene clusters govern invasion of host epithelial cells by *Salmonella typhimurium* and *Shigella flexneri*", *EMBO J.*, 12(10):3779-87(1993).

Brown et al., "Molecular analysis of the *rfb* gene cluster of *Salmonella serovar* muenchen (strain M67): the genetic basis of the polymorphism between groups C2 and B," *Mol. Microbiol* 6:1385-1394 (1992).

Camilli et al., "Insertional Mutagenesis of *Listeria monocytogenes* with a Novel Tn917 Derivative That Allows Direct Cloning of DNA Flanking Transposon Insertions," *J. Bacteriol.* 172:3738-3744 (1990).

Carter, et al., "The Route of Enteric Infection in Normal Mice," *J. Exp. Med.* 139:1189-1203 (1974).

Cheung et al. "Regulation of exoprotein expression in *Staphylococcus aureus* by a locus (sar) distinct from agr," *Proc. Natl. Acad. Sci. USA* 89:6462-6466 (1992).

Chiang & Mekalanos (1998) "Use of signature-tagged transposon mutagenesis to identify Vibrio cholerae genes critical for colonization," *Mol. Microbiol.* 27:797-805 (1998).

Chuang et al. "Global regulation of gene expression in *Escherichia coli*," *J. Bacteriol.* 175:2026-2036 (1993).

Cirillo, et al., "Macrophage-dependent induction of the *Salmonella* pathogenicity island 2 type III secretion system and its role in intracellular survival," Mol. Microbiol. 30: 175-188 (1998).

Coghlan, "Bar codes to tag 'bad genes,'" *New Scientist* p. 18 (Jul. 29, 1995).

Correia et al. "Insertional inactivation of binding determinants of *Streptococcus crista* CC5A using Tn916," *Oral Microbiol. Immunol.* 10:220-226 (1995).

Dolganov & Grossman "Insertional inactivation of genes to isolate mutants of *Synechococcus* sp. strain PCC 7942: isolation of filamentous strains," *J. Bacteriol.* 175:7644-7651 (1993).

Dunyakl, et al., "Identification of *Salmonella* pathogenecity island 2 (SPI2) genes in *Salmonella cholaraesuis* using signature-tagged mutagenesis," *Abstracts of the 97th General Meeting of the American Society for Microbiology* B-275, May 4-8, 1997.

Fields, et al., "A *Salmonella* Locus That Controls Resistance To Microbicidal Proteins From Phagocytic Cells," *Science* 243:1059-1062 (1989).

Finlay, et al., "Identification And Characterization Of TnphoA Mutants Of *Salmonella* That Are Unable To Pass Through a Polarized MDCK Epithelial Cell Monolayer," *Mol. Microbiol.* 2:757-766 (1988).

Fitts, "Development of a DNA-DNA Hybridization Test for the Presence of *Salmonella* in Foods," *Food Technology* pp. 95-102 (Mar. 1985).

Freestone, et al., "Stabilized 17D strain yellow fever vaccina:dose response studies, clinical reactions and effects on hepatic function," *Journal of Biological Standardization* 5:181-186 (1977).

Gaillard et al. (1986) "Transposon mutagenesis as a tool to study the role of hemolysin in the virulence of Listeria monocytogenes," *Infect. Immun.* 52:50-55 (1986).

Galan, et al., "Molecular And Functional Characterization Of The *Salmonella* Invasion Gene invA: Homology Of InvA To Members Of A New Protein Family," (1992).

GenBank Accession No. A51688 "*Salmonella typhimurium*" (1997).

GenBank Accession No. A51689 "*Salmonella typhimurium*" (1997).

GenBank Accession No. AF0208080 "*Salmonella typhimurium* pathogenicity island 2, partial sequence," (1998).

GenBank Accession No. AJ224892 "*Salmonella typhimurium* ssaE, sseA, sseB, sscA, sseC, sseD, sseE, sscB, sseF, sseG, ssaG, ssaH, ssaI genes and partial ssaD, ssaJ genes," (1998).

GenBank Accession No. AJ224978 "*Salmonella typhimurium*," (1999).

GenBank Accession No. J05534 "*Escherichia coli* ATP-dependent clp protease proteolytic component (clpP) gene, complete cds," (1990).

GenBank Accession No. U51927 "*Salmonella typhimurium* SpiR and SpiB genes, partial cds, and SpiC and SpiA genes, complete cds," (1996).

GenBank Accession No. X56793 "*S. enterica* (group B) rfb gene cluster," (1991).

GenBank Accession No. X61917 "*S. enterica* (group B) rfb gene cluster," (1991).

GenBank Accession No. X99944 "*S. typhimurium* ssaQ, ssaR, ssaT and ssaU genes," (1997).

GenBank Accession No. Y09357 "*S. typhimurium* ssaJ, ssaK, ssaL, ssaM, ssaV, ssaN, ssa0, ssaP, ssaQ genes," (1997).

GenBank Accession No. Z23278 "*E. coli* CtpX gene, complete cds," (1993).

GenBank Accession No. Z95891 "*Salmonella tyhpimurium* ssrA and ssrB genes," (1998).

Groisman & Ochman, "How To Become A Pathogen," *Trends Microbiol.* 2:289-293 (1994).

Groisman & Saie, "*Salmonella* Virulence: New Clues To Intramacrophage Survival," *Trends in Biochem. Sci.* 15:30-33 (1990).

Gentschev, et al., "The *Escherichia coli* hemolysin secretion apparatus—a versatile antigen delivery system in attenuated *Salmonella*," Behring Inst. Mitl. 98: 103-113 (1997), abstract only.

Gentschev, et al., "Development of antigen-delivery systems, based on the *Escherichia coli* hemolysin secretion pathway," Gene 179: 133-140 (1996), abstract only.

Gentschev, et al., "Synthesis and secretion of bacterial antigens by attenuated *Salmonella* via the *Escherichia coli* hemolysin secretion system," Behring Inst. Mitl. 95: 57-66 (1994), abstract only.

Groisman, et al., "Molecular, Functional And Evolutionary Analysis Of Sequences Specific To *Salmonella*," *Proc. Natl. Acad. Sci. USA* 90:1033-1037 (1993).

Groisman, et al., "*Salmonella typhimurium* phoP Virulence Gene Is A Transcriptional Regulator," *Proc. Natl. Acad. Sci. USA* 86:7077-7081 (1989).

Guzman, et al., "Antibody Responses in the Lungs of Mice following Oral Immunization with *Salmonella typhimurium aroA* and Invasive *Escherichia coli* Strains Expressing the Filamentous Hemagglutinin of *Bordetella pertussis*," *Inf. Immun.* 59:4391-4397 (1991).

Guzman, et al., "Direct Expression of *Bordetella pertussis* Filamentous Hemagglutinin in *Escherichia coli* and *Salmonella typhimurium aroA*," *Inf. Immun.* 39:3787-3795 (1991).

Guzman, et al., "Expression of *Bordetella pertussis* filamentous hemagglutinin in *Escherichia coli* using a two cistron system," *Microbiol. Pathogenics* 12:383-389 (1992).

Guzmán, et al., "Use of *Salmonella* spp carrier strains to delivery *Bordetella pertussis* antigens in mice using the oral route," in Biology of *Salmonella* (Cabello, et al., eds.) Plenum Press: New York, NY (1993).

Han et al. (1997) "Tn5 tagging of the phenol-degrading gene on the chromosome of *Pseudomonas putida*," *Mol. Cells* 7:40-44 (1997).

Hensel, "*Salmonella* Pathogenicity Island 2," *Mol. Microbiol.* 36:1015-1023 (2000).

Hensel, et al., "Functional analysis of ssaJ and the *ssaK/U* operon, 13 genes encoding components of the type III secretion apparatus of *Salmonella* Pathogenicity Island 2," *Mol. Microbiol.* 24:155-167 (1997).

Hensel, et al., "Genes encoding putative effector proteins of the type III secretion system of *Salmonella* pathogenicity island 2 are required for bacterial virulence and proliferation in macrophages," *Mol. Microbiol.* 30:163-174 (1998).

Hensel, et al., "Molecular and functional analysis indicates a mosaic structure of *Salmonella* pathogenicity island 2," *Mol. Microbiol.* 31:489-498 (1999).

Hensel, et al., "Simultaneous Identification Of Bacterial Virulence Genes By Negative Selection," *Science* 269:400-403 (1995).

Hensel, et al., "The genetic basis of tetrathionate respiration in *Salmonella typhimurium*," *Mol. Microbiol.* 32:275-287 (1999).

Hensel, et al., "Analysis of the boundaries of *Salmonella* pathogenicity island 2 and the corresponding chromosomal region of *Escherichia coli* K-12," *Journal of Bacteriology* 179:1105-1111 (1997).

Holden, "The type III secretion system of *Salmonella* pathogenicity island 2," *FEBS Advanced Course—Protein Export and Assembly in Bacteria*, Lunteren, The Netherlands (1998).

Holland, et al., "Tn916 Insertion Mutagenesis in *Escherichia coli* and *Haemophilus Influenzae* Type b Following Conjugative Transfer," *J. Gen. Microbiol.* 138:509-515 (1992).

Jiang, et al., "Structure and sequence of the rfb (O antigen) gene cluster of *Salmonella serovar typhimurium* (strain LT2)," *Mol Miocrobiol* 5:695-713 (1991).

Juntenen-Backman, et al., "Safe immunization of allergic children against measles, mumps, and rubella," *AJDC* 141:1103-1105 (1987).

Kahrs et al. "Generalized transposon shuttle mutagenesis in *Neisseria gonorrhoeae*: a method for isolating epithelial cell invasion-defective mutants," *Mol. Microbiol.* 12:819-831 (1994).

Kim et al. "The hrpA and hrpC operons of *Erwinia amylovora* encode components of a type III pathway that secretes harpin," *J. Bacteriol.* 179(5):1690-1697 (1997).

Leahy et al. "Transposon mutagenesis in *Acinetobacter calcoaceticus* RAG-1," *J. Bacteriol.* 175:1838-1840 (1993).

Lee, "Type III secretion systems: machines to deliver bacterial proteins into eukaryotic cells?" Trends Microbiol. 5(4): 148-156 (1997).

Lee & Falkow, "Isolation of Hyperinvasive Mutants of *Salmonella*," *Methods Enzymol.* 265:531-545 (1994).

Levine, et al., "Salmonella vaccines" in *New Antibacterial Strategies* (Neu, HC, ed.), pp. 89-104, (Churchill Livingstone:London, 1990).

Levine, et al., eds., "Attenuated *Salmonella* as a live vector for expression of foreign antigens," in New Generation Vaccines, 2$^{nd}$ ed., Marcell Dekker: New York, Chapter 27, pp. 331-361 (1997).

Lisitsyn, et al., "Cloning The Difference Between Two Complex Genomes," *Science* 259:946-951(1993).

Lisitsyn, et al., "Direct Isolation Of Polymorphic Markers Linked To A Trait By Genetically Directed Representational Difference Analysis," *Nature Genetics* 6:57-63 (1994).

Lu, et al., "Tagged Mutations At The Tox 1 Locus Of *Cochliobolus Heterostrophus* By Restriction Enzyme-Mediated Integration," *Proc. Natl. Acad. Sci. USA* 91:12649-12653 (1994).

Mahan, et al., "Selection Of Bacterial Virulence Genes That Are Specifically Induced In Host Tissues," *Science* 259:686-688 (1993).

Maurizi et al., "Sequence and Structure of Clp P, the Proteolytic Component of the ATP-Dependent Clp Protease of *Escherichia coli*," *J. Biol. Chem.* 265(21):12536-45 (1990).

Mecsas & Strauss, "Molecular mechanisms of bacterial virulence: type III secretion and pathogenicity islands," *Emerging Infectious Diseases* 2(4): 271-288 (1996).

Medina, et al., "Pathogenicity Island 2 Mutants of *Salmonella typhimurium* Are Efficient Carriers for Heterologous Antigens and Enable Modulation of Immune Responses," *Infect. Immun.* 67:1093-1099 (1999).

Mei et al. "Identification of *Staphylococcus aureus* virulence genes in a murine model of bacteraemia using signature-tagged mutagenesis," *Mol. Microbiol.* 26:399-407 (1997).

Mejia-Ruiz et al. "Isolation and characterization of an *Azotobacter vinelandii* algK mutant.," *FEMS Microbiol. Lett.* 156:101-106 (1997).

Miller, et al., "A Two-Component Regulatory System (phoPphoO) Controls *Salmonella typhimurium* Virulence," *Proc. Natl. Acad. Sci. USA* 86:5054-5058 (1989).

Miller, et al., "Isolation Of Orally Attenuated *Salmonella Typhimurium* Following TnphoA Mutagenesis," *Infection Immun.* 57:2758-2763 (1989).

Morrison et al. "Isolation of transformation-deficient *Streptococcus pneumoniae* mutants defective in control of competence, using insertion-duplication mutagenesis with the erythromycin resistance determinant of pAM beta 1," *J. Bacteriol.* 159:870-876 (1984).

Myers & Myers "Isolation and characterization of a transposon mutant of *Shewanella putrefaciens* MR-1 deficient in fumarate reductase," *Lett. Appl. Microbiol.* 25:162-168 (1997).

Nelson, et al., "Genomic Mismatch Scanning: A New Approach To Genetic Linkage Mapping," *Nature Genetics* 4:11-17 (1993).

Norgren et al. "A method for allelic replacement that uses the conjugative transposon Tn916: deletion of the emm6.1 allele in *Streptococcus pyogenes* JRS4," *Infect. lmmun.* 57:3846-3850 (1989).

Ochman & Groisman, "Distribution of pathogenicity islands in *Salmonella* spp." *Infection and Immunity* 64:5410-12 (1996).

Ochman, et al., "Identification of a pathogenicity island required for *Salmonella* survival in host cells," *Proc. Natl. Acad. Sci. USA* 93:7800-7804 (1996).

Pang et al. "Typhoid fever—important issues still remain," *Trends Microbiol.* 6:131-133 (1998).

Pascopella, et al., "Use Of In Vivo Complementation In Mycobacterium Tuberculosis To Identify A Genomic Fragment Associated With Virulence," *Infection Immun.* 62:1313-1319 (1994).

Pellcic et al. "Genetic advances for studying Mycobacterium tuberculosis pathogenicity," *Molecular Microbiology* 28:413-420 (1998).

Piatti, et al., "Cloning and Characterization of S. typhi," Sociela Italiana di Microbiologia Medica Odontoiatrica e Clinica '93 (Translation), p. 82.

Plunkett, EMBL ID NO:EC29479, Accession No. U29579 (Mar. 4, 2000).

Polissi et al. *Fourth European Meeting on the Molecular Biology of the Pneumococcus*, Abstract A.18 (1997).

Ramakrishnan et al. "Mycobacterium marinum causes both long-term subclinical infection and acute disease in the leopard frog (*Rana pipiens*)," *Infect. Immun.* 65:767-773 (1997).

Regue et al. "A generalized transducing bacteriophage for *Serratia marcescens*," *Res. Microbiol.* 142:23-27 (1991).

Rella et al. "Transposon insertion mutagenesis of *Pseudomonas aeruginosa* with a Tn5 derivative: application to physical mapping of the arc gene cluster," *Gene* 33:293-303 (1985).

Roberts et al. "Cloning of the egl gene of *Pseudomonas solanacearum* and analysis of its role in phytopathogenicity," *J. Bacteriol.* 170:1445-1451 (1988).

Roos et al. "Tagging genes and trapping promoters in *Toxoplasma gondii* by insertional mutagenesis," *Methods* 13:112-122 (1997).

Rott et al. "At least two separate gene clusters are involved in albicidin production by *Xanthomonas albilineans*," *J. Bacteriol.* 178:4590-4596 (1996).

Roudier et al. "Characterization of translation termination mutations in the spy operon of the *Salmonella* virulence plasmid pSDL2," *J. Bacteriology* 174:6418-6423 (1992).

Rüssman, et al., "Delivery of epitopes by the *Salmonella* type III secretion system for vaccine development," *Science* 281: 565-568 (1998).

Schiestl & Petes "Integration of DNA fragments by illegitimate recombination in *Saccharomyces cerevisiae*," *Proc. Natl. Acad. Sci. USA* 88:7585-7589 (1991).

Sharetzsky et al. "A novel approach to insertional mutagenesis of *Haemophilus influenzae*," *J. Bacteriol.* 173:1561-1564 (1991).

Shea, et al., "Identification of a virulence locus encoding a second type III secretion system in *Salmonella typhimurium*," *Proc. Natl. Sci. USA* 93:2593-2597 (1996).

Shea, et al., "Influence of the *Salmonella typhimurium* pathogenicity island 2 type III secretion system on bacterial growth in the mouse," *Infection and Immunity* 67:213-219 (1999).

Slauch, et al., "In Vivo Expression Technology For Selection Of Bacterial Genes Specifically Induced In Host Tissues," *Methods Enzymol*, 235:481-492 (1994).

Smith, et al., "Genetic Footprinting: A Genomic Strategy For Determining A Gene's Function Given Its Sequence" *Proc. Natl. Acad. Sci. USA* 92:6479-6483 (1995).

Smith, et al., "Virulence Of *Aspergillus Fumigatus* Double Mutants Lacking Restriction And An Alkaline Protease In A Low-Dose Model Of Invasive Pulmonary Aspergillosis," *Infection Immun.* 62(4):1313-1319 (1994).

Staendner, et al., "Identification of *Salmonella typhi* promoters activated by invasion of eukaryotic cells," *Mol. Microbiol*, 18:891-902 (1995).

Stein, EMBL ID NO:ST51867, Accession No. U51867 (Mar. 4, 2000).

Stojiljkovik et al., "Ethanolamine utilization in *Salmonella typhurium*: nucleotide sequence, protein expression, and mutational analysis of the cchA cchB eutE eutJ eutG eutH gene cluster," *J. Bacteriol*. 177(5)1357-66 (1995).

Subramanian et al. "Rapid mapping of *Escherichia coli*::Tn5 insertion mutations by REP-Tn5 PCR" *PCR Methods* 1:187-192 (1992).

Sutherland & Springett, "Effectiveness of BCG vaccination in England and Wales in 1983," *Tubercle* 68(2):81-92 (1987).

Tam & Lefebvre "Cloning of flagellar genes in *Chlamydomonas reinhardtii* by DNA insertional mutagenesis," *Genetics* 135:375-384 (1993).

Trieu-Cuot et al. "An integrative vector exploiting the transposition properties of Tn1545 for insertional mutagenesis and cloning of genes from gram-positive bacteria," *Gene* 106:21-27 (1991).

Tzschaschel, et al., "An *Escherichia coli* hemolysin transport system-based vector for the export of polypeptides: export of Shiga-like toxin IIeB subunit by *Salmonella tyhphimurium* aroA," Nature Biotechnol. 14: 765-769 (1996).

Valdivia & Falkow, "Fluorescence-based isolation of bacterial genes expressed within host cells," Science 277: 2007-2011 (1997).

Valentine, et al., "Identification of Three Highly Attenuated *Salmonella typhimurium* Mutants That are More Immunogenic and Protective in Mice than a Prototypical *aroA* Mutant," *Infect. Immun*. 66:3378-3383 (1998).

Walker, et al., "Specific Lung Mucosal and Systemic Immune Responses after Oral Immunization of Mice with *Salmonella typhimurium aroA, Salmonella typhi* Ty21a, and Invasive *Escherichia coli* expressing Recombinant Pertussis Toxin S1 Subunit," *Inf. Immun*. 60:4260-4268 (1992).

Walsh & Cepko, "Widespread Dispersion Of Neuronal Clones Across Functional Regions of the Cerebral Cortex," Science 255:434-40 (1992).

Woolley et al. "Transfer of Tn1545 and Tn916 to *Clostridium acetobutylicum*," Plasmid 22:169-174 (1989).

Adachi, et al., "Isolation of *Dictyostelium discoideum* Cytokinesis Mutants by Restriction Enzyme-Mediated Integration of the Blasticidin S Resistance Marker," *Biochem. Biophys. Res. Comm*. 205:1808-1814 (1994).

Albus et al. "Virulence of Staphylococcus aureus mutants altered in type 5 capsule production," *Infect. Immun*. 59:1008-1014 (1991).

Aldhous, "Fast Tracks to Disease Genes," *Science* 265:2008-2010 (1994).

Anthony, et al., "Transformation and allelic replacement in *Francisella* spp.," *J. Gen. Microbiol*. 137:2697-2703 (1991).

Artiguenave, et al., "High-efficiency transposon mutagenesis by electroporation of a *Pseudomonas fluorescens* strain," *FEMS Microbiol. Lett*. 153:363-369 (1997).

Bainton, et al., "Immunity of children to diphtheria, tetanus, and poliomyelitis," *British Medical Journal* 1:854-57 (1979).

Black, et al., "Restriction enzyme-mediated integrated elevates transformation frequency and enables co-transfection of *Toxoplasma gondii*," *Mol. Biochem. Parasitol*. 74:55-63 (1995).

Blasco, et al., "Nitrate reductases of *Escherichia coli*: Sequence of the second nitrate reductase and comparison with that encoded by the narGHJI operon," *Mol. Gen. Genet*. 222:104-111 (1990).

Bölker, et al., "Tagging pathogenicity genes in *Ustilago maydis* by restriction enzyme-mediated integration (REMI)," *Mol. Gen. Genet*. 248:547-552 (1995).

Brown et al. (1997) 19th Fungal Genetics Conference, Mar. 18-23, 1997 (Asilomar Conference Centre, Pacific Grove, CA).

Abaev, et al. (1997) "Stable expresion of heterologous proteins in Salmonella: Problems and approaches to their desinging," Vestn. Ross Akad Med Nauk 6:48-52 Abstract Only.

Agrawal and Goodchild (1987) "Oligodeoxynucleotide methylphosphonate: synthesis and enzymatic degradation." Tetrahedron Letters, 28:3536-3542.

Agrawal and Tang (1990) "Efficient synthesis of oligoribonucleotide and its phosphorothioate analogue using H-Phosphonate Approach," Tetradhedron Letters, 31:7541-7544.

Agrawal (1998) "Oligodeoxynucleoside phosphoramidates and phosphorothioates as inhibitors of human immunodeficiency virus," PNAS 85:7079-7083.

Agrawal (1990) "Site-specific excision from Rna by RNase H and mixed phosphate-backbone oligodeoxyribonucleotides." PNAS 87:1401-1405.

Agrawal et al. (1991) "Pharmacokinetics, biodistribution and stability of oligodeoxynucleotide phosphorothioates in mice," PNAS, 88:7595-7599.

Allaoui, et al. (1993) "MxiD, an outer membrane protein necessary for the secretion of Shigella flexneri 1pa invasins," Mol. Microbiol., 7:59-68.

Altmeyer, et al. (1993) "Cloning and molecular characterization of gene involved in Salmonella adherence and invasion of cultured epithelial cells," Mol. Microbiol., 7:89-98.

Andrews and Maurelli (1992) "MxiA of Shigella flexneria 2a, which facilitates export of invasion plasmid antigens encodes a homol of low-calcium-response protein LcrD, of Yersinia pestis," Infect. Immun. 60:3287-3295.

Bachman (1990) "Linkage map of E. coli K-12," Micro. Rev. 54:130-197.

"Bajaj, et al. (1996) "Co-ordinate regulation of Salmonella typhimurium invasion genes by environmental and regulatory factor is mediated by control of expression," Mol. Microbiol. 18:715727.

Bajaj, et al. (1995) "*hilA* is notvel *ompR/toxR* family member that activates the expression of *Salmonella typhimurium* invasion genes." Mol. Microbiol. 18:715-727.

Bannwarth (1988) "Solid-phase synthesis of oligodeoxynucleotides containing phosphoramidate internucleotide linkages and their specific chemical cleavage," Helv. Chim. Acta. 71:1517-1527.

Baudry, et al. (1988) "Nucleotide sequence of the invasion plasmid antigen B and C genes (ipaB and ipaC) of Shigella flexneri," Microb. Pathog. 4:345-357.

Benson and Goldman (1992) "Rapid mapping in *Salmonella typhimurium* with Mud-P22 prophages," J. Bacteriol. 175:1673-1681.

Boddikcer, et al. (2006) "Signature-tagged mutagenesis of *Klebsiella pneumoniae* to identify genes that influence biofilm formation on extracellular matrix material," Infect. Immun. 74:45904597.

Bogdanove, et al. (1996) "Unified nomenclature for broadly conserved hrp genes of phytopathogenic bacteria," Mol. Microbiol. 20:681-683.

Bourgogne, et al. (1998) "*Salmonella abortusivusm* strain RV6, new vaccinal vehicle for small ruminants," Vet. Microbiol. 61:199-213 Abstract Only.

Cardenas, et al. (1994) "Influence of strain viability and antigen done on the use of attenuated mutants of Salmonella as vaccine carriers," Vaccine 12:883-840.

Cardenas, et al. (1993) "Stability, immunogenicity and expression of foreign antigens in bacterial vaccine vectors," Vaccine 11:122-125 Abstract Only.

Cardenas, et al. (1992) "Oral administration using live attenuated Salmonella spp. as carriers of foreign antigens," Clin. Microbiol. Rev. 5:328-342.

Cattozzo, et al. (1997) "Expression of immunogenicity of V3 loop epitopes of HIV isolates SC and WMJ2, inserted in *Salmonella flagellin*," J. Biotechnol. 56:191-203 Abstract Only.

Chabalgoity, et al. (1996) "A *Salmonella typhimurium* htrA live vaccine expressing multiple copies of a peptide comprising amino acids 8-23 of herpes simplex virus glycoprotein D as a genetic fusion to tetanus toxin fragment C protects mice from herpes simplex virus infection," Mol. Microbiol. 19:791-801.

Chacon, et al. (1996) "Heterologous expression of the citicular glutathione peroxidase of lymphatic filariae in an attenuated vaccine strain of *Salmonella typhimurium* abrogates H-2 restriction of specific antibody response," Parasite Immunol. 18:307-316 Abstract Only.

Chang, et al. (1978) "Construction and characterization of amplifiable multicopy DNA cloning vehicles derived from the P15A cryptic miniplasmid" J. Bacteriol. 134:1141-1156.

Charles, et al. (1990) "Gene expression an the development of live enteric vaccines," Trends Biotechnol. 8:117-121 Abstract Only.
Chatfield, et al (1992) "Construction of a genetically defined Salmonella typhi Ty2 aro A, aroC mutain for the engineering of a candidate oral typhoid-tetanus vaccine," Vaccine 10:53-60.
Chatfield, et al. (1994) "The use of live attenuated Salmonella for oral vaccination," Dev. Biol. Stand. 82:35-42.
Chatfield, et al. (1993) "The development of oral vaccines based on live attenuated *Salmonella* strains," FEMS Immunol. Med. Microbiol. 7:1-7.
Chatfield, et al. (1995) "The development of oral vaccines against parasitic diseases utilizing live attenuated Salmonella," Paristology 110Suppl.:S17-S24.
Chatfield, et al. (1989) "Live Salmonella vaccines and carriers of foreign antigenic determinants," Vaccine 7:495-498.
Cirillo, et al. (1995) "Bacterial vaccine vectors and bacillus Calmette-Guerin," Clin. Infect. Dis. 30:1001-1009.
Clemens (1987) "Use of attenuated mutants of Salmonella as carriers for delivery of heterologous antigens to the secretory immune system," Pathol. Immunopathol. Res. 6:137-146.
Clements (1990) "Vaccines against enterotoxigenic bacterial pathogens based on hybrid Salmonella that express heterologous antigens," Res. Microbiol. 141:981-993. Abstract Only.
Cohen, et al. (1990) "Microbial isopenicillin n. synthase genes: structure, function, diversity and evolution," Trends in Biotechnol. 8:105-111.
Collazo, et al. (1995) "Functional analysis of the Salmonella typhimurium invasion genes invl and invJ and identification of a target of the protein secretion apparatus encoded in the inv. locus," Mol. Microbiol. 15:25-38.
Cosstick and Vyle (1989) "Solid phase synthesis of oliogonucleotides containing 3'- thioymidase," Tetrahedron Letters, 30:4693:4696.
Covone, et al. (1998) "Levels of expression and immunogenicity of attenuated Salmonella enterica servar typhimurium strains expression Escherichia coli mutant heat-labile enterotoxin," Infect. Immun. 66:224-231.
Coynault, et al. (1992) "Growth phase and SpvR regulation of transcription in Salmonella typhimurium spvANC virulence genes," Microb. Pathog. 13:133-143. Abstract Only.
Curtiss, et al. (1990) "Stabilization of recombinant avirulent vaccine strains in vivo," Res. Microbiol. 141:797-805. Abstract Only.
Davidson, et al. (1995) "Lung disease in the cystic fibrosis mouse exposed to bacterial pathogens," Nat. Genet. 9:351-357.
De Lorenzo, et al. (1990) "Mino-Tn5 transposon derivatives for insertion mutagenesis promoter probing, and chromosomal insertion of cloned Dna in gram-negative eubacteria," J. Bacteriol. 172:6568-6572.
De Lorenzo and Timis (1994) "Analysis of stable phenotypes in gram negative bacteria with Tn5 and Tn10-derived minitransposons," Methods Enzymol. 235:386-405.
Degroote, et al (1997) "Periplasmic superoxide dismutase protects Salmonella from products of phagocyte Nadph-oxidase and nitric oxide synthase," PNAS 94:13997-14001.
Deiweick, et al. (1999) "Environmental regulation of Salmonella pathogenicity island 2 gene expression," Mol. Microbiol. 31:1759-1773.
Diederich, et at. (2000) "In search for specific inhibitors of human IIbeta-hydroxysteroiddehydrogenases (11beta-HSDs): Chenodeoxycholic acid selectivity inhibits 11beta-Hsd-1" Eur. J. Endocrinol. 142:200-207.
Deiwick and Hensel (1999) "Regulation of virulence genes by environmental signal in Salmonella typhimurium electrophoresis," 20:813-817. Abstract Only.
Doggett, et al. (1993) "Immune response to Streptococcus sobrinus surface protein antigen a expressed by recombinant Salmonella typhimurium," Infect. Immun. 61:1859-1866.
Donnenberg, et al. (1991) "Construction of an eae deletion mutant of enterophatic Escherichia coli using a positive-selection suicide vector," Infect. Immunol. 59:4310-4317.
Dougan, et al. (1989) "Live bacterial vaccines and their application as carrier for foreign antigen," Adv, in Vet. Sci. and Comp. Med. 33:277-300.

Dougan, et al. (1987) "Live oral Salmonella vaccines: potential use of attenuated strains as carriers of heterologous antigens to the immune system," Parasite Immunol. 9:151-160.
Eichelberg, et al. (1994) "Molecular and functional characterization of the Salmonella typhimurium invasion.genes invB and invC: homology of invC to the FOF1 ATPase family of proteins," J. Bacteriol. 176:4501-4510.
Elliot, et al. (1998) "The complete sequence of the locus of enterocyte affeacement (LEE) from enteropathogenic Escherichia coli E2348/49," Mol. Microbiol. 28:1-4.
Everst, et al. (1995) "Expression of LacZ from the hrtA, nirB and groE promoters in a Salmonella vaccine strain: influence of growth in mammalian cells," FEMS Microbiol. Letters 126:97-101.
Fayole, et al. (1994) "Genetic control of antibody responses induced against an antigen delivered by recombinant attenuated Salmonella typhimurium,: Infect. Immun. 62:4310-4319 .
Fields, et al. (1986) "Mutants of Salmonella typhimurium that cannot survive within the macrophage are invirulent," PNAS 83:5189-5193.
Fierer, et al. (1993) "Expression of the Salmonella virulence plasmid gene spvB in cultured macrophages and nonphagocytic cells," Infect. Immun. 61:5231-5236.
Finlay, et al. (1991) "Cytoskeletal rearrangements accompanying Salmonella entry into epithelial cells," 99:283-296.
Finlay (1994) "Molecular and cellular mechanisms of Salmonella pathogenesism" Curr. Top. Microbiol. Immunol. 192:163-185.
Foulongne, et al. (2000) "Identification of Brucella suis genes affecting intracellular survival in an in vitro human macrophage infection model by signature-tagged transposon mutagenesis," Infect. 68:1297-1303.
Forsberg, et al. (1994) "Use of transcriptional fusions to monitor gene expression: a cautionary tale," J. Bacteriol. 176:2128-2132 .
Fouts, et al. (1995) "Construction and immunogenicity of Salmonella typhimurium vaccine vectors that express HIV-1 gp120," Vaccine 13:1697-1705. Abstract Only.
Fouts, et al. (1995) "Construction and characterization of Salmonella-typhi based human immunodeficiency virus type 1 vector vaccine," Vaccine 13:561-569. Abstract'Only.
Francis et al. (1992) Morphological and cytoskeletal changes in epithelial cells occur immediately upon interaction with Salmonella typhumurium grown under low-oxygen conditions," Mol. Microbiol. 6:3077-3087.
Gentschev, et al. (1998) "Delivery of the p67 sporozite antigen Theileria parva by using recombinant Salmonella dublin: secretion of the product enhances specific antibody responses in cattle," Infect. Immun. 66:2060-2064.
Ginnochio, et al. (1992) "Identification and molecular characterization of a Salmonella typhimurium gene involved in triggering the internalization of Salmonella into cultured epithelial cells," Pnas 89:1575-5980.
Ginnocchio, et al. (1994) "Contact with epithelial cells induces the formation of surface appendages on Salmonella typhimurium," Cell 76:717-724.
Guillobel, et al. (1998) "Immunization against the colonization factor antigen I of enterotoxigenic Escherichia coli by administration of a bivalent Salmonella typhimurium aroA strain," Braz. J. Med. Biol. Res. 31:545-554. Abstract Only.
Gunn and Miller (1996) "PhoP-PhoQ activates transcription of pmrAB, encoding a two-component regulatory system involved in Salmonella typhimurium antimicrobial peptide resistance," J. Bacteriol. 178:6857-6864.
Guy, et al. (2000) "Aggregation of host endosomes by Salmonella requires SP12 translocation of SseGF and involves SpvR and the fms-aroE intergenic region," Mol. Microbiol. 37:1417-1435. Abstract Only.
Haddad, et al. (1995) "Surface display compared to periplasmic expression of a malarial antigen in Salmonella typhimurium and its implications for immunogencity," FEMS Immunol. Med. Microbiol. 12:175-186. Abstract Only.
Hahn, et al. (1998) A Salmonella typhimurium strain genetically engineered to secrete a bioactive human interleukin (hIL)-6 via the Escherichia coli hemolysin secretion apparatus, FEMS Immunol. Med. Microbiol. 20:111-119. Abstract Only.

Hakansson, et al. (1996) "The YoB protein of Yersinia pseudotuberculosis is essential for the translocation of Yop effector proteins accrsoos the target cell plasma membrane and displays a contact-dependent membrane disrupting activity," EMBO J. 15:5812-5823.

Harokopakis et al. (1997) "Mucosal immunogenicity of a recombinant Salmonella typhimurium-cloned heterologous antigen in the absence or presence of co-expressed cholera toxin A2 and B subunits," Infect. Immun. 65:1445-1454.

Hauser, et al. (1998) "Defects in type III secretion correlate with internalization of Pseudomonas aeruginosa by epithelial cells," Infect. Immun. 66:1413-1420.

Havaarstein, et al. (1995) "An unmodified heptadecapeptide phermone induces competence for genetic transformation in Streptococcus pneumoniae," PNAS 92:11140-11 144.

He, et al. (2000) "Function of human brain short chain L-3 hydroxyl coenzyme a dehydrogenase in androgen metabolism," Biochemica Et. Biophysica Acta:1484:267-277.

Heithoff, et al. (1999) "An essential role for DNA adenine methylation in bacterial virulence," Science 284:967-970.

Hensel and Holden (1996) "Molecular genetic approaches for the study of virulcence in both pathogenic bacteria and fungi," Microbiol. 142:1049-1058.

Herrero, et al. (1990) "Transposon vectors containing non-antibiotic resistance selection markers for cloning and stable chromosomal insertion of foreign genes in gram negative bacteria," J. Bacteriol. 172:6557-6567.

Hess, et al. (1997) "Protection against murine listerioisis by an attenuated recombinant Salmonella typhimurium vaccine strain that secretes the naturally somatic antigen superoxide dismutase," Infect. Immun. 65:1286-1292.

Hess, et al. (1995) "Listeria monocytogenes p60 supports host cell invasion by and in vivo survival of attenuated Salmonella typhimurium," Infect. Immun. 63:2047-2053.

Hess, et al. (1996) "Superior efficacy of secreted over somatic antigen display in recombinant Salmonella vaccine induced protection against listeriosis," PNAS 93:1458-1463.

Hess, et al. (1997) "Modulation of antigen display by attenuated Salmonella typhimurium strains and its impact on protective immunity against listeriosis," Behring Inst. Mitt. 160-171.

Hirakata, et al. (1992) "Efficacy of erythromycin lactobionate for treating Pseudomonas aeuginosa bacteremia in mice," Antimicrob. Agents Chemother. 36:1198-1203.

Hoffman and Stoffel (1993) "TMbase-a database of membrane spanning protein segments," Biol. Chem. Hoppe-Seyler 347:166.

Hohmann, et al. (1995) "Macrophage-inducible expression of a model antigen in Salmonella typhimurium enhances immunogenicity," PNAS 92:2904-2908.

Hohmann, et al. (1996) "Evaluation of phoP/phoQ-deleted aroA-deleted live oral Salmonella typhi vaccine strain in human volunteers," Vaccine 14:19-24.

Holden, et al. (1989) "Mutation in heat-regulated hsp70 gene of Ustilago maydis," EMBO J. 8:1927-1934.

Holtel, et al. (1992) "Upstream binding sequences of the XyIR activator protein and integration host factor in the xylS gene promoter region of the Pseudomonas TOL plasmid," Nucl. Acid Res. 20:1755-1762.

Hone, et al. (1988) "A chromosomal integration system for stabilzation of heterologous genes in Salmonella based vaccine strains," Microb. Pathog. 5:407-418. Abstract Only.

Hormaeche, et al. (1996) "Protection against oral challenge three months after i.v. immunization of BALB/c mice with live Aro Salmonella typhimurium and Salmonella enteritidis vaccines is serotype (species)-dependent and only partially determined by the main LPS O antigen," Vaccine 14:251-259. Abstract Only.

Hormaeche, et al. (1991) "Live attenuated Salmonella vaccines and their potential as oral combined vaccines carrying heterologous antigens," J. lmmunol. 142:113-120. Abstract Only.

Hueck (1998) "Type III protein secretion systems in bacterial pathogens of animals and plants," Microbiol. Mol. Biol. Rev. 62:379-433.

Hueck, et al. (1995) "Salmonella typhimurium secreted invasion determinants are homologous to Shigella Ipa proteins," Mol. Microbiol. 18:479-490.

Jager, et al. (1988) "Oligonucleotide N-alkylphosphoramidates: synthesis and binding to polynucleotides," Biochemistry 20:7237-7246.

Janssen, et al. (1995) "Induction of the phoE promoter upon invasion of Salmonella typhimurium into eukaryotic cells," Microb. Pathog. 19:193-201. Abstract Only.

Jornvall, et al. (1995) "Short chain dehydrogenases/reductases (SDR)" Biochemistry 34:60036013.

Jornvall, et al. (1999) "SDR and MDR: Completed genome sequences show these protein families to be large, of old origin and complex nature," FEBS Letters 445:261-264.

Kaniga, et al. (1995) "Homologs of the Shigella Ipa and IpC invasins are required for Salmonella typhimurium entry into cultured epithelial cells," J. Bacteriol. 177:3965-3971.

Kaniga, et al. (1994) "The Salmonella typhimurium invasion genes invF and invG encode homologs of the AraC and PulD family of proteins," Mol. Microbiol. 13L555-568.

Karem, et al. (1996) "Cytokine expression in the gut associated lymphoid tissue after oral administration of attenuated Salmonella vaccine strains," Vaccine 14:1495-1502. Abstract Only.

Kirsch and Di Domenico (1993) "The discovery of natural products with a therapeutic potential," V.P. Gallo, Ed. Chapter 6, pages 1770221, Buttersworth, V.K.

Krul, et al. (1996) "Induction of an antibody response in mice against human papilloma virus (HPV) type 16 after immunization with HPV recombinant Salmonella strains," Cancer Immunol. 43:44-48.

Kuwajiia, et al. (1989) "Export of N-terminal fragment of Escherichia coli flagellin by a flagellum-specific pathway," PNAS, 86:4953-4957.

Laemmli (1970) "Cleavage of structural proteins during the assembly of the head of bacteriophage T4," Nature 227:680-685.

Leary, et al. (1997) "Expression of an F I/V fusion protein in attenuated Salmonella typhimurium and protection of mice against plague," Microb. Pathog. 23:167-179. Abstract Only.

Lee, et al. (1992) "Identification of a Salmonella typhimurium invasion locus by selection for hyperinvasive mutants," PNAS 89:1847-1851.

Leiter, et al. (1990) "Inhibition of influenza virus replication by phosphorothioate oligodeoxynucleotides," PNAS 87:3430-3434.

Lenz, et al. (2000) "Chemical ligands, genomics and drug delivery," Drug Discovery Today 5:145156.

Levine, et al. (1996) "Attenuated Salmonella as live oral vaccines against typhoid fecer and as live vectors." J. Biotechnol. 44(1-3):193-196.

Liljevist, et al. (1996) "A novel expression system for Salmonella typhimurium, allowing hight production levels, product secretion and efficient recovery," Biochem. Biophys. Res. Corn. 218:356359. Abstract Only.

Lingberg (1995) "The history of live bacterial vaccines," Dev. Biol. Stand. 84:211-219. Abstract Only.

Li, et al. (1995) "Relationship between evolutionary rate and cellular location among the Inv/Spa invasion proteins of Salmonella enterica," PNAS 92:7252-7256.

Lo-Man, et al. (1996) "Control by H-2 genes of the Th1 response induced against foreign antigen expressed by attenuated Salmonella typhimurium," Infect. Immun. 64:4424-4432.

Lowe, et al. (1999) "Characterization of candidate live oral Salmonella typhi vaccine strains harboring defined mutations in aroA, aroC and htrA" Infect. Imm. 67:700-707.

Macnab (1996) "Flagella and motility in Escherichia coli and Salmonella: cellular and molecular biology," F.C. Neidardt, et al. (eds.) Washington, D.C.:ASM Press: 123-145.

Maskell, et al . (1987) "Salmonella typhimurium aroA mutants as carriers of Escherichia coli heat labile enerotoxin B subunit to the murine secretory and systemic immune systems," Microb. Pathog. 2:2211-221. Abstract Only.

Maurer, et al. (1984) "Functional interchangeability of DNA replication genes in Salmonella typhimurium and Escherichia coli demonstrated by a general complementation procedure," Genetics 108:1-23.

Mcsorley, et al. (1997) "Vaccine efficacy of Salmonella strains expressing glycoprotein 63 with different promoters," Infect. Immun. 65:171-178.

Michiels, et al. (1991) "Analysis of virC, an operon involved in the secretion of Ypo proteins by Yersinea enterocolitica," J. Bacteriol. 173:4994-5009.

Milich, et al. (1995) "The hepatitis nucleocapsid as a vaccine carrier moiety," Ann. NY Acad. Sci. 754:187-201. Abstract Only.

Miller and Mekalanos (1998) "A novel suicide vector and its use in construction of inversion mutations: osmoregulation of outer membrane proteins and virulence determinants in Vibrio cholerae requires ToxR," J Bacteriol. 170:2575-2593.

Miller et al. (1993) "The PhoP virulence regulon and live oral Salmonella vaccines," Vaccine 11:122-125.

Minamino, et at (1999) "Components of the Salmonella flagellar export apparatus and classification of export substrates," J. Bacteriol. 181:1388-1394.

Miras, et al. (1995) "Nucleotide sequence of iagA and iagB genes involved in invasion of HeLa cells by Salmonella enterica subsp. Enterica Ser. Typhi" Res. Micorbiol. 146:17-20.

Monack, et al. (1996) "*Salmonella typhimurium* invasion induces apoptosis in infected macrophages," PNAS 93:9833-9838.

Newton, et al. (1995) "Studies of the anaerobically induced promoter pnirB and the improved expression of bacterial antigens" 146:193-202.

Nielson, et al. (1998) "Synthesis and characterization of dinucleoside phosphorodithoates," Tetrahedron Letters, 29:291 Jan. 2914.

Ocallaghan and Charbit (1990) "High efficiency transformation of *Salmonella typhimurium* and *Salmonella typhi* by electroporation," Mol. Gen. Genet. 223:156-158.

Obeysekere et at (1998) "Serines at the active site of 11 beta-hydroxysteroid dehydrogenase type I determine the rate of catalysis" Biochem. Biophys. Res. Commun. 250:469-473.

Ohara, et al. (1989) "Direct genomic sequencing of bacterial DNA: the pyruvate kinase I gene of *Escherichia coli*," PNAS 86:6883-6887.

Okahashi, et al. (1996) "Oral immunization of interleukin-4 (IL-4) knockout mice with a recombinant Salmonell strain or cholera toxin reveals CD4+ Th2 cells producing 1L-6 and Il-10 are associated with mucosal immunoglobulin a responses," Infect. Immun. 64:1516-1525.

Opperman, et al. (1997) "Structure function relationships of SDR hydroxysteroid dehydrogenases," Advances in Exp. Med. And Biol. 414:403-415.

Orr, et al. (1999) "Expression and immunogenicity of a mutant diptheria toxin molecule, CRM197, and its fragments in *Salmonella typhi* vaccine strain CVD 908-htrA" Infect. Immun. 67:4290-4294.

Pallen, et al. (1997) "Coiled-coil domains in proteins secreted by type III secreion systems," Mol. Microbiol. 25:423-425.

Pearce, et al (1993) "Genetic identification of exported proteins in *Streptococcus pneumoniae*," Mol. Microbiol. 9:1037-1050.

Perlman and Freedman (1971) "Experimental endocarditis. II Staphlococcol infection of the aortic valve following placement of polyethylne catheter in the left side of the heart." Yale J. Biol. Med. 44:203-213.

Plano, et al. (1991) "LcrD, a membrane-bound reegulator of the Yersinia pestis low-calcium response," J. Bacteriol. 173:7293-7303.

Pozza, et al.. (1998) "Construction and characterization of *Salmonella typhimurium* aroA simultaneously expressing the five pertussis toxin subunits," Vaccine 16:522-529. Abstract Only.

Ralph, et al. (1975) "Reticulum cell sarcoma: and effector cell in antibody-dependent cell-mediated immunity," J. Immunol. 114:898-905•.

Reed and Muench (1938)"A simple method of estimating fifty per cent end points," Am J. Hyg. 27:493-497.

Rhen, et al. (1993) "Transcriptional regulation of Salmonella enterica virulence plasmid genes in cultured macrophages," Mol. Microbiol. 10:45-56. Abstract Only.

Ronson, et al. (1987) "Conserved domains in bacterial regulatory proteins that respond to environmental stimuli," Cell 49:579-581.

Roy and Coleman (1994) "Mutations in firA, encoding the seond acyltransferase in lippolysaccharide biosynthesis, affect mulitple steps in lipopolysaccharide biosynthesis," 176:16391646.

Saiki et al. (1988) "Primer directed enzymatic ampliifcation of DNA with a thermostable DNA polymerase," Science 4839:487-491.

Salmond and Reeves (1993) "Membrane traffic wardens and protein secretion in gram negative bacteria," Trends in Biochem. Sci. 18:7-12.

Sanderson, et al. (1995) "Genetic map of *Salmonella typhimurium*,edition VIII," Microbiol. Rev. 59:241-303.

Sanger, et al. (1977) "DNA seqeunce with chain terminating inhibitors," PNAS 74:5463-5467.

Sarin, et al. (1988) "Inhibition of acquired immunodeficiency syndrome virus by oligodeoxynucleoside methylphosphonates," PNAS 85:7448-7451•.

Sasakawa, et al. (1993) "Eigh genes in region 5 that form an operon are essential for invasion of epithelial cells by Shigella flexneria 2a," J. Bacteriol. 175:2334-2346.

Schmitt et al. (1996) "The attenuated phenotype of a *Salmonella typhimurium* flgM mutant is related to expression of FliC flagellin," J. Bacteriol. 178:2911-2915.

Schodel, et al. (1990) "Hepatitis B Virus Nucleocapsid/pre-S2 fusion proteins expressed in attenuated Salmonella for oral vaccination" J. Immunol. 145:4317-4321.

Schodel (1990) "Oral vaccination using recombinant bacteria," Semin. Immunol. 12:341-349.

Shaw et al. (1991) "Modified deoxyoligonucleotides stable to exonuclease degradation in serum," Nucelic Acids Res. 19:747-750.

Sigwart, et al. (1989) "Effect of purA mutation on efficacy of Salmonella live-vaccine vectors," Infect. lmmun. 57:1858-1861.

Skorupski and Taylor (1996) "Positive selection vectors for allelic exhange," Gene 169:47-52.

Strugnell et at (1990) "Stable expression of foreign antigens from the chromosome of *Salmonella typhimurium* vaccine strains," Gene 88:57-63. Abstract Only.

Strugnell et al. (1992) "Characterization of a *Salmonella typhimurium* aro vaccine strain expressing the p69 antigen of *Bordella pertussis*," Infect. Immun. 60:3994-4002.

Su et al. (1992) "Extracellular export of Shiga toxin B-subunit haemolysin a (C-terminus) fusion proteins expressed in *Salmonella typhimurium* aro-A mutant and stimulation of B-subunit specific antibody responses," Microb. Pathog. 13:465-476. Abstract Only.

Sullivan et al (1993) "Evaluation of the efficacy of ciprofloxacin against Streptococcus pneumoniae by using a mouse protection model," Antimicrob. Agents Chemother. 37:234-239.

Tacket at al. (1990) "Safety and immunogenicity, and efficacy against cholera challenge in humans of a typhoid-cholera hybrid vaccine derived from Salmonella typhi2la" Infect. Immun. 58:1620-1627.

Tacket et al. (1997) "Safely and immunogenicity in humans of an attenuated *Salmonella typhi* vaccine vector strain expressing plasmid encoded hepatitis B antigens stabilized by the Asd-balanced lethal vector system," Infect. Immun. 65:3381-3385.

Takeuchi (1967) "Electron microscope studies of experimental Salmonella infection. I. Penetration into the intestinal epithelium by *Salmonella typhimurium*," Am. J. Pathol. 50:109-136.

Tang et al. (1993) "Self-stabilized antisense oligodeoxynucleotide phosphorothioates: properties and anti-HIV activity," Nucleic Acids Res. 21:2729-2735 ,.

Tijhaar et al. (1997) "Induction of feline immunodeficiency virus specific antibodies in cats with an attenuated Salmonella strain expressing the Gag protein," Vaccine 15:587-596.

Tijhaar et al. (1997) "Salmonella typhimurium aroA recombinants and immune-stimulating complexes as vaccine candidates for feline immunodeficiency virus," J. Gen. Virol. 46:129-138.

Uznanski et al. (1987) "Deoxyribonucleoside 3'-phosphordiamidites as substrates for solid supported synthesis of oligodeoxyribonucleotides," Tetrahedron Letters 28:3401-3404.

Valentine et al. (1996) "Induction of Siv capsid specific CTL and mucosal sIgA in mice immunized with recombinant S. typhimurium aroA mutant," Vaccine 14:138-146.

Van Gijsegem et al (1993) "Conservation of secretion pathways for pathogenicity determinants of plant and animal bacteria," Trends Microbiol. 1:175-180.

Veber et al. (1993) "Correlation between macrolide lung pharmacokinetics and therapeutic efficacy in a mouse model of pneumococcal pneumonia," J. Antimicrob. Chemother. 32:473-483.

Venkatesan et al. (1992) "Surface presentation of Shigella flexneri invasion plasmid antigens requires the products of the spa locus," J. Bacteriol. 174:1990-2001.

Verma et al. (1995) "Induction of a cellular immune response to a defined T cell epitope as an insert in the flagellin of a live vaccine strain of Salmonella," Vaccine 13:235-234. Abstract Only.

Villafane et al. (1987) "Replication control genes of plasmid pE194," J. Bacteriol. 169:48224829.

Viret et al. (1993) "Molecular cloning and characterization of the genetic determinants that express the complete Shigella serotype D (shigella sonnei) lipopolysaccharide in heterologous live attenuated vaccine strains." Mol. Microbiol. 7:239-252. Abstract Only.

Wang et al, (2006) "Application of signature tagged mutagenesis to the study of Erwina amylovora" FEMS Microbiol. Lett. 265:164-171.

Wattiau et al. (1994) "Individual chaperones required for Yop secretion by Wattiau et al. (1994) "Individual chaperones required for Yop secretion by *Yersinia* " PNAS 91:10493-10497.

Whitman et al (1993) "Antibiotic treatment of experimental endocarditis due to vancomycin- and ampicillin-resistant *Enterococcus faecium*," Antimicrob. Agents Chemother. 37:2069-2073.

Whittle et al. (1997) "Immune response to a Murray Valley encephalitis virus epitope expressed in the flagellin of an attenuated strain of Salmonella," J. Med. Microbiol. 46:129-138.

Whittle and Verma (1997) "The immune response to a B-cell epitope delivered by Salmonella is enhanced by prior immunological experience," Vaccine 15:1737-1740. Abstract Only.

Wirth et al. (1986) "Highly efficient protoplast transformation system for *Streptococcus faecalis* and a new Escherichia coli-S. Faecalis shuttle vector," J. Bacteriol. 165:831-836.

Woods et al. (1982) "Contribution of toxin a and elastase to virulence of *Pseudomonas aeruginosa* in chronic lung infections of rats," Infect. Immun. 36:1223-1228.

Yan et al. (1996) "Mixed population approach for vaccination with live recombinant Salmonella strains." J. Biotechnol. 44:197-201. Abstract Only.

Yancey (1993) "Recent advances in bovine vaccine technology," J. Dairy Sci. 76:2418-2436.

Yang et al., (1990) "Oral *Salmonella typhimurium* (AroA-) vaccine expressing a major leishmanial surface ptorin (gp63) preferentially induces T helper 1 cells and protective immunity agaist leishmaniasis," J. Immunol. 145:2281-2285. Abstract Only.

Yanisch-Perron et al. (1985) "Improved M 13 phage cloning vectors and host strains: nucleotide sequences of the M13mp18 and pUC19 vectors." Gene 33:103-119.

Youderain et al. (1988) "Packaging specific segments of the Salmonella chromosome locked-in Mud-P22 prophages," Genetics, 118:581-592.

Young et al (1999) "A new pathway for the secretion of virulence factors by bacteria: the flagellar export apparatus functions as a protein secretion system." PNAS 96:6456-6461.

Zhu et al. (1993) "Systemic gene expression intravenous DNA delivery into adult mice." Science 261:209-211.

Acharya et al. (1987) "Prevention of typhoid fever in nepal with the vi capsular polyscharaide of *Salmonella typhi*," NEJM, 317:1101-1104.

Ahmer et al. (1999) "*Salmonella* SirA is a global regulator of genes mediating enteropathogenesis," Mol. Microbiol. 31(3):971-982.

Altare et al. (1998) "Inherited interleukin 12 deficiency in a child with Bacille Calmette-Guerin and *Salmonella enteritidis* disseminated infection," J. Clin. Invest. 102:2035-2040.

Angelakopoulos and Hohmann (2000) "Pilot study of *phoP/phoQ*-deleted *Salmonella enterica* serovar Typhimurium expressing Helicobacter pylori urease in adult volunteers," Infect. Immun., 68:2134-2141.

Aranda et al. (1992) "*Salmonella typhimurium* activates virulence gene transcription within acidified macrophage phagosomes," PNAS, 89:10079-10083.

Arricau et al. (1998) "The RcsB-RcsC regulatory system of *Salmonella typhi* differentially modulates the expression of invasion proteins, flagellin and Vi antigen in response to osmolarity," Mol. Microbiol. 29:835-850.

Ascon, et al. (1998) "Oral immunization with a *Salmonella typhimurium* vaccine vector expressing recombinant enterotoxigenic Eschericia coli K99 fimbrae elicits elevated antibody titers for protective immunity," Infect. Immun. 66:5470-5476.

Attridge (1991) "Oral immunization with *Salmonella typhi* Ty2 1 a-based clones expressing *Vibrio cholerae* O-antigen: serum bactericidal antibody responses in man in relation to pre-immunization antibody levels," Vaccine, 9:877-882.

Bao and Clements (1991) "Prior immunologic experience potentiates the subsequent antibody response when *Salmonella* strains are used as vaccine carriers," Infect. Immun. 59:3841-3845.

Barry et al. (1996) "Expression and Immunogenicity of Pertussis Toxin S1 subunit-tetanus toxin fragment C fusion in *Salmonella typhi* vaccine strain CVD 908," Infect. Immun. 64:7472-4781.

Basso et al. (2002) "Characterization of a novel intracellularly activated gene from *Salmonella enterica* serovar typhi," Infect. Immun. 70:5404-5411.

Benjamin et al. (1991) "A *hemA* mutation renders *Salmonella typhimurium* avirulent in mice, yet capable of eliciting protection against intravenous infection with *S. typhimurium*," Microb. Pathog. 11:289-295.

Beuzon et al. (1999) "pH-dependant secretion of SseB, a product of the SPI-2 type III secretion system of *Salmonella typhimurium*," Mol. Microbiol. 33:806-816.

Beuzon et al. (2000) "*Salmonella* maintains the integrity of its intracellular vaciole through the action of SifA," Embo J., 19:3235-3249.

Black, et al. (1983) "Immunogenicity of Ty2la Attenuated *Salmonella typhi* given with sodium bicarbonate or in enteric-coated capsules," Develop. Biol. Stand., 53:9-14.

Bost and Clements (1995) "In vivo induction of interleukin-12 mRNA epxression after oral immunization with *Salmonella dublin* or the B subunit of *Escherichia coli* heat-labile enterotoxin," Infect. Immun. 63:1076-1083.

Brennan et al. (1994) "Differences in the immune responses of mice and sheeo ti an aromatic-dependent mutant of *Salmonella typhimurium*," J. Med. Microbiol. 41:20-28.

Brown and Hormaeche (1989) " The antibody response to salmonellae in mice and humans studied y immunoblots and ELISA," Microb. Pathog. 6:445-454.

Brown et al. (1987) "An attenuated *aroA Salmonella typhimurium* vaccine elicits humoral and cellular immunity to cloned β-galactosidase in mice," J. Infect. Dis. 155:86-92.

Browne et al. (2002) "Genetic requirements for *Salmonella*-induced cytopathology in human monocyte-derived macrophages," Infect. Immun. 70:7126-7135.

Buchmeier and Libby (1997) "Dynamics of growth and death within a *Salmonella typhimurium* population during infection of macrophages," Can. J. Microbiol. 43:29-34.

Bumann et al. (2000) "Recombinant live *Salmonella* spp. For human vaccination against heterologous pathogens," Fems Immunol. Med. Microbiol. 27:357-364.

Bumann et al. (2002) "Safety and immunogenicity of live recombinant *Salmonella enterica* serovar typhi Ty2la expressing urease A and B from *Helicobacter pylori* in human volunteers," Vaccine, 20:845-852.

Butler, et al. (1991) "Pattern of morbidity and mortality in typhoid fever dependent on age and gender: review of 552 hospitalized patients with diarrhea," Rev. Infect. Dis. 13:85-90.

Cameron and Fuls (1976) "Immunizaion of mice and calves agaisnt *Salmonella dublin* with attenuated live and inactivated vaccines," J. Vet. Res. 43:31-38.

Cancellieri and Fara (1985) "Demonstration of specific IgA in human feces after immunization with live Ty2la *Salmonella typhi* vaccine," J. Infect. Dis. 151:482-484.

Caro, et al. (1999) "Physiological changes of *Salmonella typhimurium* cells under osomotic and starvation conditions by image analysis," FEMS Microbiol. Lett. 179:265-273.

Carrier, et al. (1992) "Expression of Human IL-1βin *Salmonella typhimurium*, a model system for the delivery of recombinant therapeutic proteins in vivo," J. Immunol. 148:176-181.

Carter and Collins (1974) "Growth of typhoid and paratyphoid Bacilli in travenously infected mice," Infect. Immun. 10:816-822.

Casadevall (1998) "Antibody-mediated protection against intracellular pathogens," Trends in Microbiol. 6:102-107.

Chabalgoity et al. (1995) "Influence of preimmunization with tetanus toxioid on immune responses to tetanus toxin fragment c-guest antigen fusions in *Salmonella* vaccine carrier," Infect. Immun. 63:2564-2569.

Chabalgoity et al. (1997) "Expression and immunogenicity of an *Echinococcus granulosus* fatty acid-binding protein in live attenuated Salmonella vaccine strains," Infect. Immun. 65;2402- 2412.

Charles et al. (1990) "Isolation, characterization and nucleotide sequences of the aroC genes encoding chorismate synthase from *Salmonella typhi* and *Escherichia coli*," J. Gen. Microbiol. 136:353-358.

Chatfield, et al. (1992) "Use of the nirB promoter to direct the stable expression of heterologous antigens in *Salmonella* oral vaccine strains: development of a single-dose oral tetanus vaccine," Biotechnol. 10:888-892.
Chatfield, et al. (1992) "Evaluation of *Salmonella typhimurium* strains harbouring defined mutations in *htrA* and *aroA* in the murine salmonelloisis model," in Microbial Pathog. 12:145-151.
Chatfield, et al. (1994) "Progress in Development of Mutlivalent Oral Vaccines Based on Live Attenuated *Salmonella*" *Modern Vaccinology* E. Kurstak, ed., Plenum Medical,New York, NY. 55-85.
Chen and Schifferli (2001) "Enhanced immune responses to viral epitopes by combining macrophage-inducible expression with multimeric display on a *Salmonella* vector," Vaccine, 19:3009-3018.

Chen, et al (1996) "Salmonella spp. are cytotoxic for cultured macrophages," Mol. Microbio]. 21:1101-1115.

Chuttani, et al. (1973) "Ineffectiveness of an oral killed typhoid vaccine in a field trial," Bull. Org. Mond. Sante, 48:756-757.

Chuttani, et al. (1977) "Controlled field trial of a high-dose oral killed typhoid vaccine in India," Who 55:643-644.

Ciacci-Woolwine et al. (1997) "Salmonellae activate tumor necrosis factor apha production in a human promonocytic cell line via a released polypeptide," Infect. Immun. 65:4624-4633.

Cieslak et al. (1993) "Expression of a recombinant *Entamoeba histolytica* antigen in a *Salmonella* typhimurium vaccine strain," Vaccine 11:773-776.
Clairmont et al. (2000) "Biodistribution and genetic stability of the novel antitumor agent VPN20009, a genetically modified strain of *Salmonella typhimurium* " J. Infect. Dis. 181:1996-2002.
Clark, et al. (1996) "Invasion of murine intestinal M cells by *Salmonella typhimurium inv* mutants severely deficient for invasion of cultured cells," Infect. Immun. 64:4363-4368.
Clark, et al. (1998) "Inoculum composition and *Salmonella* pathogenicity island 1 regulate M-cell invasion and epithelial destruction by *Salmonella typhimurium*," Infect. lmmun. 66:724-731.

Clements and El-Morshidy (1984) "Construction of a potential live oral bivalent vaccine for typhoid fever and cholera-*Escherichia coil*-Related diarrheas," Infect. Immun. 46:564-569.

Clements et al. (1986) "Oral immunization of mice with attenuated *Salmonella enteritidis* containing a recombinant plasmid which codes for production of the B subunit of heat-labile *Escherichia coli* enterotoxin," Infect. Immun. 53:685-692.

Cobelens, et al. (2000) "Typhoid fever in groups of travelers: Opporotunity for studying vaccine efficacy," J. Travel Med. 7:19-24.

Collins and Carter (1972) "Comparative immunogenicity of heat-killed and living oral Salmonella vaccines," Infect. Immun. 6:451-458.

Collins (1972) "Salmonellosis in orally infected specific pathogen-free C57B1 mice," Infect. Immun. 5:191-198.

Cooper et al. (1992) "Vaccination of chickens with chicken-derived *Salmonella enteritidis* phage type 4 aroA live oral salmonella vaccines," Vaccine 10:247-254.

Corbel (1996) "Reasons for instablitiy of bacterial vaccines," Dev. Biol. Stand. 87:113-124.
Coulson et al. (1994) "*Bacillus anthracis* protective antigen, expressed in Salmonella typhimurium Sl 3261, affords protection against antrhax spore challenge," Vaccine, 12:1395-1401.
Coulson et al. (1994) "Effect of different plasmids on colonization of mouse tissues by the aromatic amino acid dependent *Salmonella typhimurium*, Sl 3261," Microbial Pathog. 16:305-311.
Coynault and Noral (1999) "Comparison of the abilities of *Salmonella typhimurium rpoS, aroA* and *rpoS aroA* strains to elicit humor immune responses in BALB/c mice to cause lethal infection in athymic BALB/c mice," Microbial Pathog. 26:299-305.
Coynault et al. (1996) "Virulence and vaccine potential of *Salmonella typhimurium* mutants deficient in the expression of the RpoS $\sigma^5$ regulon," Mol. Microbiol. 22:149-160.
Cryz et al. (1989) "Construction and characterization of a Vi-positive variant of the *Salmonella typhi* live oral vaccine strain Ty21a," Infect. Immun. 57:3863-3868.
Cryz et al. (1995) "Safety and immunogenicity of a live oral bivalent typhoid fever (*Salmonella typhi* Ty21a)-cholera (*Vibrio cholerae* CVD 103-HgR) vaccine in healthy adults," Infect. Immun. 63:1336-1339.
Curtiss and Kelly (1987) "*Salmonella typhimurium* deletion mutants lacking adenylate cyclase and cyclic Amp receptor protein are avirulent and immunogenic," Infect. Immun. 55:3035-3043.
Curtiss et al. (1989) "Recombinant avirulent Salmonella vaccine strains with stable maintenance and high level expression of cloned genes in vivo," Immunol. Invest. 18:583-596.
D'Amelio et al. (1988) "Comparative analysis of immunological responses to oral (Ty21a) and parenteral (Tab) typhoid vaccines," Infect. Immun.. 56:2731-2735.
De Almeida (1999) "Antibody responses against flagellin in mice orally immunized with attenuated Salmonella vaccine strains," Arch. Microbiol. 172:102-108.
Dham and Thompson (1982) "Studies of cellular and humoral immunity in typhoid fever and Tab vaccinated subjects," Clin. Exp. Immunol. 48:389-395.
Dilts, et al. (2000) "Phase I clinical trials of *aroA aroD* and *aroA aroD htrA* attenuated *S. typhi* vaccines; effect of formulation on safety and immunogenicity," Vaccine, 18:1473-1484.
Dima (1981) "Isolation and characterization of two *Salmonella typhosa* mutants for possible use as a live oral attenuated vaccinal strains," Arch. Roum. Path. Exp. Microbiol. 40:33-40.
Depetrillo (2000) "Safety and immunogenicity of *PhoP/PhoQ*-deleted *Salmonella typhi* expressing *Helicobacter pylori* urease in adult volunteers," Vaccine 18:449-459.
Djavani et al. (2001) "Mucosal immunization with *Salmonella typhimurium* expressing Lassa virus nucleocapsid protein cross-protects mice from lethal challenge with lymphocytic choriomeningitis virus," J. Hum. Virol. 4:103-108.
Dorman et al. (1989) "Characterization of porin and *ompR* mutants of a virulent strain of *Salmonella typhimurium: ompR* mutants are attenuated in vivo," Infect. Immun. 57:2136-2140.
Dorner (1995) "An overview of vaccine vectors," Dev. Biol. Stand. 84:23-32.
Douce , et al. (1991) "Invasion of HEp-2 cells by strains of *Salmonella typhimurium* different virulence in relation to gastroenteritis," J. Med. Microbiol. 35:349-357.
Dougan, et al. (1988) "Construction and characterization of vaccine strains of Salmonella harboring mutations in two different *aro* genes," J. Infect. Dis. 158:1329-1335.
Dragunsky et al. (1990) "In vitro characterization of *Salmonella typhi* mutant strains for live oral vaccines," Vaccine 8:263-268.
Dragunski et al. (1989) "*Salmonella typhi* vaccine strain in vitro; low inefectivity in human cell line U937," J. Biol. Stand. 17:353-360.
Dunstan et al. (1999) "Use of in vivo-regulated promoters to deliver antigens from attenuated *Salmonella enterica* var. Typhimurium," Infect. Immun. 67:5133-5141.
Dupont et al. (1971) "Studies of immunity in typhoid fever," Bull. Org. Mond. Sante. 44:667-672.
Edwards and Stocker (1988) "Construction of Δ*aroA his* Δ*pur strains* of *Salmonella typhi*," J. Bacteriol. 170:3991-3995.
Eichelberg and Galan (1999) "Differential regulation of *Salmonella typhimurium* type III secreted proteins by pathogenicity island 1 (SPI-1)-encoded transcriptional activators InvF and HiIA," Infect. Immun. 67:4099-4105.
Emmerth, et al. (1999) "Genomici subtraction identifies *Salmonella typhimurium* prophages, F-related plasmid sequences, and a novel fimbrial operon, stf, which are absent in *Salmonella typhi*," J. Bacteriol. 181:5652-5661.

Engels, et al. (1998) "Typhoid fever vaccines: a meta-analysis of studies on efficacy and toxicity," BMJ, 316:110-113.

Everest, et al. (1999) "Evaluation of *Salmonella typhimurium* Mutants in a model of experimental gastroenteritis," Infect. Immun. 67:2815-2821.

Fallon, et al. (1991) "Mouse hepatitis virus strain UAB infection enhances resistence to *Salmonella typhimurium* in mice by inducing supression of bacterial growth," Infect. Immun. 59:852-856.

Ferricio (1989) "Comparative efficacy of two, three or four doses of TY2la live oral vaccine in enteric coated capsules: a field trial in an endemic area," J. Infect. Dis. 159:766-769.

Finlay and Falkow (1997) "Common themes in microbial pathogenicity revisited," Microbiol. Mol. Biol. Rev. 61:136-169.

Formal et al. (1981) "Construction of a potential bivalent vaccine strain: introduction of *Shigella sonnei* form I antigen genes into the *galE Salmonella typhi* Ty2la typhoid vaccine strain," Infect. Immun. 34:746-750.

Forrest and LaBrooy (1993) "Effect of parenteral immunization on intestinal immune response to *Salmonella typhi* Ty2la as measured using peripheral blood lymphocytes," Vaccine, 11:136-139.

Fu and Galan (1998) "The *Salmonella typhimurium* tyrosine phosphatase SptP is translocated into host cells and disrupts the actin cytoskeleton," Mol. Microbiol. 27:359-368.

Gahring, et al. (1990) "Invasion and replication of *Salmonella typhimurium* in animal cells," Infect. Immun. 58:443-448.

Galan and Colimer (1999) "Type Hi secretion machines: bacterial devices for protein delivery into host cells," Science, 284:1322-1328.

Galan and Zhou (2000) Striking a balance: modulation of the actin cytoskeleton by *Salmonella*. PNAS, 97:8754-8761.

Galan, et al (1990) "Cloning and characterization of the *asd* gene of *Salmonella typhimurium*: use in a stable maintenance of recombinant plasmids in *Salmonella* vaccine strains," Gene, 94:29-35.

Galan and Levine (2001) "Can a 'flawless' love vector strain be engineered?" Trends in Microbiol. 9:372-376.

Galan (1996) "Molecular genetic bases of *Salmonella* entry into host cells," Mol. Microbiol. 20:263-271.

Galen et al. (1999) "Optimization of plasmid maintenance in attenuated live vector vaccine strain *Salmonella typhi* CVD 908-*htrA*" Infect. Immun. 67:6424-6433.

Garcia-Del Portillo, et al. (1993) "Salmonella induces the formation of filament structures containing lysosomal membrane glycoproteins in epithelial cells," PNAS, 90:10544-10548.

Garmory et al. (2002) "*Salmonella* vaccines for use in humans: present and future perspectives," FEMS Microbiol. Rev. 26:339-353.

Gautier et al. (1998) " Mouse susceptibility to infection by the *Salmonella abortusovus* vaccine strain Rv6 is controlled by the Ity/Nramp I gene and influences the antibody response but not the complement response," Microbial Pathog. 24:47-55.

Gentschev et al. (2000) "Delivery of protein antigens and DNA by virulence attenuated strains of *Salmonella typhimurium* ans *Listeria monocytogenes*," J. Bacteriol. 83:19-26.

Germanier and Furer (1975) "Isolation and characterization of *Gal E* mutant Ty21 a of *Salmonella typhi*: a candidate strain for a live oral typhoid vaccine," J. Infect. Dis. 131:553-558.

Germanier and Levine (1986) "The live typhoid vaccine Ty21a: recent field trial results," Bacterial Vaccines and Local Immunity:19-22.

Gewirtz et al (1999) "Orchestration of neutrophil movement by intestinal epithelial cells in response to *Salmonella typhimurium* can be uncoupled from bacterial internalization," Infect. Immun. 67:608-617.

Gilman (1977) "Evaluation of UDP-glucose-4-epineraseless mutant of *Salmonella typhi* as a live oral vaccine," J. Infect. Dis. 130:717-723.

Giron et al. (1995) "Simultaneous expression of CFA/I and CS3 colonization factor antigens of enterotoxifenic *Escherichia coli* by ΔaroC, ΔaroD *Salmonella typhi* vaccine strain CVD 908," Vaccine, 13:939-946.

Gonzales, et al. (1994) "*Salmonella typhi* vaccine strain CVD 908 expressing the circumsporozoite protein of *Plasmodium faliciparum*: Strain construction and safety and immunogenicity in humans," J. Infect. Dis. 169:927-931.

Gonzales et al. (1998) "Immunogenicity of a *Salmonella typhi* CVD 908 candidate vaccine strain expressing the major surface protein gp63 of *Leishmania mexicana mexicana*," Vaccine 16:10431052.

Grossman et al. (1995) "Flagellar serotypes of *Salmonella typhi* in Indonesia: Relatioships among motility, invasiveness, and clinical illness" J. Infect. Dis. 171:212-216.

Guard-Petter, et al. (1995) "Characterization of lipopolysaccharide heterogeneity in *Salmonella enteritidis* by an improved gel electrophoresis method," Appl. Eviron. Microbiol., 61;2845-2851.

Guerrant and Kosek (2001) "Polysaccharide conjugate typhoid vaccine," NEJM, 344:13221323.

Guillobel et al. (2000) "Adjuvant activity of a nontoxic mutant *Eschericia coli* heat-labile enterotoxin on systemic and mucosal immune responses elicited against a heterologous antigen carried by a live *Salmonella entericai* serovar typhimurium vaccine strain," 68:4349-4353.

Gunn et al. (1995) "Characterization of the *Salmonella typhimurium pagC/pagD* Chromosomal region," J. Bacteriol. 177:5040-5047.

Guo et al. (1997) "Regulation of lipid modifications by *Salmonella typhimurium* virulence genes *phoP-phoQ*," Science, 276:250-253.

Hacket (1993) "Use of *Salmonella* for heterologous gene expression and vaccine delivery systems," Curr. Opin. Biotechnol. 4:611-615.

Hall and Taylor (1970) "Salmonella Dublin: The relation between a living calf vaccine strain and those isolated from human and other sources," Vet. Rec. 86:534-536.

Harrison et al. (1997) "Correlates of protection induced by live Aro *Salmonella typhimurium* vaccines in the murine typhoid model," Immunol. 90:618-625.

Herrington et al. (1990) "Studies in volunteers to evaluate candidate *Shigella* vaccines: further experience with a bivalent *Salmonella typhi-Shigella sonnei* vaccine and protection conferred by previous *Shigella sonnei* disease," Vaccine, 8:353-357.

Hess et al. (1996) "*Salmonella typhimurium* aroA infection in gene-targeted immunodeficient mice; major role of CD4+34 TCR-αβ cells in IFN-γ in bacterial clearance independent of intracellular location," J. Immunol. 156:3321-3326.

Hindle et al. (2002) "Characterization of *Salmonella enterica* derivatives harboring defined *aroC* and *Salmonella* pathogenicity island 2 type III secretion system (*ssaV*) mutaions by immunization of healthy volunteers," Infect. Immun. 70:3457-3467.

Hirose et al. (1997) "Survival of Vi-capsulated and Vi-deleted *Salmonella typhi* strains in cultured macrophage expressing different levies of CD14 antigen," FEMS Microbiol. Lett. 147:259-265.

Hohmann and Oletta (1996) "*phoP/phoQ*- deleted *Salmonella typhi* (Ty800) is safe and immunogenic single-dose fever vaccine in volunteers," J. Infect. Dis. 173:1408-1414.

Hoisth and Stocker (1981) "Aromatic-dependent *Salmonella typhimurium* are non-virulent and effective as live vaccines," Nature, 291:238-239.

Holden (2002) "Trafficking of the *Salmonella* vacuole in macrophages," Traffic, 3:1-11.

Holmstrom, et al. (1999) "Physiological states of individual *Salmonella typhimurium* cells monitored by in situreverse transcription PCR," J. Bacteriol. 181:1733-1738.

Hone et al. (1988) "A *galE* via (Vi antigen-negative) mutant *Salmonella typhi* Ty2 retains virulence in humans," Infect. Immun. 56:1326-1333.

Hone et al (1991) "Construction of genetically defined double aro mutants of *Salmonella typhi*," Vaccine, 9:810-816.

Hone et al. (1992) "Evaluation in volunteers of candidate live oral attenuated *Salmonella typhi* vector vaccine," J. Clin. Invest. 90:412-420.

Hone, et al. (1994) "Adaptive acid tolerance response by *Salmonella typhi* and candidate live oral typhoid vaccine strains," Vaccine, 12:895-898.

Hopkins, et al. (1995) "A recombinant *Salmonella typhimurium* vaccine induces local immunity by four different routes of immunization," Infect. Immun. 63:3279-3286.

Hormaeche (1979) "Natural resistance to *Salmonella typhimurium* in different inbred mouse strains," Immunol. 37:311-318.

Hornick (1970) "Typhoid fever: pathogenesis and immunogic control," NEJM, 283: 739-742.

House, et al. (2001) "Typhoid fever: pathogenesis and disease," Curr. Opin. Infect. Dis. 14:573578.

Humphreys, et al. (1999) The alternative sigma factor, $\sigma^E$ is critically important for the virulence of *Salmonella typhimurium*, Infect. Immun. 67:1560-1568.

Ishibashi and Arai (1995)"*Salmonella typhi* does not inhibit phagosome-lysosome fusion n human monocyte derived macrophages," FEMS Immunol. Med. Microbiol. 12:55-62.

Ivanoff, et al. "Vaccination against typhoid fever: present status," Who Bull. DMS, 72:957-971.

Jepson et al. (1996) "Evidence for a rapid, direct effect on epithelial monolayer integrity and transepithelial transport in response to *Salmonella* invasion," Eur. J. Physiol. 432:225-233.

Johnston et al. (1996) "Transcriptional activation of *Salmonella typhimurium* invasion genes by a member of the phosphorylated response-regulator superfamily," Mol. Microbiol. 22:715-727.

Jones et al. (1981) "The invasion of HeLa cells by *Salmonella typhimurium*: Reversible and irreversable bacterial attachment and the role of bacterial motility," J. Gen. Microbiol. 127:351-360.

Kantele, et al. (1991) "Comparision o the human immune response to live oral, killed oral or killed parenteral *Salmonella typhi* Ty21A vaccines," Microbial Pathog. 10:117-126.

Kantele et al. (1998) "Differences in immune responses induced by oral and rectal immunizations with *Salmonella typhi* TY21a: Evidence for compartmentalization within the common mucosal immune system in humans," Infect. Immun. 66:5630-5635.

Karem, et al. (1995) "Differential induction of carrier antigen-specific immunity by *Salmonella typhimurium* live-vaccine strains after single mucosal or intravenous immunization of Balb/c mice," Infect. Immun. 63:4557-4563.

Karem, et al. (1997) "Protective immunity against herpes simplex (HSV) type 1 following oral administration of recombinant *Salmonella typhimurium* vaccine strains expressing HSV antigens," J. Gen. Virol. 78:427-434.

Kaufman and Hess (1999) "Impact of intracellular location of and antigen display by intracellular bacteria: implications for vaccine development," Immunol. Lett. 65:81-84.

Kawakami, et al. (1969) "Experimental Salmonellosis immunizing effect of live vaccine prepared from various mutants of *Salmonella* having different cell wall polysaccharides," Japan. J. Microbiol. 13:315-324.

Keddy, et al. (1998) "Efficacy of Vi polysaccharide vaccine against strains of *Salmonella typhi*: reply" Vaccine, 16:871-872.

Kehres, et al. (2000) "The NRAMP proteins of *Salmonella typhimurium* and *Escherichia coli* are selective manganese transporters involved in the response to reactive oxygen," Mol. Microbiol. 36:1085-1100.

Keitel, et al. (1994) "Clinical and serological responses following primary and booster immunizations with *Salmonella typhi* Vi capsular polysaccharicde vaccines," 12:195-199.

Kelly, et al. (1992) "Characterization and protective properties of attenuated mutants of *Salmonella choleraesuis*," Infect. Immun. 60:4881-4890.

Keren, et al. (1978) "The role of peyer's patches in the local immune response of rabbit ileum to live bacteria," J. Immunol. 120:1892-1896.

Khan, et al. (1998) "*Salmonella typhi rpoS* mutant is less cytotoxic than the parent strain but survives inside resting THP-1 macrophages," FEMS Microbiol. Lett. 161:201-208.

Khan et al. (1998) "A lethal role for lipid a in *Salmonella* infections," Mol. Microbiol. 29:571-579.

Khan et al. (2001) "Early responses to *Salmonella typhimurium* infection in mice occur at focal lesions in infected organs," Microbial Pathog. 30:29-38.

Khan et al. (2003)"*Salmonella typhi* and *S. typhimurium* derivatives harbouring deletions in aromatic biosynthesis and Salmonella pathogenicity island-2 (SPI-2) genes as vaccines and vectors," Vaccine, 21:538-548.

Khan, et al. (2007) "Ability of SPI2 mutant of *S. tyhpi* to effectively induce antibody responses to the mucosal antigen enterotoxigenic *E. coli* heat labile toxin B subunit after oral delivery to humans," Vaccine, 25:4175-4182.

Kingsley and Baumler (2000) "Host adaptation and the emergency of infectious disase: the *Salmonella* paradigm," 1006-1014.

Kirkpatrick, et al. (2005) "Comparison of the antibodies in lymphocyte supernatant and antibody-secreting cells assays for measuring intestinal mucosal immune response toa novel oral typhoid vaccine (M01ZH09)" Clin. Diagnostic Lab. Immunol. 12:1127-1129.

Kirkpatrick et al. (2005) "The novel oral typhoic vaccine MOIZHO9 is well tolerated and highly immunogenic in 2 vaccine presentations," J. Infect. Dis. 192:360-366.

Kirkpatrick, et al. (2006) "Evaluation of *Salmonella enterica* serovar Typhi (Ty2 *aroC-ssaV -* ) *M01ZH09*, with a defined mutation in the *Salmonella* pathogenicity island 2, as a live, oral typhoic vaccine in human volunteers," Vaccine, 24:116-123.

Klugman, et al. ( 1987) "Protease activity of Vi capsular polysaccharide vaccine against typhoid fever," Lancet, 1165-1169.

Kohbata, et al. (1986) "Cytopathogenic effect of *Salmonella typhi* GIFU 10007 on M cells of murine ileal peyer's patches in ligated ileal loops: an ultrastructural study," Microbiol. Immunol. 30:1225-1237.

Kohler et al., (2000) "Effect of preexisting immunity to *Salmonella* on the immune response to recombinant *Salmonella enterica* serovar typhimurium expressing a *Porphyromonas gingivalis* hemagglutinin," Infect. Immun. 68:3116-3120.

Kollaritsch et al. (1996) "Randomized double-blind placebo-controlled trial to evaluate the safety and immunogenicity of combined *Salmonella typhi* Ty2la and *Vibrio cholerae* CVD 103-HgR live oral vaccines," Infect. Immun. 64:1454-1457.

Kollaritsch et al. (1997) "Safety and immunogenicity of live oral Cholera and Typhoid vaccines administered alone or in combination with antimalarial drugs, oral polio vaccines, or yellow fever vaccine," J. Infect. Dis. 871-875.

Kollaritsch, et al. (2000) "Local and systemic immune responses to combined *Vibrio cholerae* CVD103-HgR and *Salmonella typhi* Ty2la live oral vaccines after primary immunization and reimmunization," Vaccine 18:3031-3039.

Kotloff, et al. (1996) "Safety, immunogenicity, and transmissibility in humans in CVD 1203 a live oral *Shigella flexneri* 2a vaccine candidate attenuated by deletions in *aroA* and *virG*," Infect. Immun. 64:4542-4548.

Kramer and Vote (2000) "Granulocyte selected live *Salmonella enteritidis* vaccine is species specific," Vaccine, 18:2239-2243.

Lalmanach and Lantier (1999) "Host cytokine response and resistance to *Salmonella* infection," Microbes Infect. 1:719-726.

Lebacq (2001) "Comparative tolerability an immunogenicity of Typherix™or Typhium Vi™in healthy adults," Drugs, 15 Suppl. 1:5-12.

Leclerc, et al. (1998) "Environmental regulation of *Salmonella typhi* invasion-defective mutants," Infect. Immun. 66:682-691.

Lee and Schneewind (1999) "Type III secretion machines and the pathogenesis of enteric infections caused by *Yersina* and *Salmonella* spp." Immunol. Rev. 168:241-255.

Lee et al. (2000) "Surface-displayed viral antigens on *Salmonella* carrier vaccine," Nature Biotechnol. 18:645-648.

Lee et al. (2000) "OmpR regulates the two-component system SsrA-SsrB in *Salmonella* pathogenicity island 2," J. Bacteriol. 182:771-781.

Lehoux et al. (1999) "Defined oligonucleotide tag pools and PCR screeing in signature-tagged mutagenesis of essential genes from bacteri," BioTechniques 26:473-480.

Leung and Finlay (1991) "Intracellular replication is essential for the virulence of *Salmonella typhimurium*," PNAS 88:11470-11474.

Levine and Sztein (1996) "Human mucosal vaccines for *Salmonella typhi* infections," in *Mucosal Vaccines*, Kiyono, et al., eds. Academic Press, San Diego.

Levine, et al. (1985) "The efficacy of attenuated *Salmonella typhi* oral vaccine strain Ty2la evaluated in controlled field trials," Dev.Vaccines and Drugs agains diarrhea, 11th nobel Conf. Stockholm, pp. 90-101.

Levine et al. (1987) "Safety, infectivity, immunogenicity, and in vivo stability of two attenuated auxotrophic mutant strains of *Salmonella typhi*, 541Ty and 543Ty, as live oral vaccines in human," J. Clin. Invest. 79:888-902.

Levine (1987) "Large-scale field trial of Ty2l a live oral typhoid vaccine in enteric-coated capsule formulation." Lancet, 1049-1052.

Levine et al. (1989) "Progress in vaccines against typhoid fever," Rev. Infect. Dis. 11:S552-S567.

Levine, et al. (1990) "Comparison of enteric-coated capsules and liquid formulation of Ty2la typhoid vaccine in randomised comtrolled field trial," Lancet, 336:891-894.

Levine et al. (1997) "Attenuated *Salmonella typhi* and *Shigella* as love oral vaccines and as live vectors," Behring Inst. Mitt. 98:120-123.

Levine, (1994) "Typhoid Fever Vaccines," in *Vaccines*, Plotkin and Mortimer, eds., W.B. Saunders Company, Philadelphia, 597-633.

Levine, et al. (1999) "Duration of efficacy of Ty2la, attenuated *Salmonella typhi* live oral vaccine," Vaccine, 17:S22-S27.

Levine, et al. (1997) "Attenuated Salmonella as a live vector for expression of foreign antigens. Part iii. Salmonella expressing protozoal antigens," in *New Generation Vaccines* $2^{nd}$ ed., Levine, et. al., eds. Marcel Dekker, New York. 351-361.

Levine et al. (2001) "Host-Salmonella interaction: human trials," Microbes Infect. 3:1271-1279.

Liang-Takasaki, et al. (1982) "Phagocytosis of bacteria by macrophages: Changing the carbohydrate of lipopolysaccharide alters interatction with complement and macrophages," J. Immunol. 128:1229-1235.

Liang-Takasaki et al. (1983) "Complement activation by polysaccharide of lipopolysaccharide: an important virulence determinant of Salmonellae," Infect. Immun. 41:563-569.

Liang-Takasaki, et al. (1983) "Salmonellae activate complement differentially via the alternative pathway depending on the structure of their lipopolysaccharide 0-antigen," J. Immunol. 130:1867-1870.

Libby et al. (1994) "A cytolysin encoded by *Salmonella* is required for survival within macrophages," PNAS, 91:489-493.

Liu, (1988) "Intact motility as *Salmonella typhi* invasion-related factor," Infect. Immun. 56:19671973.

Lodge, et al. (1995) "Biological and genetic characterization of TnphoA mutants of *Salmonella typhimurium* TML in the context of gastroenteritis," Infect. Immun. 63:762-769.

Londono et al. (1995) "Immunization of mice using *Salmonella typhimurium* expressing human papillomavirus type 16 E7 epitopes inserted into hepatitis B virus core antigen," Vaccine, 14:545552.

Low, et al. (1999) "Lipid a mutant *Salmonella* with suppressed virulence and TNFα induction retain tumor-targeting in vivo," Nature Biotechnol. 17:37-41.

Lucas, et al. (2000) "Unravelling the mysteries of virulence gene regulation in *Salmonella typhimurium*," Mol. Microbiol. 36:1024-1033.

Lundberg, et al. (1999) "Growth phase-regulated induction of *Salmonella*-induced macrophage apoptosis correlates with transient expression of SP1-1 genes," J. Bacteriol. 181:3433-3437.

Marshall, et al. (2000) "Use of the stationary phase inducible promoters, spy and dps, to drive heterologous antigen expression in Salmonella vaccine strains," Vaccine 18: 1298-1306.

Mastroeni, et al. (1998) "Interleukin-12 Is Required for Control of the Growth of Attenuated Aromatic-Compound-Dependent Salmonellae in BALB/c Mice: Role of Gamma Interferon and Macrophage Activation," Infect. Immun. 66: 4767-4776.

Mastroeni, et al. (1995) "Effect of Anti-Tumor Necrosis Factor Alpha Antibodies on Histopathology of Primary Salmonella Infections," Infect. Immun. 63: 3674-3682.

Mastroeni, et al. (1992) "Role of T cells, TNFα and IFNγ in recall of immunity to oral challenge with virulent salmonellae in mice vaccinated with live attenuated aro- salmonella vaccines," Microbial Pathogen. 13: 477-491.

Mazurkiewicz, et al. (2006) "Signature-tagged mutagenesis: barcoding mutants for genome-wide screens," Nat. Rev. Genet. 7: 929-939.

Mcfarland and Stocker (1987) "Effect of different purine auxotrophic mutations on mouse-virulence of a Vi-positive strain of Salmonella dublin and of two strains of Salmonella typhimurium," Microbial Pathogen. 3: 129-141.

Mcsorley and Jenkins (2000) "Antibody Is Required for Protection against Virulent bu Not Attenuated Salmonella enterica Serovar Typhimurium," Infect. Immun. 68: 3344-3348.

Medina and Guzman (2001) "Use of live bacterial vaccine vectors for antigen delivery: potential and limitations," Vaccine 19: 1573-1580.

Miao and Miller (2000) "A conserved amino acid sequence directing intracellular type II secretion by *Salmonella typhimuirim*," Proc. Natl. Acad. Sci. USA 97: 7539-7544.

Mills and Finlay (1994) "Comparison of *Salmonella typhi* and *Salmonella typhimurim* invasion, intracellular growth and localization in cultured human epithelial cells," Microbial. Pathogen. 17: 409-423.

Mills, et al. (1998) "Trafficking of Porin-Deficient *Salmonella typhimurium* Mutants inside HeLa Cells: ompR and envZ Mutants Are Defective for the Formation of Salmonella-Induced Filaments," Infect. Immun. 66: 1806-1811.

Mintz, et al. (1983) "Effect of Lipopolysaccharide Mutations on the Pathogenesis of Experimental Salmonella Gastroenteritis," Infect. Immun. 40: 236-244.

Mittrücker and Kaufmann (2000) "Immune response to infection with *Salmonella typhimurium* in mice," J. Leukoc. Biol. 67: 457-463.

Mittrücker, et al. (2000) "Cutting Edge: Role of B Lymphocytes in Protective Immunity Against *Salmonella typhimurium* Infection," J. Immunol 164: 1648-1652.

Mollenkopf, et al. (2001) "Protective efficacy against tuberculosis of ESAT-6 secreted by a live *Salmonella typhimurium* vaccine carrier strain and expressed by naked DNA," Vaccine 19: 40284035.

Mollenkopf, et al. (2001) "Intracellular Bacteria as Targets and Carriers for Vaccination," Biol. Chem. 382: 521-532.

Nardelli-Haefliger, et al. (2001) "Nasal vaccination with attenuated *Salmonella typhimurium* strains expressing the Hepatitis B nucleocapsid: dose response analysis," Vaccine 19: 2854-2861.

Nardelli-Haefliger, et al. (1996) "Oral and Rectal Immunization of Adult Female Volunteers with a Recombinant Attenuated *Salmonella typhi* Vaccine Strain," Infect. Immun. 64: 5219-5224.

Nauciel and Espinasse-Maes (1992) "Role of Gamma Interferon and Tumor Necrosis Factor Alpha in Resistance to *Salmonella typhimurium* Infection," Infect. Immun. 60: 450-454.

Nauciel (1990) "Role of CD4+ T Cells and T-Independent Mechanisms in Acquired Resistance to *Salmonella typhimurium* Infection," J. Immunol. 145: 1265-1269.

Nickerson and Curtiss III, et al. (1997) "Role of Sigma Factor RpoS," in Initial Stages of *Salmonella typhimurium* Infection, Infect. Immun. 65: 1814-1823.

Ornellas, et al. (1970) "The Specificity and Importance of Humoral Antibody in the Protection of Mice against Intraperitoneal Challenge with Complement-Sensistive and Complement-Resistant Salmonella," J. Infect. Disease 121: 113-123.

Paesold, et al. (2002) "Genes in the Salmonella pathogenicity island 2 and the *Salmonella virulence* plasmid are essential for Salmonella-induced apoptosis in intestinal epithelial cells," Cell. Microbiol. 4: 771-781 •.

Paglia, et al. (2000) "In vivo correction of genetic defects of monocyte/macrophages using attenuated Salmonella as oral vectors for targeted gene delivery," Gene Therapy 7: 1725-1730.

Pang, et al. (1995) "Typhoid fever and other salmonellosis: a continuing challenge," Trends Microbiol. 3: 253-255.

Pickard, et al. (1994) "Characterization of Defined ompR Mutants of *Salmonella typhi*: ompR Is Involved in the Regulation of Vi Polysaccharide Expression," Infect. Immun. 62: 3984-3993.

Pickett, et al. (2000) "In Vivo Characterization of the Murine Intranasal Model for Assessing the Immunogenicity of Attenuated Salmonella enterica Serovar Typhi Strains as Live Mucosal Vaccines and as Live Vectors," Infect. Immun. 68: 205-213.

Pie, et al. (1997) "Th1 Response in *Salmonella typhimurium*-Infected Mice with a High or Low Rate of Bacterial Clearance," Infect. Immun'. 65: 4509-4514.

Pier, et al. (1998) "Salmonella typhi uses CFTR to enter intestinal epithelial cells," Nature 393: 7982.

Poirer, et al. (1988) "Protective Immunity Evoked by Oral Administration of Attenuated aroA *Salmonella typhimurium* Expressing Cloned Streptococcal M Protein," J. Exp. Med. 168: 25-32.

Pulkkinen and Miller (1991) "A *Salmonella typhimurium* Virulence Protein Is Similar to a *Yersinia enterocolitica* Invasion Protein and a Bacteriophage Lambda Outer Membrane Protein," J. Bacteriol. 173: 86-93.

Qian and Pan (2002) "Construction of a tetR-Integrated Salmonella enterica *Serovar Typhi* CVD908 Strain That Tightly Controls Expression of the Major Merozoite Surface Protein of *Plasmodium falciparum* for Applications in Human Vaccine Production," Infect. Immun. 70: 2029- 2038.

Rakeman, et al. (1999) "A HilA-Independent Pathway to *Salmonella typhimurium* Invasion Gene Transcription," J. Bacteriol. 181: 3096-3104.

Richter-Dahlfors, et al. (1997) "Murine Salmonollosis Studied by Confocal Microscopy: *Salmonella typhimurium* Resides Intracellularly Inside Macrophages and Exerts a Cytotoxic Effect on Phagocytes in Vivo," J. Exp. Med. 186: 569-580.

Robbe-Saule, et al. (1995) "The live oral typhoid vaccine Ty2la is a rpoS mutant and is susceptible to various environmental stresses," FEMS Microbiol. Lett. 126: 171-176.

Roberts, et al. (2000) "Comparison of Abilities of *Salmonella enterica* Serovar Typhimurium aroA aroD and aroA htrA Mutants to Act as Live Vectors," Infect. Immun. 68: 6041-6043.

Roberts, et al. (1999) "Prior Immunity to Homologous and Heterologous Salmonella Serotypes Suppresses Local and Systemic Anti-Fragment C Antibody Responses and Protection from Tetanus Toxin in Mice Immunized with Salmonella Strains Expressing Fragment C," Infect. Immun. 67: 3810-3815.

Roberts, et al. (1998) "Oral Vaccination against Tetanus: Comparison of the Immunogenicities of Salmonella Strains Expressing Fragment C from the nirB and htrA Promoters," Infect. Immun. 66: 3080-3087.

Roland, et al. (1999) "Construction and Evaluation of a Δcya Δcrp *Salmonella typhimurium* Strain Expressing Avian Pathogenic *Escherichia coli* O78 LPS as a Vaccine to Prevent Airsacculitis in Chickens," Avain Diseases 43: 429-441.

Schödel, et al. (1993) "Avirulent Salmonella expressing hybrid hepatitis B virus core/pre-S genes for oral vaccination," Vaccine 11: 143-148.

Schödel, et al. (1994) "Development of Recombinant Salmonellae Expressing Hybrid Hepatitis B Virus Core Particles as Candidate Oral Vaccines," Brown F(ed): Recombinant Vectors in Vaccine Development. Dev. Biol. Stand. Basel, Karger 82: 151-158.

Schwan, et al. (2000) "Differential Bacterial Survival, Replication, and Apoptosis-Inducing Ability of Salmonella Serovars within Human and Murine Macrophages," Infect. Immun. 68: 10051013.

Shata, et al. (2000) "Recent advances with recombinant bacterial vaccine vectors," Mol. Med. Today 6: 66-70.

Sinha, et al. (1997) "*Salmonella typhimurium* aroA, htrA, and aroD htrA Mutants Cause Progressive Infections in Athymic (nu/nu) BALB/c Mice," Infect. Immun. 65: 1566-1569.

Sirard, et al. (1999) "Live attenuated Salmonella: a paradigm of mucosal vaccines," Immunol. Rev. 171: 5-26.

Smith, et al. (1984) "Aromatic-dependent Salmonella dublin as a parenteral modified live vaccine for calves," Am. J. Vet. Res. 45: 2231-2235.

Smith, et al. (1993) "Vaccination of calves with orally administered aromatic-dependent Salmonella dublin," Am. J. Vet. Res. 54: 1249-1255.

Soo, et al. (1998) "Genetic Control of Immune Response to Recombinant Antigens Carried by an Attenuated *Salmonella typhhimurium* Vaccine Strain: Nrampl Influences T-Helper Subset Responses and Protection against Leishmanial Challenge," Infect. Immun. 66: 1910-1917.

Spreng, et al. (200) "Salmonella vaccines secreting measles virus epitopes induce protective immune responses against measles virus encephalitis," Microbes Infect. 2: 1687-1692.

Stein, et al. (1996) "Identification of a *Salmonella virulence* gene required for formation of filamentous structures containing lysosomal membrane glycoproteins within epithelial cells," Mol. Microbiol. 20: 151-164.

Stocker (2000) "Aromatic-dependent Salmonella as anti-bacterial vaccines and as presenters of heterologous antigens or of Dna encoding them," J. Biotechnol. 83: 45-50.

Stocker (1990) "Aromatic-Dependent Salmonella as Live Vaccine Presenters of Foreign Epitopes as Inserts in Flagellin," Res. Microbiol. 141: 787-796.

Stocker (1988) "Auxotrophic *Salmonella typhi* as live vaccine," Vaccine 6: 141-145.

Svenson and Lindberg (1983) "Artificial Salmonella Vaccines," Prog. Allergy 33: 120-143.

Sydenham, et al. (2000) "Salmonella enterica Serovar Typhimurium surA Mutants Are Attenuated and Effective Live Oral Vaccines," Infect. Immun. 68: 1109-1115.

Sztein, et al. (1994) "Cytokine Production Patterns and Lymphoproliferative Responses in Volunteers Orally Immunized with Attenuated Vaccine Strains of *Salmonella tyhpi*," J. Infect. Disease 170: 1508-1517.

Tacket, et al. (2000) "Phase 2 Clinical Trial of Attenuated Salmonella enterica Serovar Typhi Oral Live Vector Vaccine Cvd 908-htrA in U.S. Volunteers," Infect. Immun. 68: 1196-1201.

Tacket, et al. (2000) "Safety and Immune Responses to Attenuated Salmonella enterica Serovar Typhi Oral Live Vector Vaccines Expressing Tetanus Toxin Fragment C," Clin. Immunol. 97: 146153.

Tacket, et al. (1997) "Safety of Live Oral *Salmonella typhi* Vaccine Strains with Deletions in htrA and aroC aroD and Immune Response in Humans," Infect. Immun. 65: 452-456.

Tacket, et al. (1992) "Clinical acceptability and immunogenicity of CVD 908 *Salmonella typhi* vaccine strain," Vaccine 10: 443-446.

Tacket, et al. (1992) "Comparison of the Safety and Immunogenicity of ΔaroC ΔaroD and Δcya Δcrp *Salmonella typhi* Strains in Adult Volunteers," Infect. Immun. 60: 536-541.

Tacket, et al. (1991) "Lack of Immune response to the Vi Component of a Vi-Positive Variant of *Salmonella typhi* Live Oral Vaccine Strain Ty21a in Human Studies," J. Infect. Disease 163: 901-904.

Tacket, et al. (1988) "Persistence of antibody titres three years after vaccination with Vi polysaccharide vaccine against typhoid fever," Vaccine 6: 307-308.

Tacket, et al. (1986) "Safety and Immunogenicity of Two *Salmonella typhi* Vi Capsular Polysaccharide Vaccines," J. Infect. Disease 154: 342-345.

Tagliabue (1989) "Immune Response to Oral Salmonella Vaccines," Curr. Topics Microbiol. Immunol. 146: 225-231.

Tang, et al. (2001) "Identification of bacterial genes required for in-vivo survival," J. Pharm. Pharmacol. 53: 1575-1579.

Tite, et al. (1991) "The Involvement of Tumor Necrosis Factor in Immunity to Salmonella Infection," J. Immunol. 147: 3161-3164.

Tramont, et al. (1984) "Safety and Antigenicity of Typhoid-Shigella sonnei Vaccine (Strain 5076-1C)," J. Infect. Disease 149: 133-136.

Turner, et al. (1993) "*Salmonella typhimurium* ΔaroA ΔaroD Mutants Expressing a Foreign Recombinant Protein Induce Specific Major Histocompatibility Complex Class 1-Restricted Cytotoxic T Lymphocytes in Mice," Infect. Immun. 61: 5374-5380.

Uchiya, et al. (1999) "A Salmonella virulence protein that inhibits cellular trafficking," EMBO J. 18: 3924-3933.

Urashima, et al. (2000) "An oral CD40 ligand gene therapy against lymhoma using attenuated *Salmonella typhimurium*," Blood 95: 1258-1263.

Valdivia and Falkow (1996) "Bacterial genetics by flow cytometry: rapid isolation of *Salmonella typhimurium* acid-inducible promoters by differential fluorescence induction," Mol. Microbiol. 22: 367-378.

Van Dissel, et al. (1995) "S. Typhi Vaccine Strain Ty21a Can Cause a Generalized Infection in Whole Body-Irradiated But Not in Hydrocortisone-Treated Mice," Scand. J. Immunol. 41: 457-461.

Van Velkinburgh and Gunn (1999) "PhoP-PhoQ-Regulated Loci Are Required for Enhanced Bile Resistance in Salmonella spp.," Infect. Immun. 67: 1614-1622.

Vancott, et al. (1998) "Regulation of host immune responses by modification of *Salmonella virulence* genes," Nat. Med. 4: 1247-1252.

Vancott, et al. (1996) "Regulation of Mucosal and Systemic Antibody Responses by T Helper Cell Subsets, Macrophages, and Derived Cytokines Following Oral Immunization with Live Recombinant Salmonella," J. Immunol. 1504: 1514.

Vazquez-Torres, et al. (2000) "Salmonella Pathogenicity Island 2-Dependent Evasion of the Phagocyte Nadph Oxidase," Science 287: 1655-1658.

Véscovi, et al. (1996) "MG2+ as an Extracellular Signal: Environmental Regulation of Salmonella Virulence," Cell 84: 165-174.

Villarreal, et al. (1992) "Proliferative and T-cell specific interleukin (IL-2/IL-4) production responses in spleen cells from mice vaccinated with aroA live attenuated Salmonella vaccines," Microbial Pathogen. 13: 305-315.

Viret, et al. (1999) "Mucosal and Systemic Immune Responses in Humans after Primary and Booster Immunizations with Orally Administered Invasive and Noninvasive Live Attenuated Bacteria," Infect. Immun. 67: 3680-3685.

Virlogeux, et al. (1996) "Characterization of the rcsA and rcsB Genes from Salmonella typhi: rcsB through tviA Is Involved in Regulation of Vi Antigen Synthesis," J. Bacteriol. 178: 1691-1698.

Virlogeux, et al. (1995) "Role of the viaB locus in synthesis, transport and expression of Salmonella typhi Vi antigen," Microbiol. 141: 3039-3047.

Wahdan, et al. (1982) "A Controlled Field Trial of Live Salmonella typhi Strain Ty 21a Oral Vaccine Against Typhoid: Three-Year Results," J. Infect. Dis. 145: 292-295.

Wahdan, et al. (1980) "A controlled field trial of live oral typhoid vaccine Ty2la," Bull. World Health Org. 58: 469-474.

Wallis (2001) "Salmonella Pathogenesis and Immunity: We Need Effective Multivalent Vaccines," Vet. J. 161: 104-106.

Wallis and Galyov (2000) "Molecular basis of Salmonella-induced enteritis," Mol. Microbiol. 36: 997-1005.

Wang, et al. (2000) "Constitutive Expression of the Vi Polysaccharide Capsular Antigen in Attenuated Salmonella enterica Serovar Typhi Oral Vaccine Strain CVD 909," Infect. Immun 68: 4647-4652.

Ward, et al. (1999) "Immunogenicity of a Salmonella typhimurium aroA aroD Vaccine Expressing a Nontoxic Domain of Clostridium difficile Toxin a," Infect. Immun. 67: 2145-2152.

Wedemeyer, et al. (2001) "Oral Immunization With HCV-NS3-Transformed Salmonella: Induction of HCV-Specific CTL in a Transgenic Mouse Model," Gastroenterology 121: 1158-1166.

Weinstein, et al. (1998) "Differential Early Interactions between Salmonella enterica Serovar Typhi and Two Other Pathogenic Salmonella Serovars with Intestinal Epithelial Cells," Infect. Immun. 66: 2310-2318.

Weinstein, et al. (1997) "Salmonella typhi Stimulation of Human Intestinal Epithelial Cells Induces Secretion of Epithelial Cell-Derived Interleukin-6," Infect. Immun. 65: 395-404.

Weintraub, et al. (1997) "Role of $\alpha\beta$ and $\gamma\delta$ T Cells in the Host Response to Salmonella Infection as Demonstrated in T-Cell-Receptor-Deficient Mice of Defined Ity Genotypes," Infect. Immun. 65: 2306-2312.

White, et al. (1999) "High efficiency gene replacement in Salmonella enteritidis chimeric fimbrins containing a T-cell epitope from Leishmania major," Vaccine 17: 2150-2161.

Wong, et al. (1974) "Vi Antigen from Salmonella typhosa and Immunity Against Typhoid Fever," Infect. Immun. 9: 348-353.

Woo, et al. (2001) "Unique immunogenicity of hepatitis B virus DNA vaccine presented by live attenuated Salmonella typhimurium," Vaccine 19: 2945-2954.

Wu, et al. (2000) "Construction and immunogenicity in mice of attenuated Salmonella typhi expressing Plasmodium falciparum merozoite surface protein 1 (MSP-1) fused to tetanus toxin fragment C," J. Biotechnol. 83: 125-135.

Wüthrich, et al. (1985) "Typhusepidemiologie in der Schweiz 1980-1983," Schwiez. med. Wschr. 115: 1714-1720.

Wyant, et al. (1999) "Salmonella tyohi Flagella Are Potent Inducers of Proinflammatory Cytokine Secretion by Human Monocytes," Infect. Immun 67: 3619-3624.

Zhang, et al. (1999) "Protection and immune responses induced by attenuated Salmonella typhimurium Uk-1 strains," Microbial Pathogen. 26: 121-130.

Zhou, et al. (1999) "An invasion-associated Salmonella protein modulates the actin-bundling activity of plastin," Proc. Natl. Acad. Sci. USA 96: 10176-10181.

Curtiss, et al. (1994) "Recombinant Salmonella vectors in vaccine development" Dev. Biol. Stand. 82:23-33.

Galen et al. (1997) "A murine model of intranasal immunizaiton to asses the immunogenicityy of attenuated Salmonella typhi live vector vaccines in stimulating serium antibody responses to expressed foreign antigens," Vaccine, 15:700-708.

Hormaeche, (1979) "Genetics of natural resistance to salmonellae in mice," Immunology, 37:319-327.

Jones, et al. (1991) "Oral vaccination of calves against experimental salmonellosis using a double aro mutant of Salmonella typhimurium," Vaccine, 9:29-34.

Jones-Carson et al. (2007) "Systemic CD8 T cell memory response to a Salmonella pathogenicity island 2 effector is restricted to Salmonella enterica encountered in the gastrointestinal mucosa," Infect. Immun. 75:2708-2716.

Chenoweth et al. (1990) "Efficacy of ampicilin versus trimethoprim-sulfamethoxazole in a mouse model of lethal enterococcol peritonitis," Antimicrob. Agents Chemother. 34:1800-1802.

Kohler, et al. (1998) "Oral immunization with recombinant Salmonella typhimurium expressing a cloned porphyromonas gingivalsi hemaglutinin: effect of bookstin on mucosal systemic and immunoglobulin G subclass response," Oral Microbiol. Immunol. 13:81-88. Abstract Only.

O'Callaghan, et al. (1990) " "Immunogenicity of foreign peptide epitopes expressed in bacterial envelope proteins," Res. Microbiol. 141:963-969 Abstract Only.

Schodel, et al. (1996) "Hybrid hepatitis B virus core antigen as a vaccine carrier moiety II. Expression in avirulent Salmonella spp. For mucosal immunization," Adv. Exp. Med. Biol. 397:1521. Abstract Only.

* cited by examiner

Position of mutations in MvP101, MvP102 and MvP103

FIG. 2A

Alignment of SseB to EspA

```
SseB    1   M S S G N - I L W G S Q N P I V F K N - - - S F G V S N A D T G S Q D D L S Q Q N P F A E G Y G V L   46
EspA    1   M D I S T T A S V A S A N A S T S M A Y D L G S M S K D D - V I D L F N K L G V F Q A A I L M F         49

SseB   47   L I L L M V I Q A I A N N K F I E V Q K N A E R A R N T Q E K S N E M D E V I A K A A K G - D A K T    95
EspA   50   A Y M Y Q A Q S D L S I A K F A D M N E A S K E S T T A Q K M A N L V D A K I A D V Q S S S D K N A    99

SseB   96   K E E V P E D V I K Y M R D - - N G L L I D G M T I D D Y M A K Y G D H G K L D K G L Q A I K A A       143
EspA  100   K A Q L P D E V I S Y I N D P R N D I T I S G - - I D N I N A Q L G - - - - A G D L Q T V K A A       141

SseB  144   L D N D A N R N T D L M S Q G I T I Q K M S Q E L N A V L T Q L T G L I S K W G E I S M I A Q K       193
EspA  142   I S A K A N N L I T T V N N S L E I Q Q M S N T L N L L T S A R S D M Q S L Q Y R T I S L G            191

SseB  194   T Y S 196
EspA  192   K       192
```

FIG. 2B

Alignment of SseC to EspD, YopB and PepB

Strains mutant in single SPI2 genes

Strains mutant in single SPI2 genes

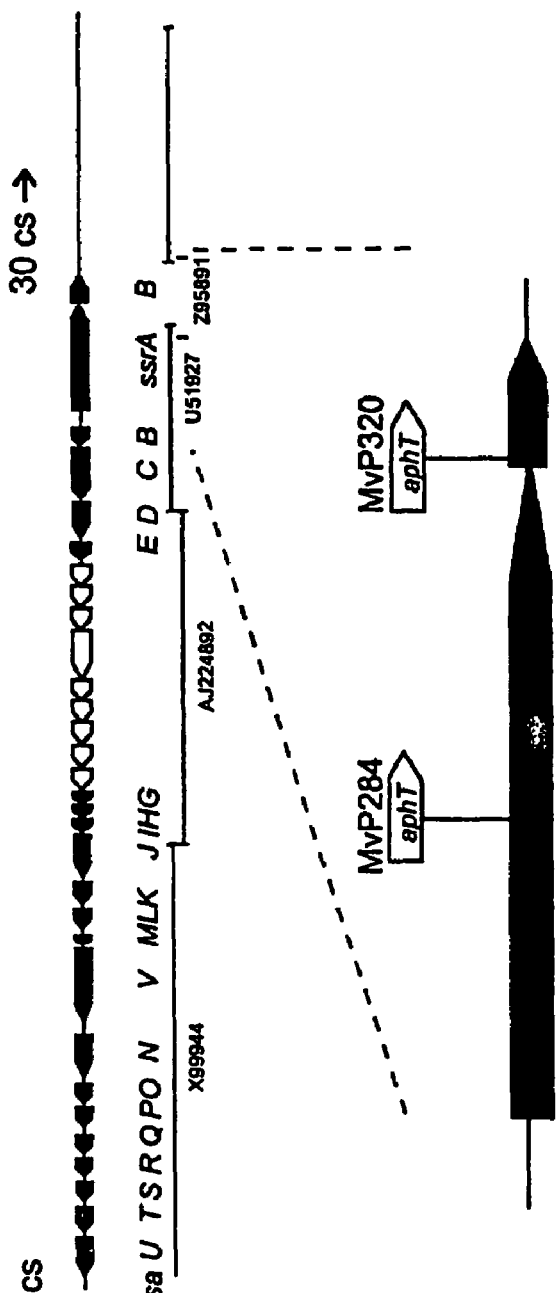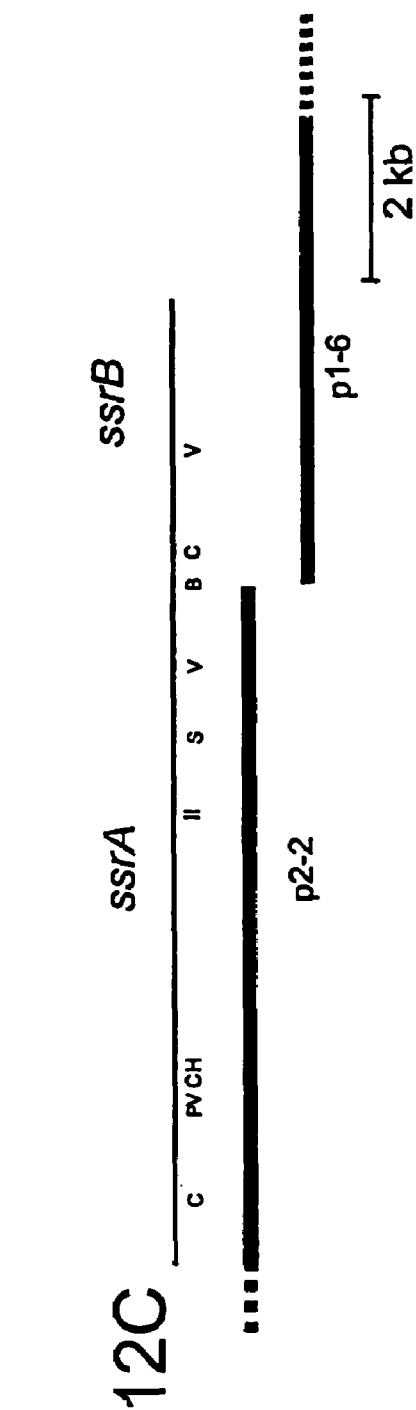
FIG. 12A  
FIG. 12B  
FIG. 12C

Model for the transcriptional units for SPI2 virulence genes

FIG. 14

Principle of Attenuation

Schematic Instruction for the Generation of Different Mutations with Increasing Grade of Attenuation ssrB ssrA   sseC sseD sseE sscB sseF sseG   aroA   Genome
                                                   mRNA

FIG. 14A

Grade of Attenuation ssrB ssrA   sseC sseD ΔsseE sscB sseF sseG   aroA   low

FIG. 14B ssrB ssrA   sseC sseD ΔsseE sscB sseF sseG   ΔaroA   medium

FIG. 14C ssrB ssrA   sseC::gene sseD sseE sscB sseF sseG   aroA   high truncated mRNA
gene

FIG. 14D

ΔssrB ssrA   sseC sseD sseE sscB sseF sseG   aroA   supreme no mRNA

Principle of insertional mutation

FIG. 16
Selective Marker Cassette (SMC)
Permanent selective marker cassette
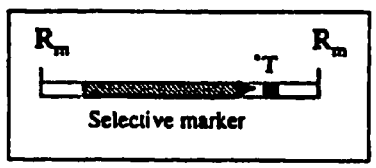
T = Optional transcriptional terminator if polar insertional mutation is required
Revertible selective marker cassette
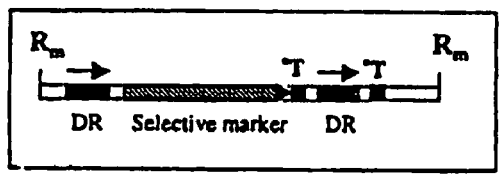
DR = direct repeat

FIG. 17

Gene Expression Cassette (GEC)

One Phase System

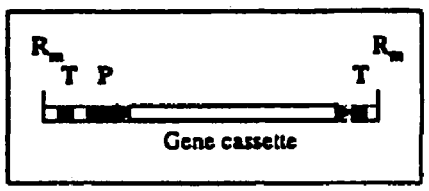
Gene cassette

P = Promoter consisting of either a
- promoter acting constitutively in *Salmonella*
- a *Salmonella in vivo* inducible promoter or
- an other promoter T = Transcriptional terminator

Two Phase System

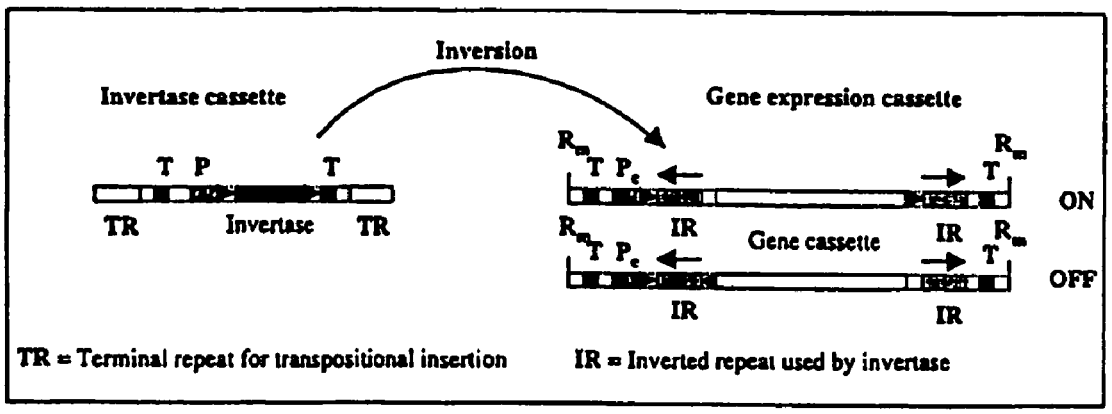

TR = Terminal repeat for transpositional insertion    IR = Inverted repeat used by invertase Gene cassette:

Single gene expression unit    or    Concatemeric gene expression units

FIG. 18

Structural requirements of the gene expression unit for the delivery of heterologous antigens into the various *Salmonella* compartments Gene sequence ⟶ Cytosolic compartment Signal peptide — Gene sequence ⟶ Periplasmic compartment Signal peptide — Gene sequence — β-barrel ⟶ Outer membrane compartment
Spacer Gene sequence ⟶ Extracellular milieu
Type III secretory protein

FIG. 19
Transactivator Cassette (TC)
P = Promoter consisting of either a
- promoter acting constitutively in *Salmonella*
- a *Salmonella in vivo* inducible promoter or
- an other promoter
$P_c$ = Constitutive promoter
One Phase System
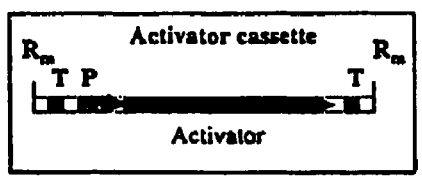
Two Phase System
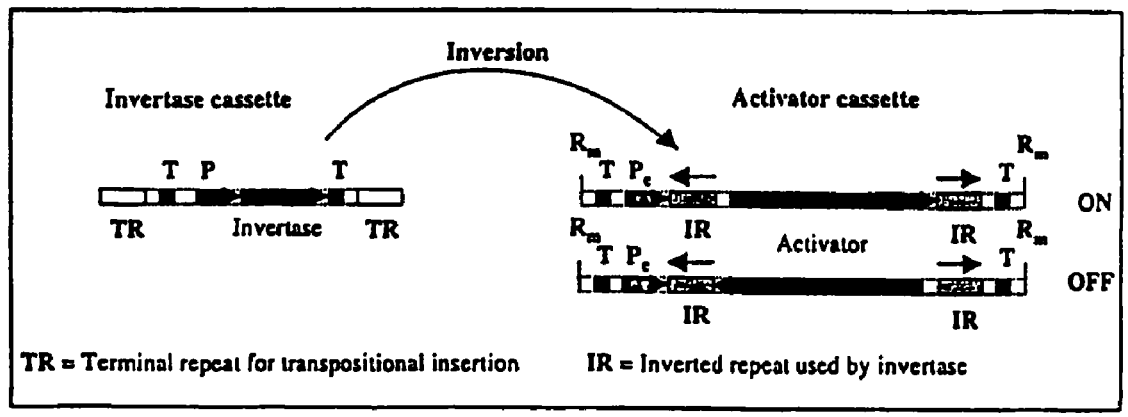
TR = Terminal repeat for transpositional insertion    IR = Inverted repeat used by invertase

FIG. 21A

```
CTGCAGTTGTCCGGTTATTGCTCGTCAAGCGAACAGATGCAAAAGGTGAGAGCGACTCTCGAATCATGGGGGGTCATGTA
TCGGGATGGTGTAATCTGTGATGACTTATTGGTACGAGAAGTGCAGGATGTTTTGATAAAAATGGGTTACCCGCATGCTG
AAGTATCCAGCGAAGGGCCGGGGAGCGTGTTAATTCATGATGATATACAAATGGATCAGCAATGGCGCAAGGTTCAACCA
TTACTTGCAGATATTCCCGGGTTATTGCACTGGCAGATTAGTCACTCTCATCAGTCTCAGGGGGATGATATATTTCTGC
GATAATAGAGAACGGTTTAGTGGGGCTTGTCAATGTTAGCCCAATGCGGCGCTCTTTTGTTATCAGTGGTGTACTGGATG
AATCTCATCAACGCATTTTGCAAGAAACGTTAGCAGCATTAAAGAAAAAGGATCCCGCTCTTTCTTTAATTTATCAGGAT
ATTGCGCCTTCCCATGATGAAAGCAAGTATCTGCCTGCGCCAGTGGCTGGCTTTGTACAGAGTCGCCATGGTAATTACTT
ATTACTGACGAATAAAGAGCGTTTACGTGTAGGGGCATTGTTACCCAATGGGGGAGAAATTGTCCATCTGAGTGCCGATG
TGGTAACGATTAAACATTATGATACTTTGATTAACTATCCATTAGATTTTAAGTGAGTGGAAAATGACAACTTTGACCCG
GTTAGAAGATTTGCTGCTTCATTCGCGTGAAGAGGCCAAAGGCATAATTTTACAATTAAGGGCTGCCCGGAAACAGTTAG
AAGAGAACAACGGCAAGTTACAGGATCCGCAGCAATATCAGCAAAACACCTTATTGCTTGAAGCGATCGAGCAGGCCGAA
AATATCATCAACATTATTTATTATCGTTACCATAACAGCGCACTTGTAGTGAGTGAGCAAGAGTAAAGTAAAAATATCTT
AGAGCCTATCCCACCAGGCGTTAATTGGCGCAGCCAGTTTGGACACGGATAGCGCGCAAAAACCGCAGCGTACACGTAGT
ACGTGAGGTTTGACTCGCTACGCTCGCCCTTCGGGCCGCCGCTAGCGGCGTTCAAAACGCTAACGCGTTTTGGCGAGCAC
TGCCCAGGTTCAAAATGGCAAGTAAAATAGCCTAATGGGATAGGCTCTTAGTTAGCACGTTAATTATCTATCGTGTATAT
GGAGGGGAATGATGATAAAGAAAAAGGCTGCGTTTAGTGAATATCGTGATTTAGAGCAAAGTTACATGCAGCTAAATCAC
TGTCTTAAAAAATTTCACCAAATCCGGGCTAAGGTGAGTCAACAGCTTGCTGAAAGGGCAGAGAGCCCCAAAAATAGCAG
AGAGACAGAGAGTATTCTTCATAACCTATTTCCACAAGGCGTTGCCGGGGTTAACCAGGAGGCCGAGAAGGATTTAAAGA
AAATAGTAAGTTTGTTTAAACAACTTGAAGTACGACTGAAACAACTTAATGCTCAAGCCCCGGTGGAGATACCGTCAGGA
AAAACAAAAAGGTAAAGCATAATGTCTTCAGGAAACATCTTATGGGGAAGTCAAAACCCTATTGTGTTTAAAAATAGCTT
CGGCGTCAGCAACGCTGATACCGGGAGCCAGGATGACTTATCCCAGCAAAATCCGTTTGCCGAAGGGTATGGTGTTTTGC
TTATTCTCCTTATGGTTATTCAGGCTATCGCAAATAATAAATTTATTGAAGTCCAGAAGAACGCTGAACGTGCCAGAAAT
ACCCAGGAAAAGTCAAATGAGATGGATGAGGTGATTGCTAAAGCAGCCAAAGGGGATGCTAAAACCAAAGAGGAGGTGCC
TGAGGATGTAATTAAATACATGCGTGATAATGGTATTCTCATCGATGGTATGACCATTGATGATTATATGGCTAAATATG
GCGATCATGGGAAGCTGGATAAAGGTGGCCTACAGGCGATCAAAGCGGCTTTGGATAATGACGCCAACCGGAATACCGAT
CTTATGAGTCAGGGGCAGATAACAATTCAAAAAATGTCTCAGGAGCTTAACGCTGTCCTTACCCAACTGACAGGGCTTAT
CAGTAAGTGGGGGGAAATTTCCAGTATGATAGCGCAGAAAACGTACTCATGAAAAAAGACCCGACCCTACAACAGGCACA
TGACACGATGCGGTTTTTCCGGCGTGGCGGCTCGCTGCGTATGTTGTTGGATGACGATGTTACACAGCCGCTTAATACTC
TGTATCGCTATGCCACGCAGCTTATGGAGGTAAAAGAATTCGCCGGCGCAGCGCGACTTTTTCAATTGCTGACGATATAT
GATGCCTGGTCATTTGACTACTGGTTTCGGTTAGGGGAATGCTGCCAGGCTCAAAAACATTGGGGGGAAGCGATATACGC
TTATGGACGCGCGGCACAAATTAAGATTGATGCGCCGCAGGCGCCATGGGCCGCAGCGGAATGCTATCTCGCGTGTGATA
ACGTCTGTTATGCAATCAAAGCGTTAAAGGCCGTGGTGCGTATTTGCGGCGAGGTCAGTGAACATCAAATTCTCCGACAG
CGTGCAGAAAAGATGTTACAGCAACTTTCTGACAGGAGCTAAAAATGAATCGAATTCACAGTAATAGCGACAGCGCCGCA
GGAGTAACCGCCTTAACACATCATCACTTAAGCAATGTCAGTTGCGTTTCCTCGGGTTCGCTGGGAAAGCGCCAGCATCG
TGTGAATTCTACTTTTGGCGATGGCAACGCCGCGTGTCTGCTATCCGGGAAAATTAGTCTTCAGGAGGCAAGCAATGCGT
TGAAGCAACTGCTTGATGCCGTACCCGGAAATCATAAGCGTCCATCATTGCCTGACTTTTTGCAGACCAATCCCGCGGTT
TTATCAATGATGATGACGTCATTAATACTCAACGTCTTTGGTAATAACGCTCAATCGTTATGCCAACAGCTTGAGCGGGC
AACTGAGGTGCAAAATGCATTACGTAATAAGCAGGTAAAGGAGTATCAGGAGCAGATCCAGAAAGCGATAGAGCAGGAGG
ATAAAGCGCGTAAAGCGGGTATTTTTGGCGCTATTTTTGACTGGATTACCGGCATATTTGAAACCGTGATTGGCGCCTTA
AAAGTTGTGGAAGGTTTTCTGTCCGAAATCCCGCAGAAATGGCTAGCGGCGTAGCTTATATGGCCGCAGGTTGTGCAGG
AATGGTTAAAGCCGGAGCCGAAACGGCAATGATGTGCGGTGCTGACCACGATACCTGTCAGGCAATTATTGACGTGACAA
GTAAGATTCAATTTGGTTGTGAAGCCGTCGCGCTGGCACTGGATGTTTTCCAGATTGGCCGTGCTTTTATGGCGACGAGA
GGTTTATCTGGCGCAGCTGCAAAAGTGCTTGACTCCGGTTTTGGCGAGGAAGTGGTTGAGCGTATGGTAGGTGCAGGGGA
AGCAGAAATAGAGGAGTTGGCTGAAAAGTTTGGCGAAGAAGTGAGCGAAAGTTTTTCCAAACAATTTGAGCCGCTTGAAC
GTGAAATGGCTATGGCGAATGAGATGGCAGAGGAGGCTGCCGAGTTTTCTCGTAACGTAGAAAATAATATGACGCGAAGC
GCGGGAAAAAGCTTTACGAAAGAGGGGGTGAAAGCCATGGCAAAAGAAGCGGCAAAAGAAGCCCTGGAAAAATGTGTGCA
AGAAGGTGGAAAGTTCCTGTTAAAAAAATTCCGTAATAAAGTTCTCTTCAATATGTTCAAAAAAATCCTGTATGCCTTAC
TGAGGGATTGTTCATTTAAAGGCTTACAGGCTATCAGATGTGCAACCGAGGGCGCCAGTCAGATGAATACTGGCATGGTT
AACACAGAAAAAGCGAAGATCGAAAAGAAAATAGAGCAATTAATAACTCAGCAACGGTTTCTGGATTTCATAATGCAACA
AACAGAAAACCAGAAAAAGATAGAACAAAAACGCTTAGAGGAGCTTTATAAGGGGACGGGTGCCGCGCTTAGAGATGTAT
TAGATACCATTGATCACTATAGTAGCGTTCAGGCGAGAATAGCTGGCTATCGCGCTTAATCTGAGGATAAAAATATGGAA
GCGAGTAACGTAGCACTGGTATTACCAGCGCCTTCCTTGTTAACACCTTCTTCCACTCCATCTCCCTCCGGGGAGGGAAT
GGGTACTGAATCAATGCTTCTGTTATTTGATGATATCTGGATGAAGCTAATGGAGCTTGCCAAAAAGCTGCGCGATATCA
TGCGCAGCTATAACGTAGAAAACAACGGCTGGCCTGGGAACTGCAAGTCAATGTTTTACAGACGCAAATGAAAACAATT
GATGAAGCGTTTAGAGCATCAATGATTACTGCGGGTGGCGCAATGTTGTCGGGTGTACTGACGATAGGATTAGGGGCCGT
```

FIG. 21A-1

```
AGGCGGGGAAACCGGTCTTATAGCGGGTCAAGCCGTAGGCCACACAGCTGGGGGCGTCATGGGCCTGGGGGCTGGTGTAG
CGCAACGTCAAAGTGATCAAGATAAAGCGATTGCCGACCTGCAACAAAATGGGGCCCAATCTTATAATAAATCCCTGACG
GAAATTATGGAGAAAGCAACTGAAATTATGCAGCAAATCATCGGCGTGGGGTCGTCACTGGTCACGGTTCTTGCTGAAAT
ACTCCGGGCATTAACGAGGTAAACATGGTGCAAGAAATAGAGCAATGGTTACGTCGGCATCAGGTGTTTACTGAGCCTGC
ATATTTAGGGGAGACCGCCATATTACTTGGGCAGCAGTTTATATTATCGCCTTACCTGGTGATCTATCGTATTGAGGCAA
AAGAAATGATTATTTGTGAGTTCAGGCGCCTGACGCCCGGGCAACCTCGACCACAGCAATTGTTTCACTTACTGGGACTT
TTACGCGGGATATTTGTGCATCACCCGCAGTTAACATGTTTAAAGATGTTGATAATCACCGACGTTCTGGATGAAAAAAA
AGCCATGCTACGCAGGAAATTATTGCGCATCCTGACAGTAATGGGAGCGACCTTTACACAGCTTGATGGCGATAACTGGA
CAGTTTTATCCGCCGAGCATCTTATCCAGCGACGTTTTTAAATGACCTTCCTGACGTAAATCATTATCACGTGAAAATAA
CAATCAATAGGTATGATGATGAAAGAAGATCAGAAAAATAAAATACCCGAAGACATTCTGAAACAGCTATTATCCGTTGA
TCCGGAAACCGTTTATGCCAGTGGTTACGCCTCATGGCAGGAGGGGATTATTCGCGCGCCGTAATCGATTTTAGTTGGC
TGGTGATGGCCCAGCCATGGAGTTGGCGTGCCCATATTGCATTGGCTGGCACCTGGATGATGCTTAAAGAATACACGACG
GCCATTAATTTCTATGGACATGCCTTGATGCTGGATGCCAGCCATCCAGAACCGGTTTACCAAACGGGCGTCTGTCTCAA
AATGATGGGGGAACCCGGGTTGGCGAGAGAGGCTTTTCAAACCGCAATCAAGATGAGTTATGCGGATGCCTCATGGAGTG
AGATTCGCCAGAATGCGCAAATAATGGTTGATACTCTTATTGCTTAAATAACAGAACGAAATATGAAAATTCATATTCCG
TCAGCGGCAAGTAATATAGTCGATGGTAATAGTCCTCCTTCCGATATACAAGCGAAGGAGGTATCGTTTCCTCCCCCTGA
AATTCCAGCGCCTGGCACCCCGCAGCCCTGTGCTGCTTACGCCTGAACAAATAAGGCAGCAGAGGGATTATGCGATAC
ATTTTATGCAATACACTATTCGTGCGCTGGGTGCGACAGTCGTGTTTGGGTTATCGGTTGCTGCAGCGGTAATTTCTGGC
GGGGCAGGATTACCCATTGCTATTCTTGCGGGGCGGCGCTCGTGATTGCTATTGGGGATGCTTGCTGTGCGTATCATAA
TTATCAATCGATATGTCAGCAAAAGGAGCCATTACAAACCGCCAGTGATAGCGTTGCTCTTGTGGTCAGTGCGCTGGCCT
TAAAATGTGGGGCAAGTCTTAACTGCGCTAACACCCTTGCTAATTGTCTTTCTTTATTAATACGTTCAGGAATCGCTATT
TCTATGTTGGTTTTACCCCTACAGTTTCCACTGCCCGCGGCTGAAAATATTGCGGCCTCTTTGGACATGGGGAGTGTAAT
TACCCTCCGTTAGCCTGACGGCGATAGGTGCGGTACTGGATTATTGCCTTGCCCGCCCCTCTGGCGACGATCAGGAAATT
CTGTTGATGAACTTCATGCCGATCCCAGTGTGTTATTGGCGGAACAAATGGCAGCGCTCTGTCAATCTGCTACTACACCT
GCACCTGCATTAATGGACAGTTCTGATCATACATCTCGGGGAGAACCATGAAACCTGTTAGCCCAAATGCTCAGGTAGGA
GGGCAACGTCCTGTTAACGCGCCTGAGGAATCACCTCCATGTCCTTCATTGCCACATCCGGAAACCAATATGGAGAGTGG
TAGAATAGGACCTCAACAAGGAAAAGAGCGGGTATTGGCCGGACTTGCGAAACGAGTGATAGAGTGTTTTCCAAAAGAAA
TTTTTAGTTGGCAAACGGTTATTTTGGGCGGACAGATTTTATGCTGTTCCGCTGGAATAGCATTAACAGTGCTAAGTGGT
GGAGGCGCGCCGCTCGTAGCCCTGGCAGGGATTGGCCTTGCTATTGCCATCGCGGATGTCGCCTGTCTTATCTACCATCA
TAAACATCATTTGCCTATGGCTCACGACAGTATAGGCAATGCCGTTTTTTATATTGCTAATTGTTTCGCCAATCAACGCA
AAAGTATGGCGATTGCTAAAGCCGTCTCCCTGGGCGGTAGATTAGCCTTAACCGCGACGGTAATGACTCATTCATACTGG
AGTGGTAGTTTGGGACTACAGCCTCATTTATTAGAGCGTCTTAATGATATTACCTATGGACTAATGAGTTTTACTCGCTT
CGGTATGGATGGGATGGCAATGACCGGTATGCAGGTCAGCAGCCCATTATATCGTTTGCTGGCTCAGGTAACGCCAGAAC
AACGTGCGCCGGAGTAATCGTTTTCAGGTATATACCGGATGTTCATTGCTTTCTAAATTTTGCTATGTTGCCAGTATCCT
TACGATGTATTTATTTTAAGGAAAAGCATTATGGATATTGCACAATTAGTGGATATGCTCTCCCACATGGCGCACCAGGC
AGGCCAGGCCATTAATGACAAAATGAATGGTAATGATTTGCTCAACCCAGAATCGATGATTAAAGCGCAATTTGCCTTAC
AGCAGTATTCTACATTTATTAATTACGAAAGTTCACTGATCAAAATGATCAAGGATATGCTTAGTGGAATCATTGCTAAA
ATCTGAAGTTATTAGCGACGATGTTCGACGGTTGCTGCTGGAAATCATGTTTGCGGGCGTTAACCATAGCCTGATTTCCC
AGGTACATGCGATGTTACCAGCGCTAACGGTTATTGTTCCGGATAAAAAATTACAGTTGGTATGTCTGGCATTATTGTTG
GCGGGTTTAAATGAGCCGCTAAAAGCCGCGAAAATTTTATCGGATATAGATTTGCCAGAGGCTATGGCGCTGCGTCTGTT
ATTTCCTGCACCAAATGAGGGGTTTGAAAATTGAATATTTCTGATATGAGCGTAGTGCCTGTAAGCACTCAATCTTATGT
AAAGTCCTCTGCAGAACCGAGCCAGGAGCAAATTAATTTTTTTGAACAATTGCTGAAAGATGAAGCATCCACCAGTAACG
CCAGTGCTTTATTACCGCAGGTTATGTTGACCAGACAAATGGATTATATGCAGTTAACGGTAGGCGTCGATTATCTTGCC
AGAATATCAGGCGCAGCATCGCAAGCGCTTAATAAGCTGGATAACATGGCATGAAGGTTCATCGTATAGTATTTCTTACT
GTCCTTACGTTCTTTCTTACGGCATGTGATGTGGATCTTTATCGCTCATTGCCAGAAGATGAAGCGAATCAAATGCTGGC
ATTACTTATGCAGCATCATATTGATGCGGAAAAAAAACAGGAAGAGGATGGTGTAACCTTACGTGTCGAGCAGTCGCAGT
TTATTAATGCGGTTGAGCTACTTAGACTTAACGGTTATCCGCATAGGCAGTTTACAACGGCGGATAAGATGTTTCCGGCT
AATCAGTTAGTGGTATCACCCCAGGAAGAACAGCAGAAGATTAATTTTTTAAAAGAACAAAGAATTGAAGGAATGCTGAG
TCAGATGGAGGGCGTGATTAATGCAAAAGTGACCATTGCGCTACCGACTTATGATGAGGGAAGTAACGCTTCTCCGAGCT
CAGTTGCCGTATTTATAAAATATTCACCTCAGGTCAATATGGAGGCCTTTCGGGTAAAAATTAAAGATTTAATAGAGATG
TCAATCCCTGGGTTGCAATACAGTAAGATTAGTATCTTGATGCAGCCTGCTGAATTC
```

FIG. 21B

```
AGCATTGACATAAAAACTTACAATTTGAAAAATTATTTATTAAATAAACTGTTACGATGTTTTTACATCGCCATCTTATT
AAAAAGTAATTGTAGTCATCGACTGGGTTATATATGAAGAAATTTATCTTCCTAATGATAACACCATCGATTAATCTTCT
GATGAAACTATATGTACTGCGATAGTGATCAAGTGCCAAAGATTTTGCAACAGGCAACTGGAGGGAAGCATTATGAATTT
GCTCAATCTCAAGAATACGCTGCAAACATCTTTAGTAATCAGGCTAACTTTTTTATTTTTATTAACAACAATAATTATTT
GGCTGCTATCTGTGCTTACCGCAGCTTATATATCAATGGTTCAGAAACGGCAGCATATAATAGAGGATTTATCCGTTCTA
TCCGAGATGAATATTGTACTAAGCAATCAACGGTTTGAAGAAGCTGAACGTGACGCTAAAAATTTAATGTATCAATGCTC
ATTAGCGACTGAGATTCATCATAACGATATTTTCCCTGAGGTGAGCCGGCATCTATCTGTCGGTCCTTCAAATTGCACGC
CGACGCTAAACGGAGAGAAGCACCGTCTCTTTCTGCAGTCCTCTGATATCGATGAAAATAGCTTTCGTCGCGATAGTTTT
ATTCTTAATCATAAAAATGAGATTTCGTTATTATCTACTGATAACCCTTCAGATTATTCAACTCTACAGCCTTTAACGCG
AAAAAGCTTTCCTTTATACCCAACCCATGCCGGGTTTTACTGGAGTGAACCAGAATACATAAACGGCAAAGGATGGCACG
CTTCCGTTGCGGTTGCCGATCAGCAAGGCGTATTTTTGAGGTGACGGTTAAACTTCCCGATCTCATTACTAAGAGCCAC
CTGCCATTAGATGATAGTATTCGAGTATGGCTGGATCAAAACAACCACTTATTGCCGTTTTCATACATCCCGCAAAAAAT
ACGTACACAGTTAGAAAATGTAACGCTGCATGATGGATGGCAGCAAATTCCCGGATTTCTGATATTACGCACAACCTTGC
ATGGCCCCGGATGGAGTCTGGTTACGCTGTACCCATACGGTAATCTACATAATCGCATCTTAAAAATTATCCTTCAACAA
ATCCCCTTTACATTAACAGCATTGGTGTTGATGACGTCGGCTTTTTGCTGGTTACTACATCGCTCACTGGCCAAACCGTT
ATGGCGTTTTGTCGATGTCATTAATAAAACCGCAACTGCACCGCTGAGCACACGTTTACCAGCACAACGACTGGATGAAT
TAGATAGTATTGCCGGTGCTTTTAACCAACTGCTTGATACTCTACAAGTCCAATACGACAATCTGGAAAACAAAGTCGCA
GAGCGCACCCAGGCGCTAAATGAAGCAAAAAAACGCGCTGAGCGAGCTAACAAACGTAAAAGCATTCATCTTACGGTAAT
AAGTCATGAGTTACGTACTCCGATGAATGGCGTACTCGGTGCAATTGAATTATTACAAACCACCCCTTTAAACATAGAGC
AACAAGGATTAGCTGATACCGCCAGAAATTGTACACTGTCTTTGTTAGCTATTATTAATAATCTGCTGGATTTTTCACGC
ATCGAGTCTGGTCATTTCACATTACATATGGAAGAAACAGCGTTACTGCCGTTACTGGACCAGGCAATGCAAACCATCCA
GGGGCCAGCGCAAAGCAAAAAACTGTCATTACGTACTTTTGTCGGTCAACATGTCCCTCTCTATTTTCATACCGACAGTA
TCCGTTTACGGCAAATTTTGGTTAATTTACTCGGGAACGCGGTAAAATTTACCGAAACCGGAGGGATACGTCTGACGGTC
AAGCGTCATGAGGAACAATTAATATTTCTGGTTAGCGATAGCGGTAAAGGGATTGAAATACAGCAGCAGTCTCAAATCTT
TACTGCTTTTTATCAAGCAGACACAAATTCGCAAGGTACAGGAATTGGACTGACTATTGCGTCAAGCCTGGCTAAAATGA
TGGGCGGTAATCTGACACTAAAAAGTGTCCCCGGGGTTGGAACCTGTGTCTCGCTAGTATTACCCTTACAAGAATACCAG
CCGCCTCAACCAATTAAAGGGACGCTGTCAGCGCCGTTCTGCCTGCATCGGCAACTGGCTTGCTGGGGAATACGCGGTGA
ACCACCCCACCAGCAAAATGCGCTTCTCAACGCAGAGCTTTTGTATTTCTCCGGAAAACTCTACGACCTGGCGCAACAGT
TAATATTGTGTACACCAAATATGCCAGTAATAAATAATTTGTTACCACCCTGGCAGTTGCAGATTCTTTTGGTTGATGAT
GCCGATATTAATCGGGATATCATCGGCAAAATGCTTGTCAGCCTGGGCCAACACGTCACTATTGCCGCCAGTAGTAACGA
GGCTCTGACTTTATCACAACAGCAGCGATTCGATTTAGTACTGATTGACATTAGAATGCCAGAAATAGATGGTATTGAAT
GTGTACGATTATGGCATGATGAGCCGAATAATTTAGATCCTGACTGCATGTTTGTGGCACTATCCGCTAGCGTAGCGACA
GAAGATATTCATCGTTGTAAAAAAAATGGGATTCATCATTACATTACAAAACCAGTGACATTGGCTACCTTAGCTCGCTA
CATCAGTATTGCCGCAGAATACCAACTTTTACGAAATATAGAGCTACAGGAGCAGGATCCGAGTCGCTGCTCAGCGCTAC
TGGCGACAGATGATATGGTCATTAATAGCAAGATTTTCCAATCACTGGACCTCTTGCTGGCTGATATTGAAAATGCCGTA
TCGGCTGGAGAAAAAATCGATCAGTTAATTCACACATTAAAAGGCTGTTTAGGTCAAATAGGGCAGACTGAATTGGTATG
CTATGTCATAGACATTGAGAATCGCGTAAAAATGGGGAAAATCATCGCGCTGGAGGAACTAACCGACTTACGCCAGAAAA
TACGTATGATCTTCAAAAACTACACCATTACTTAATATTATCTTAATTTTCGCGAGGGCAGCAAAATGAAAGAATATAAG
ATCTTATTAGTAGACGATCATGAAATCATCATTAACGGCATTATGAATGCCTTATTACCCTGGCCTCATTTTAAAATTGT
AGAGCATGTTAAAAATGGTCTTGAGGTTTATAATGCCTGTTGTGCATACGAGCCTGACATACTTATCCTTGATCTTAGTC
TACCTGGCATCAATGGCCTGGATATCATTCCTCAATTACATCAGCGTTGGCCAGCAATGAATATTCTGGTTTACACAGCA
TACCAACAAGAGTATATGACCATTAAAACTTTAGCCGCAGGTGCTAATGGCTATGTTTAAAAAGCAGTAGTCAGCAAGT
TCTGTTAGCGGCATTGCAAACAGTAGCAGTAAACAAGCGTTACATTGACCCAACGTTGAATCGGGAAGCTATCCTGGCTG
AATTAAACGCTGACACGACCAATCATCAACTGCTTACTTTGCGCGAGCGTCAGGTTCTTAAACTTATTGACGAGGGGTAT
ACCAATCATGGGATCAGCGAAAAGCTACATATCGTAGTATAAAAACCGTCGAAACACACCGGATGAATATGATGAGAAGCT
ACAGGTTCATAAAGTGACAGAGTTACTTAACTGTGCCCGAAGAATGAGGTTAATAGAGTATTAACCAGGGGCGTCCGATG
GTATTAAGCATTGGTCATATTTTGATGAGCCTTACGCCACGCAGTATTGCTCATCATCGACAAAATCCATACGGATGCCC
TGGTATGCCGCACCATTTATCACTACCTTAGTCTTCATTTGATCATGATATAGTAGAATCCCCTTATTTAACGGGCTTTA
CCATGTCGTATTCTATCGGCGAATTTGCCAGACTATGCGGTATCAATGCCGCCACGCTAAGGGCATGGCAGCGACGCTAT
G
```

FIG. 22A sseA
ATGATGATAAAGAAAAAGGCTGCGTTTAGTGAATATCGTGATTTAGAGCAAAGTTACATGCAGCTAAATCACTGTCTTAA
AAAATTTCACCAAATCCGGGCTAAGGTGAGTCAACAGCTTGCTGAAAGGGCAGAGAGCCCCAAAAATAGCAGAGAGACAG
AGAGTATTCTTCATAACCTATTTCCACAAGGCGTTGCCGGGGTTAACCAGGAGGCCGAGAAGGATTTAAAGAAAATAGTA
AGTTTGTTTAAACAACTTGAAGTACGACTGAAACAACTTAATGCTCAAGCCCCGGTGGAGATACCGTCAGGAAAAACAAA
AAGGTAA

FIG. 22B sseB
ATGTCTTCAGGAAACATCTTATGGGGAAGTCAAAACCCTATTGTGTTTAAAAATAGCTTCGGCGTCAGCAACGCTGATAC
CGGGAGCCAGGATGACTTATCCCAGCAAAATCCGTTTGCCGAAGGGTATGGTGTTTTGCTTATTCTCCTTATGGTTATTC
AGGCTATCGCAAATAATAAATTTATTGAAGTCCAGAAGAACGCTGAACGTGCCAGAAATACCCAGGAAAAGTCAAATGAG
ATGGATGAGGTGATTGCTAAAGCAGCCAAAGGGGATGCTAAAACCAAAGAGGAGGTGCCTGAGGATGTAATTAAATACAT
GCGTGATAATGGTATTCTCATCGATGGTATGACCATTGATGATTATATGGCTAAATATGGCGATCATGGGAAGCTGGATA
AAGGTGGCCTACAGGCGATCAAAGCGGCTTTGGATAATGACGCCAACCGGAATACCGATCTTATGAGTCAGGGGCAGATA
ACAATTCAAAAAATGTCTCAGGAGCTTAACGCTGTCCTTACCCAACTGACAGGGCTTATCAGTAAGTGGGGGGAAATTTC
CAGTATGATAGCGCAGAAAACGTACTCATGA

FIG. 22C sseC
ATGAATCGAATTCACAGTAATAGCGACAGCGCCGCAGGAGTAACCGCCTTAACACATCATCACTTAAGCAATGTCAGTTG
CGTTTCCTCGGGTTCGCTGGGAAAGCGCCAGCATCGTGTGAATTCTACTTTTGGCGATGGCAACGCCGCGTGTCTGCTAT
CCGGGAAAATTAGTCTTCAGGAGGCAAGCAATGCGTTGAAGCAACTGCTTGATGCCGTACCCGGAAATCATAAGCGTCCA
TCATTGCCTGACTTTTTGCAGACCAATCCCGCGGTTTTATCAATGATGATGACGTCATTAATACTCAACGTCTTTGGTAA
TAACGCTCAATCGTTATGCCAACAGCTTGAGCGGGCAACTGAGGTGCAAAATGCATTACGTAATAAGCAGGTAAAGGAGT
ATCAGGAGCAGATCCAGAAAGCGATAGAGCAGGAGGATAAAGCGCGTAAAGCGGGTATTTTTGGCGCTATTTTTGACTGG
ATTACCGGCATATTTGAAACCGTGATTGGCGCCTTAAAAGTTGTGGAAGGTTTTCTGTCCGGAAATCCCGCAGAAATGGC
TAGCGGCGTAGCTTATATGGCCGCAGGTTGTGCAGGAATGGTTAAAGCCGGAGCCGAAACGGCAATGATGTGCGGTGCTG
ACCACGATACCTGTCAGGCAATTATTGACGTGACAAGTAAGATTCAATTTGGTTGTGAAGCCGTCGCGCTGGCACTGGAT
GTTTTCCAGATTGGCCGTGCTTTTATGGCGACGAGAGGTTTATCTGGCGCAGCTGCAAAAGTGCTTGACTCCGGTTTTGG
CGAGGAAGTGGTTGAGCGTATGGTAGGTGCAGGGAAGCAGAAATAGAGGAGTTGGCTGAAAAGTTTGGCGAAGAAGTGA
GCGAAAGTTTTTCCAAACAATTTGAGCCGCTTGAACGTGAAATGGCTATGGCGAATGAGATGGCAGAGGAGGCTGCCGAG
TTTTCTCGTAACGTAGAAAATAATATGACGCGAAGCGCGGGAAAAAGCTTTACGAAAGAGGGGGTGAAAGCCATGGCAAA
AGAAGCGGCAAAAGAAGCCCTGGAAAAAATGTGTGCAAGAAGGTGGAAAGTTCCTGTTAAAAAAATTCCGTAATAAAGTTC
TCTTCAATATGTTCAAAAAAATCCTGTATGCCTTACTGAGGGATTGTTCATTTAAAGGCTTACAGGCTATCAGATGTGCA
ACCGAGGGCGCCAGTCAGATGAATACTGGCATGGTTAACACAGAAAAAGCGAAGATCGAAAAGAAAATAGAGCAATTAAT
AACTCAGCAACGGTTTCTGGATTTCATAATGCAACAAACAGAAAACCAGAAAAAGATAGAACAAAAACGCTTAGAGGAGC
TTTATAAGGGGACGGGTGCCGCGCTTAGAGATGTATTAGATACCATTGATCACTATAGTAGCGTTCAGGCGAGAATAGCT
GGCTATCGCGCTTAA

FIG. 22D sseD
ATGGGTACTGAATCAATGCTTCTGTTATTTGATGATATCTGGATGAAGCTAATGGAGCTTGCCAAAAAGCTGCGCGATAT
CATGCGCAGCTATAACGTAGAAAAACAACGGCTGGCCTGGGAACTGCAAGTCAATGTTTTACAGACGCAAATGAAAACAA
TTGATGAAGCGTTTAGAGCATCAATGATTACTGCGGGTGGCGCAATGTTGTCGGGTGTACTGACGATAGGATTAGGGGCC
GTAGGCGGGGAAACCGGTCTTATAGCGGGTCAAGCCGTAGGCCACACAGCTGGGGCGTCATGGGCCTGGGGGCTGGTGT
AGCGCAACGTCAAAGTGATCAAGATAAAGCGATTGCCGACCTGCAACAAATGGGGCCCAATCTTATAATAAATCCCTGA
CGGAAATTATGGAGAAAGCAACTGAAATTATGCAGCAAATCATCGGCGTGGGGTCGTCACTGGTCACGGTTCTTGCTGAA
ATACTCCGGGCATTAACGAGGTAA

FIG. 22E sseE
ATGGTGCAAGAAATAGAGCAATGGTTACGTCGGCATCAGGTGTTTACTGAGCCTGCATATTTAGGGGAGACCGCCATATT
ACTTGGGCAGCAGTTTATATTATCGCCTTACCTGGTGATCTATCGTATTGAGGCAAAAGAAATGATTATTTGTGAGTTCA
GGCGCCTGACGCCCGGGCAACCTCGACCACAGCAATTGTTTCACTTACTGGGACTTTTACGCGGGATATTTGTGCATCAC
CCGCAGTTAACATGTTTAAAGATGTTGATAATCACCGACGTTCTGGATGAAAAAAAAGCCATGCTACGCAGGAAATTATT
GCGCATCCTGACAGTAATGGGAGCGACCTTTACACAGCTTGATGGCGATAACTGGACAGTTTTATCCGCCGAGCATCTTA
TCCAGCGACGTTTTTAA

FIG. 22F sseF
ATGAAAATTCATATTCCGTCAGCGGCAAGTAATATAGTCGATGGTAATAGTCCTCCTTCCGATATACAAGCGAAGGAGGT
ATCGTTTCCTCCCCCTGAAATTCCAGCGCCTGGCACCCCCGCAGCCCCTGTGCTGCTTACGCCTGAACAAATAAGGCAGC
AGAGGGATTATGCGATACATTTTATGCAATACACTATTCGTGCGCTGGGTGCGACAGTCGTGTTTGGGTTATCGGTTGCT
GCAGCGGTAATTTCTGGCGGGGCAGGATTACCCATTGCTATTCTTGCGGGGCGGCGCTCGTGATTGCTATTGGGGATGC
TTGCTGTGCGTATCATAATTATCAATCGATATGTCAGCAAAAGGAGCCATTACAAACCGCCAGTGATAGCGTTGCTCTTG
TGGTCAGTGCGCTGGCCTTAAAATGTGGGGCAAGTCTTAACTGCGCTAACACCCTTGCTAATTGTCTTTCTTTATTAATA
CGTTCAGGAATCGCTATTTCTATGTTGGTTTTACCCCTACAGTTTCCACTGCCCGCGGCTGAAAATATTGCGGCCTCTTT
GGACATGGGGAGTGTAATTACCTCCGTTAGCCTGACGGCGATAGGTGCGGTACTGGATTATTGCCTTGCCCGCCCCTCTG
GCGACGATCAGGAAAATTCTGTTGATGAACTTCATGCCGATCCCAGTGTGTTATTGGCGGAACAAATGGCAGCGCTCTGT
CAATCTGCTACTACACCTGCACCTGCATTAATGGACAGTTCTGATCATACATCTCGGGGAGAACCATGA

FIG. 22G sseG
ATGAAACCTGTTAGCCCAAATGCTCAGGTAGGAGGGCAACGTCCTGTTAACGCGCCTGAGGAATCACCTCCATGTCCTTC
ATTGCCACATCCGGAAACCAATATGGAGAGTGGTAGAATAGGACCTCAACAAGGAAAAGAGCGGGTATTGGCCGGACTTG
CGAAACGAGTGATAGAGTGTTTTCCAAAAGAAATTTTTAGTTGGCAAACGGTTATTTTGGGCGGACAGATTTTATGCTGT
TCCGCTGGAATAGCATTAACAGTGCTAAGTGGTGGAGGCGCGCCGCTCGTAGCCCTGGCAGGGATTGGCCTTGCTATTGC
CATCGCGGATGTCGCCTGTCTTATCTACCATCATAAACATCATTTGCCTATGGCTCACGACAGTATAGGCAATGCCGTTT
TTTATATTGCTAATTGTTTCGCCAATCAACGCAAAAGTATGGCGATTGCTAAAGCCGTCTCCCTGGGCGGTAGATTAGCC
TTAACCGCGACGGTAATGACTCATTCATACTGGAGTGGTAGTTTGGGACTACAGCCTCATTTATTAGAGCGTCTTAATGA
TATTACCTATGGACTAATGAGTTTTACTCGCTTCGGTATGGATGGGATGGCAATGACCGGTATGCAGGTCAGCAGCCCAT
TATATCGTTTGCTGGCTCAGGTAACGCCAGAACAACGTGCGCCGGAGTAA

FIG. 22H ssaA
ATGAAAAAAGACCCGACCCTACAACAGGCACATGACACGATGCGGTTTTTCCGGCGTGGCGGCTCGCTGCGTATGTTGTT
GGATGACGATGTTACACAGCCGCTTAATACTCTGTATCGCTATGCCACGCAGCTTATGGAGGTAAAAGAATTCGCCGGCG
CAGCGCGACTTTTTCAATTGCTGACGATATATGATGCCTGGTCATTTGACTACTGGTTTCGGTTAGGGGAATGCTGCCAG
GCTCAAAAACATTGGGGGGAAGCGATATACGCTTATGGACGCGCGGCACAAATTAAGATTGATGCGCCGCAGGCGCCATG
GGCCGCAGCGGAATGCTATCTCGCGTGTGATAACGTCTGTTATGCAATCAAAGCGTTAAAGGCCGTGGTGCGTATTTGCG
GCGAGGTCAGTGAACATCAAATTCTCCGACAGCGTGCAGAAAAGATGTTACAGCAACTTTCTGACAGGAGCTAA

FIG. 22I ssaB
ATGATGATGAAAGAAGATCAGAAAAATAAAATACCCGAAGACATTCTGAAACAGCTATTATCCGTTGATCCGGAAACCGT
TTATGCCAGTGGTTACGCCTCATGGCAGGAGGGGGATTATTCGCGCGCCGTAATCGATTTTAGTTGGCTGGTGATGGCCC
AGCCATGGAGTTGGCGTGCCCATATTGCATTGGCTGGCACCTGGATGATGCTTAAAGAATACACGACGGCCATTAATTTC
TATGGACATGCCTTGATGCTGGATGCCAGCCATCCAGAACCGGTTTACCAAACGGGCGTCTGTCTCAAAATGATGGGGGA
ACCCGGGTTGGCGAGAGAGGCTTTTCAAACCGCAATCAAGATGAGTTATGCGGATGCCTCATGGAGTGAGATTCGCCAGA
ATGCGCAAATAATGGTTGATACTCTTATTGCTTAA

FIG. 22J ssaD
ATGGCATATCTCATGGTTAATCCAAAGAGTTCCTGGAAAATACGTTTTTTAGGTCACGTTTTACAAGGCCGGGAAGTATG
GCTGAATGAAGGTAACCTGTCACTGGGGGAGAAGGGATGCGATATTTGTATTCCGCTGGCTATAAATGAAAAAAATTATTC
TGAGAGAACAGGCAGATAGTTTATTTGTTGATGCCGGGAAAGCCAGAGTTAGAGTTAATGGCCGCAGATTTAATCCAAAT
AAGCCGCTACCATCCAGTGGGGTTTTGCAGGTTGCGGGAGTGGCTATCGCGTTTGGTAAACAGGATTGTGAACTTGCTGA
TTATCAAATACCCGTTTCCAGATCAGGGTACTGGTGGTTGGCTGGCGTATTCTTGATTTTCATCGGTGGAATGGGTGTCC
TGTTAAGTATTAGTGGTCAGCCTGAAACGGTAAATGACTTACCTTTGCGGGTTAAGTTTTTATTAGACAAAAGCAATATT
CATTATGTGCGGGCGCAATGGAAAGAAGATGGCAGCCTGCAGTTGTCCGGTTATTGCTCGTCAAGCGAACAGATGCAAAA
GGTGAGAGCGACTCTCGAATCATGGGGGGTCATGTATCGGGATGGTGTAATCTGTGATGACTTATTGGTACGAGAAGTGC
AGGATGTTTTGATAAAAATGGGTTACCCGCATGCTGAAGTATCCAGCGAAGGGCCGGGGAGCGTGTTAATTCATGATGAT
ATACAAATGGATCAGCAATGGCGCAAGGTTCAACCATTACTTGCAGATATTCCCGGGTTATTGCACTGGCAGATTAGTCA
CTCTCATCAGTCTCAGGGGGATGATATTATTTCTGCGATAATAGAGAACGGTTTAGTGGGGCTTGTCAATGTTAGCCCAA
TGCGGCGCTCTTTTGTTATCAGTGGTGTACTGGATGAATCTCATCAACGCATTTTGCAAGAAACGTTAGCAGCATTAAAG
AAAAAGGATCCCGCTCTTTCTTTAATTTATCAGGATATTGCGCCTTCCCATGATGAAAGCAAGTATCTGCCTGCGCCAGT
GGCTGGCTTTGTACAGAGTCGCCATGGTAATTACTTATTACTGACGAATAAAGAGCGTTTACGTGTAGGGGCATTGTTAC
CCAATGGGGGAGAAATTGTCCATCTGAGTGCCGATGTGGTAACGATTAAACATTATGATACTTTGATTAACTATCCATTA
GATTTTAAGTGA

FIG. 22K ssaE
ATGACAACTTTGACCCGGTTAGAAGATTTGCTGCTTCATTCGCGTGAAGAGGCCAAAGGCATAATTTTACAATTAAGGGC
TGCCCGGAAACAGTTAGAAGAGAACAACGGCAAGTTACAGGATCCGCAGCAATATCAGCAAAACACCTTATTGCTTGAAG
CGATCGAGCAGGCCGAAAATATCATCAACATTATTTATTATCGTTACCATAACAGCGCACTTGTAGTGAGTGAGCAAGAG
TAA

FIG. 22L ssaG
ATGGATATTGCACAATTAGTGGATATGCTCTCCCACATGGCGCACCAGGCAGGCCAGGCCATTAATGACAAAATGAATGG
TAATGATTTGCTCAACCCAGAATCGATGATTAAAGCGCAATTTGCCTTACAGCAGTATTCTACATTTATTAATTACGAAA
GTTCACTGATCAAAATGATCAAGGATATGCTTAGTGGAATCATTGCTAAAATCTGA

FIG. 22M ssaH
ATGTTTGCGGGCGTTAACCATAGCCTGATTTCCCAGGTACATGCGATGTTACCAGCGCTAACGGTTATTGTTCCGGATAA
AAAATTACAGTTGGTATGTCTGGCATTATTGTTGGCGGGTTTAAATGAGCCGCTAAAAGCCGCGAAAATTTTATCGGATA
TAGATTTGCCAGAGGCTATGGCGCTGCGTCTGTTATTTCCTGCACCAAATGAGGGGTTTGAAAATTGA

FIG. 22N ssaI
ATGAGCGTAGTGCCTGTAAGCACTCAATCTTATGTAAAGTCCTCTGCAGAACCGAGCCAGGAGCAAATTAATTTTTTTGA
ACAATTGCTGAAAGATGAAGCATCCACCAGTAACGCCAGTGCTTTATTACCGCAGGTTATGTTGACCAGACAAATGGATT
ATATGCAGTTAACGGTAGGCGTCGATTATCTTGCCAGAATATCAGGCGCAGCATCGCAAGCGCTTAATAAGCTGGATAAC
ATGGCATGA

FIG. 22O ssaJ
ATGAAGGTTCATCGTATAGTATTTCTTACTGTCCTTACGTTCTTTCTTACGGCATGTGATGTGGATCTTTATCGCTCATT
GCCAGAAGATGAAGCGAATCAAATGCTGGCATTACTTATGCAGCATCATATTGATGCGGAAAAAAAACAGGAAGAGGATG
GTGTAACCTTACGTGTCGAGCAGTCGCAGTTTATTAATGCGGTTGAGCTACTTAGACTTAACGGTTATCCGCATAGGCAG
TTTACAACGGCGGATAAGATGTTTCCGGCTAATCAGTTAGTGGTATCACCCCAGGAAGAACAGCAGAAGATTAATTTTTT
AAAAGAACAAAGAATTGAAGGAATGCTGAGTCAGATGGAGGGCGTGATTAATGCAAAAGTGACCATTGCGCTACCGACTT
ATGATGAGGGAAGTAACGCTTCTCCGAGCTCAGTTGCCGTATTTATAAAATATTCACCTCAGGTCAATATGGAGGCCTTT
CGGGTAAAAATTAAAGATTTAATAGAGATGTCAATCCCTGGGTTGCAATACAGTAAGATTAGTATCTTGATGCAGCCTGC
TGAATTCAGAATGGTAGCTGACGTACCCGCGAGACAAACATTCTGGATTATGGACGTTATCAACGCCAATAAAGGGAAGG
TGGTGAAGTGGTTGATGAAAATACCCTTATCCGTTGATGTTATCGTTGACAGGACTGTTATTAGGAGTGGGCATCCTGATC
GGCTATTTTTGCCTGAGACGCCGTTTTTGA

FIG. 22P ssrA
ATGAATTTGCTCAATCTCAAGAATACGCTGCAAACATCTTTAGTAATCAGGCTAACTTTTTTATTTTTATTAACAACAAT
AATTATTTGGCTGCTATCTGTGCTTACCGCAGCTTATATATCAATGGTTCAGAAACGGCAGCATATAATAGAGGATTTAT
CCGTTCTATCCGAGATGAATATTGTACTAAGCAATCAACGGTTTGAAGAAGCTGAACGTGACGCTAAAAATTTAATGTAT
CAATGCTCATTAGCGACTGAGATTCATCATAACGATATTTTCCCTGAGGTGAGCCGGCATCTATCTGTCGGTCCTTCAAA
TTGCACGCCGACGCTAAACGGAGAGAAGCACCGTCTCTTTCTGCAGTCCTCTGATATCGATGAAAATAGCTTTCGTCGCG
ATAGTTTTATTCTTAATCATAAAAATGAGATTTCGTTATTATCTACTGATAACCCTTCAGATTATTCAACTCTACAGCCT
TTAACGCGAAAAAGCTTTCCTTTATACCCAACCCATGCCGGGTTTTACTGGAGTGAACCAGAATACATAAACGGCAAAGG
ATGGCACGCTTCCGTTGCGGTTGCCGATCAGCAAGGCGTATTTTTTGAGGTGACGGTTAAACTTCCCGATCTCATTACTA
AGAGCCACCTGCCATTAGATGATAGTATTCGAGTATGGCTGGATCAAAACAACCACTTATTGCCGTTTTCATACATCCCG
CAAAAAATACGTACACAGTTAGAAAATGTAACGCTGCATGATGGATGGCAGCAAATTCCCGGATTTCTGATATTACGCAC
AACCTTGCATGGCCCCGGATGGAGTCTGGTTACGCTGTACCCATACGGTAATCTACATAATCGCATCTTAAAAATTATCC
TTCAACAAATCCCCTTTTACATTAACAGCATTGGTGTTGATGACGTCGGCTTTTTGCTGGTTACTACATCGCTCACTGGCC
AAACCGTTATGGCGTTTTGTCGATGTCATTAATAAAACCGCAACTGCACCGCTGAGCACACGTTTACCAGCACAACGACT
GGATGAATTAGATAGTATTGCCGGTGCTTTTAACCAACTGCTTGATACTCTACAAGTCCAATACGACAATCTGGAAAACA
AAGTCGCAGAGCGCACCCAGGCGCTAAATGAAGCAAAAAAACGCGCTGAGCGAGCTAACAAACGTAAAAGCATTCATCTT
ACGGTAATAAGTCATGAGTTACGTACTCCGATGAATGGCGTACTCGGTGCAATTGAATTATTACAAACCACCCCTTTAAA
CATAGAGCAACAAGGATTAGCTGATACCGCCAGAAATTGTACACTGTCTTTGTTAGCTATTATTAATAATCTGCTGGATT
TTTCACGCATCGAGTCTGGTCATTTCACATTACATATGGAAGAAACAGCGTTACTGCCGTTACTGGACCAGGCAATGCAA
ACCATCCAGGGGCCAGCGCAAAGCAAAAAACTGTCATTACGTACTTTTGTCGGTCAACATGTCCCTCTCTATTTTCATAC
CGACAGTATCCGTTTACGGCAAATTTTGGTTAATTTACTCGGGAACGCGGTAAAATTTACCGAAACCGGAGGGATACGTC
TGACGGTCAAGCGTCATGAGGAACAATTAATATTTCTGGTTAGCGATAGCGGTAAAGGGATTGAAATACAGCAGCAGTCT
CAAATCTTTACTGCTTTTTATCAAGCAGACACAAATTCGCAAGGTACAGGAATTGGACTGACTATTGCGTCAAGCCTGGC
TAAAATGATGGGCGGTAATCTGACACTAAAAAGTGTCCCCGGGGTTGGAACCTGTGTCTCGCTAGTATTACCCTTACAAG
AATACCAGCCGCCTCAACCAATTAAAGGGACGCTGTCAGCGCCGTTCTGCCTGCATCGGCAACTGGCTTGCTGGGGAATA
CGCGGTGAACCACCCCACCAGCAAAATGCGCTTCTCAACGCAGAGCTTTTGTATTTCTCCGGAAAACTCTACGACCTGGC
GCAACAGTTAATATTGTGTACACCAAATATGCCAGTAATAAATAATTTGTTACCACCCTGGCAGTTGCAGATTCTTTTGG
TTGATGATGCCGATATTAATCGGGATATCATCGGCAAAATGCTTGTCAGCCTGGCCAACACGTCACTATTGCCGCCAGT
AGTAACGAGGCTCTGACTTTATCACAACAGCAGCGATTCGATTTAGTACTGATTGACATTAGAATGCCAGAAATAGATGG
TATTGAATGTGTACGATTATGGCATGATGAGCCGAATAATTTAGATCCTGACTGCATGTTTGTGGCACTATCCGCTAGCG
TAGCGACAGAAGATATTCATCGTTGTAAAAAAAATGGGATTCATCATTACATTACAAAACCAGTGACATTGGCTACCTTA
GCTCGCTACATCAGTATTGCCGCAGAATACCAACTTTTACGAAATATAGAGCTACAGGAGCAGGATCCGAGTCGCTGCTC
AGCGCTACTGGCGACAGATGATATGGTCATTAATAGCAAGATTTTCCAATCACTGGACCTCTTGCTGGCTGATATTGAAA
ATGCCGTATCGGCTGGAGAAAAAATCGATCAGTTAATTCACACATTAAAAGGCTGTTTAGGTCAAATAGGGCAGACTGAA
TTGGTATGCTATGTCATAGACATTGAGAATCGCGTAAAAATGGGGAAAATCATCGCGCTGGAGGAACTAACCGACTTACG
CCAGAAAATACGTATGATCTTCAAAAACTACACCATTACTTAA

FIG. 22Q ssrB
ATGAAAGAATATAAGATCTTATTAGTAGACGATCATGAAATCATCATTAACGGCATTATGAATGCCTTATTACCCTGGCC
TCATTTTAAAATTGTAGAGCATGTTAAAAATGGTCTTGAGGTTTATAATGCCTGTTGTGCATACGAGCCTGACATACTTA
TCCTTGATCTTAGTCTACCTGGCATCAATGGCCTGGATATCATTCCTCAATTACATCAGCGTTGGCCAGCAATGAATATT
CTGGTTTACACAGCATACCAACAAGAGTATATGACCATTAAAACTTTAGCCGCAGGTGCTAATGGCTATGTTTTAAAAAG
CAGTAGTCAGCAAGTTCTGTTAGCGGCATTGCAAACAGTAGCAGTAAACAAGCGTTACATTGACCCAACGTTGAATCGGG
AAGCTATCCTGGCTGAATTAAACGCTGACACGACCAATCATCAACTGCTTACTTTGCGCGAGCGTCAGGTTCTTAAACTT
ATTGACGAGGGGTATACCAATCATGGGATCAGCGAAAAGCTACATATCAGTATAAAAACCGTCGAAACACACCGGATGAA
TATGATGAGAAAGCTACAGGTTCATAAAGTGACAGAGTTACTTAACTGTGCCCGAAGAATGAGGTTAATAGAGTATTAA

FIG. 23A

SseA
MMIKKKAAFSEYRDLEQSYMQLNHCLKKPHQIRAKVSQQLAERAESPKNSRETESILHNLPPQGVAGVNQEAEKDLKKIV
SLFKQLEVRLKQLNAQAPVEIPSGKTKR

FIG. 23B

SseB
MSSGNILWGSQNPIVFKNSFGVSNADTGSQDDLSQQNPFAEGYGVLLILLMVIQAIANNKFIEVQKNAERARNTQEKSNE
MDEVIAKAAKGDAKTKEEVPEDVIKYMRDNGILIDGMTIDDYMAKYGDHGKLDKGGLQAIKAALDNDANRNTDLMSQGQI
TIQKMSQELNAVLTQLTGLISKWGEISSMIAQKTYS

FIG. 23C

SseC
MNRIHSNSDSAAGVTALTHHHLSNVSCVSSGSLGKRQHRVNSTFGDGNAACLLSGKISLQEASNALKQLLDAVPGNHKRP
SLPDFLQTNPAVLSMMMTSLILNVFGNNAQSLCQQLERATEVQNALRNKQVKEYQEQIQKAIEQEDKARKAGIFGAIFDW
ITGIFETVIGALKVVEGFLSGNPAEMASGVAYMAAGCAGMVKAGAETAMMCGADHDTCQAIIDVTSKIQFGCEAVALALD
VFQIGRAFMATRGLSGAAAKVLDSGFGEEVVERMVGAGEAEIEELAEKFGEEVSESFSKQFEPLEREMAMANEMAEEAAE
FSRNVENNMTRSAGKSFTKEGVKAMAKEAAKEALEKCVQEGGKFLLKKFRNKVLFNMFKKILYALLRDCSFKGLQAIRCA
TEGASQMNTGMVNTEKAKIEKKIEQLITQQRFLDFIMQQTENQKKIEQKRLEELYKGTGAALRDVLDTIDHYSSVQARIA
GYRA

FIG. 23D

SseD
MEASNVALVLPAPSLLTPSSTPSPSGEGMGTESMLLLFDDIWMKLMELAKKLRDIMRSYNVEKQRLAWELQVNVLQTQMK
TIDEAFRASMITAGGAMLSGVLTIGLGAVGGETGLIAGQAVGHTAGGVMGLGAGVAQRQSDQDKAIADLQQNGAQSYNKS
LTEIMEKATEIMQQIIGVGSSLVTVLAEILRALTR

FIG. 23E

SseE
MVQEIEQWLRRHQVFTEPAYLGETAILLGQQFILSPYLVIYRIEAKEMIICEFRRLTPGQPRPQQLFHLLGLLRGIFVHH
PQLTCLKMLIITDVLDEKKAMLRRKLLRILTVMGATFTQLDGDNWTVLSAEHLIQRRF

FIG. 23F

SseF
MKIHIPSAASNIVDGNSPPSDIQAKEVSFPPPEIPAPGTPAAPVLLTPEQIRQQRDYAIHFMQYTIRALGATVVFGLSVA
AAVISGGAGLPIAILAGAALVIAIGDACCAYHNYQSICQQKEPLQTASDSVALVVSALALKCGASLNCANTLANCLSLLI
RSGIAISMLVLPLQFPLPAAENIAASLDMGSVITSVSLTAIGAVLDYCLARPSGDDQENSVDELHADPSVLLAEQMAALC
QSATTPAPALMDSSDHTSRGEP

FIG. 23G

SseG
MKPVSPNAQVGGQRPVNAPEESPPCPSLPHPETNMESGRIGPQQGKERVLAGLAKRVIECFPKEIFSWQTVILGGQILCC
SAGIALTVLSGGGAPLVALAGIGLAIAIADVACLIYHHKHHLPMAHDSIGNAVFYIANCFANQRKSMAIAKAVSLGGRLA
LTATVMTHSYWSGSLGLQPHLLERLNDITYGLMSFTRFGMDGMAMTGMQVSSPLYRLLAQVTPEQRAPE

FIG. 23H

SscA
MKKDPTLQQAHDTMRFFRRGGSLRMLLDDDVTQPLNTLYRYATQLMEVKEFAGAARLFQLLTIYDAWSFDYWFRLGECCQ
AQKHWGEAIYAYGRAAQIKIDAPQAPWAAAECYLACDNVCYAIKALKAVVRICGEVSEHQILRQRAEKMLQQLSDRS

FIG. 23I

SscB
MMMKEDQKNKIPEDILKQLLSVDPETVYASGYASWQEGDYSRAVIDFSWLVMAQPWSWRAHIALAGTWMMLKEYTTAINF
YGHALMLDASHPEPVYQTGVCLKMMGEPGLAREAFQTAIKMSYADASWSEIRQNAQIMVDTLIA

FIG. 23J

SsaD

MAYLMVNPKSSWKIRFLGHVLQGREVWLNEGNLSLGEKGCDICIPLAINEKIILREQADSLFVDAGKARVRVNGRRFNPN
KPLPSSGVLQVAGVAIAFGKQDCELADYQIPVSRSGYWWLAGVFLIFIGGMGVLLSISGQPETVNDLPLRVKFLLDKSNI
HYVRAQWKEDGSLQLSGYCSSSEQMQKVRATLESWGVMYRDGVICDDLLVREVQDVLIKMGYPHAEVSSEGPGSVLIHDD
IQMDQQWRKVQPLLADIPGLLHWQISHSHQSQGDDIISAIIENGLVGLVNVSPMRRSFVISGVLDESHQRILQETLAALK
KKDPALSLIYQDIAPSHDESKYLPAPVAGFVQSRHGNYLLLTNKERLRVGALLPNGGEIVHLSADVVTIKHYDTLINYPL
DPK

FIG. 23K

SsaE

MTTLTRLEDLLLHSREEAKGIILQLRAARKQLEENNGKLQDPQQYQQNTLLLEAIEQAENIINIIYYRYHNSALVVSEQE

FIG. 23L

SsaG

MDIAQLVDMLSHMAHQAGQAINDKMNGNDLLNPESMIKAQPALQQYSTFINYESSLIKMIKDMLSGIIAKI

FIG. 23M

SsaH

MFAGVNHSLISQVHAMLPALTVIVPDKKLQLVCLALLLAGLNEPLKAAKILSDIDLPEAMALRLLFPAPNEGFEN

FIG. 23N

SsaI

MSVVPVSTQSYVKSSAEPSQEQINFFEQLLKDEASTSNASALLPQVMLTRQMDYMQLTVGVDYLARISGAASQALNKLDN
MA

FIG. 23O

SsaJ

MKVHRIVFLTVLTFFLTACDVDLYRSLPEDEANQMLALLMQHHIDAEKKQEEDGVTLRVEQSQFINAVELLRLNGYPHRQ
PTTADKMPPANQLVVSPQEEQQKINFLKEQRIEGMLSQMEGVINAKVTIALPTYDEGSNASPSSVAVFIKYSPQVNMEAP
RVKIKDLIEMSIPGLQYSKISILMQPAEFRMVADVPARQTFWIMDVINANKGKVVKWLMKYPYPLMLSLTGLLLGVGILI
GYFCLRRRF

FIG. 23P

SsrA

MNLLNLKNTLQTSLVIRLTFLFLLTTIIIWLLSVLTAAYISMVQKRQHIIEDLSVLSEMNIVLSNQRFEEAERDAKNLMY
QCSLATEIHHNDIFPPEVSRHLSVGPSNCTPTLNGEKHRLFLQSSDIDENSFRRDSFILNHKNEISLLSTDNPSDYSTLQP
LTRKSPPLYPTHAGFYWSEPEYINGKGWHASVAVADQQGVFFEVTVKLPDLITKSHLPLDDSIRVWLDQNNHLLPFSYIP
QKIRTQLENVTLHDGWQQIPGFLILRTTLHGPWSLVTLYPYGNLHNRILKIILQQIPPFTLTALVLMTSAFCWLLHRSLA
KPLWRFVDVINKTATAPLSTRLPAQRLDELDSIAGAFNQLLDTLQVQYDNLENKVAERTQALNEAKKRAERANKRKSIHL
TVISHELRTPMNGVLGAIELLQTTPLNIEQQGLADTARNCTLSLLAIINNLLDFSRIESGHFTLHMEETALLPLLDQAMQ
TIQGPAQSKKLSLRTFVGQHVPLYFHTDSIRLRQILVNLLGNAVKFTETGGIRLTVKRHEEQLIFLVSDSGKGIEIQQQS
QIFTAFYQADTNSQGTGIGLTIASSLAKMMGGNLTLKSVPGVGTCVSLVLPLQEYQPPQPIKGTLSAPFCLHRQLACWGI
RGEPPHQQNALLNAELLYFSGKLYDLAQQLILCTPNMPVINNLLPPWQLQILLVDDADINRDIIGKMLVSLGQHVTIAAS
SNEALTLSQQQRFDLVLIDIRMPEIDGIECVRLWHDEPNNLDPDCMPVALSASVATEDIHRCKKNGIHHYITKPVTLATL
ARYISIAAEYQLLRNIELQEQDPSRCSALLATDDMVINSKIFQSLDLLLADIENAVSAGEKIDQLIHTLKGCLGQIGQTE
LVCYVIDIENRVKMGKIIALEELTDLRQKIRMIFKNYTIT

FIG. 23Q

SarB
MKEYKILLVDDHEIIINGIMNALLPWPHFKIVEHVKNGLEVYNACCAYEPDILILDLSLPGINGLDIIPQLHQRWPAMNI
LVYTAYQQEYMTIKTLAAGANGYVLKSSSQQVLLAALQTVAVNKRYIDPTLNREAILAELNADTTNHQLLTLRERQVLKL
IDEGYTNHGISEKLHISIKTVETHRMNMMRKLQVHKVTELLNCARRMRLIEY

FIG. 24A

Promoter A2
GCTTCCCTCCAGTTGCCTGTTGCAAAATCTTTGGCACTTGATCACTATCGCAGTACATATAGTTTCATCAGAAGATTAAT
CGATGGTGTTATCATTAGGAAGATAAATTTCTTCATATATAACCCAGTCGATGACTACAATTACTTTTTAATAAGATGGC
GATGTAAAAACATCGTAACAGTTTATTTAATAAATAATTTTTCAAATTGTAAGTTTTTATGTCAATGCTGAAAATGTAAT
TGTGAATTTATCGGAAAATCCGAATGATAGAATCGCCTGTGACAAGGTATATGTAGACAGCATCCTGATATTGTACAAGA
AGAGATAGTCGAAATAAATGTGAATCAGGCTTTTTACGGATGTGGTTGTGAGCGAATTTGATAGAAAC

FIG. 24B

Promoter B
TAAAAATATCTTAGAGCCTATCCCACCAGGCGTTAATTGGCGCAGCCAGTTTGGACACGGATAGCGCGCAAAAACCGCAG
CGTACACGTAGTACGTGAGGTTTGACTCGCTACGCTCGCCCTTCGGGCCGCCGCTAGCGGCGTTCAAAACGCTAACGCGT
TTTGGCGAGCACTGCCCAGGTTCAAAATGGCAAGTAAAATAGCCTAATGGGATAGGCTCTTAGTTAGCACGTTAATTATC
TATCGTGTATATGGAGGGGAAT

ATTENUATED *SALMONELLA* SP12 MUTANTS AS ANTIGEN CARRIERS

This application is a divisional of U.S. Ser. No. 09/763,620 filed Mar. 2, 2001, now U.S. Pat. No. 6,936,425 issued Aug. 30, 2005, entitled "Attenuated *Salmonella* SP 12 Mutants as Antigen Carriers", which is a filing under 35 USC §371 of PCT/EP99/06514 (WO 00/14240) filed on Sep. 3, 1999, which claims priority to European Patent Application No. 98116827.1 filed Sep. 4, 1998.

BACKGROUND OF THE INVENTION

In 1996, over 17 million people world-wide, mainly in developing countries, were killed by various infections. The appearance and spread of antibiotic resistances coupled with the increase in world-wide travel has led to an increasing risk for the outbreak of pandemic infections. This possibility must be taken very seriously since, for some pathogenic bacteria, the therapeutic alternatives available have been reduced to a single option. Intriguingly, pathogenic bacteria have also been discovered to be a relevant factor in many chronic diseases. Stomach cancer, for example, is the second most common cancer world-wide and is directly linked with chronic *Helicobacter pylori* infections. *Chlamydia pneumoniae* has been detected in arteriosclerotic plaques and recently this bacterium has been found in the diseased regions of the brain of people suffering from Alzheimer's disease. Many autoimmune diseases, such as rheumatoid arthritis, seem to have bacterial origin. *Borrelia burgdorferi* is, in addition to many other bacteria, a prominent example of an organism causing disease affecting increasing numbers of people. Finally, Nanobacteria have been identified in the chronically diseased kidneys of patients with crystalline deposits. Other serious chronic diseases are caused by viral pathogens, the most clinically relevant are Hepatitis B and C viruses (liver cancer) and the human papilloma virus (cervical cancer).

The increasing clinical importance of bacterial pathogens has provoked increased discussion regarding the paradigm of medicinal treatment or prevention as the means to handle chronic diseases. Consistently, some chronic diseases have been successfully cured by antibiotic treatment. However, as indicated above, all micro-organisms are genetically capable of rapidly generating progenies with adequate antibiotic resistances, thus impeding efficient routine treatment. Conclusively, vaccines represent an excellent alternative to pharmacological drugs, and, considering the financial aspect that disease prevention is less cost-intensive than therapy, the option of vaccination is even more attractive. Therefore, the therapeutic vaccination approach has become particularly relevant, especially with respect to the treatment of cancer and chronic bacterial or viral diseases.

The most frequently practised approach uses oral delivery of either inactivated pathogens (dead vaccine) or parenteral injections of a defined mixture of purified components (subunit vaccines). Most of the dead vaccines are efficacious, however, the risk that the inactivation procedure was incomplete and that the vaccinee may become infected remains a problem. Furthermore, dead vaccines very often do not cover all genetic variants that appear in nature. The subunit vaccines abolish most of the disadvantages of the traditional dead vaccines. However, they require technologically advanced antigen and adjuvant preparations, which makes such vaccines relatively expensive. Furthermore, the subunit vaccines are preferentially inoculated by the parenteral route, which is not the optimal route for eliciting a broad immune response. In particular, the mucosal branch of the immune system, which is the primary line of protection against many pathogens, is strongly neglected by parenteral immunisations.

Another generation of vaccines is represented by live attenuated vaccines, which are based on pathogenic bacteria or viruses that have been mutated to apathogenic variants. These variants multiply in vivo for a limited period of time before they are completely cleared by the host. Their limited prevalence in the host tissue is sufficient to adequately provoke the host immune system, which is then able to establish a protective immune response. From the safety aspect, live attenuated bacterial vaccines are more favoured than live attenuated viral vaccines. Should a live bacterial vaccine becomes threating for a vaccinee, the attenuated bacteria can generally be controlled by antibiotic treatment. In contrast, live viral vaccines, which use the replication apparatus of the host cell, are almost impossible to control. Live bacterial vaccines are typically administered orally and serve as excellent stimulators of the mucosal immune system. Moreover, live bacterial vaccines are also good stimulators of the systemically active immune system, namely the humoral and cellular branches. Due to these excellent immuno-stimulatory characteristics, live bacterial vaccine strains, such as *Salmonella*, are ideal carriers for expressing antigens from a heterologous pathogen. Such bivalent (or multivalent) vaccines mediate protection against two pathogens: the pathogen homologous to the carrier as well as the pathogen whose protective antigen(s) are expressed by the carrier. Although no bivalent bacterial vaccine expressing heterologous antigens is currently in use, potential carriers currently under investigation include Bacille Calmette-Guerin (BCG), *Salmonella* species, *Vibrio cholerae* and *Escherichia coli*.

In the attenuation process, mutations are preferentially targeted to genes that support the survival of the pathogen in the host. Initially, chemical mutation regimes were applied to the *Salmonella typhi* strain Ty2, resulting in what were thought to be perfectly attenuated pathogens capable of mediating protective immunity, in contrast to the dead homologue. However, subsequent large-scale clinical trails revealed that such strains were still not sufficiently efficacious in the prevention of typhoid fever. It appears that such strains were mutated in several genes, resulting in an over-attenuation, which adversely affects the immunogenic potential of the strain. Novel typhoid vaccine strains have been developed by the introduction of genetically defined mutations. Most of these mutations have been established in *S. typhimurium*. Infection with *S. typhimurium* causes typhoid fever-like symptoms in mice and murine salmonellosis is a well accepted model for human typhoid. Such vaccine strains contain mutations in proteins causing deficiencies in the biosynthesis of aromatic amino acids (e.g. aroA, aroC and aroD) or purines (e.g. purA and purE), in the adenylate cyclase gene (cya) or the cAMP receptor protein (crp), or possess mutations affecting the regulation of several virulence factors (phoP and phoQ). However, although a number of attenuated mutants have been generated and characterised in the mouse model with regard to their role in virulence, relatively few of them have been evaluated as vaccine carriers in humans. The reason for this is that the mutants used are either still too virulent, causing severe side effects in the host, or are not sufficiently immunogenic, due to inadequate presentation to the immune system, which requires a critical level of persistence of the vaccine strain in the host for activation.

A recent study revealed that the inactivation of individual *Salmonella* genes causing attenuation of virulence directly influences the quality of an immune response against the vaccine carrier strain. From this finding, one can conclude that it might be possible to generate a variety of differently attenuated *Salmonella* vaccine strains, each with a unique profile and individual capabilities for eliciting an immune response. With this repertoire, it might be possible to tailor a vaccine strain according to specific immunological demands. As a logical consequence, one should also be able to develop attenuated *Salmonella* vaccine strains for either prophylactic or therapeutic purposes. However, the means by which such a representative repertoire of *Salmonella* vaccine strains is obtained and further developed into an efficacious vaccine must be determined.

In cases in which a *Salmonella* vaccine strain is used as a carrier for heterologous antigens, additional parameters must be considered. Traditionally, heterologous antigens have been expressed in the *Salmonella* cytosol. In the mouse typhoid model, it was demonstrated that, when heterologous antigens are expressed at high levels in the *Salmonella* cytosol, inclusion bodies are often formed, which negatively influence the immunogenicity of the recombinant live vaccine strain in the vaccinated host. It was concluded that the formation of inclusion bodies might be fatal for the bacterium, further decreasing vitality and increasing attenuation, and thus lowering the immunogenicity. Indeed, specific expression systems that circumvent this secondary attenuation principle, e.g. the 2-phase regulated expression system, can improve the efficacy of the presentation of heterologous antigens to the host immune system.

It has been demonstrated that secretion of antigens by live attenuated *Salmonella* can be superior to intracellular expression of the same antigens both in eliciting protective T-cell responses (Hess et al., 1996; Hess et al., 1997b) and in eliciting elevated levels of antigen-specific antibody (Gentschev et al., 1998). Efficiencies of HlyA-directed secretion systems, however, are usually low (30% or less of total synthesized antigen) (Hess et al., 1997a; Hess et al., 1996), and the system seems to be problematical in *S. typhi* for export of heterologous antigens (Orr et al., 1999).

A similar immunological profile is induced by the two type III secretion systems, which are encoded by the *Salmonella* Pathogenicity Islands 1 and 2. These complex secretion machineries naturally deliver "effector proteins" into the cytosol of the infected host cell, supporting the survival of the pathogen within the host cell. By means of gene technology, the "effector proteins" can be converted into carrier vehicles for epitopes from heterologous antigens. Such chimeric "effector proteins" lose their virulent character but retain their secretory character. Consequently, the chimeric "effector protein" is delivered into the lumen of the host cell, where it is appropriately processed and subsequently stimulates the cytotoxic branch of the host immune system.

The most abundant protein secreted by *Salmonella* is flagellin (see, for example (Hueck et al., 1995)). In *S. typhimurium*, flagellin occurs in two allelic variants, FliC or FljB, while *S. typhi* carries only the FliC gene. Flagellin is secreted via the flagellum-specific export (FEX) pathway (Macnab, 1996; Minamino and Macnab, 1999), which is homologous to the type III secretion pathway (Hueck, 1998). It also has been shown recently that the FEX pathway functions in secretion of non-flagella proteins in *Yersinia enterocolitica* (Young et al., 1999). Like in type III secretion, the amino terminus of FliC directs secretion. Thus, a truncated version of 183 amino terminal amino acids of FliC (full length is 495 aa) is constitutively secreted in large amounts (Kuwajima et al., 1989). In analogy to type III secretion, the effective secretion signal in FliC may be as short as 10 to 20 amino acids. The FliC or FljB secretion signals can potentially be used to secrete large quantities of a heterologous protein which can serve as an antigen in heterologous vaccination. It is likely that the amount of secreted antigen can be even further increased in regulatory mutants affecting the expression of flagella biosynthesis genes (Macnab, 1996; Schmitt et al., 1996) or by using recombinant promoters to drive expression of the flagellin gene.

Secretion via the FEX pathway can allow the delivery of large amounts of antigen into the *Salmonella*-containing phagosome for early and efficient antigen processing and antigen presentation to the host immune system. Especially the MHC class II dependent branch of the host immune system is strongly supported by the FEX pathway mediated antigen delivery.

The other known export machineries and surface display systems of Gram-negative bacteria can be also applied to bacterial vaccine carriers such as *Salmonella*. In general, a good immune response is achieved when the antigen is presented on the *Salmonella* surface. However, as little is known about the immunological consequence of such antigen presentation systems, further experimental work is needed.

Additional immuno-modulatory effects can be achieved when environmentally regulated *Salmonella* promoters are used for the expression of heterologous antigens. For instance, the expression of a heterologous gene in a *Salmonella* carrier strain under control of the in vivo regulated stress response htrA gene promoter resulted in a stronger immune response than was obtained when under control of the anaerobically inducible promoter of the nirB gene.

According to a first aspect, the present invention relates to an isolated nucleic acid molecule comprising a nucleic acid sequence comprising at least 50 nucleotides a) of the nucleic acid sequence of one of FIGS. 21A, B, b) of an allele of the nucleic acid sequence of one of FIGS. 21A, B or c) of a nucleic acid sequence which under stringent conditions hybridizes with the nucleic acid sequence of one of FIGS. 21A, B.

Stringent hybridization conditions in the sense of the present invention are defined as those described by Sambrook et al., Molecular Cloning, A Laboratory Manual, Cold Spring Harbor Laboratory Press (1989), 1.101-1.104. According to this, hybridization under stringent conditions means that a positive hybridization signal is still observed after washing for 1 hour with 1×SSC buffer and 0.1% SDS at 55° C., preferably at 62° C. and most preferably at 68° C., in particular, for 1 hour in 0.2×SSC buffer and 0.1% SDS at 55° C., preferably at 62° C. and most preferably at 68° C.

In particular, the present invention relates to such a nucleic acid molecule which comprises the complete coding regions or parts thereof of the genes ssaD, ssaE, sseA, sseB, sscA, sseC, sseD, sseE, sscB, sseF, sseG, ssaG, ssaH, ssaE, ssaJ, ssrA and ssrB. The invention pertains also to such nucleic acids, wherein at least one coding region of said genes is functionally deleted.

In one embodiment, the nucleic acid molecule comprises an insertion cassette to facilitate the insertion of a heterologous nucleic acid molecule by transposon or phage mediated mechanism.

Furthermore, said nucleic acid molecules can comprise at least one heterologous nucleic acid molecule. In this case the heterologous nucleic acid molecule may be fused 5' or 3', inserted or deletion-inserted to the inventive nucleic acid molecule. By the term "deletion-inserted" it is understood that the insertion of the heterologous nucleic acid molecule is associated with a concurrent deletion of parts of the inventive nucleic acid molecule. Preferably, the nucleic acid molecule is inserted or deletion-inserted and in one preferred embodiment the heterologous nucleic acid molecule is flanked 5' and 3' by sequences of the nucleic acid molecule according to the invention, wherein each of said sequences has a length of at least 50 nucleotides, preferably 200-250 nucleotides.

Preferred, the heterologous nucleic acid molecule codes for a polypeptide or peptide, more preferred it codes for a bacterial or viral antigen or a homologue thereof or for a tumor antigen.

It is preferred that the nucleic acid molecule also comprises at least one gene expression cassette to allow for efficient expression of the heterologous nucleic acid molecule. Such gene expression cassette usually comprises elements such as promoters and/or enhancers which improve the expression of the heterologous nucleic molecule acids. Usually, such gene expression cassette comprises elements for the termination of transcription. The presence of transcription terminators, however, may be not preferred in cases where the heterologous nucleic acid molecule is to be transcribed together with other genes into a cistronic mRNA.

The nucleic acid molecule, one or more selective marker cassettes and one or more transactivator cassettes and optionally invertase cassettes for allowing the expression of the heterologous nucleic acid molecules in a one-phase system or a two-phase system. Furthermore, sequences may be present which code for a polypeptide or peptide-targeting domain and, thus, allow for the targeting of the expression product of the heterologous nucleic acid molecule to a predetermined cell compartment such as cytosol, periplasma or outer membrane, or the secretion of said expression product, or which code for an immunostimulatory domain.

According to another aspect, the invention relates to a recombinant vector which comprises the nucleic acid molecule described above. Another aspect of the invention pertains to a cell comprising a modified inventive nucleic acid molecule as described above by insertion of a heterologous sequence or the recombinant vector. The cell may be a prokaryotic cell such as a gram-negative cell, e.g. a *Salmonella* cell, or it can be a eukaryotic cell such as a mammalian cell, e.g. a human cell, and, in particular, a macrophage.

According to a still further aspect, the present invention relates to a peptide or polypeptide comprising a peptide sequence comprising at least 20 amino acids a) of the sequence of one of FIGS. 23A-Q, or b) of a sequence which is 60%, preferred 65% and more preferred 70% homologous to the sequence of one of FIGS. 23A-Q. In particular, the invention relates to a polypeptide comprising the sequence a) of one of FIGS. 23A-Q, or b) which is 60%, preferred 65% and more preferred 70% homologous to the sequence of one of FIGS. 23A-Q.

Percent (%) homology are determined according to the following equation:

$$H = \frac{n}{L} \times 100$$

wherein H are % homology, L is the length of the basic sequence and n is the number of nucleotide or amino acid differences of a sequence to the given basic sequence.

Another aspect of the present invention relates to an antibody which is directed against an epitope which is comprised of the aforementioned peptide or polypeptide. The antibody may be polyclonal or monoclonal. Methods for producing such an antibody are known to the person skilled in the art.

A further aspect of the present invention relates to a fusion protein comprising the polypeptide according to any one of the claims 17 and 18 having inserted or deletion-inserted or being fused C- or NH$_2$-terminally with at least one heterologous polypeptide. The heterologous polypeptide preferred is an antigen, more preferred a bacterial or viral antigen or a tumor antigen.

The present invention furthermore provides instructions for the development of a variety of potential live *Salmonella* vaccine strains with different attenuation levels, which subsequently serve as platforms for the development of recombinant live *Salmonella* vaccine carrier strains that express antigens from heterologous pathogens, thus serving as multivalent vaccines. Such recombinant live *Salmonella* vaccine carriers are equipped with modules comprising variable gene cassettes that regulate the expression of heterologous antigens in *Salmonella* and determine presentation of the heterologous antigens to the host immune system. By combinations of both systems, differently attenuated live *Salmonella* vaccine strains and variable gene cassettes, a variety of recombinant live vaccine carrier strains can be generated that have, due to their variable immunogenic characteristics, a broad application spectrum for both prophylactic and therapeutic use. The basic attenuation principle originates from novel mutations in the *Salmonella* Pathogenicity Island 2 (SPI2) gene locus. Additional mutations, which can be used either alone or in combination with mutations in sse or SPI-2 genes or in combination with the aroA mutation for optimal attenuation of live vaccine carrier strains, have been reported recently (Heithoff et al., 1999; Valentine et al., 1998). By combination of the individual mutations in the SPI-2 gene locus with each other and with other known attenuating gene mutations, such as aroA, etc., a broad repertoire of attenuation and immunogenicity can be achieved. Different expression cassettes can be introduced on these platforms, allowing further modulation of the immune response directed against the heterologous antigens. Finally, a library of individual recombinant live *Salmonella* vaccine carrier strains is generated, covering a broad spectrum of immuno-stimulatory potential, from which a genuine live vaccine strain can be tailored for the optimal protection or treatment of humans and/or animals against specific pathogens or disease.

Thus, in a further aspect, the present invention is an attenuated gram-negative cell comprising the SPI2 gene locus, wherein at least one gene of the SPI2 locus is inactivated, wherein said inactivation results in an attenuation/reduction of virulence compared to the wild type of said cell.

Genes present in the *Salmonella* pathogenicity island 2 that encode for a variety of proteins involved in type III secretion and those that are required for systemic spread and survival within phagocytic cells are ideal candidates for attenuation of pathogenic *Salmonella* ssp.

Several gram-negative bacterial pathogens secrete certain virulence proteins via specialised type III secretion systems. Virulence factors enable pathogenic bacteria to colonise a niche in the host despite specific attacks of the immune system. The type III secretion systems comprise a large number of proteins required to transfer specific effector proteins into eukaryotic host cells in a contact-dependent manner, thus they have also been called contact-dependent secretory systems. Although several components of the secretion system apparatus show evolutionary and functional conservation across bacterial species, the effector proteins are less well conserved and have different functions. The *Yersinia* effectors YpkA and YopH have threoninelserine kinase and tyrosine phosphatase activities, respectively. The actions of these and other Yops inhibit bacterial phagocytosis by host cells, which is thought to enable extracellular bacterial proliferation. The *Shigella* Ipa proteins, secreted by the mxi/spa type III secretion system, promote entry of this bacterium into epithelial cells. EspA, EspB and EspD, encoded by the locus of enterocyte effacement (LEE) of enteropathogenic *Escherichia coli* (EPEC) are required for translocation of proteins that cause cytoskeletal rearrangements and the formation of pedestal-like structures on the host cell surface.

For the purposes of the present invention an "gram-negative cell comprising the SPI2 gene locus" is a cell having a gene locus that harbors genes required for the systemic spread and survival within phagocytic cells and, thus, is a homologue or functional equivalent of the SPI2 locus from *Salmonella*. Preferred, the inventive attenuated gram-negative cell is an Enterobactericae cell, more preferred, a *Salmonella* cell, a *Shigella* cell or a *Vibrio* cell. In general, cells having a broad host range are preferred. Typical hosts are mammals, e.g. man, and birds, e.g. chicken. *Salmonella* cells are more preferred, and particularly preferred is *Salmonella* serotype *typhimurium* Definitive Type 104 (DT 104).

*Salmonella typhimurium* is unusual in that it contains two type III secretion systems for virulence determinants. The first controls bacterial invasion of epithelial cells, and is encoded by genes within a 40 kb pathogenicity island (SPI1). The other is encoded by genes within a second 40 kb pathogenicity island (SPI2) and is required for systemic growth of this pathogen within its host. The genes located on pathogenicity island SPI1 are mainly responsible for early steps of the infection process, the invasion of non-phagocytic host cells by the bacterium. For most of the SPI1 genes, mutations result in a reduced invasiveness in vitro. However, mutants that are defective in invasion are not necessarily avirulent; studies in mice demonstrated that, while these mutations in SPI1 genes significantly reduced virulence upon delivery by the oral route, they had no influence on virulence following an intraperitoneal route of infection. Taken together, these results indicate that mutations in genes within the pathogenicity island SPI1 do not abolish systemic infection and are therefore not very useful for the development of a safe, attenuated *Salmonella* carrier strain. In comparison, virulence studies of SPI2 mutants have shown them to be attenuated by at least five orders of magnitude compared with the wild-type strain after both oral and intraperitoneal inoculation of mice.

Many of the genes encoding components of the SPI2 secretion system are located in a 25 kb segment of SPI2. SPI2 contains genes for a type III secretion apparatus (ssa) and a two component regulatory system (ssr), as well as candidate genes for a set of secreted effectors (sse) and their specific chaperones (ssc). On the basis of similarities with genes present in other bacterial pathogens, the first 13 genes within the ssaK/U operon and ssaJ encode components of the secretion system apparatus. A number of additional genes, including ssaC (orf 11 in Shea et al., 1996; spiA in Ochman et al., 1996) and ssrA (orf 12 in Shea et al., 1996; spiR in Ochman et al., 1996), which encode a secretion system apparatus protein and a two component regulatory protein, respectively, are found in a region approximately 8 kb from ssaJ.

Preferably, the inventive attenuated gram-negative cell has inactivated at least one gene selected from effector (sse) gene secretion apparatus (ssa) genes, chaperon (ssc) genes and regulation (ssr) genes. More preferably, the at least one inactivated gene is an sse, ssc and/or ssr gene, even more preferred is an sse and/or ssc gene.

As far as the sse genes are affected by the inactivation, the inactivated gene is preferably sseC, sseD, sseE or a combination thereof. As far as the ssr genes are affected by the inactivation, preferably at least ssrB is inactivated. As far as the ssc genes are affected by the inactivation, preferably at least sscB is inactivated.

The inactivation of said gene of the SPI2 locus (or functional homologue thereof in cells other than *Salmonella*) is effected by a mutation which may comprise deletion. Preferred are deletions of at least six nucleotides, and more preferred is a deletion of the partial and, in particular, the complete coding sequence for said gene. The mutation may also comprise the insertion of a heterologous nucleic acid molecule into said gene to be inactivated or a combination of deletion and insertion.

Pathogenic *Salmonella* ssp. serve a basis for the construction of a panel of different live *Salmonella* vaccine prototypes generated by gradual attenuations accomplished through the introduction of defined SPI2 gene locus mutations. Each resulting individual live *Salmonella* vaccine prototype is further transformed into a multivalent recombinant vaccine by the introduction of exchangeable DNA modules carrying (1) genetically engineered genes from heterologous pathogens and (2) adequate expression systems executing efficacious antigen presentation to the host immune system. In concert, these features elicit a specific immune response that either protects vaccinated hosts against subsequently invading *Salmonella* and/or other pathogens (prophylactic vaccination) or eliminates persistant pathogens, such as *Helicobacter pylori* (therapeutic vaccination).

Pathogenic *Salmonella* ssp. are gradually attenuated by mutations in individual virulence genes that are part of the SPI2 gene locus, e.g. an sse gene coding for an effector protein, such as sseC, ssed or sseE, or an ssc gene, such as sscB, coding for a chaperone, or an ssr gene, such as ssrB, coding for a regulator. Individual mutation of each of these genes leads to a unique individual grade of attenuation, which, in turn, effects a characteristic immune response at the mucosal, humoral and cellular levels. The individual grade of attenuation can be moderately increased by combinations of at least two gene mutations within the SPI2 gene locus or by combination with a mutation in another *Salmonella* gene known to attenuate virulence, e.g. an aro gene, such as aroA. A stronger grade of attenuation is achieved by mutation of a virulence gene that is part of a polycistronic gene cluster encoding several virulence factors, such as the transcriptional unit comprising the sseC, sseD, sseE and sscB genes, such that the mutation exerts a polar effect, disrupting expression of the following genes. The grade of attenuation may directly depend on the number of virulence genes that are affected by the polar mutation as well as their individual characteristics. Finally, the strongest attenuation is achieved when regulatory genes, such as ssrB, are mutated. Again, each mode of attenuation of a *Salmonella* ssp. leads to the generation of a live *Salmonella* vaccine strain that evokes an immune response at the mucosal, humoral and cellular levels that is characteristic for the type and/or combination of attenuating mutations present in that strain. The panel of differently attenuated live *Salmonella* vaccine strains that is generated represents a pool of potential carrier strains from which that carrier can be selected that provokes the most efficacious immune response for either the prevention or eradiction of disease in conjunction with the heterologous antigens that are expressed.

Mutations leading to attenuation of the indicated *Salmonella* virulence genes are preferentially introduced by recombinant DNA technology as defined deletions that either completely delete the selected virulence gene or result in a truncated gene encoding an inactive virulence factor. In both cases, the mutation involves a single gene and does not affect expression of neighbouring genes (non-polar mutation). An insertional mutation in one of the indicated virulence genes is preferred when the selected gene is part of a polycistronic virulence gene cluster and all of the following virulence genes are included in the attenuation process (polar mutation). Insertional mutations with non-polar effects are in general restricted to genes that are either singly transcribed or are localised at the end of a polycistronic cluster, such as ssrB. However, other attenuating mutations can arise spontaneously, by chemical, energy or other forms of physical mutagenesis or as a result of mating or other forms of genetic exchange.

Thus, the mutation which results in the preparation of the inventive attenuated gram-negative cell may be a polar or non-polar mutation. Furthermore, the grade of attenuation may be modified by inactivating an additional gene outside of the SPI2 locus, for example, another virulence gene or a gene that is involved in the biosynthesis of a metabolite or a precursor thereof such as the aro genes, in particular, aroA, or any other suitable gene such as superoxide dismutase (SOD).

The attenuated cell according to the invention may furthermore comprise elements which facilitate the detection of said cell and/or the expression of an inserted heterologous nucleic acid molecule. An example of an element which facilitates the detection of the attenuated cell is a selective marker cassette, in particular, a selective marker cassette which is capable of conferring antibiotic resistance to the cell. In one embodiment, the selective marker cassette confers an antibotic resistance for an antibiotic which is not used for therapy in a mammal. Examples of elements which facilitate the expression of a heterologous nucleic acid molecule are a gene expression cassette which may comprise one or more promoter, enhancer, optionally transcription terminator or a combination thereof, a transactivator cassette, an invertase cassette for 1-phase or 2-phase expression of a heterologous nucleic acid. An example of an element which facilitates the insertion of a heterologous nucleic acid molecule is an insertion cassette.

In another aspect, the invention provides a carrier for the presentation of an antigen to a host, which carrier is an attenuated gram-negative cell according to any one of the claims 22 to 49, wherein said cell comprises at least one heterologous nucleic acid molecule comprising a nucleic acid sequence coding for said antigen, wherein said cell is capable of expressing said nucleid acid molecule or capable of causing the expression of said nucleic acid molecule in a target cell.

Preferably, said nucleic acid molecules comprises a nucleic acid sequence coding for a bacterial or viral antigen or for a tumor antigen. Examples of bacterial antigens are antigens from *Helicobacter pylori, Chlamydia pneumoniae, Borrelia burgdorferi* and Nanobacteria. Examples of viral antigens are antigens from Hepatitis virus, e.g. Hepatitis B and C, human papilloma virus and Herpes virus. The heterologous nucleic acid molecule may comprise a nucleic acid sequence which codes for at least one polypeptide or peptide-targeting domain and/or immunostimulatory domain. Thus, the expression product of said heterologous nucleic acid molecule may be targeted specifically to predetermined compartments such as periplasma, outer membrane, etc. The heterologous nucleic acid molecule may code for a fusion protein.

According to one embodiment the heterologous nucleic acid molecule is inserted into the SPI2 locus, preferred, into an sse gene and, more preferred, into sseC, sseD and/or sseE, in particular, sseC.

The insertion may be a polar insertion or an unpolar insertion. Generally, the introduction of an unpolar insertion is preferred, since it allows for the expression of the remaining genes of a polycistronic gene cluster, which can be used for the generation of carriers having different grades of attenuation.

Attenuated live *Salmonella* vaccines are used as carriers for specific antigens from heterologous pathogens, e.g. *Helicobacter*, etc., thus acting as a multivalent vaccine. The heterologous antigens are provided by a gene expression cassette (GEC) that is inserted by genetic engineering into the genome of an attenuated *Salmonella* strain. Preferentially, insertion of the gene expression cassette is targeted to one of the indicated virulence genes, thereby causing an insertional mutation as described in previous paragraph. In another application form, expression of the heterologous genes in the gene expression cassette is regulated by trans-acting factors encoded by a trans-activator cassette (TC) or an invertase cassette performing a 2-phase variable expression mode. Preferentially, the insertion of the trans-activator cassette is targeted to a second chosen virulence gene, which is then inactivated. Alternatively, the gene expression cassette or the trans-activator cassette or the invertase cassette can be introduced into the *Salmonella* genome by transposon-mediated insertion, which has no attenuation effect.

The principles of genetic engineering are required to generate either deletion or insertional mutations in *Salmonella* virulence genes. Generally, a suicide plasmid carrying a mutated virulence gene cassette containing a selective marker cassette (SMC) either alone or in combination with a gene expression cassette or a trans-activator cassette or the invertase cassette is introduced into the receptor *Salmonella* strain by conjugation. The original virulence gene is replaced with the mutated virulence gene cassette via homologous recombination, and the suicide plasmid, unable to replicate in the *Salmonella* receptor strain, becomes rapidly depleted. Successfully recombined *Salmonella* can be selected based on properties (such as, but not limited to, antibiotic resistance) conferred by the product of the gene(s) within the selective marker cassette. The mutated virulence gene cassette comprises DNA sequences that are homologous to the genome of the receptor *Salmonella* strain where the original virulence gene is localised. In the case where the original virulence gene is to be completely deleted, only those genomic DNA sequences that border the original virulence gene (indicated as flanking regions) are included in the mutated virulence gene cassette. The general architecture of a mutated virulence gene cassette includes at each end a DNA sequence of at least 50 nucleotides, ideally 200-250 nucleotides, that is homologous to the genome segment where the original virulence gene is localised. These DNA sequences flank a selective marker cassette and the other cassettes, such as the gene expression cassette (GEC) or the trans-activator cassette (TC) or the invertase cassette. As indicated above, these cassettes are used to generate insertional mutations which disrupt original gene expression. For in-frame deletions, a selective marker cassette is preferentially used.

The selective marker cassette (SMC) principally consists of a gene mediating resistance to an antibioticum which is able to inactivate the receptor *Salmonella* strain but which is actually not used in the treatment of *Salmonellosis*. Alternatively, another selectable marker can be used. The selective marker cassette is inserted in-frame in the targeted virulence gene and, consequently, the expression of the marker gene is under the control of the virulence gene promoter. Alternatively, the cassette is inserted within a polycistronic transcriptional unit, in which case the marker gene is under control of the promoter for this unit. In another application, the selective marker gene is under control of its own promoter; in this case a transcriptional terminator is included downstream of the gene. The selective marker is needed to indicate the successful insertion of the mutated virulence gene cassette into the genome of the receptor *Salmonella* strain. Furthermore, the antibiotic resistance marker is needed to facilitate the preclinical immunological assessment of the various attenuated *Salmonella* strains. In another application form, the selective marker is flanked by direct repeats, which, in the absence of selective pressure, lead to the recombinatorial excision of the selective marker cassette from the genome, leaving the short sequence of the direct repeat. Alternatively, the selective marker cassette can be completely removed by recombinant DNA technology. Firstly, the selective marker cassette is removed by adequate restriction endonuclease from the original mutated virulence gene cassette on the suicide plasmid leaving the flanking region sequences which are homologous to the *Salmonella* genome. The suicide plasmid is then transfered into the attenuated receptor *Salmonella* strain by conjugation where the SMC-depleted mutated virulence gene cassette replaces the SMC-carrying mutated virulence gene cassette by recombination. After removal of the selective marker, the attenuated *Salmonella* strain is free for the application in humans. Transcriptional terminator sequences are generally included in the cassettes when polar mutations are established.

The gene expression cassette (GEC) comprises elements that allow, facilitate or improve the expression of a gene. In a functional mode the gene expression cassette additionally comprises one or more gene expression units derived from either complete genes from a heterologous source or fragments thereof, with a minimal size of an epitope. Multiple gene expression units are preferentially organised as a concatemeric structure. The genes or gene fragments are further genetically engineered, such that the resulting proteins or fusion proteins are expressed in the cytosol, in the periplasm, surface displayed or secreted. Furthermore the genes or gene fragments can be fused with DNA sequences encoding immunologically reactive protein portions, e.g. cytokines or attenuated bacterial toxins. The genes or gene fragments are either controlled in a one-phase mode from a promoter within the gene expression cassette or in a 2-phase mode or indirectly by a trans-activator cassette (TC). In the one-phase mode the promoter is preferentially a *Salmonella* promoter that is activated, i.e. induced, by environmental signals but also constitutive promoters of different strength can be used. In the 2-phase mode, the expression of the gene cassette is controlled by an invertase that derived from an invertase cassette. The invertase catalyses the inversion of a DNA segment comprising the gene cassette. The DNA segment is flanked on each end by an inverted repeat which is the specific substrate for the invertase finally causing two orientation of the gene cassette with respect to the gene expression cassette promoter. In the ON-orientation the gene cassette is correctly placed allowing transcription of the gene cassette. In OFF, the orientation of the gene cassette is incorrect and no transcription occurs. The invertase cassette comprises of an invertase that is controlled by a constitutive promoter or a *Salmonella* promoter induced or derepressed by environmental signals.

Heterologous antigens encoded within the gene expression cassette can be expressed under the control of a promoter, e.g. a tissue-specific promoter, which may be constitutive or inducible. The expression can be activated in a target cell, whereby a signal is transmitted from the target cell to the interior of the *Salmonella* cell, which signal induces the expression. The target cell, for example, can be a macrophage. The expression product may comprise a targeting domain or immunostimulatory domain, e.g. in the form of a fusion protein. The heterologous protein itself also may be a fusion protein. The heterologous antigens can be optionally expressed as cytosolic, periplasmic, surface displayed or secretory proteins or fusion proteins in order to achieve an efficacious immune response. The antigen encoding sequences may be fused to accessory sequences that direct the proteins to the periplasm or outer membrane of the *Salmonella* cell or into the extracellular milieu. If the heterologous polypeptides are secreted, secretion can occur using a type III secretion system. Secretion by the SPI2 type III secretion system is suitable. Proteins that are destined for the cytosolic compartment of the *Salmonella* do not need accessory sequences, in this case, naturally occurring accessory sequences must be removed from the genes encoding such antigens.

The accessory sequences for the periplasmatic compartment of *Salmonella* comprise a DNA sequence deduced from the amino-terminally localised signal peptide of a heterologous protein naturally translocated via the general secretion pathway, e.g. CtxA, etc.

The accessory sequences for the outer membrane compartment of *Salmonella* preferentially comprise DNA sequences deduced from the functionally relevant portions of a type IV secretory (autotransporter) protein, e.g. AIDA or IgA protease. The appropriate fusion protein contains an amino-terminally localised signal peptide and, at the carboxy-terminus, a β-barrel shaped trans-membrane domain to which the foreign passenger protein is coupled via a spacer that anchors the passenger protein to the bacterial surface.

The accessory sequences for secretion into the extracellular milieu comprise DNA sequences deduced from proteins naturally secreted by the type III secretion system. In a generally functional fusion protein, the heterologous antigen is fused in the centre of a protein naturally secreted by the type III pathway or at the carboxy-terminal end of the respective protein.

The transactivator cassettes (TC) provide activators which generally improve expression of the heterologous antigens encoded by the various gene expression cassettes. Such activators either directly (RNA polymerase) or indirectly (transcriptional activator) act on the transcription level in a highly specific order. Preferentially, the expression of such activators are controlled by *Salmonella* promoters which are induced in vivo by environmental signals. In another application form the synthesis of the activator within the transactivator cassette is regulated in a 2-phase mode. The invertase expressed by the invertase cassette places the activator encoding DNA fragment in two orientations with respect to the transcriptional promoter. In the ON-orientation the activator gene is in the correct transcriptional order. In the OFF-modus the activator is incorrectly orientated and no expression occurs.

In the simple system, the gene product of the transactivator cassette exerts its effect directly on the promoter present in the gene expression cassette, directly activating or de-repressing expression of the heterologous gene. In the complex system, activation of the promoter in the heterologous gene expression cassette is dependent upon two or more interacting factors, at least one of which (encoded in the transactivator cassette) may be regulated by external signals. Further complexity is found in cascade systems, in which the external signal does not directly exert its effect on the transactivator cassette, but rather through a multi-step process, or in which the gene product of the transactivator cassette does not directly exert its effect on the heterologous gene expression cassette, but rather through a multi-step process.

According to still another aspect, the present invention is an attenuated gram-negative cell comprising the SPI2 gene locus, characterized by a lack of at least one SPI2 polypeptide, wherein said lack results in an attenuation/reduction of virulence compared to the wild type of said cell. Preferably, said missing SPI2 polypeptide is one or more effector polypeptide, secretion apparatus polypeptide, chaperon polypeptide or regulatory polypeptide. Furthermore, said attenuated cell may be a carrier which then is characterized by the presence of at least one heterologous peptide or polypeptide having immunogenic properties.

A further aspect of the present invention is a pharmaceutical composition which comprises as an active agent an immunologically protective living vaccine which is an attenuated gram-negative cell or carrier according to the invention. The pharmaceutical composition will comprise additives such as pharmaceutically acceptable diluents, carriers and/or adjuvants. These additives are known to the person skilled in the art. Usually, the composition will administered to a patient via a mucosa surface or via or via the parenteral route.

Further aspects of the present invention include a method for the preparation of a living vaccine, which comprises providing a living gram-negative cell comprising the SPI2 locus and inactivating at least one gene of the SPI2 locus to obtain an attenuated gram-negative cell of the invention, and optionally inserting at least one heterologous nucleic acid molecule coding for an antigen to obtain a carrier according to the invention. A further aspect pertains to a method for the preparation of a living vaccine composition comprising formulating an attenuated cell or a carrier according to the invention in a pharmaceutically effective amount together with pharmaceutically acceptable diluents, carriers and/or adjuvants. A further aspect of the invention relates to a method for the detection of an attenuated cell or a carrier according to the invention, comprising providing a sample containing said cell and detecting a specific property not present in a wild type cell. Methods for detecting a specific property of the attenuated cell or carrier, which is not present in wild type, are known to the person skilled in the art. For example, if this specific property of the attenuated cell comprises a deletion of one or more parts of the SPI2 locus, then the presence of said cell can be detected by providing a pair of specific primers which are complementary to sequences flanking this deletion and amplifying a fragment of specific length using amplification methods such as PCR. Methods for detecting the presence of an inventive carrier comprise PCR amplification of an inserted fragment or a fragment spanning the insertion boundary, hybridization methods or the detection of the heterologous expression product or of a selective marker.

A further aspect of the invention is a method for establishing a library of attenuated gram-negative cells or carriers, respectively, according to the invention. The method comprises the preparation of attenuated recombinant vaccine strains, each having a different mutation in the SPI2 locus which results in a different degree of attenuation. The pathogenicity or virulence potential of said strains can then be determined using known methods such as determination of the LD50, and the strains are rated according to the different pathogenicities, i.e. a different grade of attenuation. Preferably, the method comprises also the determination of other parameters of interest such as the immunogenicity or the immuno-stimulatory response raised in a host. Methods for determining the immuno-stimulatory potential are known to the person skilled in the art and some of them are described in Example 6. Preferably, the immuno-stimulatory potential of the inventive attenuated cells or carriers is determined at humoral, cellular and/or mucosal level. In this way it is possible to establish a library of attenuated cells or carriers having a predetermined attenuation degree and predetermined immuno-stimulatory properties. Thus, for each application, the strain having the desired properties can be selected specifically. For example, it will be usually preferred to select a strong attenuated strain for administration to patients which receive immunosuppressive drugs.

In a similar way, the invention allows for the establishment of libraries of attenuated carriers having defined pathogenicities and optionally immunogenicities. The establishment of a carrier library additionally will comprise the determination of the antigen presentation of said carrier strains to a host, whereby a panel of different carriers strains will be obtained having defined properties with respect to pathogenicity, immuno-stimulatory potential of carrier antigens and immuno-stimulatory potential of the heterologous antigen.

Another aspect of the invention is the use of the attenuated cell or carrier according to the invention for the preparation of a drug for the preventive or therapeutic treatment of an acute or chronic disease caused essentially by a bacterium or virus. For example, for the prevention or treatment of a *Salmonella* infection one will administer an attenuated *Salmonella* cell to raise the immune response of an affected patient. Similarly, a carrier according to the invention may be used for the preparation of a drug for the preventive or therapeutic treatment of a tumor.

The individual immuno-protective potential of each of the established recombinant *Salmonella* vaccine strains is determined in a mouse model using a pathogenic *Salmonella typhimurium* as the challenge strain.

Determination of the virulence potential of the recombinant *Salmonella* vaccine strain: (1) Competitive index or LD50; (2) Systemic prevalence in blood, liver and spleen strictly excluded.

Determination of the immuno-stimulatory potential of the carrier strain with a cytosolically expressed heterologous test antigen: (1) Single oral immunisation and subsequent evaluation of the short- and long-term immune response: (a) analysis of the humoral immune response profile, (b) analysis of the mucosal immune response profile, (c) analysis of the cellular immune response profile; (2) Multiple oral immunisations and subsequent evaluation of the short- and long-term immune response: (a) analysis of the humoral immune response profile, (b) analysis of the mucosal immune response profile, (c) analysis of the cellular immune response profile.

Determination of the immuno-stimulatory potential of the carrier strain for the delivery of heterologous DNA (DNA vaccination).

Preferentially, the *Salmonella* acceptor strain has a broad host range, exhibiting significant pathogenicity in both animals and humans. Ideally, this is a *Salmonella* strain that is strongly pathogenic for mice, such as *S. typhimurium*. After successful development of the recombinant *Salmonella* vaccine strain, the strain is directly applicable for use in both animals and humans. If such an ideal *Salmonella* acceptor strain is not satisfactory for the respective host, other host-specific *Salmonella* must be selected, such as *S. typhi* for humans.

Other aspects of the invention relate to the use of a nucleic acid molecule as shown in FIG. 21A or B or one of the FIGS. 22A-Q, optionally modified as described hereinabove or of a vector as described hereinabove for the preparation of an attenuated cell, a living vaccine or a carrier for the presentation of an antigen to a host and to the use of the *Salmonella* SPI2 locus for the preparation of an attenuated cell, a living vaccine or preferably a carrier for the presentation of an antigen to a host. In this context the term "*Salmonella* SPI2 locus" refers to any nucleic acid sequence, coding or not coding, and to the expression product of coding sequences.

A still further aspect of the present invention is the use of a virulence gene locus of a gram-negative cell for the preparation of a carrier for the presentation of an antigen to a host.

Another aspect of the invention relates to a method of therapeutically or prophylactically vaccinating an animal, e.g. a mammal, e.g. a human, against a chronic disease caused primarily by a infectious organism including preparation and administering a vaccine of the invention.

Still another aspect of the present invention is an isolated nucleic acid molecule comprising a nucleic acid of at least 100 nucleotides a) of the nucleic acid sequence of one of FIGS. 24A, B, b) of a nucleic acid sequence which under stringent conditions hybridizes with the nucleic acid sequence of one of FIGS. 24A, B.

In particular, said aspect relates to said nucleic acid molecule which is capable of inducing the expression of a nucleic acid sequence conding for a peptide or polypeptide operatively linked to said nucleic acid molecule.

The in vivo inducible promoter Pivi comprises a DNA fragment which carries sequences for an operator and a transcriptional promoter. Such in vivo inducible promoter can be identified by applying an adequate reporter gene approach. Two of such in vivo inducible promoters have been identified within the SPI2 locus which initiate expression of the ssaB-CDE operon (promoter A2) and the sseABsscAsseCDEsscB-sseFG operon (promoter B), respectively. These promoters are induced by a regulative system comprising the ssrA and ssrB gene products. This regulative system is part of the SPI2 locus responsible for the activation of additional SPI2 locus genes. The regulative system is activated in macrophages by environmental signal(s) via sensor protein SsrA. The SsrB protein finally binds at a defined DNA sequence which initiates transcription through the RNA polymerase.

In an application form the DNA fragment comprising operator/promoter sequences is inserted in front of an invertase gene or an activator gene or a gene expression cassette, thereby executing an in vivo inducible expression in bacteria carrying at least the ssrA and ssrB genes or the complete SPI2 locus.

Thus, in a further aspect, the invention relates to an expression system for the in vivo inducible expression of a heterologous nucleic acid in a target cell, comprising a carrier cell for said heterologous nucleic acid, wherein said carrier cell comprises (a) a polypeptide having the amino acid sequence shown in FIG. 23P (ssrA) or a functional homologue thereof, (b) a polypeptide having the amino acid sequence shown in FIG. 23Q (ssrB) or a functional homologue thereof, and (c) the nucleic acid molecule of one of FIGS. 24A, B or a functional homologue thereof, as described above.

The target cell may be any suitable cell but preferably it is a macrophage. The carrier cell preferably is a *Salmonella* cell. The target cell may also comprise one or more of the elements described above such as selective marker cassettes, gene expression cassettes, transactivator cassettes, invertase cassettes and/or insertion cassettes. Furthermore, it may comprise a heterologous nucleic acid, in particular, the heterologous nucleic acids may be inserted into a gene expression cassette, thus rendering the GEC functional.

A still further aspect of the invention relates to the use of a nucleic acid molecule comprising at least 100 nucleotides of the nucleic acid sequence shown in one of FIGS. 24A, B or hybridizing therewith and having promoter activity, for the in vivo inducible expression of a heterologous nucleic acid molecule.

A further aspect of the present invention is the use of said nucleic acid molecule for the detection of in vivo inducible promoters.

EXPERIMENTAL PROCEDURES

The strains, material, and methods used in the type III secretion system of the *Salmonella* Pathogenicity Island 2 (SPI2) work described above are as follows:

Mice

Female BALB/c (H-$2^d$) of 6-12 weeks of age were maintained under standard conditions according to institutional guidelines. This study was approved by an ethic committee for animal use in experimental research.

Bacterial Strains, Phages and Plasmids

The bacterial strains, phages and plasmids used in this study are listed in Table 1. Unless otherwise indicated, bacteria were grown at 37° C. in Luria Bertani (LB) broth or agar, supplemented with ampicillin (50 µg/ml), kanamycin (50 µg/ml), or chloramphenicol (50 µg/ml) where appropriate. Eukaryotic cells were grown in RPMI 1640 supplemented with 10% of foetal calf serum (FCS), 100 U/ml penicillin, 50 µg/ml streptomycin, $5 \times 10^{-5}$ M 2-mercaptoethanol and 1 mM L-glutamine (GIBCO BRL; Prisley, Scotland). To achieve constitutive expression of β-gal, the plasmid pAH97 (Holtel et al., 1992) was electroporated into the carrier strains as described elsewhere (O'Callaghan and Charbit, 1990).

TABLE 1

Phages, plasmids and bacterial strains used in this work.

| Phage, plasmid or strain | Description | Reference |
|---|---|---|
| Phages | | |
| λ1 | clone from a library of *S. typhimurium* genomic DNA in λ1059 | Shea et al., 1996 |
| λ2 | clone from a library of *S. typhimurium* genomic DNA in λ1059 | Shea et al., 1996 |
| λ5 | clone from a library of *S. typhimurium* genomic DNA in λ1059 | Shea et al., 1996 |
| Plasmids | | |
| pBluescriptKS+, pBluescriptSK+ | Amp$^r$; high copy number cloning vectors | Stratagene, Heidelberg |
| pUC18 | Amp$^r$; high copy number cloning vector | Gibco-BRL, Eggenstein |
| pT7-Blue | Amp$^r$; high copy number cloning vector | Novagen, Heidelberg |
| pCVD442 | suicide vector | Donnenberg et al., 1991 |
| pACYC184 | Cm$^r$, Tet$^r$; low copy number cloning vector | Chang and Cohen, 1978 |
| pGPL01 | R6K ori, Amp$^r$; λpir-dependent suicide vector for luc fusions | Gunn and Miller, 1996 |
| pLB02 | R6K ori, Amp$^r$; λpir-dependent suicide vector for luc fusions | Gunn and Miller, 1996 |
| pGP704 | R6K ori, Amp$^r$; λpir-dependent suicide vector | Miller and Mekalanos, 1988 |
| pKAS32 | Amp$^r$; λpir-dependent suicide vector; rpsl$^s$ | Skorupski and Taylor, 1996 |
| pNQ705 | R6K ori, Cm$^r$; λpir-dependent suicide vector | Forsberg et al., 1994 |
| pSB315 | Kan$^r$, Amp$^r$ | Galán et al., 1992 |
| p1-6 | Amp$^r$, 4.8 kb PstI/BamHI fragment of λ1 in pT7-Blue | this work |
| p1-20 | 1.7 kb BamHI/HincII fragment of p1-6 in pKS+ | this work |

TABLE 1-continued

Phages, plasmids and bacterial strains used in this work.

| Phage, plasmid or strain | Description | Reference |
|---|---|---|
| p1-21 | aphT cassette in EcoRV site of p1-20 | this work |
| p1-22 | XbaI/KpnI insert of p1-21 in pKAS32 | this work |
| p2-2 | Amp$^r$; 5.7 kb BamHI fragment of λ2 in pUC18 | this work |
| p2-20 | 1.6 kb HindIII/HincII fragment of p2-2 in HindIII/SmaI-digested pKS+ | this work |
| p2-21 | aphT cassette in HincII site of p2-20 | this work |
| p2-22 | insert of p2-21 in pKAS32 | this work |
| p2-50 | 3.7 kb BamHI/KpnI fragment of p2-2 in pKS+ | this work |
| p5-2 | Amp$^r$; 5.7 kb EcoRI fragment of λ5 in pKS+ | this work |
| p5-30 | 3.0 kb PstI/EcoRI fragment of p5-2 in pUC18 | this work |
| p5-31 | aphT cassette in EcoRV site of p5-30 | this work |
| p5-33 | SphI/EcoRI insert of p5-31 in pGP704 | this work |
| p5-4 | Amp$^r$; 5.8 kb HindIII fragment of λ5 in pSK+ | this work |
| p5-40 | 4.5 kb SstI/HindIII fragment of p5-2 in pKS+ | this work |
| p5-41 | aphT cassette in SmaI site of p5-40 | this work |
| p5-43 | KpnI/SstI insert of p5-41 in pNQ705 | this work |
| p5-5 | Amp$^r$; PstI digestion of p5-4 and religation of the larger fragment | this work |
| p5-50 | 2.6 kb BamHI/ClaI fragment of p5-2 in pKS+ | this work |
| p5-51 | aphT cassette in HindIII site of p5-50 after Klenow fill-in | this work |
| p5-53 | XbaI/SalI insert of p5-51 in pGP704 | this work |
| p5-60 | ClaI-digestion of p5-2 and religation of larger fragment | this work |
| p5-8 | Amp$^r$; 2.2 kb PstI/HindIII fragment of p5-2 in pSK+ | this work |
| psseA | Cm$^r$; sseA in pACYC184 | this study |
| psseB | Cm$^r$; sseB in pACYC184 | this study |
| psseC | Cm$^r$; sseC in pACYC184 | this work |
| *E. coli* strains | | |
| DH5α | see reference | Gibco-BRL |
| S17-1 λpir | λpir phage lysogen (see reference) | Miller and Mekalanos, 1988 |
| CC118 λpir | λpir phage lysogen (see reference) | Herrero et al., 1990 |
| XL1-Blue | see reference | Stratagene |
| *S. typhimurium* strains | | |
| NCTC12023 | wild-type | Colindale, UK |
| CS015 | phoP-102::Tn10d-Cm | Miller et al., 1989 |
| CS022 | phoP$^c$ | Miller et al., 1989 |
| P2D6 | ssaV::mTn5 | Shea et al., 1996 |
| P3F4 | ssrA::mTn5 | Shea et al., 1996 |
| P4H2 | hilA::mTn5 | Monack et al., 1996 |
| P6E11 | spaRS::mTn5 | Shea et al., 1996 |
| P8G12 | ssrB::mTn5 | Shea et al., 1996 |
| P9B6 | ssaV::mTn5 | Shea et al., 1996 |
| P9B7 | ssaT::mTn5 | Shea et al., 1996 |
| P11D10 | ssaJ::mTn5 | Shea et al., 1996 |
| NPssaV | ssaV::aphT, Km$^r$; non-polar mutation | Deiwick et al., 1998 |
| HH100 | sseAΔ::aphT, Km$^r$; non-polar mutation | this study |
| HH101 | HH100 containing psseA | this study |
| HH102 | sseBΔ::aphT, Km$^r$; non-polar mutation | this study |
| HH103 | HH102 containing psseB | this study |
| HH107 | sseFΔ::aphT, Km$^r$; non-polar mutation | this study |
| HH108 | sseG::aphT, Km$^r$; non-polar mutation | this study |
| MvP102 | ΔsseEsscB, Km$^r$; non-polar mutation | this work |
| MvP103 | sseC::aphT, Km$^r$; non-polar mutation | this work |
| MvP103[psseC] | MvP103 containing psseC | this work |
| MvP131 | ssaB::luc in *S. typhimurium* NCTC12023 | this work |
| MvP127 | sseA::luc in *S. typhimurium* NCTC12023 | this work |
| MvP239 | sipC::lacZY, EE638 in *S. typhimurium* NCTC12023 | Hueck et al., 1995; this work |
| MvP244 | ssaB::luc in *S. typhimurium* P8G12 | this work |
| MvP266 | ssaH::luc in *S. typhimurium* NCTC12023 | this work |
| MvP284 | ssrA::aphT, Km$^r$; non-polar mutation | this work |
| MvP320 | ssrB::aphT, Km$^r$; non-polar mutation | this work |
| MvP337 | in-frame deletion in sseC | this work |
| MvP338 | in-frame deletion in sseD | this work |
| MvP339 | in-frame deletion in sscB | this work |
| MvP340 | in-frame deletion in ssrA | this work |
| SL7207 | *S. typhimurium* 2337-65 hisG46, DEL407 aroA::TnI(Tc-s) | gift from B. A. D. Stocker |
| III-57 sseC | Δ sseC | this work |

Example 1

Distribution of the Pathogenicity Island SPI-2 within Different *Salmonella* Strains The presence of open reading frames of the SPI-2 region in various *Salmonella* isolates and *E. coli* K-12 was analyzed by Southern hybridization as shown in Table 2.

TABLE 2

Prevalence of SPI-2 genes in various *Salmonella* ssp. deduced from representative gene probes

| Species | subspec. | serovar/serotype | ssrAB | ORF |
|---|---|---|---|---|
| *S. enterica* | I | typhimurium | + | + |
| *S. enterica* | I | typhi | + | + |
| *S. enterica* | II | | + | + |
| *S. enterica* | IIIa | | + | + |
| *S. enterica* | IIIb | | + | + |
| *S. enterica* | IV | | + | + |
| *S. enterica* | VI | | + | + |
| *S. enterica* | VII | | + | + |
| *S. bongori* | | 66:z41:— | − | + |
| *S. bongori* | | 44:z48:— | − | + |
| *E. coli* K-12 | | | − | − |

Presence or absence of hybridizing bands is indicated by + or −, respectively.

Hybridization

Genomic DNA of various *Salmonella* strains and *E. coli* K-12 was prepared as previously described (Hensel et al., 1997a). For Southern hybridization analysis, genomic DNA was digested with EcoRI or EcoRV, fractionated on 0.6% agarose gels and transferred to Hybond N$^+$ membranes (Amersham, Braunschweig). Various probes corresponding to the SPI-2 region were obtained as restriction fragments of the subcloned insert of λ1. Probes corresponding to ORF 242 and ORF 319 were generated by PCR using primer sets D89 (5'-TTTTTACGTGAAGCGGGGTG-3') (SEQ ID NO:44) and D90 (5'-GGCATTAGCGGATGTCTGACTG-3') (SEQ ID NO:45), and D91 (5'-CACCAGGAAC-CATTTTCTCTGG-3') (SEQ ID NO:46) and D92 (5'-CAGC-GATGACGATATTCGACAAG-3') (SEQ ID NO:47), respectively. PCR was performed according to the specifications of the manufacturer (Perkin-Elmer, Weiterstadt). PCR products were submitted to agarose gel electrophoresis and fragments of the expected size were recovered and purified. Hybridization probes were labeled using the DIG labeling system as described by the manufacturer (Boehringer, Mannheim).

Example 2

Characterization of sse Genes and Construction of sseC::aphT, sseD::aphT and sseEΔ Mutant *S. Typhimurium* Strains MvP103, MvP101 and MvP102

Organization of sse and ssc Genes

In order to characterize SPI2 genetically and functionally, a central region of the pathogenicity island (FIG. 1A) has been cloned and sequenced. DNA fragments covering the region between ssaC and ssaJ were subcloned in plasmids p5-2 and p5-4 as indicated in FIG. 1C. The arrangement and designation of genes in the 8 kb region between ssaC and ssaK is shown in FIG. 1B. This sequence will be available from the EMBL database under accession number AJ224892 in the near future. The sequenced region extends the open reading frame (ORF) of a gene encoding a putative subunit of the type III secretion apparatus referred to as spiB (Ochman et al., 1996). For consistency with the universal nomenclature for type III secretion system subunits (Bogdanove et al., 1996) and the nomenclature of other SPI2 genes (Hensel et al., 1997b), this gene has been designated ssaD. The deduced amino acid sequence of ssaD is 24% identical to YscD of *Y. enterocolitica*. This is followed by an ORF with coding capacity for a 9.3 kDa protein, 34% identical to YscE of *Y. enterocolitica*. Therefore, this gene is designated ssaE. A sequence of 263 bp separates ssaE and a set of nine genes, several of which encode proteins with sequence similarity to secreted effector proteins or their chaperones from other pathogens. These genes are separated by short intergenic regions or have overlapping reading frames and it is likely that some are co-transcribed and translationally coupled. Therefore, the genes with similarity to those encoding chaperones were designated sscA and sscB, and the others sseA-E. The amino acid sequence deduced from sscA shows 26% identity/49% similarity over 158 amino acid residues to SycD, the product of lcrH of *Y. pseudotuberculosis* which acts as a secretion-specific chaperone for YopB and YopD (Wattiau et al., 1994). The amino acid sequence deduced from sscB shows 23% identity/36% similarity over 98 amino acid residues to Ippi of *Shigella flexneri*. Ippl is a chaperone for *S. flexneri* invasion proteins (Ipas) (Baundry et al., 1988). As is the case for the secretion chaperones SycD, Ippl and SicA (Kaniga et al., 1995), SscB has an acidic pI (Table 3), whereas SscA has an unusually high pI of 8.8. SseB is 25% identical/47% similar to EspA of EPEC over the entire length of the 192 amino acid residue protein (FIG. 2b). SseD is 27% identical/51% similar to EspB of EPEC over 166 amino acid residues. SseC has sequence similarity to a class of effector proteins involved in the translocation of other effectors into the target host cell. These include YopB of *Y. enterocolitica*, EspD of EPEC and PepB of *Pseudomonas aerugunosa*. SseC is approximately 24% identical/48% similar to both EspD of EPEC and YopB of *Y. enterocolitica* (FIG. 2a). EspD and YopB have two hydrophobic domains that are predicted to insert into target cell membranes (Pallen et al., 1997). SseC contains three hydrophobic regions that could represent membrane-spanning domains. Other features of these predicted effector proteins are shown in Table 1. Using the TMpredict program (Hofmann and Stoffel, 1993), transmembrane helices are predicted for all the effector proteins apart from SseA which is very hydrophilic. Alignments of SseC to homologs in other pathogens are shown in FIG. 2b. Conserved amino acids are mainly clustered in the central, more hydrophobic portion of the protein, but unlike YopB, there is no significant similarity to the RTX family of toxins. The conserved residues in SseD are present mainly in the N-terminal half of the protein. Comparison of the deduced amino acid sequences of sseABCDEF with entries in the PROSITE database did not reveal the presence of any characteristic protein motifs. We subjected the predicted amino acid sequences of the sse genes to searches using the programs COIL and MULTICOIL as described by Pallen et al. (1997). SseA and SseD are predicted to have one trimeric coil each, and SseC is predicted to have two trimeric coils (Table 3). Since EspB and EspD are predicted to have one and two trimeric coils, respectively (Pallen et al., 1997), this provides further evidence that these proteins are functionally related.

TABLE 3

Features of predicted proteins.

| Protein | $M_r$ (kDa) | pI | Tm predictions | Predicted coils |
|---------|-------------|-----|----------------|-----------------|
| SseA | 12.5 | 9.3 | hydrophilic | at least one (trimer) |
| SseB | 21.5 | 4.7 | one transmembrane helix | none |
| SseC | 52.8 | 6.3 | three transmembrane helices | at least two (trimers) |
| SseD | 20.6 | 4.8 | three transmembrane helices | at least one (trimer) |
| SseE | 16.3 | 9.7 | one transmembrane helix | none |
| SscA | 18.1 | 8.8 | hydrophilic | none |
| SscB | 16.4 | 4.7 | hydrophilic | none |

Expression of SPI2 Genes

Generation of Antibodies Against Recombinant SPI2 Proteins

In order to monitor the expression of the SPI2 genes sseB, sscA and ssaP, a Western blot analysis of total bacterial cells with polyclonal antibodies raised against recombinant SPI2 proteins SseB, SscA, and SsaP was performed.

Protein gel electrophoresis and Western blotting were performed as described elsewhere (Laemmli, 1970 and Sambrook et al., 1989). Plasmids for the expression of recombinant SPI2 protein were constructed by cloning the individual SPI2 genes in plasmids pQE30, pQE31 or pQE32 (Qiagen, Hilden) in order to generate in-frame fusion to the N-terminal 6His tag. Recombinant SPI2 genes were expressed in *E. coli* M 5 [pREP] (Qiagen) and purified by metal chelating chromotography according to recommendations of the manufacturer (Qiagen). For immunisation, about 1 mg of recombinant SPI2 proteins were emulsified with complete and incomplete Freund's adjuvant for primary and booster immunizations, respectively. Rabbits were immunized subcutaneously according to standard protocols (Harlow and Lane, 1988). SPI2 proteins were detected with antisera raised against recombinant SPI2 proteins after electrophoretical separation of proteins from total cells and transfered onto a nitrocellulose membrane (Schleicher and Schuell) using a 'Semi-Dry' blotting device (Bio-Rad) according to the manufacturers manual. Bound antibody was visualized using a secondary antibody-alkaline phosphatase conjugate according to standard protocols (Harlow and Lane).

Generation of Reporter Gene Fusions:

Fusions of the reporter gene firefly luciferase (luc) to various genes in SPI2 were obtained using the suicide vectors pLB02 and pGPL01 (Gunn and Miller, 1996), which were kindly provided by Drs. Gunn and Miller (Seattle).

For the generation of a fusion to ssaB, a 831 bp EcoRV fragment of p2-2 was subcloned in EcoRV digested pSK$^+$. For the generation of a transcriptional fusion to sseA, a 1060 bp SmaI/HincII fragment of p5-4 was subcloned in pSK$^+$. The inserts of the resulting constructs were recovered as a EcoRI/KpnI fragment and ligated with EcoRI/KpnI digested reporter vectors pGPL01 and pLB02. For the generation of a transcriptional fusion to ssaJ, a 3 kb SmaI/KpnI fragment of p5-2 was directly subcloned in pGPL01 and pLB02.

Constructs with transcriptional fusions of SPI2 genes to luc were than integrated into the chromosome of *S. typhimurium* by mating between *E. coli* S17-1 λpir harbouring the respective construct and a spontaneous mutant of *S. typhimurium* resistant to 100 μgxml$^{-1}$ nalidixic acid and selection for exconjugants resistant to carbenicillin and nalidixic acid. The targeted integration in SPI2 (for constructs using pGLP01) or the zch region (for constructs using pLB02) was confirmed by Southernanalysis. Fusions were then moved into a mouse-passaged strain of *S. typhimurium* NCTC12023 by P22 transduction according to standard procedures (Maloy et al., 1996).

Assay of Reporter Genes

β-galactosidase activities of reporter gene fusions were determined according to standard procedures (Miller, 1992).

Bacterial strains harbouring firefly luciferase fusions to SPI2 genes (strain MvP127, sseA::luc, strain MvP131, ssaB::luc, strain MvP266, ssaH::luc) were grown in medium with various Mg$^{2+}$ concentrations. The luciferase activity of aliquots of the cultures was determined using the Promega (Heidelberg) luciferase assay kit or custom made reagents accordingly. Briefly, bacteria were pelleted by centrifugation for 5 min. at 20000×g at 4° C. and resuspended in lysis buffer (100 mM KHPO$_4$, pH 7.8, 2 mM EDTA, 1% Triton X-100, 5 mgxml$^{-1}$ bovine serum albumin, 1 mM DTT, 5 mgxml$^{-1}$ lysozyme). Lysates were incubated for 15 min at room temperature with repeated agitation and subjected to a freeze/thaw cycle. Aliquots of the lysates (25 μl) were transferred to microtiter plates (MicroFLUOR, Dynatech) and immediately assayed after addition of 50 μl luciferase reagent (20 mM Tricine-HCl, pH 7.8, 1.07 mM (MgCO$_3$)$_4$Mg(OH)$_2$, 100 μM EDTA, 33.3 mM DTT, 270 μM_Li$_3$-coenzyme A, 470 μM D(-)-luciferin, 530 μM Mg-ATP) for photon emission using the TriLux MicroBeta luminometer (Wallac, Turku). All assays were done in triplicates and repeated on independent occasions.

Expression of SPI2 Genes such as ssaB and ssaH is Induced by low Mg$^{2+}$ Concentrations of the Growth Medium

*S. typhimurium* wild-type strain and strains harbouring luc reporter-gene fusions to ssaB (strain MvP131) and to ssaH (strain MvP266) were grown to mid-log phase (OD at 600 nm of about 0.5) in minimal media containing high amounts of Mg$^{2+}$ (10 mM MgCl$_2$). This medium is referred to as medium G. Bacteria were recovered by centrifugation, washed three times in minimal medium containing 8 μM Mg$^{2+}$. This medium is referred to as medium F. Bacteria were resuspended in medium F or medium G and growth at 37° C. was continued. Aliquots of the cultures of strains MvP131 and MvP266 were withdrawn at the several different time points indicated and subjected to analysis of luciferase activity. Aliquots of the wild-type strain were withdrawn at the same time points. Protein from total bacterial cells was separated by SDS-PAGE and transferred to nicrocellulose membranes. These blots were incubated with antibodies raised against recombinant SsaP and SscA protein in order to detect proteins synthesized after the magnesium concentration shift in the magnesium concentration. After shifting bacteria from a growth medium with high amounts of Mg$^{2+}$ to a medium with limiting amounts of Mg$^{2+}$, the expression of SPI2 genes was highly induced. This induction can be monitored by using the reporter gene luc fused into different positions of SPI2. Furthermore, proteins synthesized after induction of SPI2 were detected by Western Blots. However, even in the presence of high amounts of Mg$^{2+}$, a low level of expression of SPI2 genes was observed.

Expression of SPI2 Genes Such as sseA and ssaB is Modulated by PhoP/PhoQ Regulation No expression of sseb or sscA was observed during growth in various rich media, or cell culture media with or without serum. However, low amount of SsaP were detected after growth in Lysogeny Broth (LB) or other rich media such as brain heart infusion (BHI). Growth in minimal medium containing less than 30 μM Mg$^{2+}$ induces the expression of SPI2 genes. Such effect of the Mg$^{2+}$ concentration has so far only been observed for PhoP/PhoQ-regulated genes. This observation is in contrast to a previous report by Valdivia and Falkow (1997) who postulated that SPI2 gene expression is independent of PhoP/PhoQ. However, in a PhoP$^c$ (constitutive) strain background (CSO22, Miller et al., 1989) expression of SPI2 genes was not constitutive but still dependent on the Mg$^{2+}$ concentration of the medium. This indicates that SPI2 gene expression is modulated by PhoP/PhoQ, but that further regulatory elements such as SsrA/B are needed.

DNA Cloning and Sequencing

DNA preparations and genetic manipulations were carried out according to standard protocols (Sambrook et al, 1989). Plasmid DNA transformation of bacterial cells was performed by electroporation (O'Callaghan and Charbit, 1990).

Clones harbouring fragments of SPI2 were identified from a library of genomic DNA of *S. typhimurium* in λ 1059 which has been described previously (Shea et al., 1996). The sse and ssc genes were subcloned from clone λ5 on a 5.7 kb EcoRI fragment (p5-2) and a 5.8 kb HindIII fragment (p5-4) in pBluescriptKS + as indicated in FIG. 1 and Table 1.

DNA sequencing was performed using a primer-walking strategy. The dideoxy method (Sanger et al., 1977) was applied using the Pharmacia T7 sequencing system for manual sequencing and the dye terminator chemistry for automatic analysis on a ABI377 sequencing instrument. Assembly of contigs from DNA sequences was performed by means of AssemblyLign and MacVector software (Oxford Molecular, Oxford). For further sequence analyses, programs of the GCG package version 8 (Devereux et al., 1984) were used on the HGMP network.

Construction of Non-polar Mutations

The construction of non-polar mutations in sseC (MvP103), sseD (MvP101) and sseE (MvP102) are described below. All chromosomal modifications were confirmed by PCR and Southern hybridization analysis (Southern, 1975, J. Mol. Biol. 98: 503-517).

Mutant MvP103, sseC. A 2.6 kb fragment was recovered after BamHI and ClaI digestion of p5-2 and subcloned in BamHI/ClaI-digested pBluescript II KS +. The resulting construct termed p5-50 was digested by HindIII, blunt ended using the Klenow fragment of DNA polymerase and ligated to the aphT cassette. A 900 bp HincII fragment of pSB315 containing an aminoglycoside 3'-phosphotransferase gene (aphT) from which the transcriptional terminator had been removed (Galán et al., 1992) was ligated in the same orientation into the blunted-ended HindIII site of plasmid p5-50. After transformation of *E. coli* XL-1 Blue and selection for resistance against kanamycin and carbenicillin (50 µg/ml each) one clone has been chosen and the harbouring plasmid isolated. This plasmid was termed p5-51 and its identity confirmed by restriction analysis. It was further digested with SalI and XbaI and the insert of 3.5 kb was ligated to SalI/XbaI-digested pGP704. This plasmid was electroporated into *E. coli* CC118 λpir and the transformants selected for resistance to kanamycin and carbenicillin (50 ig/ml each). As done before, one clone was chosen, its plasmid with the according DNA fragment in pGP704, termed p5-53, isolated and confirmed by restriction analysis. Plasmid p5-53 was electroporated into *E. coli* S 17-1 λpir and transferred into *S. typhimurium* NCTC12023 (resistant to nalidixic acid, 100 µg/ml) by conjugation as has been described previously (de Lorenzo and Timmis, 1994). Exconjugants in which the sseC gene had been replaced by the cloned gene disrupted by insertion of the aphT cassette were selected by resistance to kanamycin and nalidixic acid (100 µg/ml). The resulting exconjugants were finally tested for a lactose-negative phenotype and their sensitivity to carbenicillin. Selected clones were further examined by Southernblot analysis. In order to exclude possible mutations which have been acquired during the cloning procedure the mutated sseC allele was transferred into a fresh *Salmonella* background by P22 transduction (described by Maloy et al., 1996). The resulting *Salmonella* strain MvP103 was examined for the presence of the resistance cassette within the sseC gene by the use of PCR. Amplification was performed by using the primers E25 (5'-GAAATCCCGCAGAAATG-3') (SEO ID NO:48) and E28 (5'-AAGGCGATAATATAAAC-3') (SEO ID NO:49). The resulting fragment had a size of 1.6 kb for *S. typhimurium* wild-type and 2.5 kb for strain MvP103.

For complementation of non-polar mutations in sseC, the corresponding genes were amplified by PCR from genomic DNA using a series of primers corresponding to the region 5' of the putative start codons and to the 3' ends of the genes. These primers introduced BamHI restriction sites at the termini of the amplified genes. After digestion with BamHI, the genes were ligated to BamHI-digested pACYC184 (Chang and Cohen, 1978) and transferred into *E. coli* DH5α. The orientation of the insert was determined by PCR, and in addition, DNA sequencing was performed to confirm the orientation and the correct DNA sequence of the inserts. Plasmids with inserts in the same transcriptional orientation as the Tetr gene of pACYC184 were selected for complementation studies and electroporated into the *S. typhimurium* strains harbouring corresponding non-polar mutations.

Mutant MvP101, sseD. A 3.0 kb fragment was recovered after PstI and EcoRI digestion of p5-2 and subcloned in PstI/EcoRI-digested pUC18 The resulting construct termed p5-30 was digested by EcoRV and treated with alkaline phosphatase. The aphT cassette was isolated as described above and ligated to the linearized plasmid p5-30 in the same orientation in the unique EcoRV site. After transformation of *E. coli* XL-1 Blue and selection against kanamycin and carbenicillin (50 µg/ml each) one clone has been chosen and the harbouring plasmid isolated. This plasmid was termed p5-31 and its identity confirmed by restriction analysis. p5-31 was further digested with SphI and EcoRI, a 4.0 kb fragment isolated and ligated to SphI/EcoRI-digested pGP704. This plasmid was electroporated into *E. coli* CC118 λpir and transformants selected to kanamycin and carbenicillin (50 µg/ml each). As done before, one clone was chosen, its plasmid with the according DNA fragment in pGP704, termed p5-33, isolated and confirmed by restriction analysis. Plasmid p5-33 was electroporated into *E. coli* S17-1 λpir and transferred into *S. typhimurium* NCTC12023 (resistant to nalidixic acid) by conjugation as has been described previously (de Lorenzo and Timmis, 1994). Exconjugants in which the sseD gene had been replaced by the cloned gene disrupted by insertion of the aphT cassette were selected by resistance to kanamycin and nalidixic acid (100 µg/ml). The resulting exconjugants were finally tested for a lactose-negative phenotype and their sensitivity to carbenicillin. Selected clones were further examined by Southernblot analysis. In order to exclude possible mutations which might have been accumulated during the cloning procedure the mutated sseD allele was transferred into a fresh *Salmonella* background by P22 transduction (described by Maloy et al., 1996). The resulting *Salmonella* strain MvP1O1 was examined for the presence of the resistance cassette within the sseD gene by the use of PCR. Amplification was performed by using the primers E6 (5'-AGAGATGTAflAGATAC-3') (SEQ ID NO:50) and E28 (5'-AAGGCGATAATATAAAC-3') (SEQ ID NO:49). The resulting fragment had a size of 0.8 kb for *S. typhimurium* wild-type was used and 1.7 kb in the case of strain MvP101.

Mutant MvP102, deletion or parts of sseE and sscB. A 4.5 kb fragment was recovered after SstI and HindIII digestion of p5-2 and subcloned in SstI/HindIII-digested pKS +. The resulting construct termed p5-40 was digested by SmaI, digested with alkaline phospatase and ligated to the aphT cassette in the same orientation into the unique SmaI site created in the sseE/sseB deletion plasmid p5-40 as described above. After transformation of *E. coli* XL-1 Blue and selection against kanamycin and carbenicillin (50 µg/ml each) one clone was chosen and the harbouring plasmid isolated. This plasmid was termed p5-41 and its identity confirmed via restriction analysis. It was further digested with KpnI and SstI and the insert was ligated to KpnI/SstI-digested pNQ705. This plasmid was electroporated into *E. coli* CC118 λpir and transformed bacteria selected to kanamycin and chloramphenicol (50 µg/ml each). As done before, one clone was chosen, its plasmid with the according DNA fragment in pNQ705, termed p5-43, isolated and confirmed by restriction analysis. The resulting plasmid was used to transfer the mutated gene onto the *Salmonella* chromosome as described above. Resulting clones have been further examined by Southernblot analysis. To exclude possible mutations which might have been acquired during the cloning procedure the mutated sseE/sscB allele was transferred into a fresh *Salmonella* background by P22 transduction (described by Maloy et al., 1996). The resulting *Salmonella* strain MvP102 was examined for the presence of the resistance cassette within the sseE/sseB gene by the use of PCR. Amplification was performed by using the primers E6 (5'-AGAGATGTATTAGATAC-3') (SEQ ID NO:50) and E4 (5'-GCAATAAGAGTATCAAC-3') (SEQ ID NO:51). The resulting fragment had a size of 1.6 kb for *S. typhimurium* wild-type and a size of 1.9 kb for strain MvP102.

Construction of Mutant Strains Carrying In-frame Deletions in sseC, sseD and sscB:

Based on the observation that a non-polar in sseE did not result in a significant attenuation of virulence in the mouse model (Hensel et al., 1998), the generation of a deletion mutant for the sseE gene is not of interest for the generation of carrier strains.

Construction of an In-frame Deletion in sseC, Mutant MvP337

A deletion of 158 bp between codon 264 and 422 of sseC was generated. Plasmid p5-2 was digested by ClaI and the larger fragment containing the vector portion was recovered and self-ligated to generate p5-60. Plasmid p5-60 was linearized by digestion with HindIII, which cuts once within the sseC gene. Primers sseC-del-1 (5'-GCT AAG CTT CGG CTC AAA TTG TTT GGA AAA C-3') (SEQ ID NO:52) and sseE-del-2 (5'-GCT AAG CTT AGA GAT GTA TTA GAT ACC-3') (SEQ ID NO:53) were designed to introduce HindIII sites. PCR was performed using linearized p5-60 as template DNA. The TAQPLUS® polymerase (*Pyrococcus furiosus* DNA polymerase + recombinant *T. Aquaticus* YT1 polymerase) (Stratagene) was used according to the instructions of the manufacturer. Reactions of 100 µl volume were set up using 10 µl of 10× TAQPLUS® Precision buffer containing magnesium chloride, 0.8 µl of 100 mM dNTPs, 250 ng DNA template (linearized p5-8), 250 ng of each primer and 5 U of TAQPLUS® DNA polymerase (*Pyrococcus furiosus* DNA polymerase + recombinant *T. Aquaticus* YT1 polymerase). PCR was carried out for 35 cycles of: 95° C. for 1 minute, 60° C. for 1 minute, 72° C. for 6 minutes. Then a final step of 72° C. for 10 minutes was added. 10 µl of the PCR reaction were analyzed. A product of the expected size was recovered, digested by HindIII, self-ligated, and the ligation mixture was used to transform *E. coli* DH5α to resistance to carbenicillin. Plasmids were isolated from transformants and the integrity of the insert and the deletion was analyzed by restriction digestion and DNA sequencing. The insert of a confirmed construct was isolated after digestion with XbaI and KpnI and ligated to XbaI/KpnI-digested vector pKAS32. The resulting construct was used to transform *E. coli* S17-1 λpir to resistance to carbenicillin, and conjugational transfer of the plasmid to *S. typhimurium* (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 µg/ml streptomycin to select for colonies which had lost the integrated plasmid and undergone allelic exchange. Clones resistant to streptomycin but sensitive to carbenicillin were used for further analysis. Screening of mutants with a deletion within the sseC locus was performed by PCR using primers sseC-For (5'-ATT GGA TCC GCA AGC GTC CAG AA-3') (SEQ ID NO:54) and sseC-Rev (5-TAT GGA TCC TCA GAT TAA GCG CG-3') (SEQ ID NO:55). Amplification of DNA from clones containing the wild-type sseC allele resulted in a PCR product of 1520 bp, use of DNA from clones harbouring a sseC allele with an internal deletion resulted in a PCR product of 1050 bp. The integrity of clones harbouring the sseC deletion was further confirmed by Southern analysis of the sseC locus. Finally, the sseC locus containing the internal in-frame deletion was moved into a fresh strain background of *S. typhimurium* by P22 transduction (Maloy et al., 1996) and the resulting strain was designated MvP 337.

Construction of an In-frame Deletion in sseD, Mutant Strain MvP338

A deletion of 116 bp between codon 26 and 142 of sseD was generated. Plasmid p5-2 was digested by HindIII/PstI and a fragment of 2.1 kb was isolated and subcloned in HindIII/PstI-digested vector pBluescript SK +. The resulting construct was designated p5-8. p5-8 was linearized by digestion with EcoRV, which cuts twice within the sseD gene. Primers sseD-del-1 (5'-ATA GAA TTC GGA GGG AGA TGG AGT GGA AG -3') (SEQ ID NO:56) and sseD-del-2 (5'-ATA GAA TTC GAA GAT AAA GCG ATT GCC GAC-3') (SEQ ID NO:57) were designed to introduce EcoRI sites. PCR was performed using linearized p5-8 as template DNA. The TAQPLUS® polymerase (*Pyrococcus furiosus* DNA polymerase + recombinant *T. Aquaticus* YT1 polymerase) (Stratagene) was used according to the instructions of the manufacturer. Reactions of 100 µl volume were set up using 10 µl of 10× TAQPLUS® Precision buffer containing magnesium chloride, 0.8 µl of 100 mM dNTPs, 250 ng DNA template (linearized p5-8), 250 ng of each primer and 5 U of TAQPLUS® DNA polymerase (*Pyrococcus furiosus* DNA polymerase + recombinant *T. Aquaticus* YT1 polymerase). PCR was carried out for 35 cycles of: 95° C. for 1 minute, 60° C. for 1 minute, 72° C. for 5 minutes. Then a final step of 72° C. for 10 minutes was added. 10 µl of the PCR reaction were analyzed. A product of the expected size was recovered, digested by EcoRI, self-ligated, and the ligation mixture was used to transform *E. coli* DH5á to resistance to carbenicillin. Plasmids were isolated from transformants and the integrity of the insert and the deletion was analyzed by restriction mapping and DNA sequencing. The insert of a confirmed construct was isolated after digestion with XbaI and KpnI and ligated to XbaI/KpnI-digested vector pKAS32. The resulting construct was used to transform *E. coli* S17-1 λpir to resistance to carbenicillin, and conjugational transfer of the plasmid to *S. typhimurium* (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 ig/ml streptomycin to select for colonies which had lost the integrated plasmid and undergone allelic exchange. Clones resistant to streptomycin but sensitive to carbenicillin were used for further analysis. Screening of mutants with a deletion within the sseD locus was performed by PCR using primers sseD-For (5'-GAA GGA TCC ACT CCA TCT CCC TC-3') (SEQ ID NO:58) and sseD-Rev (5-GAA GGA TCC ATT TGC TCT ATT TCT TGC-3') (SEQ ID NO:59). Amplification of DNA from clones containing the wild-type sseD allele resulted in a PCR product of 560 bp, use of DNA from clones harbouring a sseD allele with an internal deletion resulted in a PCR product of 220 bp. The integrity of clones harbouring the sseD deletion was further confirmed by Southern analysis of the sseD locus. Finally, the sseD locus containing the internal in-frame deletion was moved into a fresh strain background of *S. typhimurium* by P22 transduction (Maloy et al., 1996) and the resulting strain was designated MvP338.

Construction of an In-frame Deletion in sscB, Mutant Strain MvP339

A deletion of 128 bp between codon 32 and 160 of sscB was generated. A 3 kb BglII fragment of plasmid p5-2 was ligated into the BamHI site of pBluescript KS + to generate plasmid p5-70. Plasmid p5-70 was linearized by digestion with NcoI, which cuts once within the sscB gene. Primers sscB-del-1 (5'-ATG GGA TCC GAG ATT CGC CAG AAT GCG CAA-3') (SEQ ID NO:60) and sscB-del-2 (5'-ATG GGA TCC ACT GGC ATA AAC GGT TTC CGG-3') (SEQ ID NO:61) were designed to introduce BamHI sites. PCR was performed using linearized p5-70 as template DNA. The TAQPLUS® polymerase (*Pyrococcus furiosus* DNA polymerase+recombinant *T. Aquaticus* YT1 polymerase) (Stratagene) was used according to the instructions of the manufacturer. Reactions of 100 µl/volume were set up using 10 µl of 10× TAQPLUS® Precision buffer containing magnesium chloride, 0.8 µl of 100 mM dNTPs, 250 ng DNA template (linearized p5-70), 250 ng of each primer and 5 U of TAQPLUS® DNA polymerase (*Pyrococcus furiosus* DNA polymerase+recombinant *T. Aquaticus* YT1 polymerase). PCR was carried out for 35 cycles of: 95° C. for 1 minute, 60° C. for 1 minute, 72° C. for 6 minutes. Then a final step of 72° C. for 10 minutes was added. 10 µl of the PCR reaction were analyzed. A product of the expected size was recovered, digested by BamHI, self-ligated, and the ligation mixture was used to transform *E. coli* DH5á to resistance to carbenicillin. Plasmids were isolated from transformants and the integrity of the insert and the deletion was analyzed by restriction analysis and DNA sequencing. The insert of a confirmed construct was isolated after digestion with XbaI and KpnI and ligated to XbaI/KpnI-digested vector pKAS32. The resulting construct was used to transform *E. coli* S17-1 λpir to resistance to carbenicillin, and conjugational transfer of the plasmid to *S. typhimurium* (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 ig/ml streptomycin to select for colonies which had lost the integrated plasmid and undergone allelic exchange. Clones resistant to streptomycin but sensitive to carbenicillin were used for further analysis. Screening of mutants with a deletion within the sseC locus was performed by PCR using primers sscB-For (5'-ATT GGA TCC TGA CGT AAA TCA TTA TCA-3') (SEQ ID NO:62) and sscB-Rev (5-ATT GGA TCC TTA AGC AAT AAG TGA ATC-3') (SEQ ID NO:63). Amplification of DNA from clones containing the wild-type sscB allele resulted in a PCR product of 480 bp, use of DNA from clones harbouring a sscB allele with an internal deletion resulted in a PCR product of 100 bp. The integrity of clones harbouring the sseC deletion was further confirmed by Southern analysis of the sscB locus. Finally, the sscB locus containing the internal in-frame deletion was moved into a fresh strain background of *S. typhimurium* by P22 transduction (Maloy et al., 1996) and the resulting strain was designated MvP339.

Construction of a Deletion Mutation in the sseC Gene

In a further approach the complete sequence of the chromosomal sseC gene was deleted by allelic replacement with a deleted copy of the gene. The deletion was constructed in a suicide plasmid (pCVD442 (Donnenberg et al., 1991). First, two DNA fragments flanking the sseC gene (fragment A, carrying artificial SalI and XbaI sites at its 5' and 3' ends, respectively; and fragment B, carrying artificial XbaI and SacI sites at its 5' and 3' ends, respectively) were amplified by PCR. The oligonucleotides used for PCR were: 1.) sseDelfor1 GCTGTCGACTTGTAGTGAGTGAGCAAG (SEQ ID NO:70) (3' nucleotide corresponds to bp 941 in included sequence: FIG. 21A); 2.) sseCDelrev2 GGATCTAGATTTTAGCTCCTGTCAGAAAG (SEQ ID NO:71) (3' nucleotide corresponds to bp 2585 in included sequence, oligo binds to reverse strand); 3.) sseCDelfor2 GGATCTAGATCTGAGGATAAAAATATGG (SEQ ID NO:72) (3' nucleotide corresponds to bp 4078 in included sequence); 4.) sseDelrev1 GCTGAGCTCTGCCGCTGACGGAATATG (SEQ ID NO:73) (3' nucleotide corresponds to bp 5592 in included sequence, oligo binds to reverse strand). The resulting PCR fragments were fused together via the XbaI site. The resulting fragment was cut with SalI and SacI and cloned into pCVD442 cut with SalI and SacI. The resulting plasmid was introduced into *S. typhimurium* NCTC12023 by conjugation and chromosomal integrants of the plasmid into the sseC locus were selected for by the plasmid-encoded ampicillin resistance marker. In a second step, clones which had lost the plasmid were screened for by loss of ampicillin resistance. The resulting clones were tested for chromosomal deletion of the sseC gene by PCR, and deletion of a 1455 bp fragment, comprising the entire sseC open reading frame, was confirmed. This ΔsseC mutant strain was named III-57ΔsseC.

Construction of a sseC-aroA Double Mutant

In order to construct a double mutant which can serve as a prototype for a live attenuated vaccine, the sseC:aphT(Km') marker from MvP103 was transferred by P22 phage transduction into *S. typhimurium* SL7207 (hisG46 DEL407 [aroA544:Tn10], Tc$^R$) a strain carrying a stable deletion in the aroA gene.

Example 3

Invasion and Intracellular Growth in Tissue Culture

Intramacrophage Replication of Mutant Strains

Several strains which are defective in their ability to replicate inside macrophages and macrophage-like cell lines have been tested, as macrophage survival and replication are thought to represent an important aspect of *Salmonella* pathogenesis in vivo (Fields et al., 1986). It has been reported previously that a number of SPI2 mutant strains were not defective for survival or replication within RAW macrophages (Hensel et al., 1997b) but subsequent experiments have revealed that some SPI2 mutants can be shown to have a replication defect if aerated stationary phase bacterial cultures opsonized with normal mouse serum are used (see also accompanying paper: Cirillo et al., 1998). The increase in cfu for different strains in RAW macrophages over a 16 h period is shown in FIG. 3. Replication defects were observed for strains carrying mutations in ssaV (encoding a component of the secretion apparatus), sseB and sseC and to a lesser extent for strains carrying mutations in sseE. Partial complementation of this defect was achieved with strains harbouring plasmids carrying functional copies of sseb and sseC, HH103 and MvP103[psseC], respectively. The ability of SPI2 mutant strains to replicate inside the J774.1 macrophage cell line (FIG. 4A) and in periodate-elicited peritoneal macrophages from C3H/HeN mice (FIG. 4B) has also been tested. Similar replication defects of *S. typhimurium* carrying transposon or non-polar mutations in SPI2 genes were observed, regardless of the phagocyte cell-type examined, although the peritoneal elicited cells had superior antimicrobial activity compared to either cell line.

Macrophage Survival Assays

RAW 264.7 cells (ECACC 91062702), a murine macrophage-like cell line, were grown in Dulbecco's modified Eagle's medium (DMEM) containing 10%$_{foetal}$ calf serum (FCS) and 2 mM glutamine at 37° C. in 5% $CO_2$. *S. typhimurium* strains were grown in LB to stationary phase and diluted to an $OD_{600}$ of 0.1 and opsonized for 20 min in DMEM containing 10% normal mouse serum. Bacteria were then centrifuged onto macrophages seeded in 24 well tissue culture plates at a multiplicity of infection of approximately 1:10 and incubated for 30 min. Following infection, the macrophages were washed twice with PBS to remove extracellular bacteria and incubated for 90 min (2h post-infection) or 16 h in medium containing gentamicin (12 μg/ml). Infected macrophages were washed twice with PBS and lysed with 1% Triton X-100 for 10 min and appropriate aliquots and dilutions were plated onto LB agar to enumerate cfu.

Survival of opsonized *S. typhimurium* strains in J774.1 cells (Ralph et al., 1975) or C3H/HeN murine peritoneal exudate cells (from Charles River Laboratories, Wilmington, Mass.) was determined essentially as described by DeGroote et al. (1997), but without the addition of interferon-γ. Briefly, peritoneal cells harvested in PBS with heat-inactivated 10%$_{foetal}$ calf serum 4 days after intraperitoneal injection of 5 mM sodium periodate (Sigma, St. Louis, Mo.) were plated in 96-well flat-bottomed microtiter plates (Becton-Dickinson, Franklin Lakes, N.J.) and allowed to adhere for 2 h. Non-adherent cells were flushed out with prewarmed medium containing 10% heat-inactivated $_{foetal}$ calf serum. In previous studies, we have established that >95% of the cells remaining after this procedure are macrophages. *S. typhimurium* from aerated overnight cultures was opsonized with normal mouse serum and centrifuged onto adherent cells at an effector to target ratio of 1:10. The bacteria were allowed to internalize for 15 min, and washed with medium containing 6 μg/ml gentamicin to kill extracellular bacteria. At 0 h and 20 h, cells were lysed with PBS containing 0.5% deoxycholate (Sigma, St. Louis, Mo.), with plating of serial dilutions to enumerate colony-forming units.

Example 4

Evaluation of Safety in the *S. typhimurium* Mouse Model of Salmonellosis

Virulence Tests with Strains Carrying Non-polar Mutations

DNA sequence analysis suggested that the sse genes might encode effector proteins of the secretion system, but apart from a possible polar effect from a transposon insertion in sscA no strains carrying mutations in these genes were recovered in the original STM screen for *S. typhimurium* virulence genes using mTn5 mutagenesis (Hensel et al., 1995), and their role in virulence was unclear. To address this question, strains carrying non-polar mutations in sseC, sseD and sseEsscB (FIG. 1) have been constructed and subjected to virulence tests. Table 4 shows that all mice inoculated with strains carrying mutations sseC and sseD survived a dose of $1 \times 10^4$ cfu, three orders of magnitude greater than the $LD_{50}$ of the wild-type strain, which is less than 10 cfu when the inoculum is administered by the i.p. route (Buchmeier et al., 1993; Shea et al, 1996). The same strains containing a plasmid carrying the corresponding wild-type allele were also inoculated into mice at a dose of $1 \times 10^4$ cfu. No mice survived these infections, which shows that each mutation can be complemented by the presence of a functional copy of each gene, and that each of these genes plays an important role in *Salmonella* virulence. Strains carrying non-polar mutations in sseEsscB caused lethal infections when approximately $1 \times 10^4$ cells of each strain were inoculated into mice by the i.p. route (Table 4) and were analyzed in more detail by a competition assay with the wild-type strain in mixed infections (five mice/test) to determine if they were attenuated in virulence. The competitive index, defined as the output ratio of mutant to wild-type bacteria, divided by the input ratio of mutant to wild-type bacteria, shows that the sseEsscB mutant was not significantly different to that of a fully virulent strain carrying an antibiotic resistance marker, which implies that this gene does not play a significant role in systemic *Salmonella* infection of the mouse.

TABLE 4

Virulence of *S. typhimurium* strains in mice.

| Strain | Genotype | Mouse survival after inoculation[a] with bacterial strain | Mouse survival after inoculation[a] with mutant + complementing plasmid | Competitive index in vivo |
|---|---|---|---|---|
| NCTC12023 | wild-type | 0/5 | n.d. | 0.98[b] |
| MvP101 | ΔsseD::aphT | 5/5 | n.d. | >0.01 |
| MvP102 | ΔsseEsscB::aphT | 4/4 | n.d. | 0.79 |
| MvP103 | sseC::aphT | 5/5 | 0/5 | >0.01 (oral) |
|  |  |  |  | >0.01 (i.p.) |

[a]Mice were inoculated intraperitoneally with $1 \times 10^4$ cells of each strain
[b]Result of competition between wild-type strain NCTC12023 and a virulent mTn5 mutant identified in the STM screen.

Example 5

Vaccination with the sseC::aphT, and ΔsseD::aphT mutant *S. Typhimurium* Strains MvP103 and MvP101

Strains Carrying Non-polar Mutations as Live Vaccine Carriers

To confirm the suitability of the MvP101 and MvP103 mutants as live vaccine carriers their level of attenuation was evaluated by determining the $LD_{50}$ after oral inoculation in mice. Groups of 10 mice were fed with serial dilutions of either MvP110, MvP103 or the wild-type parental strain NCTCNCTC12023 and dead animals were recorded within a period of 10 days postinfection. The obtained results demonstrated that both mutants are highly attenuated when given orally to BALB/c mice ($LD_{50}$ above $10^9$) when compared with the parental strain ($LD_{50}=6.9 \times 10^5$ CFU). After intraperitoneal inocoluation the $LD_{50}$ of *S. typhimurium* NCTC12023 wild-type in BALB/c is 6 bacteria, and the $LD_{50}$ of MvP103 in BALB/c is $2.77 \times 10^6$ after intraperitoneal inoculation. The mutation can be complemented by psseC, but no $LD_{50}$ determination for the complemented mutant strain was performed. $LD_{50}$ of MvP101 in BALB/c is $3.54 \times 10^6$ after intraperitoneal inoculation. A partial complementation by plasmid p5-K1 was possible. An intraperitoneal $LD_{50}$ for MvP101 [p5-K1] of $8.45 \times 10^2$ was determined. (Description of p5-K1: a 3.2 kb PstI fragment of p5-2 containing sseC'sseDsseEsscBsseF' was subcloned in low copy number cloning vector pWSK29).

Determination of the $LD_{50}$

Doses ranging from $10^5$ to $10^9$ CFU of either *S. typhimurium* NCTCNCTC12023 (wild-type) or the mutants MvP103 and MvP101 were orally inoculated into groups of 10 mice and survival was recorded over 10 days.

$LD_{50}$ of *S typhimurium* wild-type and mutant strains MvP101 and MvP103 after intraperitoneal infection was determined by inoculation of doses ranging from $10^1$ to $10^7$ CFU into groups of 5 female BALB/c mice of 6-8 weeks of age. Survival was recorded over a period of three weeks. The $LD_{50}$ dose of the challenge strains was calculated by the method of Reed and Muench (Reed and Muench, 1938).

Immunization Protocols

For vaccination, bacteria were grown overnight until they reach medium log phase. Then, they were harvested by centrifugation (3,000×g) and resuspended in 5% sodium bicarbonate. Mice were immunized four times at 15 day intervals by gently feeding them with the bacterial suspension ($10^9$ CFU/mouse) in a volume of approximately 30 µl. Control mice were vaccinated with the carrier, lacking plasmid.

Cytotoxicity Assay

Spleen cells were obtained from mice 14 days after the last immunization and $2×10^6$ effector cells were restimulated in vitro for 5 days in complete medium supplemented with 20 U/ml of rIL-2 and 20 µM of the βGP1 peptide (β-gal p876-884, TPHPARIGL), which encompasses the immunodominant $H-2L^d$-restricted β-gal epitope. After restimulation, the assay was performed using the [$^3$H]-thymidine incorporation method. In brief, $2×10^6$ of P815 cells per ml were labelled with [$^3$H]-thymidine for 4 h in either complete medium or complete medium supplemented with 20 µM of βGP1 peptide and used as target cells. Following washing, $2×10^5$ labelled targets were incubated with serial dilutions of effector cells in 200 µl of complete medium for 4 h at 37° C. Cells were harvested and specific lysis was determined as follows: [(retained c.p.m. in the absence of effectors)−(experimentally retained c.p.m. in the presence of effectors)/retained c.p.m. in the absence of effectors]×100.

Example 6

Evaluation of the Induced Immune Response

Induction of Mucosal Immune Responses After Oral Vaccination

To achieve protection against mucosal pathogens using live *Salmonella* carriers, elicitation of an efficient mucosal response is highly desirable. Therefore, the presence of β-gal-specific antibodies in intestinal washes from mice immunized with either MvP101, MvP103 or SL7207 carrying pAH97 was investigated 52 days after immunization. As shown in FIG. 5., immunization with all three carriers stimulate the production of significant amounts of β-gal-specific IgA and, to a lesser extent, favor the transudation of antigen-specific IgG in the intestinal lumen. No statistically significant differences were observed among the mucosal responses to the different recombinant clones.

Cellular Immune Responses Triggered After Oral Immunization with sseC and sseD Mutants Expressing β-gal To evaluate the efficacy of the antigen-specific T cell responses generated in immunized mice, spleen cells were enriched in CD4 + T cells and restimulated in vitro during four days with β-gal. As shown in FIG. 6, although antigen-specific CD4 +-enriched spleen cells were generated after vaccination with the three carriers, MvP103 and MvP101 were significantly more efficient than SL7207 (P 0.05) at triggering specific cellular immune response. In contrast, cells isolated from mice immunized with the carrier alone failed to proliferate in the presence of β-gal.

To investigate the Th-type of immune response triggered by immunization, the content of IFN-γ, IL-2, IL-4, IL-5, IL-6 and IL-10 was measured in the supernatant fluids of restimulated cells. The results demonstrated that a predominant Th1 response pattern was induced in mice immunized with all the carriers. IFN-γ was the only cytokine with significantly increased levels in comparison to those observed in supernatants from spleen cells isolated from mice immunized with plasmidless carriers (FIG. 7). Interestingly, in agreement with the IgG isotype patterns, the levels of IFN-γ detected in supernatants from cells of mice immunized with MvP103 [pAH97] were significantly higher (P 0.05) than those from animals receiving either MvP101 [pAH97] or SL7207 [pAH97] (FIG. 7).

Antigen-specific antibody responses generated in mice orally immunized with the attenuated *S. typhimurium* vaccine carriers expressing the model antigen β-gal Groups of mice were immunized with the recombinant strains MvP101 [pAH97] and MvP103 [pAH97]. To estimate the efficacy of the prototypes another group was vaccinated with the well-established carrier strain SL7207 [pAH97]. The abilities of the different carriers to induce a systemic humoral response was determined by measuring the titer of β-gal-specific antibodies in the serum of vaccinated mice. As shown in FIG. 8, significant titers of β-gal-specific IgG and IgM antibodies were detected at day 30 in all vaccinated animals. In contrast to the IgM titers which reach a plateau at day 30, the titers of IgG steadily increased until day 52 from immunization when the experiment was concluded. Although all tested carriers exhibit an excellent performance, the MvP103 mutant was the most efficient at inducing anti-β-gal IgG antibodies (P 0.05). No significant levels of β-gal-specific IgA were detected in mice immunized with any of the three recombinant clones (data not shown).

To determine the subclass distribution of the anti-β-gal IgG, serum samples were analyzed for specific levels of IgG1, IgG2a, IgG2b and IgG3. The results shown in FIG. 9 demonstrate that the main β-gal-specific IgG isotype present in sera of all immunized mice was IgG2, suggesting of a predominant Th1 response. Interestingly, a lower concentration of IgG1 (P 0.05) was observed in mice immunized with MvP103 than in those receiving MvP101 and SL7202, indicating a similar response pattern in animals immunized with the last two carriers.

Sample Collection

Serum samples were collected at different time points and monitored for the presence of β-gal-specific antibodies. At day 52 after immunization, intestinal ravages were obtained by flushing the small intestine with 2 ml of PBS supplemented with 50 mM EDTA, 0.1% bovine serum albumin and 0.1 mg/ml of soybean trypsin inhibitor (Sigma). Then, the ravages were centrifuged (10 min at 600×g) to remove debris, supernatants were removed and supplemented with phenylmethylsulfonyl fluoride (10 mM) and $NaN_3$, and stored at −20° C.

Antibody Assays

Antibody titres were determined by an enzyme-linked immunosorbent assay (ELISA). Briefly, 96 well Nunc-Immuno MaxiSorp™ assay plates (Nunc, Roskilde, Denmark) were coated with 50 µl/well β-gal (5 µg/ml) in coating buffer (0.1 M $Na_2HPO_4$, pH 9.0). After overnight incubation at 4° C., plates were blocked with 10% FCS in PBS for 1 h at 37°

C. Serial two-fold dilutions of serum in FCS-PBS were added (100 µl/well) and plates were incubated for 2 h at 37° C. After four washes with PBS-0.05% Tween 20, secondary antibodies were added: biotinylated γ-chain specific goat anti-mouse IgG, µ-chain specific goat anti-mouse IgM, α-chain specific goat anti-mouse IgA antibodies (Sigma, St. Louis, Mo.) or, to determine IgG subclass, biotin-conjugated rat anti-mouse IgG1, IgG2a, IgG2b and IgG3 (Pharmingen) and plates were further incubated for 2 h at 37° C. After four washes, 100 µl of peroxidase-conjugated streptavidin (Pharmingen, St. Diego, Calif.) were added to each well and plates were incubated at room temperature for 1 h. After four washes, reactions were developed using ABTS [2,2'-azino-bis-(3-ethybenzthiazoline-6-sulfonic acid)] in 0.1 M citrate-phosphate buffer (pH 4.35) containing 0.01% $H_2O_2$. Endpoint titers were expressed as the reciprocal $log_2$ of the last dilution which gave an optical density at 405 nm 0.1 unit above the values of the negative controls after a 30 min incubation.

To determine the concentration of total Ig present in the intestinal ravages, serial dilutions of the corresponding samples were incubated in microtiter plates that had been coated with goat anti-mouse IgG, IgM and IgA as capture antibodies (100 µg/well, Sigma) and serial dilutions of purified mouse IgG, IgM and IgA (Sigma) were used to generate standard curves. Detection of antigen-specific Ig was performed as described above.

Induction of Antigen-specific CTL Responses in Mice Orally Immunized with the Carrier Strains Expressing β-gal The elicitation of MHC class I restricted responses are particularly important for protection against many intracellular pathogens and tumors. It has been shown that antigen-specific CD8 + CTL can be generated both in vitro and in vivo after immunization with recombinant *Salmonella* spp. expressing heterologous antigens. Therefore, we considered it important to determine whether the tested carriers were also able to trigger a β-gal-specific CTL response. Spleen cells were collected from mice vaccinated with either MvP101 [pAH97], MvP103 [pAH97] or SL7207 [pAH97] at day 52 from immunization and restimulated in vitro with βGP1-pulsed syngenic spleen cells for 5 days. As shown in FIG. 10, the spleen cells from mice immunized with either of the three constructs induced significant lysis of βGP1-loaded target cells compared with unloaded controls. The more efficient responses were observed using the carrier strain MvP103. The lysis was mediated by CD8 + T cells since the cytotoxic activity was completely abrogated when CD8 + T effector cells were depleted (data not shown).

Cytokine Determination

Culture supernatants were collected from proliferating cells on days 2 and 4, and stored at −70° C. The determination of IL-2, IL-4, IL-5, IL-6, IL-10 and IFN-γ was performed by specific ELISA. In brief, 96-well microtiter plates were coated overnight at 4° C. with purified rat anti-mouse IL-2 mAb (clone JESG-1A12), anti-IL-4 mAb (clone 11B11), anti-IL-5 mAb (clone TRFK5), anti-IL-6 mAb (clone MP5-20F3), anti-IL-10 mAb (clone JES5-2A5), and anti-IFN-γ mAb (clone R4-6A2) (Pharmingen). After three washes, plates were blocked and two-fold dilutions of supernatant fluids were added. A standard curve was generated for each cytokine using recombinant murine IL-2 (rIL-2), rIL-4, rIL-5, rIL-6, rIFN-γ, and rIL-10 (Pharmingen). Plates were further incubated at 4° C. overnight. After washing, 100 µl/well of biotinylated rat anti-mouse IL-2 (clone JES6-5H4), IL-4 (clone BVD6-24G2), IL-5 (clone TRFK4), IL-6 (clone MP5-32C11), IL-10 (clone SXC-1) and INF-γ (clone XMG1.2) monoclonal antibodies were added and incubated for 45 min at RT. After six washes, streptavidin-peroxidase conjugated was added and incubated for 30 min at RT. Finally, the plates were developed using ABTS.

Depletion of CD8 + Spleen Cells.

The CD8 + cell subset was depleted using MINIMACS™ (cell separator) Magnetic Ly-2 Microbeads according to the manufacturer's instructions (Miltenyi Biotec). Depleted cell preparations contained 1% CD8 + cells.

FACSCAN™ (cytometer) Analysis

Approximately $5 \times 10^5$ cells were incubated in staining buffer (PBS supplemented with 2% FCS and 0.1% sodium azide) with the desired antibody or combination of antibodies for 30 min at 4° C. After washes, cells were analysed on a FACSCAN™ (cytometer) (Becton Dickinson). The monoclonal antibodies used were FITC-conjugated anti-CD4 and anti-CD8 (clones H129.19 and 53-6.7; Pharmingen).

Example 7

Cell Proliferation

Cell Proliferation Assay

Spleen cell suspensions were enriched for CD4 + T cells using MINIMACS™ (cell separator) Magnetic Ly-2 and indirect goat-anti-mouse-IgG Microbeads according to the instructions of the manufacturer (Mitenyi Biotec GmbH, Germany). Cell preparations contained >65% of CD4 + cells. Cells were adjusted to $2 \times 10^6$ cells/ml in complete medium supplemented with 20 U/ml of mouse rIL-2 (Pharmigen), seeded at 100 µl/well in a flat-bottomed 96-well microtiter plate (Nunc, Roskilde, Denmark) and incubated for four days in the presence of different concentrations of soluble 1-gal. During the final 18 hours of culture 1 µCi of [$^3$H]-thymidine (Amersham International, Amersham, U.K.) was added per well. The cells were harvested on paper filters using a cell harvester and the [$^3$H]-thymidine incorporated into the DNA of proliferating cells was determined in a .beta.-scintillation counter.

Example 8

Characterization of ssr Genes and Construction and Characterization of the ssr Mutant *S. Typhimurium* Strains MvP284, MvP320 and MvP333

Homology of the Two Component Regulator Genes ssrA and ssrB of SPI2 with Other Bacterial Proteins The SPI2 gene ssrA encodes a protein similar to sensor components of bacterial two component regulatory systems as has been described before (Ochman et al., 1996). For consistency with the nomenclature of SPI2 virulence genes (Hensel et al., 1997b; Valdivia and Falkow, 1997), this gene is designated ssrA. Downstream of ssrA, an ORF with coding capacity for a 24.3 kDa protein was identified. This gene shares significant similarity with a family of genes encoding transcriptional activators like DegU of *Bacillus subtilis*, UvrY of *E. coli* and BvgA of *Bordetella pertussis*. Therefore, it is likely that the protein acts as the regulatory component of the ssr system and the gene was designated ssrB.

Inverse Regulation of SPI1 and SPI2

The expression of the type III secretions systems of SPI1 and SPI2 is tightly regulated by environmental conditions. While SPI1 is induced during late loglearly stationary phase after growth in rich media of high osmolarity and limiting $O_2$ (oxygen) concentration, no induction of SPI2 gene expression was observed. In contrast, after growth in minimal medium with limiting amounts of $Mg^{2+}$ (8 µM) the ssaB::luc fusion was highly expressed while the sipC::lacZ fusion was not expressed. The expression of the ssaB::luc fusion is dependent on the function of SsrA/B, since there is no expression in the ssrB-negative background strain P8G12 (Hensel et al., 1998). The expression of the sipC::lacZ fusion is dependent on HilA, the transcriptional regulator of SPI1. We also observed that a mutation in ssrB affects expression of the sipC::lacZ fusion. This indicates that SPI2 has a regulatory effect on the expression of SPI1 genes.

Bacterial strains harbouring a luc fusion to ssaB in SPI2 (strain MvP131) and a lacZ fusion to sipC in SPI1 (strain MvP239) were grown under conditions previously shown to induce SPI gene expression. Bacteria were grown over night in minimal medium containing 8 µM $Mg^{2+}$ or over night in LB broth containing 1% NaCl (LB 1% NaCl). The Luc activity of strain MvP131 and β-galactosidase activity of strain MvP239 were determined. As a control, both reporter fusions were assayed in the ssrB negative strain background of P8G12.

Expression levels of lacZ Reporter-gene fusions to SPI genes were assayed as described by Miller, 1992.

Construction and Analysis of sseA Reporter Gene Fusion

A 1.1 kb SmaI/HincII fragment of p5-4 was subcloned into pGP101, a suicide vector for the generation of luc fusions (Gunn and Miller, 1996). The resulting construct, in which 1.0 kb upstream and 112 bp of sseA is transcriptionally fused to luc was used to transform E. coli S17-1 λpir, and conjugational transfer to S. typhimurium performed as described previously (Gunn and Miller, 1996). Strains that had integrated the reporter gene fusion into the chromosome by homologous recombination were confirmed by PCR and Southern hybridization analysis. Subsequently, the fusion was moved by P22 transduction into the wild-type and various mutant strain backgrounds with mTn5 insertions in SPI1 or SPI2 genes (Maloy et al., 1996). As a control, a strain was constructed harbouring a chromosomal integration of pLB02, a suicide plasmid without a promoter fusion to the luc gene (Gunn and Miller, 1996). For the analysis of gene expression, strains were grown for 16 h in minimal medium with aeration. Aliquots of the bacterial cultures were lysed and luciferase activity was determined using a luciferase assay kit according to the manufacturer's protocol (Boehringer Mannheim). Photon detection was performed on a Microplate scintillation/luminescence counter (Wallac, Turku). All assay were done in triplicate, and replicated on independent occasions.

Expression of sseA is Dependent on SsrAB

To establish if the sse genes are part of the SPI2 secretion system, the expression of an sseA::luc reporter gene fusion, integrated by homologous recombination into the chromosome of different SPI2 mutant strains, has been investigated (FIG. 11). Transcriptional activity of sseA in a wild-type background during growth in minimal medium was dramatically reduced by inactivation of the SPI2 two-component system. Transposon insertions in ssrA (mutant strain P3F4) and ssrB (mutant strain P8G12), encoding the sensor component and the transcriptional activator, respectively, resulted in 250 to 300-fold reduced expression of sseA. Inactivation of hilA, the transcriptional activator of SPI1 (Bajaj et al., 1996), had no effect on sseA gene expression. Transposon insertions in two genes encoding components of the SPI2 type III secretion apparatus (ssaJ::mTn5 and ssaT::mTn5; mutant strains P11D10 and P9B7; Shea et al., 1996) also had no significant effect on the expression of sseA. These data show that SsrA/B is required for the expression of sseA, but that hilA is not.

Expression of SPI2 Genes within Macrophages is Dependent on SsrA/B

The presence of S. typhimurium within eukaryotic cells (macrophages) induces the expression of SPI2 genes as indicated by analysis of fusions to ssaB and ssaH. This expression is dependent on the two component regulatory system SsrA/B encoded by SPI2.

The murine macrophage-line cell line J744 was used for this experiment. Macrophages were infected at a multiplicity of infection of 10 bacteria per macrophage with MvP131 (luc fusion to ssaB), MvP266 (luc fusion of ssaH) and MvP244 (luc fusion to ssaB in a ssrB negative background). Extracellular bacteria were killed by the addition of gentamicin (20 µg/ml). At various time points, macrophages were lysed by the addition of 0.1% Triton X-100, and intracellular bacteria were enumerated by plating serial dilutions onto LB agar plates. A further aliquot of the bacteria was recovered and the luciferase activity was determined. Luciferase activities were expressed a relative light emission per bacteria.

Effects of a Mutation in ssrB on the Secreted Effector Protein of SPI1 SipC

Analysis of proteins secreted into the growth medium by the S. typhimurium SPI2 mutant strain MvP320 (non-polar mutation in a, FIG. 12) revealed the absence or strong reduction in the amounts of the secreted SPI1 effector protein (Hensel et al., 1997b). These SPI2 mutants are also reduced in their ability to invade cultured epithelial cells or cultured macrophages (Hensel et al., 1997b). To examine this phenomenon in greater detail, we expressed recombinant SipC (rSipC) and raised antibodies against rSipC in rabbits. In Western blots, antiserum against rSipC reacted with a 42 kDa protein from precipitates of culture supernatants of S. typhimurium wild-type strain NCTC12023. No reaction was observed with supernatants from cultures of EE638, a strain deficient in SipC (Hueck et al., 1995). Furthermore, in Western blots SipC could not be detected in culture supernatants of the SPI2 mutants MvP320. However, SipC was detected in culture supernatants of other SPI2 mutants like P2D6 (ssa V::mTn5), P9B6 (ssa V::mTn5) and NPssa V(ssa V::aphT) (Deiwick et al., 1998). The detection by antiserum of SipC in culture supernatants of various strains was in accord with the presence or absence of SipC as detected by SDS-PAGE. Further it was analyzed whether the absence of SipC in culture supernatants of SPI2 mutant strains was due to defective secretion of SipC via the type III secretion system or reduced synthesis of SipC in these strains. Antiserum against rSipC was used to detect SipC in pellets of cultures grown under inducing conditions for the expression of SPI1 genes (i.e. stationary phase, high osmolarity, low oxygen) (Bajaj et al., 1996). Analysis of wild-type and strains carrying various mutations in SPI1 and SPI2 genes indicated highly reduced amounts of SipC in the mutants with a non-polar mutation in ssrB. However, SipC was detected at levels comparable to those observed in pellets of wild-type cultures and SPI2 mutant strains P2D6, P9B6 and NPssa V. The effect on SipC synthesis is not due to reduced growth rates or reduced protein levels in SPI2 mutants, since both parameters were comparable for the wild-type and SPI2 mutants.

Effects of a Mutation in the SPI2 Gene ssrB on the Expression of SPI1 Genes

In order to assay the effect of SPI2 mutations on the expression of SPI1 genes, previously characterized fusions of lacZ to various SPI1 genes (Bajaj et al., 1995; Bajaj et al., 1996)

were transduced into the SPI2 mutant MvP320 and various SPI1 mutants to generate a set of reporter fusion strains. The expression of the reporter β-galactosidase in cultures grown under conditions inducing for SPI1 expression (see above) was assayed. A Tn insertion in hilA (P4H2) reduced the expression of prgK as well as sipC, while an insertion in spaRS(P6E11) only affected the expression of sipC. Some mutant strains with a mutation in the SPI2 gene ssrB encoding a components of the two component regulatory system showed reduced expression of reporter fusions to prgK and sipC (FIG. 11). The effects on the expression of both genes was similar. Other mutant strains with Tn insertions in ssaV (P2D6, P9B6), as well as mutant NPssaV harbouring a non-polar insertions in ssaV, had levels of expression of prgK and sipC comparable to that of corresponding reporter fusions in a wild-type genetic background. Analysis of lacZ fusions to prgH and invF revealed a similar effect on expression as shown for prgK and sipC.

A Mutation in the SPI2 Gene ssrB Affects Expression of the SPI1 Regulator hilA

Analysis of reporter fusions to sipC and prgK indicated that expression of genes in two different operons of SPI1 can be affected by SPI2 mutations, suggesting that these mutations affect other SPI1 genes involved in regulation of sipC and prgK. It has been demonstrated previously that the expression of SPI1 genes is under the control of the transcriptional activator HilA (Bajaj et al., 1995; Bajaj et al., 1996). The expression of hilA was therefore analyzed in the presence of a SPI2 mutation in ssrB. The SPI2 mutant strain MvP320 had largely diminished levels of hilA expression. Again, very low levels of hilA expression were observed in mutants that had reduced levels of prgK and sipC expression. To analyze whether the effect of the SPI2 mutation on sipC expression resulted from the reduced expression of hilA, we next performed complementation experiments in various mutant strains harbouring pVV135 (constitutive expression of hilA) (Bajaj et al., 1996) or pVV214 (expression of hilA from the native promoter) (Bajaj et al., 1995). In accordance with a previous study (Bajaj et al., 1995), the hilA mutation of strain P4H2 was complemented by pVV214. However, the sipC expression was not restored in the mutant strain MvP320 harbouring either pVV135 or pVV214.

Construction of the ssrA and ssrB Mutant *S. typhimurium* Strains MvP284 and MvP320

Mutant MvP284, ssrA. The ssrA gene (FIG. 12) was subcloned from the phage clone λ2 derived plasmid p2-2 on a 5.7 kb BamHI fragment in pUC18 as indicated in Table 1. A 1.6 kb fragment was recovered after HindIII and EcoRV digestion of p2-2 and subcloned in HindIII/HincII-digested pbluescript II KS +. The resulting construct termed p2-20 was digested with HincII and dephosphorylated with alkaline phosphatase. The aphT cassette was isolated as described above and ligated to the linearized plasmid p2-20 in the same orientation into the unique HincII site. After transformation of *E. coli* XL-1 Blue and selection against kanamycin and carbenicillin (50 µg/ml each) one clone has been chosen and the harbouring plasmid isolated. This plasmid was termed p2-21 and its identity proved via restriction analysis. p2-21 was further digested with KpnI and XbaI, a 2.5 kb fragment isolated and ligated to KpnI/XbaI-digested pKAS32. This plasmid was electroporated into *E. coli* CC118 λpir and transformants selected to kanamycin and carbenicillin (50 µg/ml each). As done before, one clone was chosen, its plasmid with the according DNA fragment in pKAS32, termed p2-22, isolated and confirmed by restriction analysis. Plasmid p2-22 was electroporated into *E. coli* S17-1 λpir and transferred into *S. typhimurium* NCTC12023 (streptomycin resistant) by conjugation as has been described previously (de Lorenzo and Timmis, 1994). Exconjugants in which the ssrA gene had been replaced by the cloned gene disrupted by insertion of the aphT cassette were selected by its growth on M9 + glucose minimal medium agar plates (Maloy et al., 1996) and its resistance to kanamycin and carbenicillin (100 µg/ml). The resulting exconjugants were finally shown to have a lactose negative phenotype and to be sensitive to kanamycin and streptomycin. Selected clones were further examined by Southernblot analysis. In order to exclude possible mutations which might have been developed during the cloning procedure the mutated ssrA allele was transfered into a fresh *Salmonella* background by P22 transduction (described by Maloy et al., 1996). The resulting *Salmonella* strain MvP284 was examined for the presence of the resistance cassette within the ssrA gene by the use of primers ssrA-For (5'-AAG GAA TTC AAC AGG CAA CTG GAG G-3') (SEQ ID NO:64) and ssrA-Rev (5-CTG CCC TCG CGA AAA TTA AGA TAA TA-3') (SEQ ID NO65). Amplification of DNA from clones containing the wild-type ssrA allele resulted in a PCR product of 2800 bp, use of DNA from clones harbouring a ssrA allele disrupted by the aphT cassette resulted in a PCR product of 3750 bp. The resulting *Salmonella* strain MvP320 was examined for the presence of the resistance cassette within the ssrB gene by the use of Southern hybridization analysis of total DNA of exconjugants.

Mutant MvP320, ssrB. The ssrB gene (FIG. 12) was subcloned from the phage clone λ1 derived plasmid p1-6 on a 4.8 kb PstI/BamHI-fragment in pT7-Blue as indicated in Table 1. A 1.7 kb fragment was recovered after BamHI and HincII digestion of p1-6 and subcloned in BamHI/HincII-digested pBluescript II KS +. The resulting construct termed p1-20 was digested with EcoRV and dephosphorylated with alkaline phosphatase. The aphT cassette was isolated as described above and ligated to the linearized plasmid p1-20 in the same orientation into the unique EcoRV site. After transformation of *E. coli* XL-1 Blue and selection against kanamycin and carbenicillin (50 µg/ml each) one clone has been chosen and the harbouring plasmid isolated. This plasmid was termed p1-21 and its identity confirmed by restriction analysis. p1-21 was further digested with KpnI and XbaI, a 2.5 kb fragment isolated and ligated to KpnI/XbaI-digested pKAS32. This plasmid was electroporated into *E. coli* CC118 λpir and transformed bacteria selected to kanamycin and carbenicillin (50 µg/ml each) was performed. As done before, one clone was chosen, its plasmid with the according DNA fragment in pKAS32, termed p1-22, isolated and confirmed by restriction analysis. Plasmid p1-22 was electroporated into *E. coli* S17-1 λpir and transferred into *S. typhimurium* NCTC12023 (streptomycin resistant) by conjugation as has been described previously (de Lorenzo and Timmis, 1994). Exconjugants in which the ssrB gene had been replaced by the cloned gene disrupted by insertion of the aphT cassette were selected by its growth on M9 + glucose minimal medium agar plates (Maloy et al., 1996) and its resistance to kanamycin and carbenicillin (100 µg/ml). The resulting exconjugants were finally shown to have a lactose negative phenotype and to be sensitive to kanamycin and streptomycin. Selected clones were further examined by Southernblot analysis. In order to exclude possible mutations which might have been acquired during the cloning procedure the mutated ssrB allele has been transferred into a fresh *Salmonella* background by P22 transduction (described by Maloy et al., 1996). Screening of mutants with a insertion of the aphT cassette within the ssrB locus was performed by PCR using primers ssrB-For (5'-CTT AAT TTT CGC GAG GG-3') (SEQ ID NO:66) and ssrB-Rev (5'-GGA CGC CCC TGG TTA ATA-3') (SEQ ID NO:67). Amplification of DNA from clones containing the wild-type ssrB allele resulted in a PCR product of 660 bp, use of DNA from clones harbouring a ssrB allele disrupted by insertion of the aphT cassette resulted in a PCR product of 1600 bp. The resulting *Salmonella* strain MvP320 was examined for the presence of the resistance cassette within the ssrB gene by the use of Southern hybridization analysis of total DNA of exconjugants.

Construction of the Mutant Strain MvP340 Carrying an In-frame Deletion in ssrA

A deletion of 407 codons between codon 44 and 451 of ssrB was generated. Plasmid p2-2 was digested by BamHI and KpnI, a fragment of 3.7 kb was recovered and subcloned in pBluescript KS + to generate p2-50. Plasmid p2-50 was linearized by digestion with PstI, which cuts once within the subcloned fragment of the ssrA gene. Primers ssrA-del-1 (5'-GGT CTG CAG GAT TTT TCA CGC ATC GCG TC-3') (SEQ ID NO: 68) and ssrB-del-2 (5'-GGT CTG CAG AAC CAT TGA TAT ATA AGC TGC-3') (SEQ ID NO:69) were designed to introduce PstI sites. PCR was performed using linearized p2-50 as template DNA. The TAQPLUS® polymerase (*Pyrococcus furiosus* DNA polymerase+recombinant *T. Aquaticus* YT1 polymerase) (Stratagene) was used according to the instructions of the manufacturer. Reactions of 100 μl volume were set up using 10 μl of 10× TAQPLUS® Precision buffer containing magnesium chloride, 0.8 μl of 100 mM dNTPs, 250 ng DNA template (linearized p2-50), 250 ng of each primer and 5 U of TAQPLUS® DNA polymerase (*Pyrococcus furiosus* DNA polymerase+recombinant *T. Aquaticus* YT1 polymerase). PCR was carried out for 35 cycles of: 95° C. for 1 minute, 60° C. for 1 minute, 72° C. for 6 minutes. Then a final step of 72° C. for 10 minutes was added. 10 μl of the PCR reaction were analyzed. A product of the expected size was recovered, digested by PstI, self-ligated, and the ligation mixture was used to transform *E. coli* DH5á to resistance to carbenicillin. Plasmids were isolated from transformants and the integrity of the insert and the deletion was analyzed by restriction analysis and DNA sequencing. The insert of a confirmed construct was isolated after digestion with XbaI and KpnI and ligated to XbaI/KpnI-digested vector pKAS32. The resulting construct was used to transform *E. coli* S17-1 λpir to resistance to carbenicillin, and conjugational transfer of the plasmid to *S. typhimurium* (Nal$^R$, Strep$^R$) was performed according to standard procedures (de Lorenzo and Timmis, 1994). Exconjugants that had integrated the suicide plasmid by homologous recombination were selected by resistance to nalidixic acid and carbenicillin, and screened for sensitivity to streptomycin. Such clones were grown in LB to OD600 of about 0.5 and aliquots were plated on LB containing 250 μg/ml streptomycin to select for colonies which had lost the integrated plasmid and undergone allelic exchange. Clones resistant to streptomycin but sensitive to carbenicillin were used for further analysis. Screening of mutants with a deletion within the ssrA locus was performed by PCR using primers ssrA-For (5'-AAG GAA TTC AAC AGG CAA CTG GAG G-3') (SEQ ID NO:64) and ssrA-Rev (5-CTG CCC TCG CGA AAA TTA AGA TAA TA-3') (SEQ ID NO:65). Amplification of DNA from clones containing the wild-type ssrA allele resulted in a PCR product of 2800 bp, use of DNA from clones harbouring a ssrA allele with an internal deletion resulted in a PCR product of 1580 bp. The integrity of clones harbouring the ssrA deletion was further confirmed by Southernanalysis of the ssrA locus. Finally, the ssrA locus containing the internal in-frame deletion was moved into a fresh strain background of *S. typhimurium* by P22 transduction (Maloy et al., 1996) and the resulting strain was designated MvP340.

Southern Hybridization

Genomic DNA of *Salmonella* was prepared as previously described (Hensel et al., 1997). For Southern hybridization analysis, genomic DNA was digested with EcoRI or EcoRV, fractionated on 0.6% agarose gels and transferred to Hybond N$^+$ membranes (Amersham, Braunschweig). Various probes corresponding to the ssrA and ssrB region were obtained as restriction fragments of the subcloned insert of λ1 and λ2.

Example 9

Evaluation of Safety of *S. Typhimurium* Strain MvP320

For competition assays between *S. typhimurium* wild-type and the mutant strain MvP320, bacteria were grown in LB to an optical density at 600 nm of 0.4-0.6. Cultures were diluted and aliquots of the two cultures were mixed to form an inoculum containing equal amounts of both strains. The ratio of both strains was determined by plating dilutions on LB plates containing antibiotics selective for individual strains. An inoculum of about $10^4$ colony forming units (cfu) was used to infect 6 to 8 weeks old female BALB/c mice (Charles River Breeders, Wiga) by injection into the peritoneal cavity. At several time points after infection mice were sacrificed by cervical dislocation and the bacterial load of liver and spleen was determined by plating tissue homogenates using the 'WASP' (Meintrup, Lähden) spiral plating device. Plating was performed using LB plates containing 50 μg/ml kanamycin or 100 μg/ml nalidixic acid to select for the mutant strains or the wild-type, respectively.

Strain MvP320 harbouring the aphT gene cassette in ssrB was recovered in at least 1000-fold lower numbers than the *S. typhimurium* wild-type strain. These data indicate that ssrB contributes significantly to systemic infections of *S. typhimurium* in the mouse model of salmonellosis.

Statistical Analysis of all Experiments.

Statistical significance between paired samples was determined by Student's t test. The significance of the obtained results was determined using the statgraphic plus for windows 2.0 software (Statistical Graphic Corp.).

Example 10

Characterization of the in vivo Inducible $P_{ssaE}$ Promoter (Promoter B, FIG. 24B)

The promoter which is located upstream of ssaE ($P_{ssaE}$, formerly called Promoter B) was shown to be regulated by the ssrAB locus. A DNA fragment comprising nucleotide 800 to 120 (800-1205) in the included sequence (FIG. 21A) was shown to confer ssrB-dependent regulation upon the expression of a reporter gene (gfp) fused to the promoter. The DNA fragment was cloned on a low-copy plasmid in front of the gfp gene. As has been shown previously for other reporter gene constructs, induction of expression from $P_{ssaE}$ (800-1205) was observed in magnesium minimal medium (Deiwick et al., 1999) and was dependent on the presence of a chromosomal wild type allele of ssrB. A shorter DNA fragment, comprising nucleotide 923 to 1205 (923-1205) in the included sequence, did not confer regulation upon expression of gfp. However, expression was reduced compared to the $P_{ssaE}$ (800-1205) fragment and was not induced in magnesium minimal medium nor was it dependent on ssrB. Thus, the $P_{ssaE}$ (800-1205) fragment comprises promoter active and regulatory sequences, probably including an SsrB-binding site.

DESCRIPTION OF THE DRAWINGS

Figure 2B:
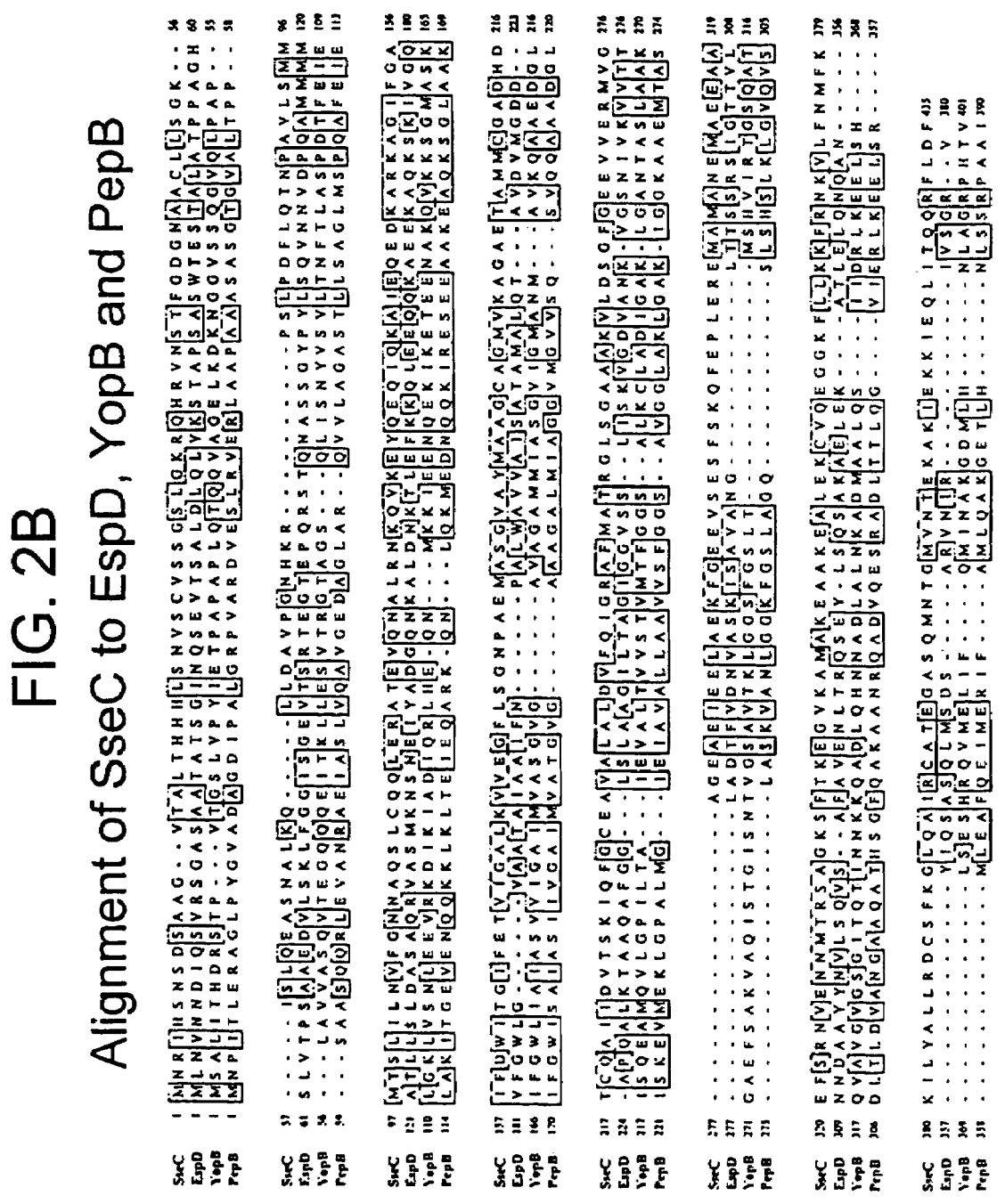

FIG. 2a. Alignment of the deduced SseB amino acid sequence (SEQ ID NO:5) to EspA of EPEC (SEQ ID NO:40) (Elliot et al., 1998). The ClustalW algorithm of the MacVector 6.0 program was used to construct the alignments. Similar amino acid residues are boxed, identical residues are boxed and shaded.

FIG. 2b. Alignment of the deduced SseC amino acid sequence (SEQ ID NO:8) to EspD of EPEC (SEQ ID NO:41) (Elliot et al., 1998), YopB of *Yersinia enterocolitica* (SEQ ID NO:42) (Hakansson et al., 1993), and PepB of *Pseudomonas aeruinosa* (SEQ ID NO:43) (Hauser et al., 1998). The ClustalW algorithm of the MacVector 6.0 program was used to construct the alignments. Positions where at least three amino acid residues are similar are boxed, where at least three residues are identical are boxed and shaded.

FIG. 12. Map of *Salmonella* Pathogenicity Island 2 (A) indicating the positions of the mutations in strains MvP284 and MvP320 (B). A partial restriction map of the genomic region is shown, and the position of inserts of plasmids relevant for this work is indicated (C). B, BamHI; C, ClaI; H, HindIII; P, PstI; V; S, SmaI; EcoRV; II, HincII.

FIG. 14 shows the principle of how mutations having a different grade of attenuation can be generated. As shown in A, the inactivation of one effector gene such as sse results in a low grade of attenuation. As shown in B, the additional inactivation of a gene located outside the SPI2 locus such as aroA results in a medium grade of attenuation. By insertional mutation with a polar effect all genes in a polycistronic cluster are affected which results in a high grade of attenuation, as shown in C. As shown in D, the inactivation of a regulatory gene such as ssrB results in a supreme attenuation.

FIG. 16 illustrates the selective marker cassette.

FIG. 17 illustrates the gene expression cassette and the induction thereof in a two-phase system. The gene expression cassette comprises a promoter, optionally a gene cassette comprising one or more expression units and optionally one or more transcriptional terminators for the expression units and/or a transcribed sequence 5' to the gene expression cassette.

FIG. 18 shows the structural requirements of the gene expression unit for the delivery of heterologous antigens into various compartments, i.e. accessory sequences that direct the targeting of the expression product.

FIG. 19 shows a transactivator cassette in a one-phase system and a two-phase system.

FIG. 21A shows the genomic sequence of a region of the SPI2 locus from *Salmonella* comprising the complete sequences of the genes ssaE to ssaI and partial sequences of ssaD and ssaJ (cf. FIG. 12) (SEQ ID NO:1).

FIG. 21B shows the nucleotide sequence of a region of the SPI2 locus from *Salmonella* comprising the coding sequences for ssrA and ssrB (SEQ ID NO:2).

FIGS. 22A-Q each show the nucleotide sequence of the respective gene indicated (SEQ ID NOS:3, 5, 7, 9, 12, 14, 16, 18, 20, 22, 24, 26, 28, 30, 32, 34, and 36).

FIGS. 23A-Q each show the amino acid sequence of the respective polypeptide indicated. (SEQ ID NO:4, 6, 8, 11, 13, 15, 17, 19, 21, 23, 25, 27, 29, 31, 33, 35, and 37)

FIGS. 24A,B each show a nucleotide sequence comprising an in vivo inducible promoter (SEQ ID NO:38 and SEQ ID NO:39).

Literature

Figure 1A:
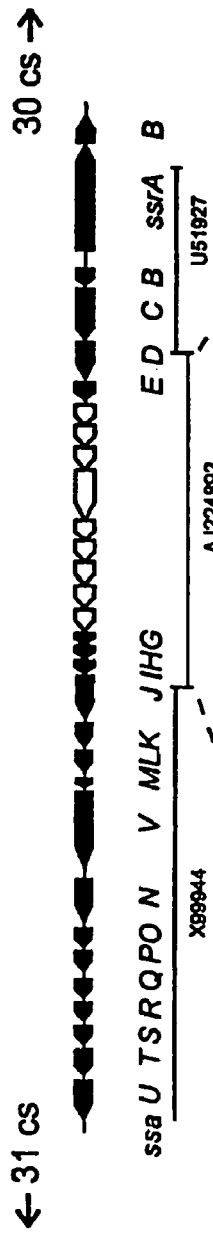
FIG. 1. Map of *Salmonella* Pathogenicity Island 2 (A) indicating the positions of the mutations in strains MvP101, MvP102, and MvP103 (B). A partial restriction map of the genomic region is shown, and the positions of plasmid inserts relevant for this work are indicated (C). B, BamHI; C, ClaI; E, EcoRI; P, PstI; V, EcoRV; S, SmaI; EMBL database accession numbers are indicated for the sequences in (A).
Figure 1B:
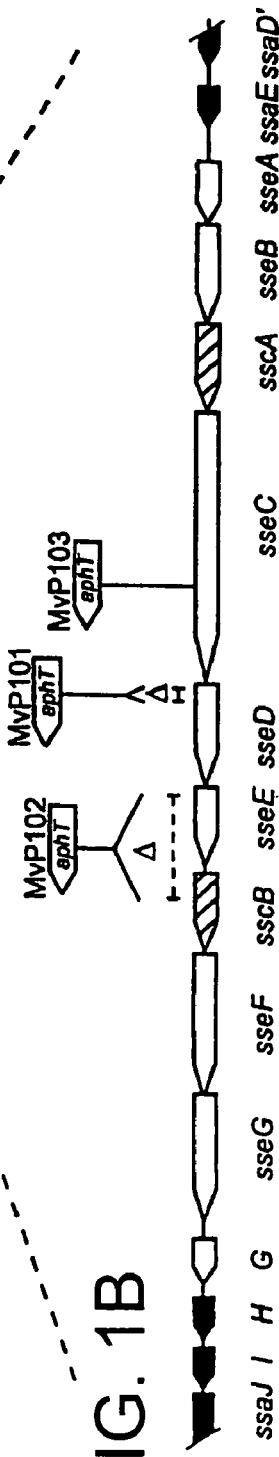
Figure 1C:
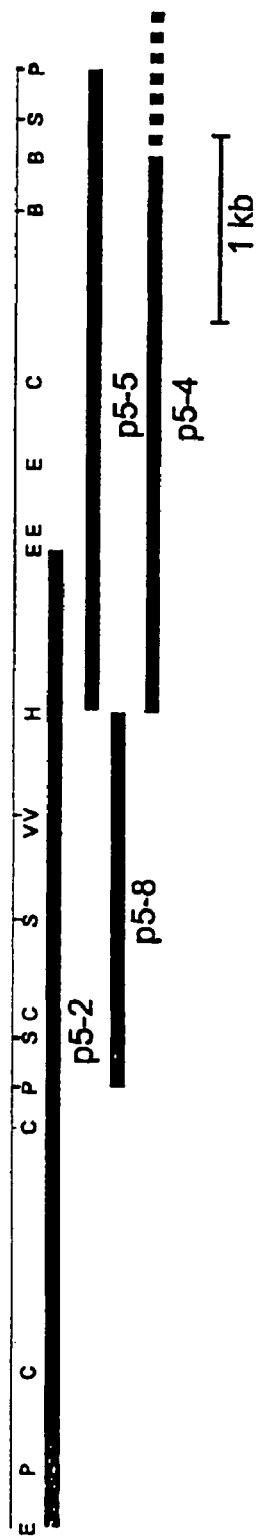
Figure 3:
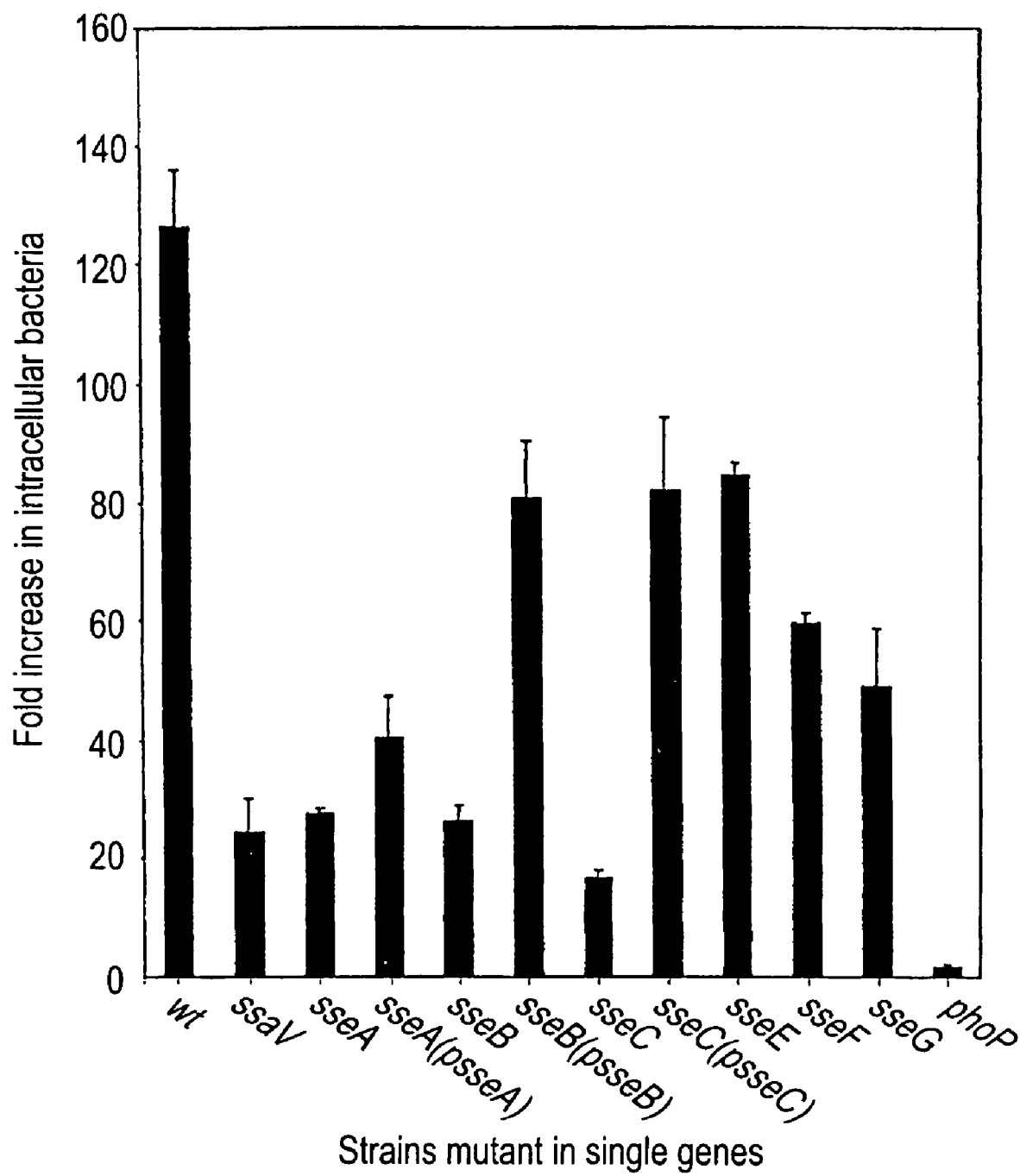
FIG. 3. Intracellular accumulation of *S. typhimurium* SPI2 mutants in RAW 264.7 macrophages. Following opsonization and infection, macrophages were lysed and cultured for enumeration of intracellular bacteria (gentamicin protected) at 2 h and 16 h post-infection. The values shown represent the fold increase calculated as a ratio of the intracellular bacteria between 2 h and 16 h post-infection. Infection was performed in in triplicates for each strain and the standard error from the mean is shown.
Figure 4A:
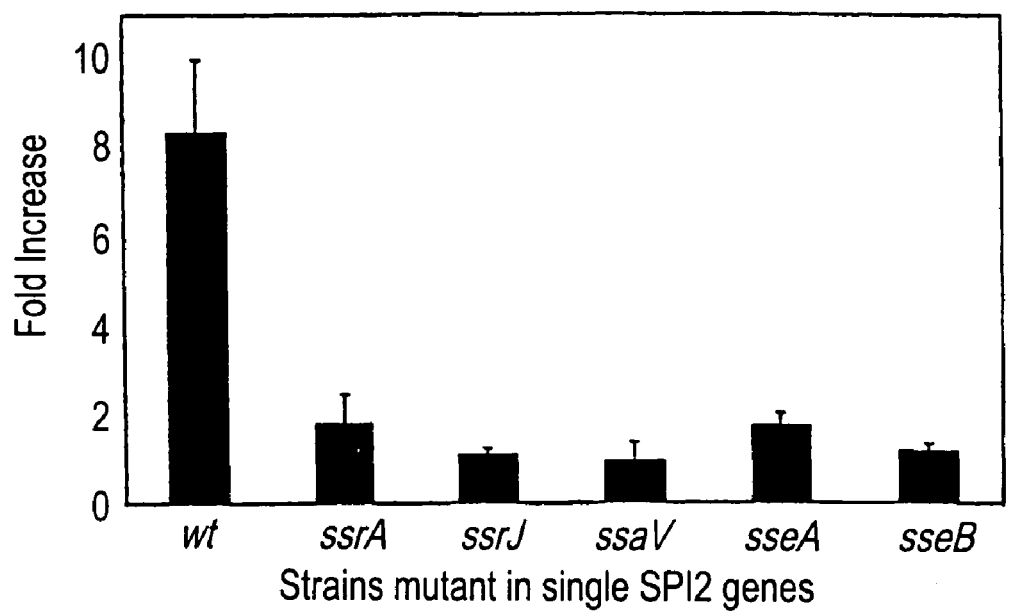
FIG. 4. Intracellular survival and replication of SPI2 mutant *S. typhimurium* in (A) J774.1 cells and (B) periodate-elicited peritoneal macrophages from C3H/HeN mice. After opsonization and internalization, phagocytes were lysed and cultured for enumeration of viable intracellular bacteria at time 0 h. The values shown represent the proportion of this intracellular inoculum viable at 20 h+the standard error of the mean. Samples were processed in triplicate, and each experiment was performed at least twice.
Figure 4B:
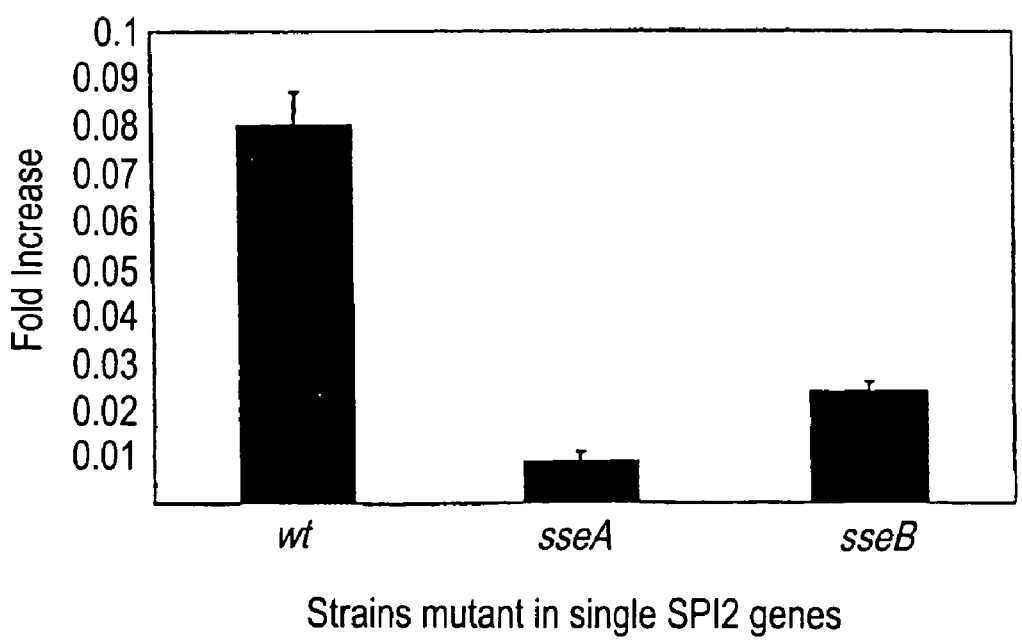
Figure 5:
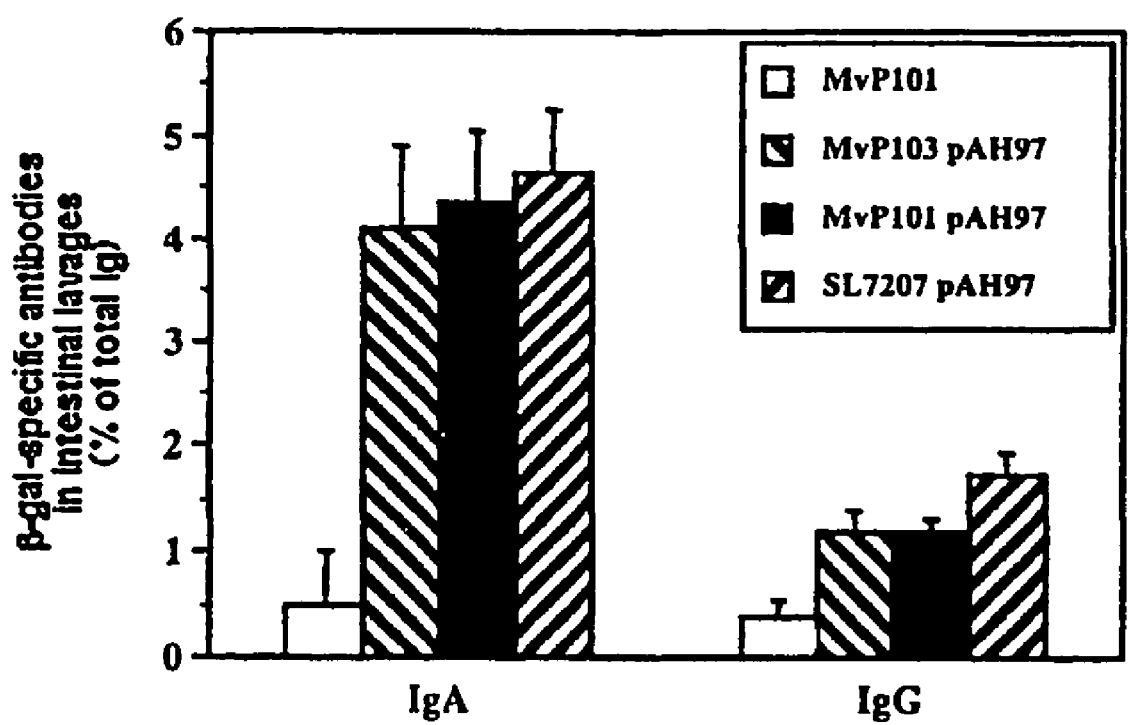
FIG. 5. β-gal-specific antibodies in intestinal lavages of mice orally immunized with either MvP101[pAH97], MvP103 [pAH97], SL7207 [pAH97] or MvP101 at day 52 after immunization. Results are expressed as percentage of the corresponding total Ig subclass present in the intestinal lavage, the SEM is indicated by vertical lines. Significant levels of antigen-specific IgM could not be detected in any of the groups. The results obtained with MvP103 and SL7207 (not shown) were similar to those for MvP101.
Figure 6:
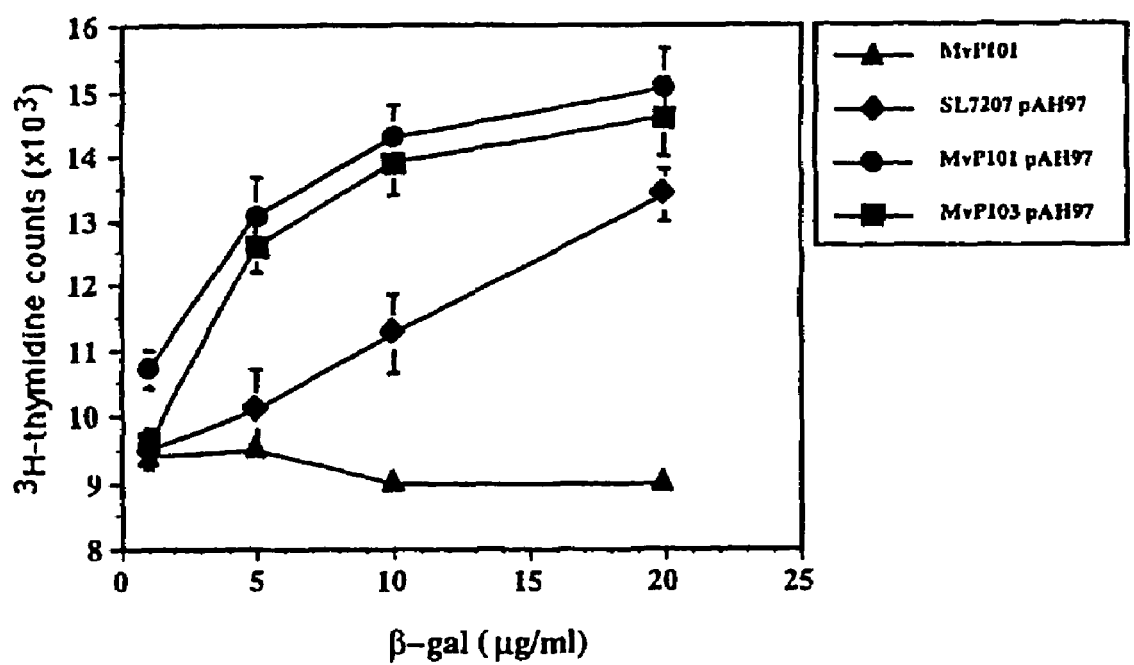
FIG. 6. β-gal-specific proliferative response of CD4 + enriched spleen cells from mice orally immunized with either MvP101 [pAH97], MvP103 [pAH97], SL7207 [pAH97] or MvP101. Cells were restimulated in vitro during a 4 day incubation with different concentrations of soluble β-gal. The values are expressed as mean cpm of triplicates; the SEM was in all cases lower than 10%. Background values obtained from wells without the stimulating antigen were subtracted. Results obtained with MvP103 and SL7207 (not shown) were similar to those obtained with MvP101.
Figure 7:
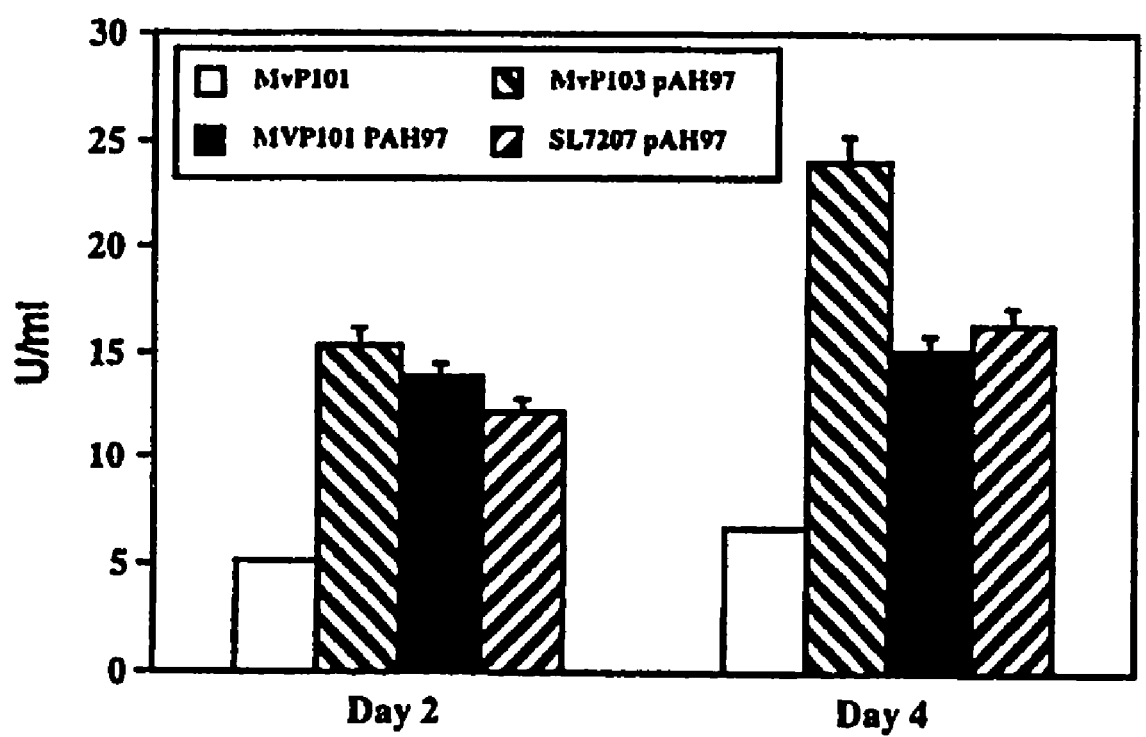
FIG. 7. IFN-γ present in supernatants from cultured CD4 + enriched spleen cells of mice orally immunized with either MvP101 [pAH97], MvP103 [PAH97], SL7207 [pAH97] or plasmidless MvP101 at day 2 and 4 of culture. Spleen cells were isolated from mice at day 52 after immunization, and CD4 + enriched populations were restimulated in vitro for four days in the presence of soluble β-gal (20 µg/ml). IFN-γ production was determined by ELISA, results represent the means of three determinations. The SEM is indicated by vertical lines, similar results were obtained using any of the plasmidless carriers (not shown). No significant differences with the control groups were observed when IL-2, IL-4, IL-5, IL-6 and IL-10 were tested (not shown).
Figure 8:
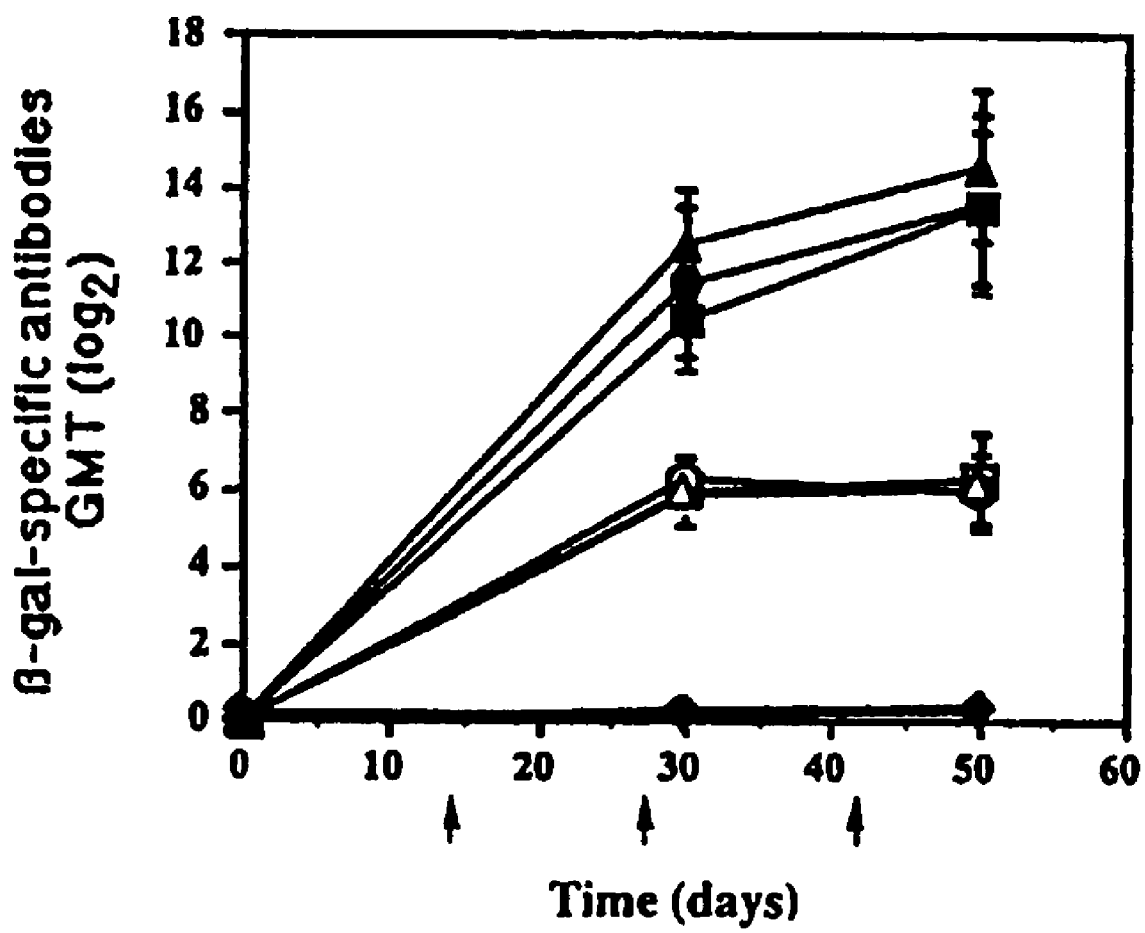
FIG. 8. Kinetics of the β-gal-specific serum IgG (closed symbols) and IgM (open symbols) antibody responses in mice (n=5) after oral immunization with either MvP101 [pAH97] (triangle), MvP103 [pAH97] (circle), SL7207 [pAH97] (square) or plasmidless MvP101 (diamond). Results are expressed as the reciprocal $\log_2$ of the geometric mean end point titer (GMT), the SEM was in all cases lower than 10%. Similar results were obtained using any of the plasmidless carriers (not shown), immunizations are indicated by arrows.
Figure 9:
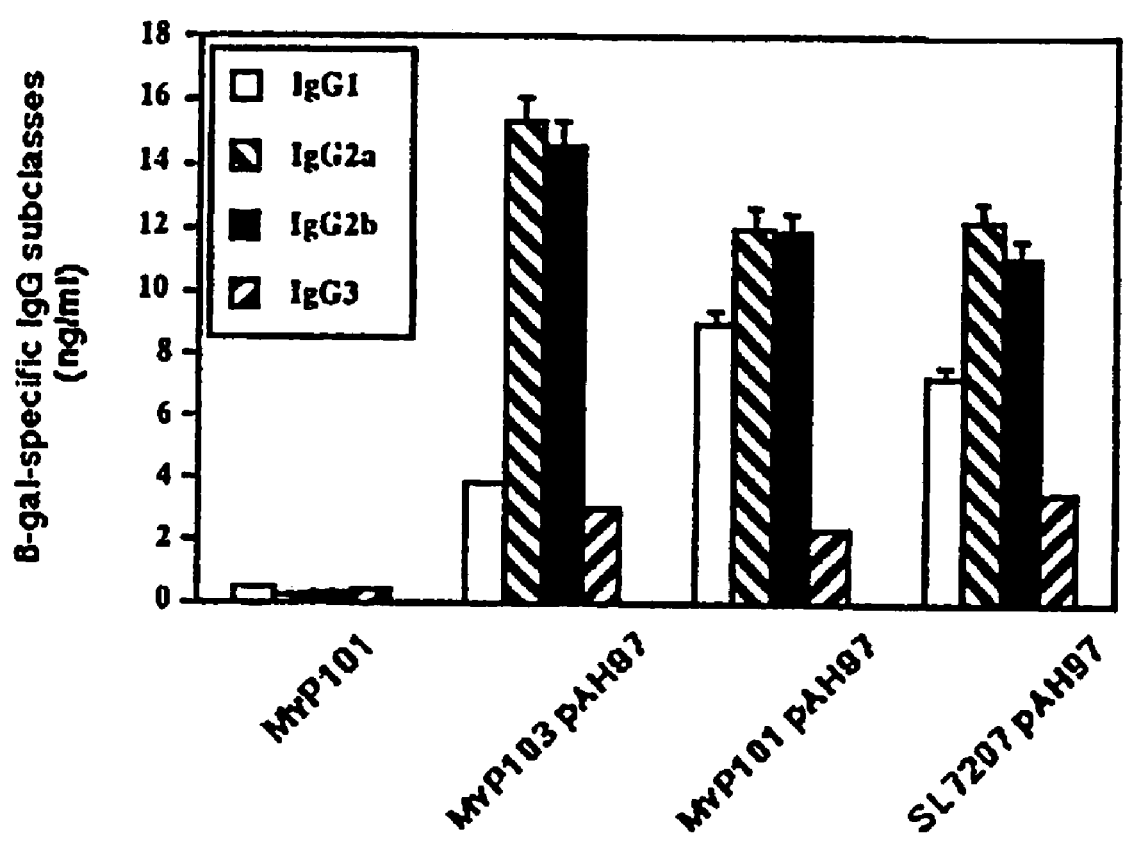
FIG. 9. Subclass profiles of the β-gal-specific IgG antibodies present in the serum of mice (n=5) orally immunized with either MvP101 [pAH97], MvP103 [pAH97], SL7207 [PAH97] or plasmidless MvP101 at day 52 post-immunization. Results are expressed as ng/ml, the SEM is indicated by vertical lines. Similar results were obtained using any of the plasmidless carriers (not shown).
Figure 10:
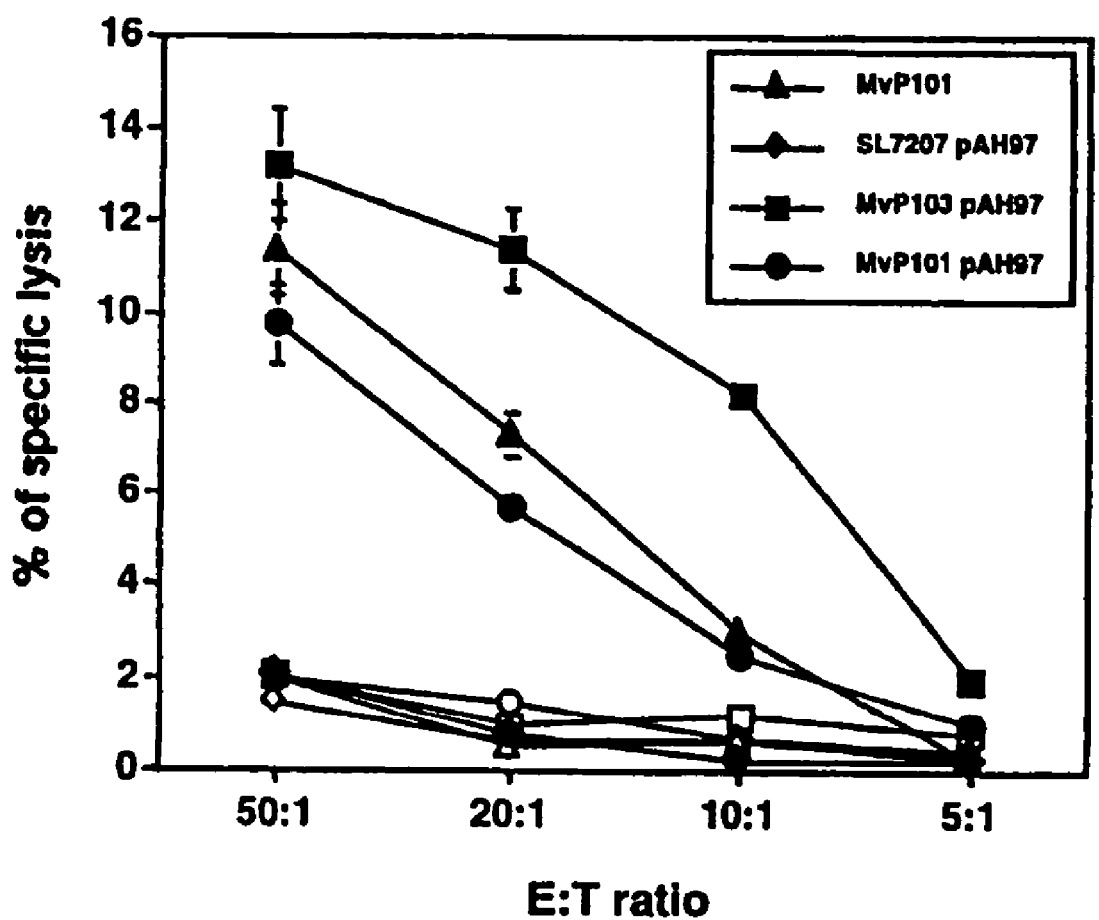
FIG. 10. Recognition of the MHC class I-restricted βGP1 epitope by lymphocytes primed in vivo in mice by oral vaccination with either MvP101 [pAH97], MvP103 [pAH97], SL7207 [pAH97] or plasmidless MvP101. Spleen cells from immunized mice were restimulated in vitro five days in the presence of 20 µM βGP1. At the end of the culture, lymphocytes were tested in a [$^3$H]-thymidine-release assay using P815 (open symbols) and βGP1-loaded P815 (closed symbols) as targets. Results are mean values of triplicate wells (one out of three independent experiments is shown) and are expressed as: [(retained cpm in the absence of effectors)–(experimentally retained cpm in the presence of effectors)/ retained cpm in the absence of effectors]×100; SEM were lower than 5% of the values. Similar results were obtained using any of the plasmidless carriers (not shown).
Figure 11:
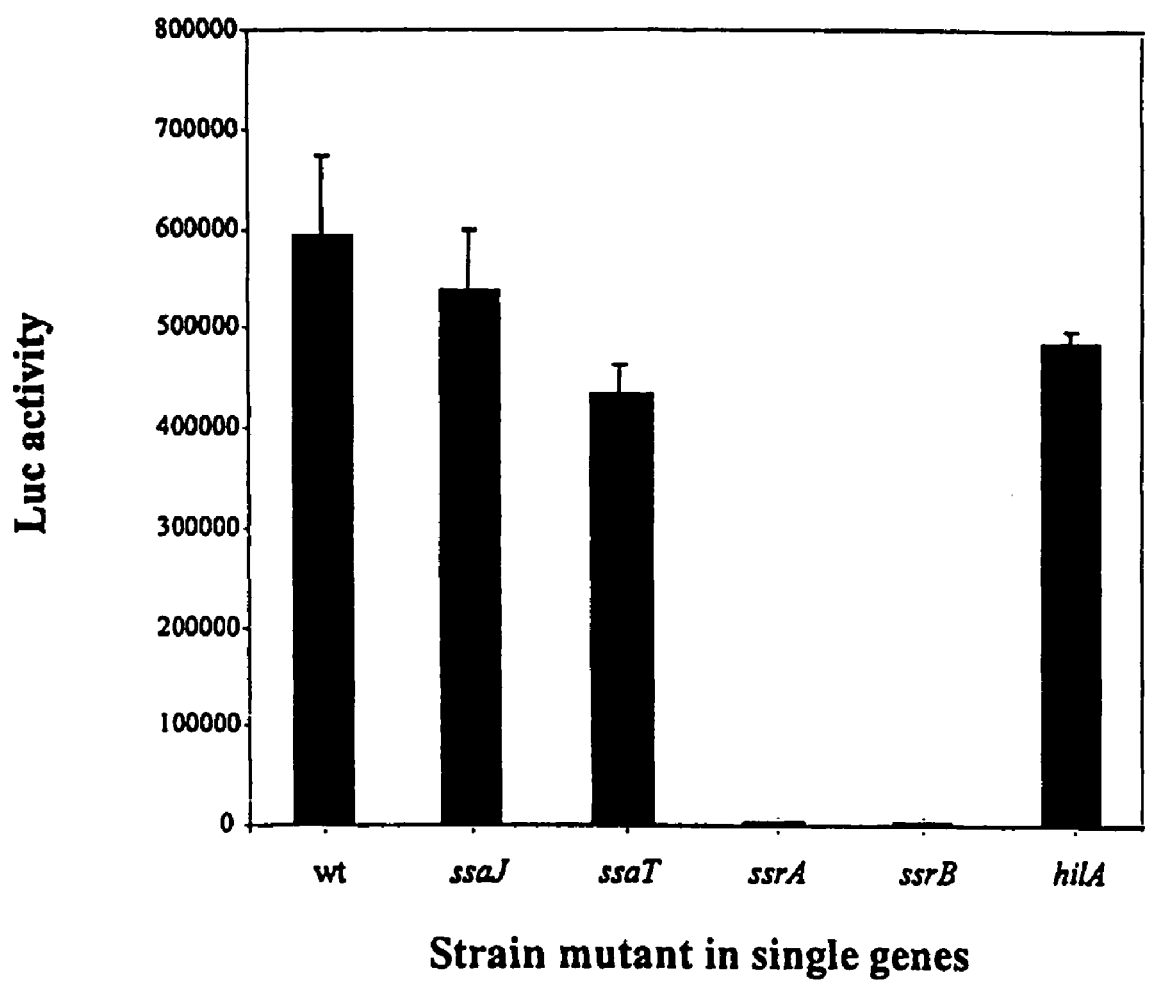
FIG. 11. Expression of an sseA::luc fusion in wild-type and mTn5 mutant strains of *S. typhimurium*.
Figure 13:
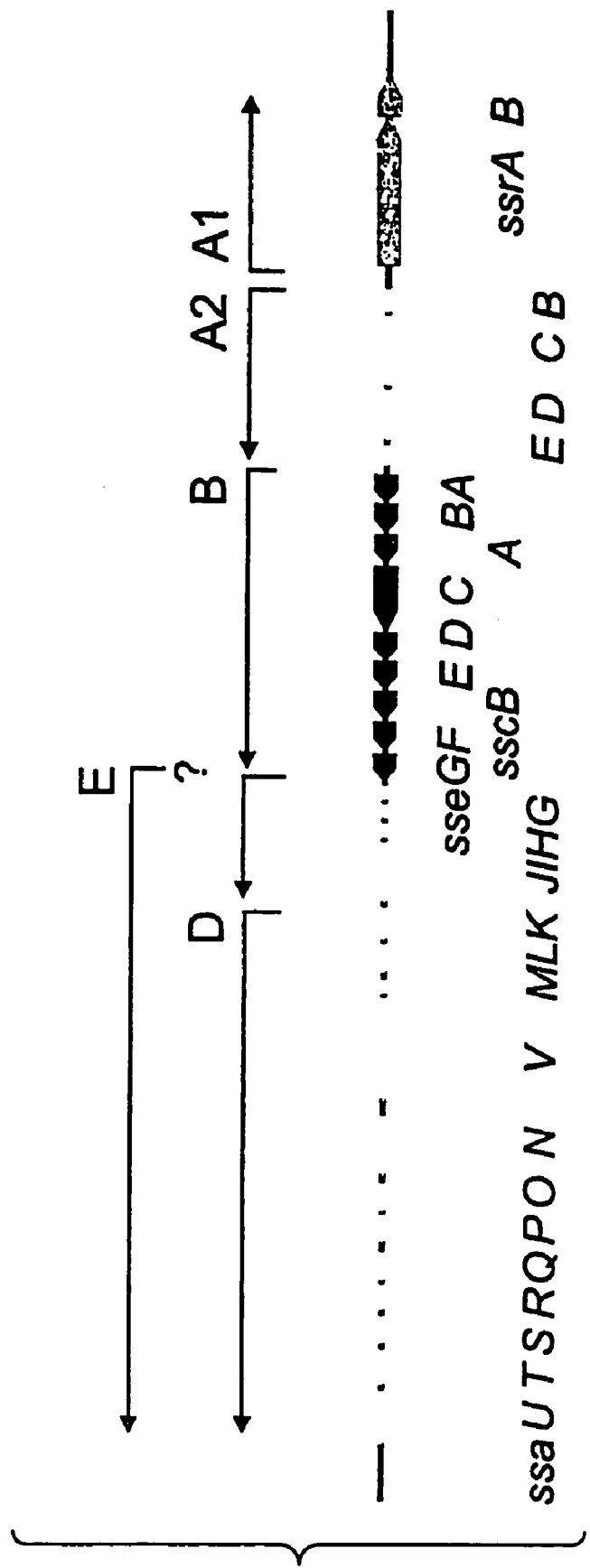
FIG. 13. Model for the transcriptional organization of SPI2 virulence genes. This model is based on the observation of the transcriptional direction of SPI2 genes, characterization of promoter activities
Figure 15:
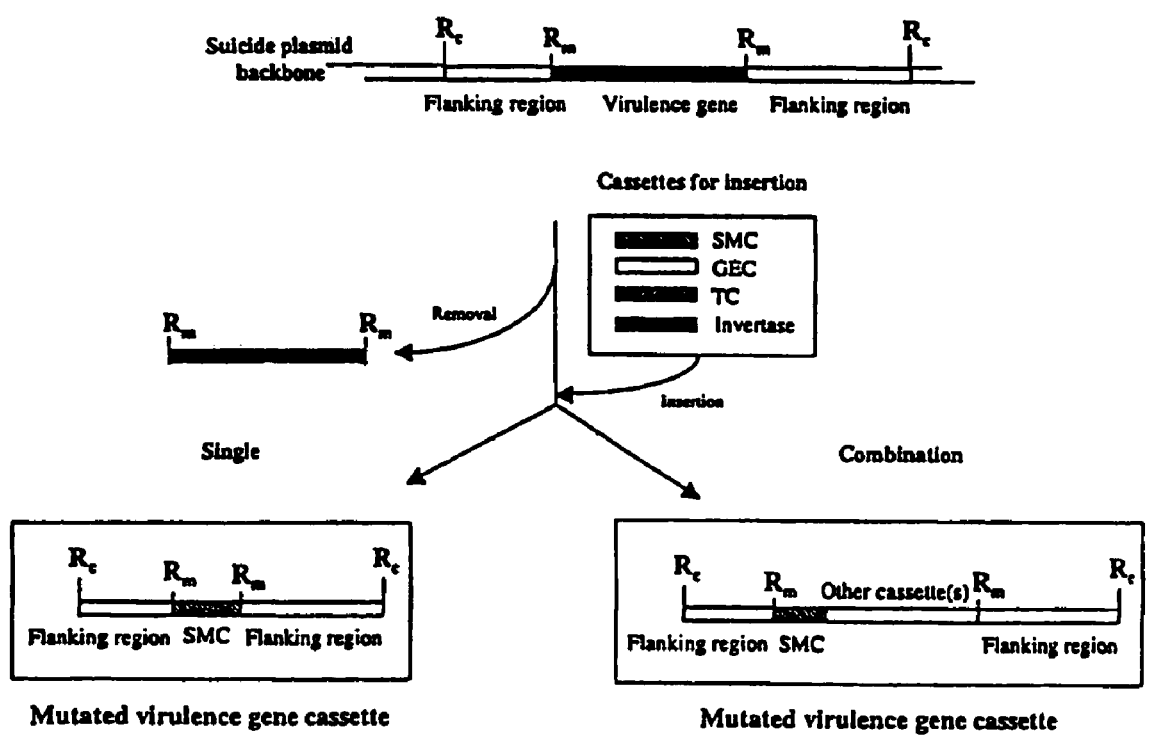
FIG. 15 shows the principle of insertional mutation by example of insertional mutation into a virulence gene. Different cassettes such as SMC, GEC, TC and/or invertase cassette may be inserted into a cloned virulence gene, thus yielding an inactivated virulence gene which may be introduced into a cell by homologous recombination using a virulence gene cassette.
Figure 20:
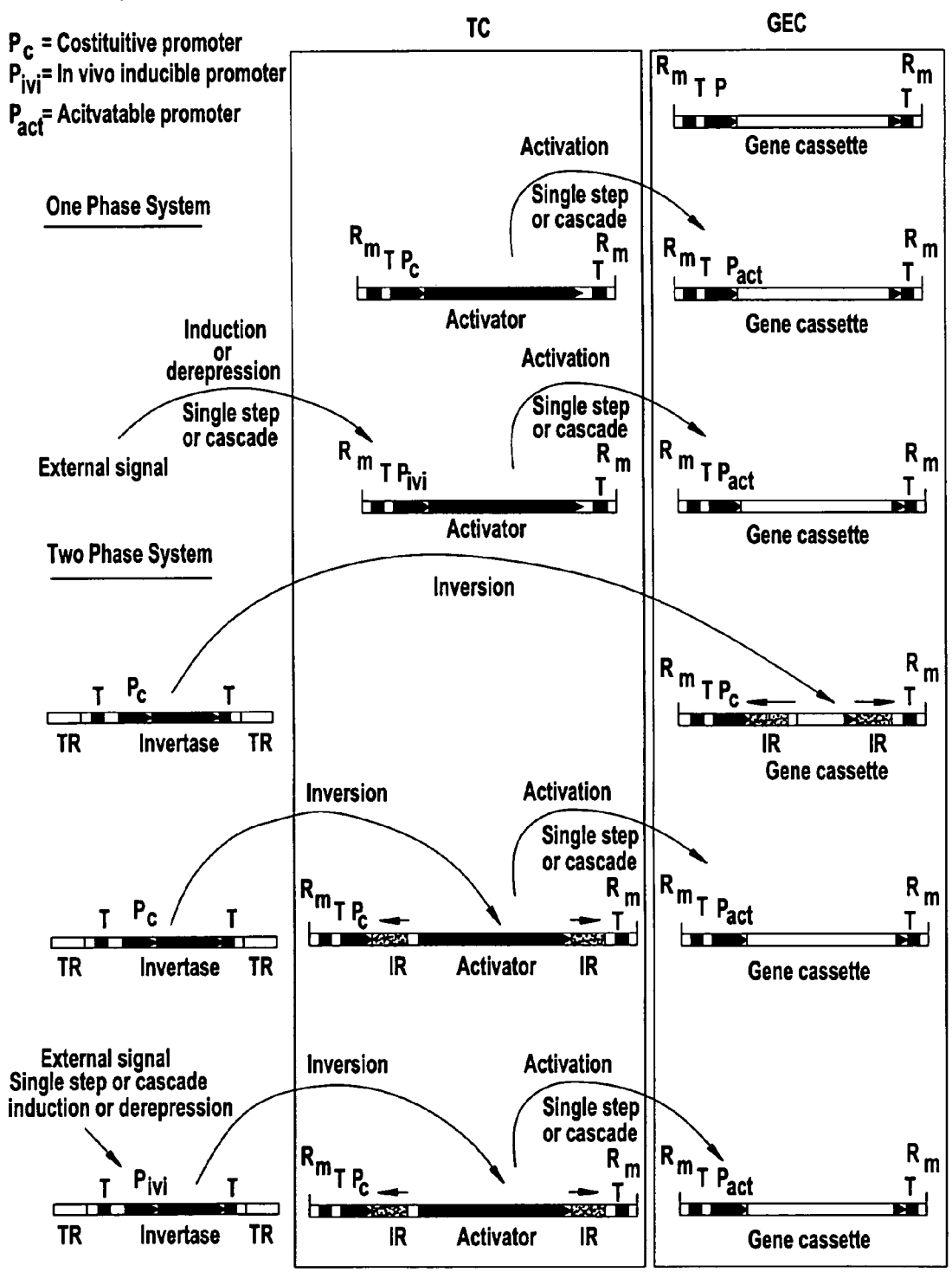
FIG. 20 shows different modes of gene expression as realized by the combination of different accessory sequences and/or cassettes in a one-phase system and a two-phase system.

Bajaj, V., Lucas, R. L., Hwang, C., Lee, C. A. (1996). Co-ordinate regulation of *Salmonella typhimurium* invasion genes by environmental and regulatory factors is mediated by control of expression. *Mol. Microbiol.* 22: 703-714.

Bajaj, V., Hwang, C., Lee, C. A. (1995). hilA is a novel ompR/toxR family member that activates the expression of *Salmonella typhimurium* invasion genes. *Mol. Microbiol.* 18: 715-727.

Baudry, B., Kaczorek, M. and Sansonetti, P. J. (1988) Nucleotide sequence of the invasion plasmid antigen B and C genes (ipaB and ipaC) of *Shigella flexneri. Microb Pathog* 4: 345-357.

Bogdanove, A. J., Beer, S. V., Bonas, U., Boucher, C. A., Collmer, A., Coplin, D. L., Cornelis, G. R., Huang, H.-C., Hutcheson, S. W., Panopoulos, N. J., and van Gijsegem, F. (1996) Unified nomenclature for broadly conserved hrp genes of phytopathogenic bacteria. *Mol Microbiol* 20: 681-683.

Buchmeier, N. A., Lipps, C. J., So, M. Y. H., Heffron, F. (1993) Recombination-deficient mutants of *Salmonella typhimurium* are avirulent and sensitive to the oxidative burst of macrophages. *Mol. Microbiol.* 7: 933-936

Chang, A. C. and Cohen, S. N. (1978). Construction and characterization of amplifiable multicopy DNA cloning vehicles derived from the P15A cryptic miniplasmid. *J Bacteriol* 134: 1141-1156.

Cirillo, D. M., Valdivia, R. H., Monack, D. M., Falkow, S. (1998) Macrophage-dependent induction of the *Salmonella* pathogenicity island 2 type III secretion system and its role in intracellular survival. *Mol. Microbiol.* 30: 175-88

Cirillo, J. D., Stover, C. K., Bloom, B. R., Jacobs, W. R. Jr., Barletta, R. G. (1995). Bacterial vaccine vectors and bacillus Calmette-Guerin. *Clin. Infect. Dis.* 20: 1001-1009.

DeGroote, M. A., Ochsner, U. A., Shiloh, M. U., Nathan, C., McCord, J. M., Dinauer, M. C., Libby, S. J., Vazquez-Torres, A., Xu, Y., and Fang, F. C. (1997) Periplasmic superoxide dismutase protects *Salmonella* from products of phagocyte NADPH-oxidase and nitric oxide synthase. *Proc Natl Acad Sci USA* 94: 13997-14001.

de Lorenzo, V. and Timmis, K. N. (1994). Analysis and construction of stable phenotypes in Gram-negative bacteria with Tn5- and Tn10-derived minitransposons. *Methods Enzymol.* 235, 386-405.

Devereux, J., Haeberli, P., and Smithies, O. (1984) A comprehensive set of sequence analysis programs for the VAX. *Nucleic Acids Res* 12: 387-395.

Deiwick, J., Nikolaus, T., Erdogan, S., Hensel, M. (1999). Environmental regulation of *Salmonella* pathogenicity island 2 gene expression. *Mol. Microbiol.* 31: 1759-1773.

Deiwick, J., Nikolaus, T., Shea, J. E., Gleeson, C., Holden, D. W., Hensel, M. (1998). Mutations in SPI2 genes affecting transcription of SPI1 genes and resistance to anti-microbial agents. *J. Bacteriol.* 180: 4775-4780.

Donnenberg, M. S., and Kaper, J. B. (1991) Construction of an eae deletion mutant of enteropathogenic *Escherichia coli* using a positive-selection suizide vector. *Infect Immun* 59: 4310-4317

Elliot, S. J., Wainwright, L. A., McDaniel, T. K., Jarvis, K. G., Deng, Y. K., Lai., L. C., McNamara, B. P., Donnenberg, M. S., and Kaper, J. B. (1998) The complete sequence of the locus of enterocyte affacement (LEE) from enteropathogenic *Escherichia coli* E2348/69. *Mol Microbiol* 28: 1-4.

Fields, P. I., Swanson, R. V., Haidaris., C. G., and Heffron, F. (1986) Mutants of *Salmonella typhimurium* that cannot survive within the macrophage are avirulent. *Proc Natl Acad Sci USA* 83: 5189-5193.

Forsberg, A., Pavitt, G. D. and Higgins, C. F. (1994). Use of transcriptional fusions to monitor gene expression: a cautionary tale. *J. Bacteriol.* 176: 2128-2132.

Galán, J. E., Ginocchio, C. and Costeas, P. (1992). Molecular and functional characterization of the *Salmonella* invasion gene invA: homology of InvA to members of a new protein family. *J. Bacteriol.* 174: 4338-4349.

Gentschev, I., Glaser, I., Goebel, W., McKeever, D. J., Musoke, A., and Heussler, V. T. (1998) Delivery of the p67 sporozoite antigen of *Theileria parva* by using recombinant *Salmonella* dublin: secretion of the product enhances specific antibody responses in cattle. *Infect Immun* 66: 2060-2064.

Gunn, J. S., Miller, S. 1. (1996). PhoP-PhoQ activates transcription of pmrAB, encoding a two-component regulatory system involved in *Salmonella typhimurium* antimicrobial peptide resistance. *J. Bacteriol.* 178: 6857-6864.

Hakansson, S., Schesser, K., Persson, C., Galyov, E. E., Rosqvist, R., Homble, F., and Wolf Watz, H. (1996) The YopB protein of *Yersinia pseudotuberculosis* is essential for the translocation of Yop effector proteins across the target cell plasma membrane and displays a contact-dependent membrane disrupting activity. *EMBO J* 15: 5812-5823.

Harlow, E., Lane, D. (1988). Antibodies: A laboratory manual. Cold Spring Harbour Laboratory Press, Cold Sprin Harbour, New York.

Hauser, A. R., Fleiszig, S., Kang, P. J., Mostov, K., and Engel, J. N. (1998) Defects in type III secretion correlate with internalization of *Pseudomonas aeruginosa* by epithelial cells. *Infect Immun* 66: 1413-1420.

Heithoff, D. M., Sinsheimer, R. L., Low, D. A., and Mahan, M. J. (1999) An essential role for DNA adenine methylation in bacterial virulence. *Science* 284: 967-970.

Hensel, M., Nikolaus, T., Egelseer, C. (1999). Molecular and functional analysis indicates a mosaic structure of *Salmonella* Pathogenicity Island 2. *Mol. Microbiol.* 31: 489-98.

Hensel, M., Shea, J. E., Baumler, A. J., Gleeson, C., and Holden, D. W. (1997a) Analysis of the boundaries of *Salmonella* pathogenicity island 2 and the corresponding chromosomal region of *Escherichia coli* K-12. *J Bacteriol* 179: 1105-1111.

Hensel, M., Shea, J. E., Raupach, B., Monack, D., Falkow, S., Gleeson, C., and Holden, D. W. (1997b) Functional analysis of ssaJ and the ssaK/U operon, 13 genes encoding components of the type III secretion apparatus of *Salmonella* pathogenicity island 2. *Mol Microbiol* 24: 155-167.

Hensel, M., Shea, J. E., Gleeson, C., Jones, M. D., Dalton, E., Holden, D. W. (1995). Simultaneous identification of bacterial virulence genes by negative selection. *Science* 269: 400-403.

Herrero, M., de Lorenzo, V., and Timmis, K. N. (1990) Transposon vectors containing non-antibiotic resistance selection markers for cloning and stable chromosomal insertion of foreign genes in gram-negative bacteria. *J Bacteriol* 172: 6557-6567.

Hess, J., Dietrich, G., Gentschev, I., Miko, D., Goebel, W., and Kaufmann, S. H. (1997a) Protection against murine listeriosis by an attenuated recombinant *Salmonella typhimurium* vaccine strain that secretes the naturally somatic antigen superoxide dismutase. *Infect Immun* 65: 1286-1292.

Hess, J., Gentschev, I., Miko, D., Weizel, M., Ladel, C., Goebel, W., and Kaufmann, S. H. (1996) Superior efficacy of secreted over somatic antigen display in recombinant *Salmonella* vaccine induced protection against listeriosis. *Proc Natl Acad Sci USA* 93: 1458-1463.

Hess, J., Miko, D., Gentschev, I., Dietrich, G., Goebel, W., Mollenkopf, H. J., Ladel, C., and Kaufmann, S. H. (1997b) Modulation of antigen display by attenuated *Salmonella typhimurium* strains and its impact on protective immunity against listeriosis. *Behring Inst Mitt* 160-171.

Hofmann, K. and Stoffel, W. (1993). TMbase—a database of membrane spanning proteins segments. *Biol Chem Hoppe-Seyler* 347: 166.

Holtel, A., Timmis, K. N., Ramos, J. L. (1992%. Upstream binding sequences of the XylR activator protein and integration host factor in the xylS gene promoter region of the *Pseudomonas* TOL plasmid. *Nucleic. Acids. Res.* 20:1755-1762.

Hueck, C. J. (1998). Type III protein secretion systems in bacterial pathogens of animals and plants. *Microbiol. Mol. Biol. Rev.* 62: 379-433.

Hueck, C. J., Hantman, M. J., Bajaj, V., Johnston, C., Lee, C. A., Miller, S. I. (1995). *Salmonella typhimurium* secreted invasion determinants are homologous to *Shigella* Ipa proteins. *Mol. Microbiol.* 18: 479-490.

Kaniga, K., Tucker, S., Trollinger, D., Galan, J. E. (1995). Homologs of the *Shigella* IpaB and IpaC invasins are required for *Salmonella typhimurium* entry into cultured epithelial cells. *J. Bacteriol.* 177: 3965-3971.

Kuwajima, G., Kawagishi, I., Homma, M., Asaka, J., Kondo, E., and Macnab, R. M. (1989) Export of an N-terminal fragment of *Escherichia coli* flagellin by a flagellum-specific pathway. *Proc Natl Acad Sci USA* 86: 4953-4957.

Laemmli, U. K. (1970). Cleavage of structural proteins during the assembly of the head of bacteriophage T4. *Nature* 227: 680-685.

Macnab, R. M. (1996) Flagella and motility. In *Escherichia coli* and *Salmonella*: cellular and molecular biology. F. C. Neidhardt, et al. (eds.). Washington, D.C.: ASM Press, pp. 123-145

Maloy, S. R., Steward, V. L. and Taylor, R. K. (1996). Genetic analysis of pathogenic bacteria, Cold Spring Harbor, N.Y.: Cold Spring Harbor Laboratory Press.

Miller, J. H. (1992). A short course in bacteria genetics. Cold Spring Harbor Laboratory Press, Cold Spring Harbor, N.Y.

Miller, S. I., Kukral, A. M., and Mekalanos, J. J. (1989) A two component regulatory system (phoP and phoQ) controls *Salmonella typhimurium* virulence. *Proc Natl Acad Sci USA* 86: 5054-5058.

Miller, V. L., Mekalanos, J. J. (1988). A novel suicide vector and its use in construction of invertion mutations: osmoregulation of outer membrane proteins and virulence determinants in *Vibrio cholerae* requires toxR. *J. Bacteriol.* 170, 2575-2583.

Minamino, T., and Macnab, R. M. (1999) Components of the *Salmonella flagellar* export apparatus and classification of export substrates. *J Bacteriol* 181: 1388-1394.

Monack, D. M., Raupach, B., Hromockyj, A. E., and Falkow, S. (1996) *Salmonella typhimurium* invasion induces apoptosis in infected macrophages. *Proc Natl Acad Sci USA* 93: 9833-9838.

O'Callaghan, D., Charbit, A. (1990). High efficiency transformation of *Salmonella typhimurium* and *Salmonella typhi* by electroporation. *Mol. Gen. Genet.* 223:156-158.

Ochman, H., Soncini, F. C., Solomon, F., Groisman, E. A. (1996). Identification of a pathogenicity island required for *Salmonella* survival in host cells. *Proc. Nat. Acad. Sci. USA* 93: 7800-7804.

Orr, N., Galen, J. E., and Levine, M. M. (1999) Expression and immunogenicity of a mutant diphtheria toxin molecule, $CRM_{197}$, and its fragments in *Salmonella typhi* vaccine strain CVD 908-htrA. *Infect Immun* 67: 4290-4294.

Pallen, M. J., Dougan, G., and Frankel, G. (1997) Coiled-coil domains in proteins secreted by type III secretion systems. *Mol Microbiol* 25: 423-425.

Ralph, P., Prichard, J., and Cohn, M. (1975). Reticulum cell sarcoma: and effector cell in antibody-dependent cell-mediated immunity. *J. Immunol.* 114: 898-905.

Reed, L. J., Muench, H. (1938). A simple method of estimating fifty percent end points. *Am. J. Hyg.* 27:493-497.

Sambrook, J., Fritsch, E. F., Maniatis, T. (1989). *Molecular cloning: a laboratory manual*. Cold Spring Harbor Laboratory Press, Cold Spring Harbor, N.Y.

Sanger, F., Nicklen, S., and Coulson, A. R. (1977) DNA sequencing with chain terminating inhibitors. *Proc Natl Acad Sci USA* 74: 5463-5467.

Schmitt, C. K., Darnell, S. C., and O'Brien, A. D. (1996) The attenuated phenotype of a *Salmonella typhimurium* flgM mutant is related to expression of FliC flagellin. *J Bacteriol* 178: 2911-2915

Shea, J. E., Hensel, M., Gleeson, C., Holden, D. W. (1996). Identification of a virulence locus encoding a second type III secretion system in *Salmonella typhimurium. Proc. Natl. Acad. Sci. USA* 93: 2593-2597.

Skorupski, K. and Taylor, R. K. (1996). Positive selection vectors for allelic exchange. *Gene* 169: 47-52.

Valdivia, R. H., and Falkow, S. (1997) Fluorescence-based isolation of bacterial genes expressed within host cells. *Science* 277: 2007-2011.

Valentine, P. J., Devore, B. P., and Heffron, F. (1998) Identification of three highly attenuated *Salmonella typhimurium* mutants that are more immunogenic and protective in mice than a prototypical aroA mutant. *Infect Immun* 66: 3378-3383

Wattiau, P., Bernier, B., Deslée, P., Michiels, T., and Cornelis, G. R. (1994) Individual chaperones required for Yop secretion by *Yersinia. Proc Natl Acad Sci USA* 91: 10493-10497.

Yanisch-Perron, C., Vieira, J. and Messing, J. (1985). *Gene* 33, 103-119.

Young, G. M., Schmiel, D. H., and Miller, V. L. (1999) A new pathway for the secretion of virulence factors by bacteria: the flagellar export apparatus functions as a protein-secretion system. *Proc Natl Acad Sci USA* 96: 6456-6461.

Zhu, N., Liggitt, D., Liu, Y., Debs, R. (1993). Systemic gene expression after intravenous DNA delivery into adult mice. *Science* 261: 209-211.

The invention claimed is:

1. An isolated attenuated gram-negative *Salmonella* cell comprising the SPI2 gene locus, wherein at least one effector (sse) gene selected from the group consisting of sseC, sseD and sseE of the SPI2 locus is inactivated, wherein said inactivation results in an attenuation/reduction of virulence compared to the wild type of said cell.

2. The isolated attenuated gram-negative *Salmonella* cell according to claim 1, wherein said cell has a broad host range.

3. The isolated attenuated gram-negative *Salmonella* cell according to claim 2, wherein said cell is a *Salmonella* serotype Typhimurium Definitive Type 104 (DT104) cell.

4. The isolated attenuated gram-negative *Salmonella* cell according to claim 1, wherein at least one gene is inactivated by a mutation comprising a deletion.

5. The isolated attenuated gram-negative *Salmonella* cell according to claim 4, wherein said deletion comprises at least 6 nucleotides.

6. The isolated attenuated gram-negative *Salmonella* cell according to claim 4, wherein the mutation comprises a deletion of the complete coding sequence for said gene.

7. The isolated attenuated gram-negative *Salmonella* cell according to claim 1, wherein at least one gene is inactivated by a mutation comprising the insertion of a heterologous nucleic acid molecule.

8. The isolated attenuated gram-negative *Salmonella* cell according to claim 7, wherein said mutation is a non-polar mutation.

9. The isolated attenuated gram-negative *Salmonella* cell according to claim 1, wherein at least one additional gene located outside of the SPI2 locus is inactivated, wherein the inactivation results in a further attenuation/reduction of virulence compared to the wild type.

10. The isolated attenuated gram-negative *Salmonella* cell according to claim 9, wherein said additional gene is superoxide dismutase.

11. The isolated attenuated gram-negative *Salmonella* cell according to claim 1, comprising at least one selective marker cassette.

12. The isolated attenuated gram-negative *Salmonella* cell according to claim 11, wherein said selective marker cassette is capable of conferring an antibiotic resistance to the cell.

13. The isolated attenuated gram-negative *Salmonella* cell according to claim 1 comprising at least one gene expression cassette.

14. The isolated attenuated gram-negative *Salmonella* cell according to claim 1 comprising at least one transactivator cassette.

15. The isolated attenuated gram-negative *Salmonella* cell according to claim 1 comprising at least one invertase cassette.

16. The isolated attenuated gram-negative *Salmonella* cell according to claim 1 further comprising at least one insertion cassette.

* * * * *

SEQUENCE LISTING

<160> NUMBER OF SEQ ID NOS: 73

<210> SEQ ID NO 1
<211> LENGTH: 8457
<212> TYPE: DNA
<213> ORGANISM: Salmonella

<400> SEQUENCE: 1

```
ctgcagttgt ccggttattg ctcgtcaagc gaacagatgc aaaaggtgag agcgactctc      60
gaatcatggg gggtcatgta tcgggatggt gtaatctgtg atgacttatt ggtacgagaa     120
gtgcaggatg ttttgataaa aatgggttac ccgcatgctg aagtatccag cgaagggccg     180
gggagcgtgt taattcatga tgatatacaa atggatcagc aatggcgcaa ggttcaacca     240
ttacttgcag atattcccgg gttattgcac tggcagatta gtcactctca tcagtctcag     300
ggggatgata ttatttctgc gataatagag aacggtttag tggggcttgt caatgttagc     360
ccaatgcggc gctcttttgt tatcagtggt gtactggatg aatctcatca acgcattttg     420
caagaaacgt tagcagcatt aaagaaaaag gatcccgctc tttctttaat ttatcaggat     480
attgcgcctt cccatgatga aagcaagtat ctgcctgcgc cagtggctgg ctttgtacag     540
agtcgccatg gtaattactt attactgacg aataaagagc gtttacgtgt aggggcattg     600
ttacccaatg ggggagaaat tgtccatctg agtgccgatg tggtaacgat taaacattat     660
gatactttga ttaactatcc attagatttt aagtgagtgg aaaatgacaa ctttgacccg     720
gttagaagat ttgctgcttc attcgcgtga agaggccaaa ggcataattt tacaattaag     780
ggctgcccgg aaacagttag aagagaacaa cggcaagtta caggatccgc agcaatatca     840
gcaaaacacc ttattgcttg aagcgatcga gcaggccgaa aatatcatca acattattta     900
ttatcgttac cataacagcg cacttgtagt gagtgagcaa gagtaaagta aaaatatctt     960
agagcctatc ccaccaggcg ttaattggcg cagccagttt ggacacggat agcgcgcaaa    1020
aaccgcagcg tacacgtagt acgtgaggtt tgactcgcta cgctcgccct tcgggccgcc    1080
gctagcggcg ttcaaaacgc taacgcgttt tggcgagcac tgcccaggtt caaaatggca    1140
agtaaaatag cctaatggga taggctctta gttagcacgt taattatcta tcgtgtatat    1200 ggagggggaat gatgataaag aaaaaggctg cgtttagtga atatcgtgat ttagagcaaa    1260
gttacatgca gctaaatcac tgtcttaaaa aatttcacca aatccgggct aaggtgagtc    1320
aacagcttgc tgaaagggca gagagcccca aaaatagcag agagacagag agtattcttc    1380
ataacctatt tccacaaggc gttgccgggg ttaaccagga ggccgagaag gatttaaaga    1440
```

-continued

```
aaatagtaag tttgtttaaa caacttgaag tacgactgaa acaacttaat gctcaagccc    1500
cggtggagat accgtcagga aaaacaaaaa ggtaaagcat aatgtcttca ggaaacatct    1560
tatgggaag  tcaaaaccct attgtgttta aaaatagctt cggcgtcagc aacgctgata    1620
ccgggagcca ggatgactta tcccagcaaa atccgtttgc cgaagggtat ggtgttttgc    1680
ttattctcct tatggttatt caggctatcg caaataataa atttattgaa gtccagaaga    1740
acgctgaacg tgccagaaat acccaggaaa agtcaaatga gatggatgag gtgattgcta    1800
aagcagccaa aggggatgct aaaaccaaag aggaggtgcc tgaggatgta attaaataca    1860
tgcgtgataa tggtattctc atcgatggta tgaccattga tgattatatg gctaaatatg    1920
gcgatcatgg gaagctggat aaaggtggcc tacaggcgat caaagcggct ttggataatg    1980
acgccaaccg gaataccgat cttatgagtc agggggcagat aacaattcaa aaaatgtctc    2040
aggagcttaa cgctgtcctt acccaactga cagggcttat cagtaagtgg ggggaaattt    2100
ccagtatgat agcgcagaaa acgtactcat gaaaaaagac ccgaccctac aacaggcaca    2160
tgacacgatg cggttttttcc ggcgtggcgg ctcgctgcgt atgttgttgg atgacgatgt    2220
tacacagccg cttaatactc tgtatcgcta tgccacgcag cttatggagg taaaagaatt    2280
cgccggcgca gcgcgacttt ttcaattgct gacgatatat gatgcctggt catttgacta    2340
ctggtttcgg ttaggggaat gctgccaggc tcaaaaacat tgggggggaag cgatatacgc    2400
ttatggacgc gcggcacaaa ttaagattga tgcgccgcag gcgccatggg ccgcagcgga    2460
atgctatctc gcgtgtgata acgtctgtta tgcaatcaaa gcgttaaagg ccgtggtgcg    2520
tatttgcggc gaggtcagtg aacatcaaat tctccgacag cgtgcagaaa agatgttaca    2580
gcaactttct gacaggagct aaaaatgaat cgaattcaca gtaatagcga cagcgccgca    2640
ggagtaaccg ccttaacaca tcatcactta agcaatgtca gttgcgtttc ctcgggttcg    2700
ctgggaaagc gccagcatcg tgtgaattct acttttggcg atggcaacgc cgcgtgtctg    2760
ctatccggga aaattagtct tcaggaggca agcaatgcgt tgaagcaact gcttgatgcc    2820
gtacccggaa atcataagcg tccatcattg cctgactttt tgcagaccaa tcccgcggtt    2880
ttatcaatga tgatgacgtc attaatactc aacgtctttg gtaataacgc tcaatcgtta    2940
tgccaacagc ttgagcgggc aactgaggtg caaaatgcat tacgtaataa gcaggtaaag    3000
gagtatcagg agcagatcca gaaagcgata gagcaggagg ataaagcgcg taaagcgggt    3060
atttttggcg ctattttttga ctggattacc ggcatatttg aaaccgtgat tggcgcctta    3120
aaagttgtgg aaggttttct gtccggaaat cccgcagaaa tggctagcgg cgtagcttat    3180
atggccgcag gttgtgcagg aatggttaaa gccgagccg  aaacggcaat gatgtgcggt    3240
gctgaccacg ataccctgtca ggcaattatt gacgtgacaa gtaagattca atttggttgt    3300
gaagccgtcg cgctggcact ggatgttttc cagattggcc gtgcttttat ggcgacgaga    3360
ggtttatctg gcgcagctgc aaaagtgctt gactccggtt ttggcgagga agtggttgag    3420
cgtatggtag gtgcagggga agcagaaata gaggagttgg ctgaaaagtt tggcgaagaa    3480
gtgagcgaaa gttttttccaa acaatttgag ccgcttgaac gtgaaatggc tatggcgaat    3540
gagatggcag aggaggctgc cgagttttct cgtaacgtag aaaataatat gacgcgaagc    3600
gcgggaaaaa gctttacgaa agagggggtg aaagccatgg caaaagaagc ggcaaaagaa    3660
gccctgaaa aatgtgtgca agaaggtgga aagttcctgt taaaaaaatt ccgtaataaa    3720
gttctcttca atatgttcaa aaaaatcctg tatgccttac tgagggattg ttcatttaaa    3780
```

```
ggcttacagg ctatcagatg tgcaaccgag ggcgccagtc agatgaatac tggcatggtt    3840
aacacagaaa aagcgaagat cgaaagaaa atagagcaat taataactca gcaacggttt    3900
ctggatttca taatgcaaca aacagaaaac cagaaaaaga tagaacaaaa acgcttagag    3960
gagctttata aggggacggg tgccgcgctt agagatgtat tagataccat tgatcactat    4020
agtagcgttc aggcgagaat agctggctat cgcgcttaat ctgaggataa aaatatggaa    4080
gcgagtaacg tagcactggt attaccagcg ccttccttgt taacaccttc ttccactcca    4140
tctccctccg gggagggaat gggtactgaa tcaatgcttc tgttatttga tgatatctgg    4200
atgaagctaa tggagcttgc caaaaagctg cgcgatatca tgcgcagcta taacgtagaa    4260
aaacaacggc tggcctggga actgcaagtc aatgttttac agacgcaaat gaaaacaatt    4320
gatgaagcgt ttagagcatc aatgattact gcgggtggcg caatgttgtc gggtgtactg    4380
acgataggat tagggccgt aggcggggaa accggtctta tagcgggtca agccgtaggc    4440
cacacagctg ggggcgtcat gggcctgggg gctggtgtag cgcaacgtca aagtgatcaa    4500
gataaagcga ttgccgacct gcaacaaaat ggggcccaat cttataataa atccctgacg    4560
gaaattatgg agaaagcaac tgaaattatg cagcaaatca tcggcgtggg gtcgtcactg    4620
gtcacggttc ttgctgaaat actccgggca ttaacgaggt aaacatggtg caagaaatag    4680
agcaatggtt acgtcggcat caggtgttta ctgagcctgc atatttaggg gagaccgcca    4740
tattacttgg gcagcagttt atattatcgc cttacctggt gatctatcgt attgaggcaa    4800
aagaaatgat tatttgtgag ttcaggcgcc tgacgcccgg gcaacctcga ccacagcaat    4860
tgtttcactt actgggactt ttacgcggga tatttgtgca tcacccgcag ttaacatgtt    4920
taaagatgtt gataatcacc gacgttctgg atgaaaaaaa agccatgcta cgcaggaaat    4980
tattgcgcat cctgacagta atgggagcga cctttacaca gcttgatggc gataactgga    5040 cagtttatc cgccgagcat cttatccagc gacgttttta aatgaccttc ctgacgtaaa    5100
tcattatcac gtgaaaataa caatcaatag gtatgatgat gaaagaagat cagaaaaata    5160 aaataccga agacattctg aaacagctat tatccgttga tccggaaacc gtttatgcca    5220
gtggttacgc ctcatggcag gagggggatt attcgcgcgc cgtaatcgat tttagttggc    5280
tggtgatggc ccagccatgg agttggcgtg cccatattgc attggctggc acctggatga    5340
tgcttaaaga atacacgacg gccattaatt tctatggaca tgccttgatg ctggatgcca    5400
gccatccaga accggtttac caaacgggcg tctgtctcaa aatgatgggg gaacccgggt    5460
tggcgagaga ggcttttcaa accgcaatca agatgagtta tgcggatgcc tcatggagtg    5520
agattcgcca gaatgcgcaa ataatggttg atactcttat tgcttaaata acagaacgaa    5580
atatgaaaat tcatattccg tcagcggcaa gtaatatagt cgatggtaat agtcctcctt    5640
ccgatataca agcgaaggag gtatcgtttc ctccccctga aattccagcg cctggcaccc    5700
ccgcagcccc tgtgctgctt acgcctgaac aaataaggca gcagagggat tatgcgatac    5760
attttatgca atacactatt cgtgcgctgg gtgcgacagt cgtgtttggg ttatcggttg    5820
ctgcagcggt aatttctggc ggggcaggat tacccattgc tattcttgcg ggggcggcgc    5880
tcgtgattgc tattggggat gcttgctgtg cgtatcataa ttatcaatcg atatgtcagc    5940
aaaaggagcc attacaaacc gccagtgata gcgttgctct tgtggtcagt gcgctggcct    6000
taaaatgtgg ggcaagtctt aactgcgcta acacccttgc taattgtctt tctttattaa    6060
tacgttcagg aatcgctatt tctatgttgg ttttaccccct acagtttcca ctgcccgcgg    6120
ctgaaaatat tgcggcctct ttggacatgg ggagtgtaat tacctccgtt agcctgacgg    6180
```

-continued

```
cgataggtgc ggtactggat tattgccttg cccgcccctc tggcgacgat caggaaaatt      6240
ctgttgatga acttcatgcc gatcccagtg tgttattggc ggaacaaatg gcagcgctct      6300
gtcaatctgc tactacacct gcacctgcat taatggacag ttctgatcat acatctcggg      6360
gagaaccatg aaacctgtta gcccaaatgc tcaggtagga gggcaacgtc ctgttaacgc      6420
gcctgaggaa tcacctccat gtccttcatt gccacatccg gaaaccaata tggagagtgg      6480
tagaatagga cctcaacaag gaaaagagcg ggtattggcc ggacttgcga aacgagtgat      6540
agagtgtttt ccaaaagaaa ttttagttg caaacggtt attttgggcg gacagatttt        6600
atgctgttcc gctggaatag cattaacagt gctaagtggt ggaggcgcgc cgctcgtagc      6660
cctggcaggg attggccttg ctattgccat cgcggatgtc gcctgtctta tctaccatca      6720
taaacatcat ttgcctatgg ctcacgacag tataggcaat gccgtttttt atattgctaa      6780
ttgtttcgcc aatcaacgca aaagtatggc gattgctaaa gccgtctccc tgggcggtag      6840
attagcctta accgcgacgg taatgactca ttcatactgg agtggtagtt tgggactaca      6900
gcctcattta ttagagcgtc ttaatgatat tacctatgga ctaatgagtt ttactcgctt      6960
cggtatggat gggatggcaa tgaccggtat gcaggtcagc agcccattat atcgtttgct      7020
ggctcaggta acgccagaac aacgtgcgcc ggagtaatcg ttttcaggta tataccggat      7080
gttcattgct ttctaaattt tgctatgttg ccagtatcct tacgatgtat ttattttaag      7140
gaaaagcatt atggatattg cacaattagt ggatatgctc tcccacatgg cgcaccaggc      7200
aggccaggcc attaatgaca aaatgaatgg taatgatttg ctcaacccag aatcgatgat      7260
taaagcgcaa tttgccttac agcagtattc tacatttatt aattacgaaa gttcactgat      7320
caaaatgatc aaggatatgc ttagtggaat cattgctaaa atctgaagtt attagcgacg      7380
atgttcgacg gttgctgctg gaaatcatgt ttgcgggcgt taaccatagc ctgatttccc      7440
aggtacatgc gatgttacca gcgctaacgg ttattgttcc ggataaaaaa ttacagttgg      7500
tatgtctggc attattgttg gcgggtttaa atgagccgct aaaagccgcg aaaattttat      7560
cggatataga tttgccagag gctatggcgc tgcgtctgtt atttcctgca ccaaatgagg      7620
ggtttgaaaa ttgaatattt ctgatatgag cgtagtgcct gtaagcactc aatcttatgt      7680
aaagtcctct gcagaaccga gccaggagca aattaatttt tttgaacaat tgctgaaaga      7740
tgaagcatcc accagtaacg ccagtgcttt attaccgcag gttatgttga ccagacaaat      7800
ggattatatg cagttaacgg taggcgtcga ttatcttgcc agaatatcag gcgcagcatc      7860
gcaagcgctt aataagctgg ataacatggc atgaaggttc atcgtatagt atttcttact      7920
gtccttacgt tctttcttac ggcatgtgat gtggatcttt atcgctcatt gccagaagat      7980
gaagcgaatc aaatgctggc attacttatg cagcatcata ttgatgcgga aaaaaaacag      8040
gaagaggatg gtgtaacctt acgtgtcgag cagtcgcagt ttattaatgc ggttgagcta      8100
cttagactta acggttatcc gcataggcag tttacaacgg cggataagat gtttccggct      8160
aatcagttag tggtatcacc ccaggaagaa cagcagaaga ttaatttttt aaagaacaa       8220 agaattgaag gaatgctgag tcagatggag ggcgtgatta atgcaaaagt gaccattgcg      8280
ctaccgactt atgatgaggg aagtaacgct tctccgagct cagttgccgt atttataaaa      8340
tattcacctc aggtcaatat ggaggccttt cgggtaaaaa ttaaagattt aatagagatg      8400
tcaatccctg ggttgcaata cagtaagatt agtatcttga tgcagcctgc tgaattc        8457
```

<210> SEQ ID NO 2

<211> LENGTH: 3921
<212> TYPE: DNA
<213> ORGANISM: Salmonella

<400> SEQUENCE: 2

```
agcattgaca taaaaactta caatttgaaa aattatttat taaataaact gttacgatgt      60
ttttacatcg ccatcttatt aaaaagtaat tgtagtcatc gactgggtta tatatgaaga     120
aatttatctt cctaatgata acaccatcga ttaatcttct gatgaaacta tatgtactgc     180
gatagtgatc aagtgccaaa gattttgcaa caggcaactg gagggaagca ttatgaattt     240
gctcaatctc aagaatacgc tgcaaacatc tttagtaatc aggctaactt ttttattttt     300
attaacaaca ataattattt ggctgctatc tgtgcttacc gcagcttata tatcaatggt     360
tcagaaacgg cagcatataa tagaggattt atccgttcta tccgagatga atattgtact     420
aagcaatcaa cggtttgaag aagctgaacg tgacgctaaa aatttaatgt atcaatgctc     480
attagcgact gagattcatc ataacgatat tttccctgag gtgagccggc atctatctgt     540
cggtccttca aattgcacgc cgacgctaaa cggagagaag caccgtctct ttctgcagtc     600
ctctgatatc gatgaaaata gctttcgtcg cgatagtttt attcttaatc ataaaaatga     660
gatttcgtta ttatctactg ataacccttc agattattca actctacagc ctttaacgcg     720
aaaaagcttt cctttatacc caacccatgc cgggttttac tggagtgaac cagaatacat     780
aaacggcaaa ggatggcacg cttccgttgc ggttgccgat cagcaaggcg tattttttga     840
ggtgacggtt aaacttcccg atctcattac taagagccac ctgccattag atgatagtat     900
tcgagtatgg ctggatcaaa caaccactt attgccgttt tcatacatcc cgcaaaaaat     960
acgtacacag ttagaaaatg taacgctgca tgatggatgg cagcaaattc ccggatttct    1020
gatattacgc acaaccttgc atggccccgg atggagtctg gttacgctgt acccatacgg    1080
taatctacat aatcgcatct taaaaattat ccttcaacaa atcccctttta cattaacagc    1140
attggtgttg atgacgtcgg cttttttgctg gttactacat cgctcactgg ccaaaccgtt    1200
atggcgtttt gtcgatgtca ttaataaaac cgcaactgca ccgctgagca cacgtttacc    1260
agcacaacga ctggatgaat tagatagtat tgccggtgct tttaaccaac tgcttgatac    1320
tctacaagtc caatacgaca atctggaaaa caaagtcgca gagcgcaccc aggcgctaaa    1380
tgaagcaaaa aaacgcgctg agcgagctaa caaacgtaaa agcattcatc ttacggtaat    1440
aagtcatgag ttacgtactc cgatgaatgg cgtactcggt gcaattgaat tattacaaac    1500
caccccttta aacatagagc aacaaggatt agctgatacc gccagaaatt gtacactgtc    1560
tttgttagct attattaata atctgctgga ttttcacgc atcgagtctg gtcatttcac     1620
attacatatg gaagaaacag cgttactgcc gttactggac caggcaatgc aaaccatcca    1680
ggggccagcg caaagcaaaa aactgtcatt acgtactttt gtcggtcaac atgtccctct    1740
ctattttcat accgacagta tccgtttacg gcaaattttg gttaatttac tcgggaacgc    1800
ggtaaaattt accgaaaccg gagggatacg tctgacggtc aagcgtcatg aggaacaatt    1860
aatatttctg gttagcgata gcggtaaagg gattgaaata cagcagcagt ctcaaatctt    1920
tactgctttt tatcaagcag acacaaattc gcaaggtaca ggaattggac tgactattgc    1980
gtcaagcctg gctaaaatga tgggcggtaa tctgacacta aaaagtgtcc ccggggttgg    2040
aacctgtgtc tcgctagtat taccccttaca agaataccag ccgcctcaac caattaaagg    2100
gacgctgtca gcgccgttct gcctgcatcg gcaactggct tgctggggaa tacgcggtga    2160
accacccac cagcaaaatg cgcttctcaa cgcagagctt ttgtatttct ccggaaaact    2220
```

-continued

```
ctacgacctg gcgcaacagt taatattgtg tacaccaaat atgccagtaa taaataattt    2280
gttaccaccc tggcagttgc agattctttt ggttgatgat gccgatatta atcgggatat    2340
catcggcaaa atgcttgtca gcctgggcca acacgtcact attgccgcca gtagtaacga    2400
ggctctgact ttatcacaac agcagcgatt cgatttagta ctgattgaca ttagaatgcc    2460
agaaatagat ggtattgaat gtgtacgatt atggcatgat gagccgaata atttagatcc    2520
tgactgcatg tttgtggcac tatccgctag cgtagcgaca gaagatattc atcgttgtaa    2580
aaaaaatggg attcatcatt acattacaaa accagtgaca ttggctacct tagctcgcta    2640
catcagtatt gccgcagaat accaactttt acgaaatata gagctacagg agcaggatcc    2700
gagtcgctgc tcagcgctac tggcgacaga tgatatggtc attaatagca agattttcca    2760
atcactggac ctcttgctgg ctgatattga aaatgccgta tcggctggag aaaaaatcga    2820
tcagttaatt cacacattaa aaggctgttt aggtcaaata gggcagactg aattggtatg    2880
ctatgtcata gacattgaga atcgcgtaaa aatggggaaa atcatcgcgc tggaggaact    2940
aaccgactta cgccagaaaa tacgtatgat cttcaaaaac tacaccatta cttaatatta    3000
tcttaatttt cgcgagggca gcaaaatgaa agaatataag atcttattag tagacgatca    3060
tgaaatcatc attaacggca ttatgaatgc cttattaccc tggcctcatt ttaaaattgt    3120
agagcatgtt aaaaatggtc ttgaggttta taatgcctgt tgtgcatacg agcctgacat    3180
acttatcctt gatcttagtc tacctggcat caatggcctg gatatcattc ctcaattaca    3240
tcagcgttgg ccagcaatga atattctggt ttacacagca taccaacaag agtatatgac    3300
cattaaaact ttagccgcag gtgctaatgg ctatgtttta aaaagcagta gtcagcaagt    3360
tctgttagcg gcattgcaaa cagtagcagt aaacaagcgt tacattgacc caacgttgaa    3420
tcgggaagct atcctggctg aattaaacgc tgacacgacc aatcatcaac tgcttacttt    3480
gcgcgagcgt caggttctta aacttattga cgaggggtat accaatcatg ggatcagcga    3540
aaagctacat atcagtataa aaaccgtcga acacaccgg atgaatatga tgagaaagct    3600
acaggttcat aaagtgacag agttacttaa ctgtgcccga agaatgaggt taatagagta    3660
ttaaccaggg gcgtccgatg gtattaagca ttggtcatat tttgatgagc cttacgccac    3720
gcagtattgc tcatcatcga caaaatccat acggatgccc tggtatgccg caccatttat    3780 cactaccta gtcttcattt gatcatgata tagtagaatc cccttattta acgggcttta    3840
ccatgtcgta ttctatcggc gaatttgcca gactatgcgg tatcaatgcc gccacgctaa    3900
gggcatggca gcgacgctat g                                              3921
```

<210> SEQ ID NO 3
<211> LENGTH: 327
<212> TYPE: DNA
<213> ORGANISM: Salmonella
<220> FEATURE:
<221> NAME/KEY: CDS
<222> LOCATION: (1)..(324)

<400> SEQUENCE: 3

```
atg atg ata aag aaa aag gct gcg ttt agt gaa tat cgt gat tta gag      48
Met Met Ile Lys Lys Lys Ala Ala Phe Ser Glu Tyr Arg Asp Leu Glu
1               5                   10                  15 caa agt tac atg cag cta aat cac tgt ctt aaa aaa ttt cac caa atc     96
Gln Ser Tyr Met Gln Leu Asn His Cys Leu Lys Lys Phe His Gln Ile
            20                  25                  30 cgg gct aag gtg agt caa cag ctt gct gaa agg gca gag agc ccc aaa    144
```

| | | | | | | | | | | | | |
|---|---|---|---|---|---|---|---|---|---|---|---|---|
|Arg|Ala|Lys|Val|Ser|Gln|Gln|Leu|Ala|Glu|Arg|Ala|Glu|Ser|Pro|Lys|
| | |35| | | |40| | | |45| | | | | |

```
aat agc aga gag aca gag agt att ctt cat aac cta ttt cca caa ggc      192
Asn Ser Arg Glu Thr Glu Ser Ile Leu His Asn Leu Phe Pro Gln Gly
     50                  55                  60 gtt gcc ggg gtt aac cag gag gcc gag aag gat tta aag aaa ata gta      240
Val Ala Gly Val Asn Gln Glu Ala Glu Lys Asp Leu Lys Lys Ile Val
 65                  70                  75                  80 agt ttg ttt aaa caa ctt gaa gta cga ctg aaa caa ctt aat gct caa      288
Ser Leu Phe Lys Gln Leu Glu Val Arg Leu Lys Gln Leu Asn Ala Gln
                 85                  90                  95 gcc ccg gtg gag ata ccg tca gga aaa aca aaa agg taa                  327
Ala Pro Val Glu Ile Pro Ser Gly Lys Thr Lys Arg
            100                 105
```

<210> SEQ ID NO 4
<211> LENGTH: 108
<212> TYPE: PRT
<213> ORGANISM: Salmonella

<400> SEQUENCE: 4

```
Met Met Ile Lys Lys Lys Ala Ala Phe Ser Glu Tyr Arg Asp Leu Glu
 1               5                  10                  15

Gln Ser Tyr Met Gln Leu Asn His Cys Leu Lys Lys Phe His Gln Ile
                20                  25                  30

Arg Ala Lys Val Ser Gln Gln Leu Ala Glu Arg Ala Glu Ser Pro Lys
             35                  40                  45

Asn Ser Arg Glu Thr Glu Ser Ile Leu His Asn Leu Phe Pro Gln Gly
         50                  55                  60

Val Ala Gly Val Asn Gln Glu Ala Glu Lys Asp Leu Lys Lys Ile Val
 65                  70                  75                  80

Ser Leu Phe Lys Gln Leu Glu Val Arg Leu Lys Gln Leu Asn Ala Gln
                 85                  90                  95

Ala Pro Val Glu Ile Pro Ser Gly Lys Thr Lys Arg
            100                 105
```

<210> SEQ ID NO 5
<211> LENGTH: 591
<212> TYPE: DNA
<213> ORGANISM: Salmonella
<220> FEATURE:
<221> NAME/KEY: CDS
<222> LOCATION: (1)..(588)

<400> SEQUENCE: 5

```
atg tct tca gga aac atc tta tgg gga agt caa aac cct att gtg ttt      48
Met Ser Ser Gly Asn Ile Leu Trp Gly Ser Gln Asn Pro Ile Val Phe
 1               5                  10                  15 aaa aat agc ttc ggc gtc agc aac gct gat acc ggg agc cag gat gac      96
Lys Asn Ser Phe Gly Val Ser Asn Ala Asp Thr Gly Ser Gln Asp Asp
                20                  25                  30 tta tcc cag caa aat ccg ttt gcc gaa ggg tat ggt gtt ttg ctt att     144
Leu Ser Gln Gln Asn Pro Phe Ala Glu Gly Tyr Gly Val Leu Leu Ile
             35                  40                  45 ctc ctc atg gtt att cag gct atc gca aat aat aaa ttt att gaa gtc     192
Leu Leu Met Val Ile Gln Ala Ile Ala Asn Asn Lys Phe Ile Glu Val
         50                  55                  60 cag aag aac gct gaa cgt gcc aga aat acc cag gaa aag tca aat gag     240
Gln Lys Asn Ala Glu Arg Ala Arg Asn Thr Gln Glu Lys Ser Asn Glu
 65                  70                  75                  80
```

```
atg gat gag gtg att gct aaa gca gcc aaa ggg gat gct aaa acc aaa         288
Met Asp Glu Val Ile Ala Lys Ala Ala Lys Gly Asp Ala Lys Thr Lys
             85                  90                  95 gag gag gtg cct gag gat gta att aaa tac atg cgt gat aat ggt att         336
Glu Glu Val Pro Glu Asp Val Ile Lys Tyr Met Arg Asp Asn Gly Ile
        100                 105                 110 ctc atc gat ggt atg acc att gat gat tat atg gct aaa tat ggc gat         384
Leu Ile Asp Gly Met Thr Ile Asp Asp Tyr Met Ala Lys Tyr Gly Asp
    115                 120                 125 cat ggg aag ctg gat aaa ggt ggc cta cag gcg atc aaa gcg gct ttg         432
His Gly Lys Leu Asp Lys Gly Gly Leu Gln Ala Ile Lys Ala Ala Leu
130                 135                 140 gat aat gac gcc aac cgg aat acc gat ctt atg agt cag ggg cag ata         480
Asp Asn Asp Ala Asn Arg Asn Thr Asp Leu Met Ser Gln Gly Gln Ile
145                 150                 155                 160 aca att caa aaa atg tct cag gag ctt aac gct gtc ctt acc caa ctg         528
Thr Ile Gln Lys Met Ser Gln Glu Leu Asn Ala Val Leu Thr Gln Leu
                165                 170                 175 aca ggg ctt atc agt aag tgg ggg gaa att tcc agt atg ata gcg cag         576
Thr Gly Leu Ile Ser Lys Trp Gly Glu Ile Ser Ser Met Ile Ala Gln
            180                 185                 190 aaa acg tac tca tga                                                     591
Lys Thr Tyr Ser
        195

<210> SEQ ID NO 6
<211> LENGTH: 196
<212> TYPE: PRT
<213> ORGANISM: Salmonella

<400> SEQUENCE: 6

Met Ser Ser Gly Asn Ile Leu Trp Gly Ser Gln Asn Pro Ile Val Phe
  1               5                  10                  15

Lys Asn Ser Phe Gly Val Ser Asn Ala Asp Thr Gly Ser Gln Asp Asp
             20                  25                  30

Leu Ser Gln Gln Asn Pro Phe Ala Glu Gly Tyr Gly Val Leu Leu Ile
         35                  40                  45

Leu Leu Met Val Ile Gln Ala Ile Ala Asn Asn Lys Phe Ile Glu Val
     50                  55                  60

Gln Lys Asn Ala Glu Arg Ala Arg Asn Thr Gln Glu Lys Ser Asn Glu
 65                  70                  75                  80

Met Asp Glu Val Ile Ala Lys Ala Ala Lys Gly Asp Ala Lys Thr Lys
             85                  90                  95

Glu Glu Val Pro Glu Asp Val Ile Lys Tyr Met Arg Asp Asn Gly Ile
        100                 105                 110

Leu Ile Asp Gly Met Thr Ile Asp Asp Tyr Met Ala Lys Tyr Gly Asp
    115                 120                 125

His Gly Lys Leu Asp Lys Gly Gly Leu Gln Ala Ile Lys Ala Ala Leu
130                 135                 140

Asp Asn Asp Ala Asn Arg Asn Thr Asp Leu Met Ser Gln Gly Gln Ile
145                 150                 155                 160

Thr Ile Gln Lys Met Ser Gln Glu Leu Asn Ala Val Leu Thr Gln Leu
                165                 170                 175

Thr Gly Leu Ile Ser Lys Trp Gly Glu Ile Ser Ser Met Ile Ala Gln
            180                 185                 190

Lys Thr Tyr Ser
        195
```

<210> SEQ ID NO 7
<211> LENGTH: 1455
<212> TYPE: DNA
<213> ORGANISM: Salmonella
<220> FEATURE:
<221> NAME/KEY: CDS
<222> LOCATION: (1)..(1452)

<400> SEQUENCE: 7

| | | | | | | | | | | | | | | | | |
|---|---|---|---|---|---|---|---|---|---|---|---|---|---|---|---|---|
| atg | aat | cga | att | cac | agt | aat | agc | gac | agc | gcc | gca | gga | gta | acc | gcc | 48 |
| Met | Asn | Arg | Ile | His | Ser | Asn | Ser | Asp | Ser | Ala | Ala | Gly | Val | Thr | Ala | |
| 1 | | | | 5 | | | | | 10 | | | | | 15 | | |

| tta | aca | cat | cat | cac | tta | agc | aat | gtc | agt | tgc | gtt | tcc | tcg | ggt | tcg | 96 |
|---|---|---|---|---|---|---|---|---|---|---|---|---|---|---|---|---|
| Leu | Thr | His | His | His | Leu | Ser | Asn | Val | Ser | Cys | Val | Ser | Ser | Gly | Ser | |
| | | | | 20 | | | | | 25 | | | | | 30 | | |

| ctg | gga | aag | cgc | cag | cat | cgt | gtg | aat | tct | act | ttt | ggc | gat | ggc | aac | 144 |
|---|---|---|---|---|---|---|---|---|---|---|---|---|---|---|---|---|
| Leu | Gly | Lys | Arg | Gln | His | Arg | Val | Asn | Ser | Thr | Phe | Gly | Asp | Gly | Asn | |
| | | 35 | | | | | 40 | | | | | 45 | | | | |

| gcc | gcg | tgt | ctg | cta | tcc | ggg | aaa | att | agt | ctt | cag | gag | gca | agc | aat | 192 |
|---|---|---|---|---|---|---|---|---|---|---|---|---|---|---|---|---|
| Ala | Ala | Cys | Leu | Leu | Ser | Gly | Lys | Ile | Ser | Leu | Gln | Glu | Ala | Ser | Asn | |
| 50 | | | | | 55 | | | | | 60 | | | | | | |

| gcg | ttg | aag | caa | ctg | ctt | gat | gcc | gta | ccc | gga | aat | cat | aag | cgt | cca | 240 |
|---|---|---|---|---|---|---|---|---|---|---|---|---|---|---|---|---|
| Ala | Leu | Lys | Gln | Leu | Leu | Asp | Ala | Val | Pro | Gly | Asn | His | Lys | Arg | Pro | |
| 65 | | | | | 70 | | | | | 75 | | | | | 80 | |

| tca | ttg | cct | gac | ttt | ttg | cag | acc | aat | ccc | gcg | gtt | tta | tca | atg | atg | 288 |
|---|---|---|---|---|---|---|---|---|---|---|---|---|---|---|---|---|
| Ser | Leu | Pro | Asp | Phe | Leu | Gln | Thr | Asn | Pro | Ala | Val | Leu | Ser | Met | Met | |
| | | | | 85 | | | | | 90 | | | | | 95 | | |

| atg | acg | tca | tta | ata | ctc | aac | gtc | ttt | ggt | aat | aac | gct | caa | tcg | tta | 336 |
|---|---|---|---|---|---|---|---|---|---|---|---|---|---|---|---|---|
| Met | Thr | Ser | Leu | Ile | Leu | Asn | Val | Phe | Gly | Asn | Asn | Ala | Gln | Ser | Leu | |
| | | | | 100 | | | | | 105 | | | | | 110 | | |

| tgc | caa | cag | ctt | gag | cgg | gca | act | gag | gtg | caa | aat | gca | tta | cgt | aat | 384 |
|---|---|---|---|---|---|---|---|---|---|---|---|---|---|---|---|---|
| Cys | Gln | Gln | Leu | Glu | Arg | Ala | Thr | Glu | Val | Gln | Asn | Ala | Leu | Arg | Asn | |
| | | | 115 | | | | | 120 | | | | | 125 | | | |

| aag | cag | gta | aag | gag | tat | cag | gag | cag | atc | cag | aaa | gcg | ata | gag | cag | 432 |
|---|---|---|---|---|---|---|---|---|---|---|---|---|---|---|---|---|
| Lys | Gln | Val | Lys | Glu | Tyr | Gln | Glu | Gln | Ile | Gln | Lys | Ala | Ile | Glu | Gln | |
| | | 130 | | | | | 135 | | | | | 140 | | | | |

| gag | gat | aaa | gcg | cgt | aaa | gcg | ggt | att | ttt | ggc | gct | att | ttt | gac | tgg | 480 |
|---|---|---|---|---|---|---|---|---|---|---|---|---|---|---|---|---|
| Glu | Asp | Lys | Ala | Arg | Lys | Ala | Gly | Ile | Phe | Gly | Ala | Ile | Phe | Asp | Trp | |
| 145 | | | | | 150 | | | | | 155 | | | | | 160 | |

| att | acc | ggc | ata | ttt | gaa | acc | gtg | att | ggc | gcc | tta | aaa | gtt | gtg | gaa | 528 |
|---|---|---|---|---|---|---|---|---|---|---|---|---|---|---|---|---|
| Ile | Thr | Gly | Ile | Phe | Glu | Thr | Val | Ile | Gly | Ala | Leu | Lys | Val | Val | Glu | |
| | | | | 165 | | | | | 170 | | | | | 175 | | |

| ggt | ttt | ctg | tcc | gga | aat | ccc | gca | gaa | atg | gct | agc | ggc | gta | gct | tat | 576 |
|---|---|---|---|---|---|---|---|---|---|---|---|---|---|---|---|---|
| Gly | Phe | Leu | Ser | Gly | Asn | Pro | Ala | Glu | Met | Ala | Ser | Gly | Val | Ala | Tyr | |
| | | | | 180 | | | | | 185 | | | | | 190 | | |

| atg | gcc | gca | ggt | tgt | gca | gga | atg | gtt | aaa | gcc | gga | gcc | gaa | acg | gca | 624 |
|---|---|---|---|---|---|---|---|---|---|---|---|---|---|---|---|---|
| Met | Ala | Ala | Gly | Cys | Ala | Gly | Met | Val | Lys | Ala | Gly | Ala | Glu | Thr | Ala | |
| | | | 195 | | | | | 200 | | | | | 205 | | | |

| atg | atg | tgc | ggt | gct | gac | cac | gat | acc | tgt | cag | gca | att | att | gac | gtg | 672 |
|---|---|---|---|---|---|---|---|---|---|---|---|---|---|---|---|---|
| Met | Met | Cys | Gly | Ala | Asp | His | Asp | Thr | Cys | Gln | Ala | Ile | Ile | Asp | Val | |
| | | 210 | | | | | 215 | | | | | 220 | | | | |

| aca | agt | aag | att | caa | ttt | ggt | tgt | gaa | gcc | gtc | gcg | ctg | gca | ctg | gat | 720 |
|---|---|---|---|---|---|---|---|---|---|---|---|---|---|---|---|---|
| Thr | Ser | Lys | Ile | Gln | Phe | Gly | Cys | Glu | Ala | Val | Ala | Leu | Ala | Leu | Asp | |
| 225 | | | | | 230 | | | | | 235 | | | | | 240 | |

| gtt | ttc | cag | att | ggc | cgt | gct | ttt | atg | gcg | acg | aga | ggt | tta | tct | ggc | 768 |
|---|---|---|---|---|---|---|---|---|---|---|---|---|---|---|---|---|
| Val | Phe | Gln | Ile | Gly | Arg | Ala | Phe | Met | Ala | Thr | Arg | Gly | Leu | Ser | Gly | |
| | | | | 245 | | | | | 250 | | | | | 255 | | |

| gca | gct | gca | aaa | gtg | ctt | gac | tcc | ggt | ttt | ggc | gag | gaa | gtg | gtt | gag | 816 |
|---|---|---|---|---|---|---|---|---|---|---|---|---|---|---|---|---|
| Ala | Ala | Ala | Lys | Val | Leu | Asp | Ser | Gly | Phe | Gly | Glu | Glu | Val | Val | Glu | |
| | | | | 260 | | | | | 265 | | | | | 270 | | |

```
cgt atg gta ggt gca ggg gaa gca gaa ata gag gag ttg gct gaa aag    864
Arg Met Val Gly Ala Gly Glu Ala Glu Ile Glu Glu Leu Ala Glu Lys
        275                 280                 285 ttt ggc gaa gaa gtg agc gaa agt ttt tcc aaa caa ttt gag ccg ctt    912
Phe Gly Glu Glu Val Ser Glu Ser Phe Ser Lys Gln Phe Glu Pro Leu
    290                 295                 300 gaa cgt gaa atg gct atg gcg aat gag atg gca gag gag gct gcc gag    960
Glu Arg Glu Met Ala Met Ala Asn Glu Met Ala Glu Glu Ala Ala Glu
305                 310                 315                 320 ttt tct cgt aac gta gaa aat aat atg acg cga agc gcg gga aaa agc   1008
Phe Ser Arg Asn Val Glu Asn Asn Met Thr Arg Ser Ala Gly Lys Ser
                325                 330                 335 ttt acg aaa gag ggg gtg aaa gcc atg gca aaa gaa gcg gca aaa gaa   1056
Phe Thr Lys Glu Gly Val Lys Ala Met Ala Lys Glu Ala Ala Lys Glu
            340                 345                 350 gcc ctg gaa aaa tgt gtg caa gaa ggt gga aag ttc ctg tta aaa aaa   1104
Ala Leu Glu Lys Cys Val Gln Glu Gly Gly Lys Phe Leu Leu Lys Lys
        355                 360                 365 ttc cgt aat aaa gtt ctc ttc aat atg ttc aaa aaa atc ctg tat gcc   1152
Phe Arg Asn Lys Val Leu Phe Asn Met Phe Lys Lys Ile Leu Tyr Ala
    370                 375                 380 tta ctg agg gat tgt tca ttt aaa ggc tta cag gct atc aga tgt gca   1200
Leu Leu Arg Asp Cys Ser Phe Lys Gly Leu Gln Ala Ile Arg Cys Ala
385                 390                 395                 400 acc gag ggc gcc agt cag atg aat act ggc atg gtt aac aca gaa aaa   1248
Thr Glu Gly Ala Ser Gln Met Asn Thr Gly Met Val Asn Thr Glu Lys
                405                 410                 415 gcg aag atc gaa aag aaa ata gag caa tta ata act cag caa cgg ttt   1296
Ala Lys Ile Glu Lys Lys Ile Glu Gln Leu Ile Thr Gln Gln Arg Phe
            420                 425                 430 ctg gat ttc ata atg caa caa aca gaa aac cag aaa aag ata gaa caa   1344
Leu Asp Phe Ile Met Gln Gln Thr Glu Asn Gln Lys Lys Ile Glu Gln
        435                 440                 445 aaa cgc tta gag gag ctt tat aag ggg acg ggt gcc gcg ctt aga gat   1392
Lys Arg Leu Glu Glu Leu Tyr Lys Gly Thr Gly Ala Ala Leu Arg Asp
    450                 455                 460 gta tta gat acc att gat cac tat agt agc gtt cag gcg aga ata gct   1440
Val Leu Asp Thr Ile Asp His Tyr Ser Ser Val Gln Ala Arg Ile Ala
465                 470                 475                 480 ggc tat cgc gct taa                                                1455
Gly Tyr Arg Ala <210> SEQ ID NO 8
<211> LENGTH: 484
<212> TYPE: PRT
<213> ORGANISM: Salmonella

<400> SEQUENCE: 8

Met Asn Arg Ile His Ser Asn Ser Asp Ser Ala Ala Gly Val Thr Ala
 1               5                  10                  15

Leu Thr His His His Leu Ser Asn Val Ser Cys Val Ser Ser Gly Ser
                20                  25                  30

Leu Gly Lys Arg Gln His Arg Val Asn Ser Thr Phe Gly Asp Gly Asn
            35                  40                  45

Ala Ala Cys Leu Leu Ser Gly Lys Ile Ser Leu Gln Glu Ala Ser Asn
        50                  55                  60

Ala Leu Lys Gln Leu Leu Asp Ala Val Pro Gly Asn His Lys Arg Pro
 65                 70                  75                  80

Ser Leu Pro Asp Phe Leu Gln Thr Asn Pro Ala Val Leu Ser Met Met
```

```
                    85                  90                  95
Met Thr Ser Leu Ile Leu Asn Val Phe Gly Asn Asn Ala Gln Ser Leu
                100                 105                 110

Cys Gln Gln Leu Glu Arg Ala Thr Glu Val Gln Asn Ala Leu Arg Asn
            115                 120                 125

Lys Gln Val Lys Glu Tyr Gln Glu Gln Ile Gln Lys Ala Ile Glu Gln
        130                 135                 140

Glu Asp Lys Ala Arg Lys Ala Gly Ile Phe Gly Ala Ile Phe Asp Trp
145                 150                 155                 160

Ile Thr Gly Ile Phe Glu Thr Val Ile Gly Ala Leu Lys Val Val Glu
                165                 170                 175

Gly Phe Leu Ser Gly Asn Pro Ala Glu Met Ala Ser Gly Val Ala Tyr
            180                 185                 190

Met Ala Ala Gly Cys Ala Gly Met Val Lys Ala Gly Ala Glu Thr Ala
        195                 200                 205

Met Met Cys Gly Ala Asp His Asp Thr Cys Gln Ala Ile Ile Asp Val
    210                 215                 220

Thr Ser Lys Ile Gln Phe Gly Cys Glu Ala Val Ala Leu Ala Leu Asp
225                 230                 235                 240

Val Phe Gln Ile Gly Arg Ala Phe Met Ala Thr Arg Gly Leu Ser Gly
                245                 250                 255

Ala Ala Ala Lys Val Leu Asp Ser Gly Phe Gly Glu Glu Val Val Glu
            260                 265                 270

Arg Met Val Gly Ala Gly Glu Ala Glu Ile Glu Glu Leu Ala Glu Lys
        275                 280                 285

Phe Gly Glu Glu Val Ser Glu Ser Phe Ser Lys Gln Phe Glu Pro Leu
    290                 295                 300

Glu Arg Glu Met Ala Met Ala Asn Glu Met Ala Glu Ala Ala Glu
305                 310                 315                 320

Phe Ser Arg Asn Val Glu Asn Asn Met Thr Arg Ser Ala Gly Lys Ser
                325                 330                 335

Phe Thr Lys Glu Gly Val Lys Ala Met Ala Lys Glu Ala Ala Lys Glu
            340                 345                 350

Ala Leu Glu Lys Cys Val Gln Glu Gly Gly Lys Phe Leu Leu Lys Lys
        355                 360                 365

Phe Arg Asn Lys Val Leu Phe Asn Met Phe Lys Lys Ile Leu Tyr Ala
    370                 375                 380

Leu Leu Arg Asp Cys Ser Phe Lys Gly Leu Gln Ala Ile Arg Cys Ala
385                 390                 395                 400

Thr Glu Gly Ala Ser Gln Met Asn Thr Gly Met Val Asn Thr Glu Lys
                405                 410                 415

Ala Lys Ile Glu Lys Ile Glu Gln Leu Ile Thr Gln Arg Phe
            420                 425                 430

Leu Asp Phe Ile Met Gln Gln Thr Glu Asn Gln Lys Lys Ile Glu Gln
        435                 440                 445

Lys Arg Leu Glu Glu Leu Tyr Lys Gly Thr Gly Ala Ala Leu Arg Asp
    450                 455                 460

Val Leu Asp Thr Ile Asp His Tyr Ser Ser Val Gln Ala Arg Ile Ala
465                 470                 475                 480

Gly Tyr Arg Ala

<210> SEQ ID NO 9
<211> LENGTH: 504
```

```
<212> TYPE: DNA
<213> ORGANISM: Salmonella
<220> FEATURE:
<221> NAME/KEY: CDS
<222> LOCATION: (1)..(501)

<400> SEQUENCE: 9 atg ggt act gaa tca atg ctt ctg tta ttt gat gat atc tgg atg aag      48
Met Gly Thr Glu Ser Met Leu Leu Leu Phe Asp Asp Ile Trp Met Lys
 1               5                  10                  15 cta atg gag ctt gcc aaa aag ctg cgc gat atc atg cgc agc tat aac      96
Leu Met Glu Leu Ala Lys Lys Leu Arg Asp Ile Met Arg Ser Tyr Asn
             20                  25                  30 gta gaa aaa caa cgg ctg gcc tgg gaa ctg caa gtc aat gtt tta cag     144
Val Glu Lys Gln Arg Leu Ala Trp Glu Leu Gln Val Asn Val Leu Gln
         35                  40                  45 acg caa atg aaa aca att gat gaa gcg ttt aga gca tca atg att act     192
Thr Gln Met Lys Thr Ile Asp Glu Ala Phe Arg Ala Ser Met Ile Thr
     50                  55                  60 gcg ggt ggc gca atg ttg tcg ggt gta ctg acg ata gga tta ggg gcc     240
Ala Gly Gly Ala Met Leu Ser Gly Val Leu Thr Ile Gly Leu Gly Ala
 65                  70                  75                  80 gta ggc ggg gaa acc ggt ctt ata gcg ggt caa gcc gta ggc cac aca     288
Val Gly Gly Glu Thr Gly Leu Ile Ala Gly Gln Ala Val Gly His Thr
                 85                  90                  95 gct ggg ggc gtc atg ggc ctg ggg gct ggt gta gcg caa cgt caa agt     336
Ala Gly Gly Val Met Gly Leu Gly Ala Gly Val Ala Gln Arg Gln Ser
            100                 105                 110 gat caa gat aaa gcg att gcc gac ctg caa caa aat ggg gcc caa tct     384
Asp Gln Asp Lys Ala Ile Ala Asp Leu Gln Gln Asn Gly Ala Gln Ser
        115                 120                 125 tat aat aaa tcc ctg acg gaa att atg gag aaa gca act gaa att atg     432
Tyr Asn Lys Ser Leu Thr Glu Ile Met Glu Lys Ala Thr Glu Ile Met
    130                 135                 140 cag caa atc atc ggc gtg ggg tcg tca ctg gtc acg gtt ctt gct gaa     480
Gln Gln Ile Ile Gly Val Gly Ser Ser Leu Val Thr Val Leu Ala Glu
145                 150                 155                 160 ata ctc cgg gca tta acg agg taa                                     504
Ile Leu Arg Ala Leu Thr Arg
                165

<210> SEQ ID NO 10
<211> LENGTH: 167
<212> TYPE: PRT
<213> ORGANISM: Salmonella

<400> SEQUENCE: 10

Met Gly Thr Glu Ser Met Leu Leu Leu Phe Asp Asp Ile Trp Met Lys
 1               5                  10                  15

Leu Met Glu Leu Ala Lys Lys Leu Arg Asp Ile Met Arg Ser Tyr Asn
             20                  25                  30

Val Glu Lys Gln Arg Leu Ala Trp Glu Leu Gln Val Asn Val Leu Gln
         35                  40                  45

Thr Gln Met Lys Thr Ile Asp Glu Ala Phe Arg Ala Ser Met Ile Thr
     50                  55                  60

Ala Gly Gly Ala Met Leu Ser Gly Val Leu Thr Ile Gly Leu Gly Ala
 65                  70                  75                  80

Val Gly Gly Glu Thr Gly Leu Ile Ala Gly Gln Ala Val Gly His Thr
                 85                  90                  95

Ala Gly Gly Val Met Gly Leu Gly Ala Gly Val Ala Gln Arg Gln Ser
```

-continued

```
                         100                 105                 110
Asp Gln Asp Lys Ala Ile Ala Asp Leu Gln Gln Asn Gly Ala Gln Ser
            115                 120                 125

Tyr Asn Lys Ser Leu Thr Glu Ile Met Glu Lys Ala Thr Glu Ile Met
130                 135                 140

Gln Gln Ile Ile Gly Val Gly Ser Ser Leu Val Thr Val Leu Ala Glu
145                 150                 155                 160

Ile Leu Arg Ala Leu Thr Arg
                165

<210> SEQ ID NO 11
<211> LENGTH: 195
<212> TYPE: PRT
<213> ORGANISM: Salmonella

<400> SEQUENCE: 11

Met Glu Ala Ser Asn Val Ala Leu Val Leu Pro Ala Pro Ser Leu Leu
  1               5                  10                  15

Thr Pro Ser Ser Thr Pro Ser Pro Ser Gly Glu Gly Met Gly Thr Glu
                 20                  25                  30

Ser Met Leu Leu Leu Phe Asp Asp Ile Trp Met Lys Leu Met Glu Leu
             35                  40                  45

Ala Lys Lys Leu Arg Asp Ile Met Arg Ser Tyr Asn Val Glu Lys Gln
         50                  55                  60

Arg Leu Ala Trp Glu Leu Gln Val Asn Val Leu Gln Thr Gln Met Lys
 65                  70                  75                  80

Thr Ile Asp Glu Ala Phe Arg Ala Ser Met Ile Thr Ala Gly Gly Ala
                 85                  90                  95

Met Leu Ser Gly Val Leu Thr Ile Gly Leu Gly Ala Val Gly Gly Glu
                100                 105                 110

Thr Gly Leu Ile Ala Gly Gln Ala Val Gly His Thr Ala Gly Gly Val
            115                 120                 125

Met Gly Leu Gly Ala Gly Val Ala Gln Arg Gln Ser Asp Gln Asp Lys
130                 135                 140

Ala Ile Ala Asp Leu Gln Gln Asn Gly Ala Gln Ser Tyr Asn Lys Ser
145                 150                 155                 160

Leu Thr Glu Ile Met Glu Lys Ala Thr Glu Ile Met Gln Gln Ile Ile
                165                 170                 175

Gly Val Gly Ser Ser Leu Val Thr Val Leu Ala Glu Ile Leu Arg Ala
            180                 185                 190

Leu Thr Arg
        195

<210> SEQ ID NO 12
<211> LENGTH: 417
<212> TYPE: DNA
<213> ORGANISM: Salmonella
<220> FEATURE:
<221> NAME/KEY: CDS
<222> LOCATION: (1)..(414)

<400> SEQUENCE: 12 atg gtg caa gaa ata gag caa tgg tta cgt cgg cat cag gtg ttt act       48
Met Val Gln Glu Ile Glu Gln Trp Leu Arg Arg His Gln Val Phe Thr
  1               5                  10                  15 gag cct gca tat tta ggg gag acc gcc ata tta ctt ggg cag cag ttt       96
Glu Pro Ala Tyr Leu Gly Glu Thr Ala Ile Leu Leu Gly Gln Gln Phe
                 20                  25                  30
```

```
ata tta tcg cct tac ctg gtg atc tat cgt att gag gca aaa gaa atg      144
Ile Leu Ser Pro Tyr Leu Val Ile Tyr Arg Ile Glu Ala Lys Glu Met
        35                  40                  45 att att tgt gag ttc agg cgc ctg acg ccc ggg caa cct cga cca cag      192
Ile Ile Cys Glu Phe Arg Arg Leu Thr Pro Gly Gln Pro Arg Pro Gln
 50                  55                  60 caa ttg ttt cac tta ctg gga ctt tta cgc ggg ata ttt gtg cat cac      240
Gln Leu Phe His Leu Leu Gly Leu Leu Arg Gly Ile Phe Val His His
 65                  70                  75                  80 ccg cag tta aca tgt tta aag atg ttg ata atc acc gac gtt ctg gat      288
Pro Gln Leu Thr Cys Leu Lys Met Leu Ile Ile Thr Asp Val Leu Asp
                 85                  90                  95 gaa aaa aaa gcc atg cta cgc agg aaa tta ttg cgc atc ctg aca gta      336
Glu Lys Lys Ala Met Leu Arg Arg Lys Leu Leu Arg Ile Leu Thr Val
            100                 105                 110 atg gga gcg acc ttt aca cag ctt gat ggc gat aac tgg aca gtt tta      384
Met Gly Ala Thr Phe Thr Gln Leu Asp Gly Asp Asn Trp Thr Val Leu
        115                 120                 125 tcc gcc gag cat ctt atc cag cga cgt ttt taa                          417
Ser Ala Glu His Leu Ile Gln Arg Arg Phe
    130                 135

<210> SEQ ID NO 13
<211> LENGTH: 138
<212> TYPE: PRT
<213> ORGANISM: Salmonella

<400> SEQUENCE: 13

Met Val Gln Glu Ile Glu Gln Trp Leu Arg Arg His Gln Val Phe Thr
 1               5                  10                  15

Glu Pro Ala Tyr Leu Gly Glu Thr Ala Ile Leu Leu Gly Gln Gln Phe
            20                  25                  30

Ile Leu Ser Pro Tyr Leu Val Ile Tyr Arg Ile Glu Ala Lys Glu Met
        35                  40                  45

Ile Ile Cys Glu Phe Arg Arg Leu Thr Pro Gly Gln Pro Arg Pro Gln
 50                  55                  60

Gln Leu Phe His Leu Leu Gly Leu Leu Arg Gly Ile Phe Val His His
 65                  70                  75                  80

Pro Gln Leu Thr Cys Leu Lys Met Leu Ile Ile Thr Asp Val Leu Asp
                 85                  90                  95

Glu Lys Lys Ala Met Leu Arg Arg Lys Leu Leu Arg Ile Leu Thr Val
            100                 105                 110

Met Gly Ala Thr Phe Thr Gln Leu Asp Gly Asp Asn Trp Thr Val Leu
        115                 120                 125

Ser Ala Glu His Leu Ile Gln Arg Arg Phe
    130                 135

<210> SEQ ID NO 14
<211> LENGTH: 789
<212> TYPE: DNA
<213> ORGANISM: Salmonella
<220> FEATURE:
<221> NAME/KEY: CDS
<222> LOCATION: (1)..(786)

<400> SEQUENCE: 14 atg aaa att cat att ccg tca gcg gca agt aat ata gtc gat ggt aat       48
Met Lys Ile His Ile Pro Ser Ala Ala Ser Asn Ile Val Asp Gly Asn
 1               5                  10                  15
```

```
agt cct cct tcc gat ata caa gcg aag gag gta tcg ttt cct ccc cct    96
Ser Pro Pro Ser Asp Ile Gln Ala Lys Glu Val Ser Phe Pro Pro Pro
            20                  25                  30 gaa att cca gcg cct ggc acc ccc gca gcc cct gtg ctg ctt acg cct   144
Glu Ile Pro Ala Pro Gly Thr Pro Ala Ala Pro Val Leu Leu Thr Pro
                35                  40                  45 gaa caa ata agg cag cag agg gat tat gcg ata cat ttt atg caa tac   192
Glu Gln Ile Arg Gln Gln Arg Asp Tyr Ala Ile His Phe Met Gln Tyr
 50                  55                  60 act att cgt gcg ctg ggt gca aca gtc gtg ttt ggg tta tcg gtt gct   240
Thr Ile Arg Ala Leu Gly Ala Thr Val Val Phe Gly Leu Ser Val Ala
 65                  70                  75                  80 gca gcg gta att tct ggc ggg gca gga tta ccc att gct att ctt gcg   288
Ala Ala Val Ile Ser Gly Gly Ala Gly Leu Pro Ile Ala Ile Leu Ala
                 85                  90                  95 ggg gcg gcg ctc gtg att gct att ggg gat gct tgc tgt gcg tat cat   336
Gly Ala Ala Leu Val Ile Ala Ile Gly Asp Ala Cys Cys Ala Tyr His
            100                 105                 110 aat tat caa tcg ata tgt cag caa aag gag cca tta caa acc gcc agt   384
Asn Tyr Gln Ser Ile Cys Gln Gln Lys Glu Pro Leu Gln Thr Ala Ser
        115                 120                 125 gat agc gtt gct ctt gtg gtc agt gcg ctg gcc tta aaa tgt ggg gca   432
Asp Ser Val Ala Leu Val Val Ser Ala Leu Ala Leu Lys Cys Gly Ala
130                 135                 140 agt ctt aac tgc gct aac acc ctt gct aat tgt ctt tct tta tta ata   480
Ser Leu Asn Cys Ala Asn Thr Leu Ala Asn Cys Leu Ser Leu Leu Ile
145                 150                 155                 160 cgt tca gga atc gct att tct atg ttg gtt tta ccc cta cag ttt cca   528
Arg Ser Gly Ile Ala Ile Ser Met Leu Val Leu Pro Leu Gln Phe Pro
                165                 170                 175 ctg ccc gcg gct gaa aat att gcg gcc tct ttg gac atg ggg agt gta   576
Leu Pro Ala Ala Glu Asn Ile Ala Ala Ser Leu Asp Met Gly Ser Val
            180                 185                 190 att acc tcc gtt agc ctg acg gcg ata ggt gcg gta ctg gat tat tgc   624
Ile Thr Ser Val Ser Leu Thr Ala Ile Gly Ala Val Leu Asp Tyr Cys
        195                 200                 205 ctt gcc cgc ccc tct ggc gac gat cag gaa aat tct gtt gat gaa ctt   672
Leu Ala Arg Pro Ser Gly Asp Asp Gln Glu Asn Ser Val Asp Glu Leu
    210                 215                 220 cat gcc gat ccc agt gtg tta ttg gcg gaa caa atg gca gcg ctc tgt   720
His Ala Asp Pro Ser Val Leu Leu Ala Glu Gln Met Ala Ala Leu Cys
225                 230                 235                 240 caa tct gct act aca cct gca cct gca tta atg gac agt tct gat cat   768
Gln Ser Ala Thr Thr Pro Ala Pro Ala Leu Met Asp Ser Ser Asp His
                245                 250                 255 aca tct cgg gga gaa cca tga                                        789
Thr Ser Arg Gly Glu Pro
            260

<210> SEQ ID NO 15
<211> LENGTH: 262
<212> TYPE: PRT
<213> ORGANISM: Salmonella

<400> SEQUENCE: 15

Met Lys Ile His Ile Pro Ser Ala Ala Ser Asn Ile Val Asp Gly Asn
 1               5                  10                  15

Ser Pro Pro Ser Asp Ile Gln Ala Lys Glu Val Ser Phe Pro Pro Pro
            20                  25                  30

Glu Ile Pro Ala Pro Gly Thr Pro Ala Ala Pro Val Leu Leu Thr Pro
```

-continued

```
                   35                  40                  45
Glu Gln Ile Arg Gln Arg Asp Tyr Ala Ile His Phe Met Gln Tyr
     50                  55                  60

Thr Ile Arg Ala Leu Gly Ala Thr Val Val Phe Gly Leu Ser Val Ala
 65                  70                  75                  80

Ala Ala Val Ile Ser Gly Gly Ala Gly Leu Pro Ile Ala Ile Leu Ala
                 85                  90                  95

Gly Ala Ala Leu Val Ile Ala Ile Gly Asp Ala Cys Cys Ala Tyr His
                100                 105                 110

Asn Tyr Gln Ser Ile Cys Gln Gln Lys Glu Pro Leu Gln Thr Ala Ser
            115                 120                 125

Asp Ser Val Ala Leu Val Val Ser Ala Leu Ala Leu Lys Cys Gly Ala
    130                 135                 140

Ser Leu Asn Cys Ala Asn Thr Leu Ala Asn Cys Leu Ser Leu Leu Ile
145                 150                 155                 160

Arg Ser Gly Ile Ala Ile Ser Met Leu Val Leu Pro Leu Gln Phe Pro
                165                 170                 175

Leu Pro Ala Ala Glu Asn Ile Ala Ala Ser Leu Asp Met Gly Ser Val
                180                 185                 190

Ile Thr Ser Val Ser Leu Thr Ala Ile Gly Ala Val Leu Asp Tyr Cys
            195                 200                 205

Leu Ala Arg Pro Ser Gly Asp Asp Gln Glu Asn Ser Val Asp Glu Leu
    210                 215                 220

His Ala Asp Pro Ser Val Leu Leu Ala Glu Gln Met Ala Ala Leu Cys
225                 230                 235                 240

Gln Ser Ala Thr Thr Pro Ala Pro Ala Leu Met Asp Ser Ser Asp His
                245                 250                 255

Thr Ser Arg Gly Glu Pro
                260
```

```
<210> SEQ ID NO 16
<211> LENGTH: 690
<212> TYPE: DNA
<213> ORGANISM: Salmonella
<220> FEATURE:
<221> NAME/KEY: CDS
<222> LOCATION: (1)..(687)

<400> SEQUENCE: 16 atg aaa cct gtt agc cca aat gct cag gta gga ggg caa cgt cct gtt      48
Met Lys Pro Val Ser Pro Asn Ala Gln Val Gly Gly Gln Arg Pro Val
 1               5                  10                  15 aac gcg cct gag gaa tca cct cca tgt cct tca ttg cca cat ccg gaa      96
Asn Ala Pro Glu Glu Ser Pro Pro Cys Pro Ser Leu Pro His Pro Glu
                20                  25                  30 acc aat atg gag agt ggt aga ata gga cct caa caa gga aaa gag cgg     144
Thr Asn Met Glu Ser Gly Arg Ile Gly Pro Gln Gln Gly Lys Glu Arg
            35                  40                  45 gta ttg gcc gga ctt gcg aaa cga gtg ata gag tgt ttt cca aaa gaa     192
Val Leu Ala Gly Leu Ala Lys Arg Val Ile Glu Cys Phe Pro Lys Glu
 50                  55                  60 att ttt agt tgg caa acg gtt att ttg ggc gga cag att tta tgc tgt     240
Ile Phe Ser Trp Gln Thr Val Ile Leu Gly Gly Gln Ile Leu Cys Cys
 65                  70                  75                  80 tcc gct gga ata gca tta aca gtg cta agt ggt gga ggc gcg ccg ctc     288
Ser Ala Gly Ile Ala Leu Thr Val Leu Ser Gly Gly Gly Ala Pro Leu
                85                  90                  95
```

|  |  |
|---|---:|
| gta gcc ctg gca ggg att ggc ctt gct att gcc atc gcg gat gtc gcc<br>Val Ala Leu Ala Gly Ile Gly Leu Ala Ile Ala Ile Ala Asp Val Ala<br>            100                      105                        110 | 336 |
| tgt ctt atc tac cat cat aaa cat cat ttg cct atg gct cac gac agt<br>Cys Leu Ile Tyr His His Lys His His Leu Pro Met Ala His Asp Ser<br>115                        120                        125 | 384 |
| ata ggc aat gcc gtt ttt tat att gct aat tgt ttc gcc aat caa cgc<br>Ile Gly Asn Ala Val Phe Tyr Ile Ala Asn Cys Phe Ala Asn Gln Arg<br>      130                      135                        140 | 432 |
| aaa agt atg gcg att gct aaa gcc gtc tcc ctg ggc ggt aga tta gcc<br>Lys Ser Met Ala Ile Ala Lys Ala Val Ser Leu Gly Gly Arg Leu Ala<br>145                        150                        155                        160 | 480 |
| tta acc gcg acg gta atg act cat tca tac tgg agt ggt agt ttg gga<br>Leu Thr Ala Thr Val Met Thr His Ser Tyr Trp Ser Gly Ser Leu Gly<br>            165                      170                        175 | 528 |
| cta cag cct cat tta tta gag cgt ctt aat gat att acc tat gga cta<br>Leu Gln Pro His Leu Leu Glu Arg Leu Asn Asp Ile Thr Tyr Gly Leu<br>                180                      185                        190 | 576 |
| atg agt ttt act cgc ttc ggt atg gat ggg atg gca atg acc ggt atg<br>Met Ser Phe Thr Arg Phe Gly Met Asp Gly Met Ala Met Thr Gly Met<br>                    195                      200                        205 | 624 |
| cag gtc agc agc cca tta tat cgt ttg ctg gct cag gta acg cca gaa<br>Gln Val Ser Ser Pro Leu Tyr Arg Leu Leu Ala Gln Val Thr Pro Glu<br>210                        215                        220 | 672 |
| caa cgt gcg ccg gag taa<br>Gln Arg Ala Pro Glu<br>225 | 690 |

<210> SEQ ID NO 17
<211> LENGTH: 229
<212> TYPE: PRT
<213> ORGANISM: Salmonella

<400> SEQUENCE: 17

Met Lys Pro Val Ser Pro Asn Ala Gln Val Gly Gly Gln Arg Pro Val
1               5                   10                  15

Asn Ala Pro Glu Glu Ser Pro Pro Cys Pro Ser Leu Pro His Pro Glu
            20                  25                  30

Thr Asn Met Glu Ser Gly Arg Ile Gly Pro Gln Gln Gly Lys Glu Arg
        35                  40                  45

Val Leu Ala Gly Leu Ala Lys Arg Val Ile Glu Cys Phe Pro Lys Glu
    50                  55                  60

Ile Phe Ser Trp Gln Thr Val Ile Leu Gly Gln Ile Leu Cys Cys
65                  70                  75                  80

Ser Ala Gly Ile Ala Leu Thr Val Leu Ser Gly Gly Ala Pro Leu
                85                  90                  95

Val Ala Leu Ala Gly Ile Gly Leu Ala Ile Ala Ile Ala Asp Val Ala
            100                 105                 110

Cys Leu Ile Tyr His His Lys His His Leu Pro Met Ala His Asp Ser
        115                 120                 125

Ile Gly Asn Ala Val Phe Tyr Ile Ala Asn Cys Phe Ala Asn Gln Arg
    130                 135                 140

Lys Ser Met Ala Ile Ala Lys Ala Val Ser Leu Gly Gly Arg Leu Ala
145                 150                 155                 160

Leu Thr Ala Thr Val Met Thr His Ser Tyr Trp Ser Gly Ser Leu Gly
                165                 170                 175

Leu Gln Pro His Leu Leu Glu Arg Leu Asn Asp Ile Thr Tyr Gly Leu
            180                 185                 190

-continued

```
Met Ser Phe Thr Arg Phe Gly Met Asp Gly Met Ala Met Thr Gly Met
            195                 200                 205

Gln Val Ser Ser Pro Leu Tyr Arg Leu Leu Ala Gln Val Thr Pro Glu
        210                 215                 220

Gln Arg Ala Pro Glu
225

<210> SEQ ID NO 18
<211> LENGTH: 474
<212> TYPE: DNA
<213> ORGANISM: Salmonella
<220> FEATURE:
<221> NAME/KEY: CDS
<222> LOCATION: (1)..(471)

<400> SEQUENCE: 18 atg aaa aaa gac ccg acc cta caa cag gca cat gac acg atg cgg ttt      48
Met Lys Lys Asp Pro Thr Leu Gln Gln Ala His Asp Thr Met Arg Phe
  1               5                  10                  15 ttc cgg cgt ggc ggc tcg ctg cgt atg ttg ttg gat gac gat gtt aca      96
Phe Arg Arg Gly Gly Ser Leu Arg Met Leu Leu Asp Asp Asp Val Thr
                 20                  25                  30 cag ccg ctt aat act ctg tat cgc tat gcc acg cag ctt atg gag gta     144
Gln Pro Leu Asn Thr Leu Tyr Arg Tyr Ala Thr Gln Leu Met Glu Val
             35                  40                  45 aaa gaa ttc gcc ggc gca gcg cga ctt ttt caa ttg ctg acg ata tat     192
Lys Glu Phe Ala Gly Ala Ala Arg Leu Phe Gln Leu Leu Thr Ile Tyr
         50                  55                  60 gat gcc tgg tca ttt gac tac tgg ttt cgg tta ggg gaa tgc tgc cag     240
Asp Ala Trp Ser Phe Asp Tyr Trp Phe Arg Leu Gly Glu Cys Cys Gln
 65                  70                  75                  80 gct caa aaa cat tgg ggg gaa gcg ata tac gct tat gga cgc gcg gca     288
Ala Gln Lys His Trp Gly Glu Ala Ile Tyr Ala Tyr Gly Arg Ala Ala
                 85                  90                  95 caa att aag att gat gcg ccg cag gcg cca tgg gcc gca gcg gaa tgc     336
Gln Ile Lys Ile Asp Ala Pro Gln Ala Pro Trp Ala Ala Ala Glu Cys
            100                 105                 110 tat ctc gcg tgt gat aac gtc tgt tat gca atc aaa gcg tta aag gcc     384
Tyr Leu Ala Cys Asp Asn Val Cys Tyr Ala Ile Lys Ala Leu Lys Ala
        115                 120                 125 gtg gtg cgt att tgc ggc gag gtc agt gaa cat caa att ctc cga cag     432
Val Val Arg Ile Cys Gly Glu Val Ser Glu His Gln Ile Leu Arg Gln
    130                 135                 140 cgt gca gaa aag atg tta cag caa ctt tct gac agg agc taa             474
Arg Ala Glu Lys Met Leu Gln Gln Leu Ser Asp Arg Ser
145                 150                 155

<210> SEQ ID NO 19
<211> LENGTH: 157
<212> TYPE: PRT
<213> ORGANISM: Salmonella

<400> SEQUENCE: 19

Met Lys Lys Asp Pro Thr Leu Gln Gln Ala His Asp Thr Met Arg Phe
  1               5                  10                  15

Phe Arg Arg Gly Gly Ser Leu Arg Met Leu Leu Asp Asp Asp Val Thr
                 20                  25                  30

Gln Pro Leu Asn Thr Leu Tyr Arg Tyr Ala Thr Gln Leu Met Glu Val
             35                  40                  45

Lys Glu Phe Ala Gly Ala Ala Arg Leu Phe Gln Leu Leu Thr Ile Tyr
```

```
              50                  55                  60
Asp Ala Trp Ser Phe Asp Tyr Trp Phe Arg Leu Gly Glu Cys Cys Gln
 65                  70                  75                  80

Ala Gln Lys His Trp Gly Glu Ala Ile Tyr Ala Tyr Gly Arg Ala Ala
                 85                  90                  95

Gln Ile Lys Ile Asp Ala Pro Gln Ala Pro Trp Ala Ala Glu Cys
            100                 105                 110

Tyr Leu Ala Cys Asp Asn Val Cys Tyr Ala Ile Lys Ala Leu Lys Ala
            115                 120                 125

Val Val Arg Ile Cys Gly Glu Val Ser Glu His Gln Ile Leu Arg Gln
130                 135                 140

Arg Ala Glu Lys Met Leu Gln Gln Leu Ser Asp Arg Ser
145                 150                 155

<210> SEQ ID NO 20
<211> LENGTH: 435
<212> TYPE: DNA
<213> ORGANISM: Salmonella
<220> FEATURE:
<221> NAME/KEY: CDS
<222> LOCATION: (1)..(432)

<400> SEQUENCE: 20 atg atg atg aaa gaa gat cag aaa aat aaa ata ccc gaa gac att ctg      48
Met Met Met Lys Glu Asp Gln Lys Asn Lys Ile Pro Glu Asp Ile Leu
 1               5                  10                  15 aaa cag cta tta tcc gtt gat ccg gaa acc gtt tat gcc agt ggt tac      96
Lys Gln Leu Leu Ser Val Asp Pro Glu Thr Val Tyr Ala Ser Gly Tyr
                 20                  25                  30 gcc tca tgg cag gag ggg gat tat tcg cgc gcc gta atc gat ttt agt     144
Ala Ser Trp Gln Glu Gly Asp Tyr Ser Arg Ala Val Ile Asp Phe Ser
             35                  40                  45 tgg ctg gtg atg gcc cag cca tgg agt tgg cgt gcc cat att gca ttg     192
Trp Leu Val Met Ala Gln Pro Trp Ser Trp Arg Ala His Ile Ala Leu
         50                  55                  60 gct ggc acc tgg atg atg ctt aaa gaa tac acg acg gcc att aat ttc     240
Ala Gly Thr Trp Met Met Leu Lys Glu Tyr Thr Thr Ala Ile Asn Phe
 65                  70                  75                  80 tat gga cat gcc ttg atg ctg gat gcc agc cat cca gaa ccg gtt tac     288
Tyr Gly His Ala Leu Met Leu Asp Ala Ser His Pro Glu Pro Val Tyr
                 85                  90                  95 caa acg ggc gtc tgt ctc aaa atg atg ggg gaa ccc ggg ttg gcg aga     336
Gln Thr Gly Val Cys Leu Lys Met Met Gly Glu Pro Gly Leu Ala Arg
            100                 105                 110 gag gct ttt caa acc gca atc aag atg agt tat gcg gat gcc tca tgg     384
Glu Ala Phe Gln Thr Ala Ile Lys Met Ser Tyr Ala Asp Ala Ser Trp
            115                 120                 125 agt gag att cgc cag aat gcg caa ata atg gtt gat act ctt att gct     432
Ser Glu Ile Arg Gln Asn Ala Gln Ile Met Val Asp Thr Leu Ile Ala
         130                 135                 140 taa                                                                  435

<210> SEQ ID NO 21
<211> LENGTH: 144
<212> TYPE: PRT
<213> ORGANISM: Salmonella

<400> SEQUENCE: 21

Met Met Met Lys Glu Asp Gln Lys Asn Lys Ile Pro Glu Asp Ile Leu
 1               5                  10                  15
```

```
Lys Gln Leu Leu Ser Val Asp Pro Glu Thr Val Tyr Ala Ser Gly Tyr
         20                  25                  30

Ala Ser Trp Gln Glu Gly Asp Tyr Ser Arg Ala Val Ile Asp Phe Ser
     35                  40                  45

Trp Leu Val Met Ala Gln Pro Trp Ser Trp Arg Ala His Ile Ala Leu
 50                  55                  60

Ala Gly Thr Trp Met Met Leu Lys Glu Tyr Thr Thr Ala Ile Asn Phe
 65                  70                  75                  80

Tyr Gly His Ala Leu Met Leu Asp Ala Ser His Pro Glu Pro Val Tyr
                 85                  90                  95

Gln Thr Gly Val Cys Leu Lys Met Met Gly Glu Pro Gly Leu Ala Arg
            100                 105                 110

Glu Ala Phe Gln Thr Ala Ile Lys Met Ser Tyr Ala Asp Ala Ser Trp
        115                 120                 125

Ser Glu Ile Arg Gln Asn Ala Gln Ile Met Val Asp Thr Leu Ile Ala
    130                 135                 140
```

<210> SEQ ID NO 22
<211> LENGTH: 1212
<212> TYPE: DNA
<213> ORGANISM: Salmonella
<220> FEATURE:
<221> NAME/KEY: CDS
<222> LOCATION: (1)..(1209)

<400> SEQUENCE: 22

```
atg gca tat ctc atg gtt aat cca aag agt tcc tgg aaa ata cgt ttt    48
Met Ala Tyr Leu Met Val Asn Pro Lys Ser Ser Trp Lys Ile Arg Phe
 1               5                  10                  15 tta ggt cac gtt tta caa ggc cgg gaa gta tgg ctg aat gaa ggt aac    96
Leu Gly His Val Leu Gln Gly Arg Glu Val Trp Leu Asn Glu Gly Asn
             20                  25                  30 ctg tca ctg ggg gag aag gga tgc gat att tgt att ccg ctg gct ata   144
Leu Ser Leu Gly Glu Lys Gly Cys Asp Ile Cys Ile Pro Leu Ala Ile
         35                  40                  45 aat gaa aaa att att ctg aga gaa cag gca gat agt tta ttt gtt gat   192
Asn Glu Lys Ile Ile Leu Arg Glu Gln Ala Asp Ser Leu Phe Val Asp
 50                  55                  60 gcc ggg aaa gcc aga gtt aga gtt aat ggc cgc aga ttt aat cca aat   240
Ala Gly Lys Ala Arg Val Arg Val Asn Gly Arg Arg Phe Asn Pro Asn
 65                  70                  75                  80 aag ccg cta cca tcc agt ggg gtt ttg cag gtt gcg gga gtg gct atc   288
Lys Pro Leu Pro Ser Ser Gly Val Leu Gln Val Ala Gly Val Ala Ile
                 85                  90                  95 gcg ttt ggt aaa cag gat tgt gaa ctt gct gat tat caa ata ccc gtt   336
Ala Phe Gly Lys Gln Asp Cys Glu Leu Ala Asp Tyr Gln Ile Pro Val
            100                 105                 110 tcc aga tca ggg tac tgg tgg ttg gct ggc gta ttc ttg att ttc atc   384
Ser Arg Ser Gly Tyr Trp Trp Leu Ala Gly Val Phe Leu Ile Phe Ile
        115                 120                 125 ggt gga atg ggt gtc ctg tta agt att agt ggt cag cct gaa acg gta   432
Gly Gly Met Gly Val Leu Leu Ser Ile Ser Gly Gln Pro Glu Thr Val
    130                 135                 140 aat gac tta cct ttg cgg gtt aag ttt tta tta gac aaa agc aat att   480
Asn Asp Leu Pro Leu Arg Val Lys Phe Leu Leu Asp Lys Ser Asn Ile
145                 150                 155                 160 cat tat gtg cgg gcg caa tgg aaa gaa gat ggc agc ctg cag ttg tcc   528
His Tyr Val Arg Ala Gln Trp Lys Glu Asp Gly Ser Leu Gln Leu Ser
                165                 170                 175
```

```
ggt tat tgc tcg tca agc gaa cag atg caa aag gtg aga gcg act ctc    576
Gly Tyr Cys Ser Ser Ser Glu Gln Met Gln Lys Val Arg Ala Thr Leu
        180                 185                 190 gaa tca tgg ggg gtc atg tat cgg gat ggt gta atc tgt gat gac tta    624
Glu Ser Trp Gly Val Met Tyr Arg Asp Gly Val Ile Cys Asp Asp Leu
        195                 200                 205 ttg gta cga gaa gtg cag gat gtt ttg ata aaa atg ggt tac ccg cat    672
Leu Val Arg Glu Val Gln Asp Val Leu Ile Lys Met Gly Tyr Pro His
    210                 215                 220 gct gaa gta tcc agc gaa ggg ccg ggg agc gtg tta att cat gat gat    720
Ala Glu Val Ser Ser Glu Gly Pro Gly Ser Val Leu Ile His Asp Asp
225                 230                 235                 240 ata caa atg gat cag caa tgg cgc aag gtt caa cca tta ctt gca gat    768
Ile Gln Met Asp Gln Gln Trp Arg Lys Val Gln Pro Leu Leu Ala Asp
                245                 250                 255 att ccc ggg tta ttg cac tgg cag att agt cac tct cat cag tct cag    816
Ile Pro Gly Leu Leu His Trp Gln Ile Ser His Ser His Gln Ser Gln
            260                 265                 270 ggg gat gat att att tct gcg ata ata gag aac ggt tta gtg ggg ctt    864
Gly Asp Asp Ile Ile Ser Ala Ile Ile Glu Asn Gly Leu Val Gly Leu
        275                 280                 285 gtc aat gtt agc cca atg cgg cgc tct ttt gtt atc agt ggt gta ctg    912
Val Asn Val Ser Pro Met Arg Arg Ser Phe Val Ile Ser Gly Val Leu
    290                 295                 300 gat gaa tct cat caa cgc att ttg caa gaa acg tta gca gca tta aag    960
Asp Glu Ser His Gln Arg Ile Leu Gln Glu Thr Leu Ala Ala Leu Lys
305                 310                 315                 320 aaa aag gat ccc gct ctt tct tta att tat cag gat att gcg cct tcc   1008
Lys Lys Asp Pro Ala Leu Ser Leu Ile Tyr Gln Asp Ile Ala Pro Ser
                325                 330                 335 cat gat gaa agc aag tat ctg cct gcg cca gtg gct ggc ttt gta cag   1056
His Asp Glu Ser Lys Tyr Leu Pro Ala Pro Val Ala Gly Phe Val Gln
            340                 345                 350 agt cgc cat ggt aat tac tta tta ctg acg aat aaa gag cgt tta cgt   1104
Ser Arg His Gly Asn Tyr Leu Leu Leu Thr Asn Lys Glu Arg Leu Arg
        355                 360                 365 gta ggg gca ttg tta ccc aat ggg gga gaa att gtc cat ctg agt gcc   1152
Val Gly Ala Leu Leu Pro Asn Gly Gly Glu Ile Val His Leu Ser Ala
    370                 375                 380 gat gtg gta acg att aaa cat tat gat act ttg att aac tat cca tta   1200
Asp Val Val Thr Ile Lys His Tyr Asp Thr Leu Ile Asn Tyr Pro Leu
385                 390                 395                 400 gat ttt aag tga                                                   1212
Asp Phe Lys <210> SEQ ID NO 23
<211> LENGTH: 403
<212> TYPE: PRT
<213> ORGANISM: Salmonella

<400> SEQUENCE: 23

Met Ala Tyr Leu Met Val Asn Pro Lys Ser Ser Trp Lys Ile Arg Phe
  1               5                  10                  15

Leu Gly His Val Leu Gln Gly Arg Glu Val Trp Leu Asn Glu Gly Asn
             20                  25                  30

Leu Ser Leu Gly Glu Lys Gly Cys Asp Ile Cys Ile Pro Leu Ala Ile
         35                  40                  45

Asn Glu Lys Ile Ile Leu Arg Glu Gln Ala Asp Ser Leu Phe Val Asp
     50                  55                  60
```

```
Ala Gly Lys Ala Arg Val Arg Val Asn Gly Arg Arg Phe Asn Pro Asn
 65                  70                  75                  80

Lys Pro Leu Pro Ser Ser Gly Val Leu Gln Val Ala Gly Val Ala Ile
                 85                  90                  95

Ala Phe Gly Lys Gln Asp Cys Glu Leu Ala Asp Tyr Gln Ile Pro Val
            100                 105                 110

Ser Arg Ser Gly Tyr Trp Trp Leu Ala Gly Val Phe Leu Ile Phe Ile
        115                 120                 125

Gly Gly Met Gly Val Leu Leu Ser Ile Ser Gly Gln Pro Glu Thr Val
    130                 135                 140

Asn Asp Leu Pro Leu Arg Val Lys Phe Leu Leu Asp Lys Ser Asn Ile
145                 150                 155                 160

His Tyr Val Arg Ala Gln Trp Lys Glu Asp Gly Ser Leu Gln Leu Ser
                165                 170                 175

Gly Tyr Cys Ser Ser Ser Glu Gln Met Gln Lys Val Arg Ala Thr Leu
            180                 185                 190

Glu Ser Trp Gly Val Met Tyr Arg Asp Gly Val Ile Cys Asp Asp Leu
        195                 200                 205

Leu Val Arg Glu Val Gln Asp Val Leu Ile Lys Met Gly Tyr Pro His
    210                 215                 220

Ala Glu Val Ser Ser Glu Gly Pro Gly Ser Val Leu Ile His Asp Asp
225                 230                 235                 240

Ile Gln Met Asp Gln Gln Trp Arg Lys Val Gln Pro Leu Leu Ala Asp
                245                 250                 255

Ile Pro Gly Leu Leu His Trp Gln Ile Ser His Ser His Gln Ser Gln
            260                 265                 270

Gly Asp Asp Ile Ile Ser Ala Ile Glu Asn Gly Leu Val Gly Leu
        275                 280                 285

Val Asn Val Ser Pro Met Arg Arg Ser Phe Val Ile Ser Gly Val Leu
    290                 295                 300

Asp Glu Ser His Gln Arg Ile Leu Gln Glu Thr Leu Ala Ala Leu Lys
305                 310                 315                 320

Lys Lys Asp Pro Ala Leu Ser Leu Ile Tyr Gln Asp Ile Ala Pro Ser
                325                 330                 335

His Asp Glu Ser Lys Tyr Leu Pro Ala Pro Val Ala Gly Phe Val Gln
            340                 345                 350

Ser Arg His Gly Asn Tyr Leu Leu Leu Thr Asn Lys Glu Arg Leu Arg
        355                 360                 365

Val Gly Ala Leu Leu Pro Asn Gly Gly Glu Ile Val His Leu Ser Ala
    370                 375                 380

Asp Val Val Thr Ile Lys His Tyr Asp Thr Leu Ile Asn Tyr Pro Leu
385                 390                 395                 400

Asp Phe Lys

<210> SEQ ID NO 24
<211> LENGTH: 243
<212> TYPE: DNA
<213> ORGANISM: Salmonella
<220> FEATURE:
<221> NAME/KEY: CDS
<222> LOCATION: (1)..(240)

<400> SEQUENCE: 24 atg aca act ttg acc cgg tta gaa gat ttg ctg ctt cat tcg cgt gaa    48
Met Thr Thr Leu Thr Arg Leu Glu Asp Leu Leu Leu His Ser Arg Glu
```

```
                1               5              10              15
gag gcc aaa ggc ata att tta caa tta agg gct gcc cgg aaa cag tta        96
Glu Ala Lys Gly Ile Ile Leu Gln Leu Arg Ala Ala Arg Lys Gln Leu
                        20                  25                  30 gaa gag aac aac ggc aag tta cag gat ccg cag caa tat cag caa aac       144
Glu Glu Asn Asn Gly Lys Leu Gln Asp Pro Gln Gln Tyr Gln Gln Asn
            35                  40                  45 acc tta ttg ctt gaa gcg atc gag cag gcc gaa aat atc atc aac att       192
Thr Leu Leu Leu Glu Ala Ile Glu Gln Ala Glu Asn Ile Ile Asn Ile
        50                  55                  60 att tat tat cgt tac cat aac agc gca ctt gta gtg agt gag caa gag       240
Ile Tyr Tyr Arg Tyr His Asn Ser Ala Leu Val Val Ser Glu Gln Glu
    65                  70                  75                  80 taa                                                                    243

<210> SEQ ID NO 25
<211> LENGTH: 80
<212> TYPE: PRT
<213> ORGANISM: Salmonella

<400> SEQUENCE: 25

Met Thr Thr Leu Thr Arg Leu Glu Asp Leu Leu His Ser Arg Glu
  1               5                  10                  15

Glu Ala Lys Gly Ile Ile Leu Gln Leu Arg Ala Ala Arg Lys Gln Leu
                        20                  25                  30

Glu Glu Asn Asn Gly Lys Leu Gln Asp Pro Gln Gln Tyr Gln Gln Asn
            35                  40                  45

Thr Leu Leu Leu Glu Ala Ile Glu Gln Ala Glu Asn Ile Ile Asn Ile
        50                  55                  60

Ile Tyr Tyr Arg Tyr His Asn Ser Ala Leu Val Val Ser Glu Gln Glu
    65                  70                  75                  80

<210> SEQ ID NO 26
<211> LENGTH: 216
<212> TYPE: DNA
<213> ORGANISM: Salmonella
<220> FEATURE:
<221> NAME/KEY: CDS
<222> LOCATION: (1)..(213)

<400> SEQUENCE: 26 atg gat att gca caa tta gtg gat atg ctc tcc cac atg gcg cac cag        48
Met Asp Ile Ala Gln Leu Val Asp Met Leu Ser His Met Ala His Gln
  1               5                  10                  15 gca ggc cag gcc att aat gac aaa atg aat ggt aat gat ttg ctc aac        96
Ala Gly Gln Ala Ile Asn Asp Lys Met Asn Gly Asn Asp Leu Leu Asn
                        20                  25                  30 cca gaa tcg atg att aaa gcg caa ttt gcc tta cag cag tat tct aca       144
Pro Glu Ser Met Ile Lys Ala Gln Phe Ala Leu Gln Gln Tyr Ser Thr
            35                  40                  45 ttt att aat tac gaa agt tca ctg atc aaa atg atc aag gat atg ctt       192
Phe Ile Asn Tyr Glu Ser Ser Leu Ile Lys Met Ile Lys Asp Met Leu
        50                  55                  60 agt gga atc att gct aaa atc tga                                        216
Ser Gly Ile Ile Ala Lys Ile
    65                  70

<210> SEQ ID NO 27
<211> LENGTH: 71
<212> TYPE: PRT
<213> ORGANISM: Salmonella
```

<400> SEQUENCE: 27

| Met | Asp | Ile | Ala | Gln | Leu | Val | Asp | Met | Leu | Ser | His | Met | Ala | His | Gln |
|---|---|---|---|---|---|---|---|---|---|---|---|---|---|---|---|
| 1 | | | | 5 | | | | | 10 | | | | | 15 | |

| Ala | Gly | Gln | Ala | Ile | Asn | Asp | Lys | Met | Asn | Gly | Asn | Asp | Leu | Leu | Asn |
|---|---|---|---|---|---|---|---|---|---|---|---|---|---|---|---|
| | | | 20 | | | | | 25 | | | | | 30 | | |

| Pro | Glu | Ser | Met | Ile | Lys | Ala | Gln | Phe | Ala | Leu | Gln | Gln | Tyr | Ser | Thr |
|---|---|---|---|---|---|---|---|---|---|---|---|---|---|---|---|
| | | | 35 | | | | | 40 | | | | | 45 | | |

| Phe | Ile | Asn | Tyr | Glu | Ser | Ser | Leu | Ile | Lys | Met | Ile | Lys | Asp | Met | Leu |
|---|---|---|---|---|---|---|---|---|---|---|---|---|---|---|---|
| | 50 | | | | | 55 | | | | | 60 | | | | |

| Ser | Gly | Ile | Ile | Ala | Lys | Ile |
|---|---|---|---|---|---|---|
| 65 | | | | | 70 | |

<210> SEQ ID NO 28
<211> LENGTH: 228
<212> TYPE: DNA
<213> ORGANISM: Salmonella
<220> FEATURE:
<221> NAME/KEY: CDS
<222> LOCATION: (1)..(225)

<400> SEQUENCE: 28

```
atg ttt gcg ggc gtt aac cat agc ctg att tcc cag gta cat gcg atg       48
Met Phe Ala Gly Val Asn His Ser Leu Ile Ser Gln Val His Ala Met
 1               5                  10                  15 tta cca gcg cta acg gtt att gtt ccg gat aaa aaa tta cag ttg gta       96
Leu Pro Ala Leu Thr Val Ile Val Pro Asp Lys Lys Leu Gln Leu Val
             20                  25                  30 tgt ctg gca tta ttg ttg gcg ggt tta aat gag ccg cta aaa gcc gcg      144
Cys Leu Ala Leu Leu Leu Ala Gly Leu Asn Glu Pro Leu Lys Ala Ala
         35                  40                  45 aaa att tta tcg gat ata gat ttg cca gag gct atg gcg ctg cgt ctg      192
Lys Ile Leu Ser Asp Ile Asp Leu Pro Glu Ala Met Ala Leu Arg Leu
     50                  55                  60 tta ttt cct gca cca aat gag ggg ttt gaa aat tga                      228
Leu Phe Pro Ala Pro Asn Glu Gly Phe Glu Asn
 65                  70                  75
```

<210> SEQ ID NO 29
<211> LENGTH: 75
<212> TYPE: PRT
<213> ORGANISM: Salmonella

<400> SEQUENCE: 29

| Met | Phe | Ala | Gly | Val | Asn | His | Ser | Leu | Ile | Ser | Gln | Val | His | Ala | Met |
|---|---|---|---|---|---|---|---|---|---|---|---|---|---|---|---|
| 1 | | | | 5 | | | | | 10 | | | | | 15 | |

| Leu | Pro | Ala | Leu | Thr | Val | Ile | Val | Pro | Asp | Lys | Lys | Leu | Gln | Leu | Val |
|---|---|---|---|---|---|---|---|---|---|---|---|---|---|---|---|
| | | | 20 | | | | | 25 | | | | | 30 | | |

| Cys | Leu | Ala | Leu | Leu | Leu | Ala | Gly | Leu | Asn | Glu | Pro | Leu | Lys | Ala | Ala |
|---|---|---|---|---|---|---|---|---|---|---|---|---|---|---|---|
| | | | 35 | | | | | 40 | | | | | 45 | | |

| Lys | Ile | Leu | Ser | Asp | Ile | Asp | Leu | Pro | Glu | Ala | Met | Ala | Leu | Arg | Leu |
|---|---|---|---|---|---|---|---|---|---|---|---|---|---|---|---|
| | 50 | | | | | 55 | | | | | 60 | | | | |

| Leu | Phe | Pro | Ala | Pro | Asn | Glu | Gly | Phe | Glu | Asn |
|---|---|---|---|---|---|---|---|---|---|---|
| 65 | | | | | 70 | | | | | 75 |

<210> SEQ ID NO 30
<211> LENGTH: 249
<212> TYPE: DNA
<213> ORGANISM: Salmonella
<220> FEATURE:
<221> NAME/KEY: CDS

<222> LOCATION: (1)..(246)

<400> SEQUENCE: 30

```
atg agc gta gtg cct gta agc act caa tct tat gta aag tcc tct gca      48
Met Ser Val Val Pro Val Ser Thr Gln Ser Tyr Val Lys Ser Ser Ala
1               5                   10                  15 gaa ccg agc cag gag caa att aat ttt ttt gaa caa ttg ctg aaa gat      96
Glu Pro Ser Gln Glu Gln Ile Asn Phe Phe Glu Gln Leu Leu Lys Asp
            20                  25                  30 gaa gca tcc acc agt aac gcc agt gct tta tta ccg cag gtt atg ttg     144
Glu Ala Ser Thr Ser Asn Ala Ser Ala Leu Leu Pro Gln Val Met Leu
        35                  40                  45 acc aga caa atg gat tat atg cag tta acg gta ggc gtc gat tat ctt     192
Thr Arg Gln Met Asp Tyr Met Gln Leu Thr Val Gly Val Asp Tyr Leu
    50                  55                  60 gcc aga ata tca ggc gca gca tcg caa gcg ctt aat aag ctg gat aac     240
Ala Arg Ile Ser Gly Ala Ala Ser Gln Ala Leu Asn Lys Leu Asp Asn
65                  70                  75                  80 atg gca tga                                                         249
Met Ala
```

<210> SEQ ID NO 31
<211> LENGTH: 82
<212> TYPE: PRT
<213> ORGANISM: Salmonella

<400> SEQUENCE: 31

```
Met Ser Val Val Pro Val Ser Thr Gln Ser Tyr Val Lys Ser Ser Ala
1               5                   10                  15

Glu Pro Ser Gln Glu Gln Ile Asn Phe Phe Glu Gln Leu Leu Lys Asp
            20                  25                  30

Glu Ala Ser Thr Ser Asn Ala Ser Ala Leu Leu Pro Gln Val Met Leu
        35                  40                  45

Thr Arg Gln Met Asp Tyr Met Gln Leu Thr Val Gly Val Asp Tyr Leu
    50                  55                  60

Ala Arg Ile Ser Gly Ala Ala Ser Gln Ala Leu Asn Lys Leu Asp Asn
65                  70                  75                  80

Met Ala
```

<210> SEQ ID NO 32
<211> LENGTH: 750
<212> TYPE: DNA
<213> ORGANISM: Salmonella
<220> FEATURE:
<221> NAME/KEY: CDS
<222> LOCATION: (1)..(747)

<400> SEQUENCE: 32

```
atg aag gtt cat cgt ata gta ttt ctt act gtc ctt acg ttc ttt ctt      48
Met Lys Val His Arg Ile Val Phe Leu Thr Val Leu Thr Phe Phe Leu
1               5                   10                  15 acg gca tgt gat gtg gat ctt tat cgc tca ttg cca gaa gat gaa gcg      96
Thr Ala Cys Asp Val Asp Leu Tyr Arg Ser Leu Pro Glu Asp Glu Ala
            20                  25                  30 aat caa atg ctg gca tta ctt atg cag cat cat att gat gcg gaa aaa     144
Asn Gln Met Leu Ala Leu Leu Met Gln His His Ile Asp Ala Glu Lys
        35                  40                  45 aaa cag gaa gag gat ggt gta acc tta cgt gtc gag cag tcg cag ttt     192
Lys Gln Glu Glu Asp Gly Val Thr Leu Arg Val Glu Gln Ser Gln Phe
    50                  55                  60
```

```
att aat gcg gtt gag cta ctt aga ctt aac ggt tat ccg cat agg cag      240
Ile Asn Ala Val Glu Leu Leu Arg Leu Asn Gly Tyr Pro His Arg Gln
 65                  70                  75                  80 ttt aca acg gcg gat aag atg ttt ccg gct aat cag tta gtg gta tca      288
Phe Thr Thr Ala Asp Lys Met Phe Pro Ala Asn Gln Leu Val Val Ser
                 85                  90                  95 ccc cag gaa gaa cag cag aag att aat ttt tta aaa gaa caa aga att      336
Pro Gln Glu Glu Gln Gln Lys Ile Asn Phe Leu Lys Glu Gln Arg Ile
            100                 105                 110 gaa gga atg ctg agt cag atg gag ggc gtg att aat gca aaa gtg acc      384
Glu Gly Met Leu Ser Gln Met Glu Gly Val Ile Asn Ala Lys Val Thr
        115                 120                 125 att gcg cta ccg act tat gat gag gga agt aac gct tct ccg agc tca      432
Ile Ala Leu Pro Thr Tyr Asp Glu Gly Ser Asn Ala Ser Pro Ser Ser
130                 135                 140 gtt gcc gta ttt ata aaa tat tca cct cag gtc aat atg gag gcc ttt      480
Val Ala Val Phe Ile Lys Tyr Ser Pro Gln Val Asn Met Glu Ala Phe
145                 150                 155                 160 cgg gta aaa att aaa gat tta ata gag atg tca atc cct ggg ttg caa      528
Arg Val Lys Ile Lys Asp Leu Ile Glu Met Ser Ile Pro Gly Leu Gln
                165                 170                 175 tac agt aag att agt atc ttg atg cag cct gct gaa ttc aga atg gta      576
Tyr Ser Lys Ile Ser Ile Leu Met Gln Pro Ala Glu Phe Arg Met Val
            180                 185                 190 gct gac gta ccc gcg aga caa aca ttc tgg att atg gac gtt atc aac      624
Ala Asp Val Pro Ala Arg Gln Thr Phe Trp Ile Met Asp Val Ile Asn
        195                 200                 205 gcc aat aaa ggg aag gtg gtg aag tgg ttg atg aaa tac cct tat ccg      672
Ala Asn Lys Gly Lys Val Val Lys Trp Leu Met Lys Tyr Pro Tyr Pro
210                 215                 220 ttg atg tta tcg ttg aca gga ctg tta tta gga gtg ggc atc ctg atc      720
Leu Met Leu Ser Leu Thr Gly Leu Leu Leu Gly Val Gly Ile Leu Ile
225                 230                 235                 240 ggc tat ttt tgc ctg aga cgc cgt ttt tga                              750
Gly Tyr Phe Cys Leu Arg Arg Arg Phe
                245
```

<210> SEQ ID NO 33
<211> LENGTH: 249
<212> TYPE: PRT
<213> ORGANISM: Salmonella

<400> SEQUENCE: 33

```
Met Lys Val His Arg Ile Val Phe Leu Thr Val Leu Thr Phe Phe Leu
 1               5                  10                  15

Thr Ala Cys Asp Val Asp Leu Tyr Arg Ser Leu Pro Glu Asp Glu Ala
            20                  25                  30

Asn Gln Met Leu Ala Leu Leu Met Gln His His Ile Asp Ala Glu Lys
        35                  40                  45

Lys Gln Glu Glu Asp Gly Val Thr Leu Arg Val Glu Gln Ser Gln Phe
    50                  55                  60

Ile Asn Ala Val Glu Leu Leu Arg Leu Asn Gly Tyr Pro His Arg Gln
 65                  70                  75                  80

Phe Thr Thr Ala Asp Lys Met Phe Pro Ala Asn Gln Leu Val Val Ser
                 85                  90                  95

Pro Gln Glu Glu Gln Gln Lys Ile Asn Phe Leu Lys Glu Gln Arg Ile
            100                 105                 110

Glu Gly Met Leu Ser Gln Met Glu Gly Val Ile Asn Ala Lys Val Thr
        115                 120                 125
```

```
Ile Ala Leu Pro Thr Tyr Asp Glu Gly Ser Asn Ala Ser Pro Ser Ser
    130                 135                 140

Val Ala Val Phe Ile Lys Tyr Ser Pro Gln Val Asn Met Glu Ala Phe
145                 150                 155                 160

Arg Val Lys Ile Lys Asp Leu Ile Glu Met Ser Ile Pro Gly Leu Gln
                165                 170                 175

Tyr Ser Lys Ile Ser Ile Leu Met Gln Pro Ala Glu Phe Arg Met Val
            180                 185                 190

Ala Asp Val Pro Ala Arg Gln Thr Phe Trp Ile Met Asp Val Ile Asn
        195                 200                 205

Ala Asn Lys Gly Lys Val Val Lys Trp Leu Met Lys Tyr Pro Tyr Pro
    210                 215                 220

Leu Met Leu Ser Leu Thr Gly Leu Leu Leu Gly Val Gly Ile Leu Ile
225                 230                 235                 240

Gly Tyr Phe Cys Leu Arg Arg Phe
                245

<210> SEQ ID NO 34
<211> LENGTH: 2763
<212> TYPE: DNA
<213> ORGANISM: Salmonella
<220> FEATURE:
<221> NAME/KEY: CDS
<222> LOCATION: (1)..(2760)

<400> SEQUENCE: 34 atg aat ttg ctc aat ctc aag aat acg ctg caa aca tct tta gta atc      48
Met Asn Leu Leu Asn Leu Lys Asn Thr Leu Gln Thr Ser Leu Val Ile
1               5                   10                  15 agg cta act ttt tta ttt tta tta aca aca ata att att tgg ctg cta      96
Arg Leu Thr Phe Leu Phe Leu Leu Thr Thr Ile Ile Ile Trp Leu Leu
                20                  25                  30 tct gtg ctt acc gca gct tat ata tca atg gtt cag aaa cgg cag cat     144
Ser Val Leu Thr Ala Ala Tyr Ile Ser Met Val Gln Lys Arg Gln His
            35                  40                  45 ata ata gag gat tta tcc gtt cta tcc gag atg aat att gta cta agc     192
Ile Ile Glu Asp Leu Ser Val Leu Ser Glu Met Asn Ile Val Leu Ser
        50                  55                  60 aat caa cgg ttt gaa gaa gct gaa cgt gac gct aaa aat tta atg tat     240
Asn Gln Arg Phe Glu Glu Ala Glu Arg Asp Ala Lys Asn Leu Met Tyr
65                  70                  75                  80 caa tgc tca tta gcg act gag att cat cat aac gat att ttc cct gag     288
Gln Cys Ser Leu Ala Thr Glu Ile His His Asn Asp Ile Phe Pro Glu
                85                  90                  95 gtg agc cgg cat cta tct gtc ggt cct tca aat tgc acg ccg acg cta     336
Val Ser Arg His Leu Ser Val Gly Pro Ser Asn Cys Thr Pro Thr Leu
            100                 105                 110 aac gga gag aag cac cgt ctc ttt ctg cag tcc tct gat atc gat gaa     384
Asn Gly Glu Lys His Arg Leu Phe Leu Gln Ser Ser Asp Ile Asp Glu
        115                 120                 125 aat agc ttt cgt cgc gat agt ttt att ctt aat cat aaa aat gag att     432
Asn Ser Phe Arg Arg Asp Ser Phe Ile Leu Asn His Lys Asn Glu Ile
    130                 135                 140 tcg tta tta tct act gat aac cct tca gat tat tca act cta cag cct     480
Ser Leu Leu Ser Thr Asp Asn Pro Ser Asp Tyr Ser Thr Leu Gln Pro
145                 150                 155                 160 tta acg cga aaa agc ttt cct tta tac cca acc cat gcc ggg ttt tac     528
Leu Thr Arg Lys Ser Phe Pro Leu Tyr Pro Thr His Ala Gly Phe Tyr
                165                 170                 175
```

| | | | | | | | | | | | | | | | | |
|---|---|---|---|---|---|---|---|---|---|---|---|---|---|---|---|---|
| tgg | agt | gaa | cca | gaa | tac | ata | aac | ggc | aaa | gga | tgg | cac | gct | tcc | gtt | 576 |
| Trp | Ser | Glu | Pro | Glu | Tyr | Ile | Asn | Gly | Lys | Gly | Trp | His | Ala | Ser | Val | |
| | | 180 | | | | | 185 | | | | | 190 | | | | |

| | | | | | | | | | | | | | | | | |
|---|---|---|---|---|---|---|---|---|---|---|---|---|---|---|---|---|
| gcg | gtt | gcc | gat | cag | caa | ggc | gta | ttt | ttt | gag | gtg | acg | gtt | aaa | ctt | 624 |
| Ala | Val | Ala | Asp | Gln | Gln | Gly | Val | Phe | Phe | Glu | Val | Thr | Val | Lys | Leu | |
| | 195 | | | | | 200 | | | | | 205 | | | | | |

| | | | | | | | | | | | | | | | | |
|---|---|---|---|---|---|---|---|---|---|---|---|---|---|---|---|---|
| ccc | gat | ctc | att | act | aag | agc | cac | ctg | cca | tta | gat | gat | agt | att | cga | 672 |
| Pro | Asp | Leu | Ile | Thr | Lys | Ser | His | Leu | Pro | Leu | Asp | Asp | Ser | Ile | Arg | |
| 210 | | | | | 215 | | | | | 220 | | | | | | |

| | | | | | | | | | | | | | | | | |
|---|---|---|---|---|---|---|---|---|---|---|---|---|---|---|---|---|
| gta | tgg | ctg | gat | caa | aac | aac | cac | tta | ttg | ccg | ttt | tca | tac | atc | ccg | 720 |
| Val | Trp | Leu | Asp | Gln | Asn | Asn | His | Leu | Leu | Pro | Phe | Ser | Tyr | Ile | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| caa | aaa | ata | cgt | aca | cag | tta | gaa | aat | gta | acg | ctg | cat | gat | gga | tgg | 768 |
| Gln | Lys | Ile | Arg | Thr | Gln | Leu | Glu | Asn | Val | Thr | Leu | His | Asp | Gly | Trp | |
| | | | | 245 | | | | | 250 | | | | | 255 | | |

| | | | | | | | | | | | | | | | | |
|---|---|---|---|---|---|---|---|---|---|---|---|---|---|---|---|---|
| cag | caa | att | ccc | gga | ttt | ctg | ata | tta | cgc | aca | acc | ttg | cat | ggc | ccc | 816 |
| Gln | Gln | Ile | Pro | Gly | Phe | Leu | Ile | Leu | Arg | Thr | Thr | Leu | His | Gly | Pro | |
| | | | 260 | | | | | 265 | | | | | 270 | | | |

| | | | | | | | | | | | | | | | | |
|---|---|---|---|---|---|---|---|---|---|---|---|---|---|---|---|---|
| gga | tgg | agt | ctg | gtt | acg | ctg | tac | cca | tac | ggt | aat | cta | cat | aat | cgc | 864 |
| Gly | Trp | Ser | Leu | Val | Thr | Leu | Tyr | Pro | Tyr | Gly | Asn | Leu | His | Asn | Arg | |
| | | 275 | | | | | 280 | | | | | 285 | | | | |

| | | | | | | | | | | | | | | | | |
|---|---|---|---|---|---|---|---|---|---|---|---|---|---|---|---|---|
| atc | tta | aaa | att | atc | ctt | caa | caa | atc | ccc | ttt | aca | tta | aca | gca | ttg | 912 |
| Ile | Leu | Lys | Ile | Ile | Leu | Gln | Gln | Ile | Pro | Phe | Thr | Leu | Thr | Ala | Leu | |
| | 290 | | | | | 295 | | | | | 300 | | | | | |

| | | | | | | | | | | | | | | | | |
|---|---|---|---|---|---|---|---|---|---|---|---|---|---|---|---|---|
| gtg | ttg | atg | acg | tcg | gct | ttt | tgc | tgg | tta | cta | cat | cgc | tca | ctg | gcc | 960 |
| Val | Leu | Met | Thr | Ser | Ala | Phe | Cys | Trp | Leu | Leu | His | Arg | Ser | Leu | Ala | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| aaa | ccg | tta | tgg | cgt | ttt | gtc | gat | gtc | att | aat | aaa | acc | gca | act | gca | 1008 |
| Lys | Pro | Leu | Trp | Arg | Phe | Val | Asp | Val | Ile | Asn | Lys | Thr | Ala | Thr | Ala | |
| | | | | 325 | | | | | 330 | | | | | 335 | | |

| | | | | | | | | | | | | | | | | |
|---|---|---|---|---|---|---|---|---|---|---|---|---|---|---|---|---|
| ccg | ctg | agc | aca | cgt | tta | cca | gca | caa | cga | ctg | gat | gaa | tta | gat | agt | 1056 |
| Pro | Leu | Ser | Thr | Arg | Leu | Pro | Ala | Gln | Arg | Leu | Asp | Glu | Leu | Asp | Ser | |
| | | | 340 | | | | | 345 | | | | | 350 | | | |

| | | | | | | | | | | | | | | | | |
|---|---|---|---|---|---|---|---|---|---|---|---|---|---|---|---|---|
| att | gcc | ggt | gct | ttt | aac | caa | ctg | ctt | gat | act | cta | caa | gtc | caa | tac | 1104 |
| Ile | Ala | Gly | Ala | Phe | Asn | Gln | Leu | Leu | Asp | Thr | Leu | Gln | Val | Gln | Tyr | |
| | | 355 | | | | | 360 | | | | | 365 | | | | |

| | | | | | | | | | | | | | | | | |
|---|---|---|---|---|---|---|---|---|---|---|---|---|---|---|---|---|
| gac | aat | ctg | gaa | aac | aaa | gtc | gca | gag | cgc | acc | cag | gcg | cta | aat | gaa | 1152 |
| Asp | Asn | Leu | Glu | Asn | Lys | Val | Ala | Glu | Arg | Thr | Gln | Ala | Leu | Asn | Glu | |
| | 370 | | | | | 375 | | | | | 380 | | | | | |

| | | | | | | | | | | | | | | | | |
|---|---|---|---|---|---|---|---|---|---|---|---|---|---|---|---|---|
| gca | aaa | aaa | cgc | gct | gag | cga | gct | aac | aaa | cgt | aaa | agc | att | cat | ctt | 1200 |
| Ala | Lys | Lys | Arg | Ala | Glu | Arg | Ala | Asn | Lys | Arg | Lys | Ser | Ile | His | Leu | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| acg | gta | ata | agt | cat | gag | tta | cgt | act | ccg | atg | aat | ggc | gta | ctc | ggt | 1248 |
| Thr | Val | Ile | Ser | His | Glu | Leu | Arg | Thr | Pro | Met | Asn | Gly | Val | Leu | Gly | |
| | | | | 405 | | | | | 410 | | | | | 415 | | |

| | | | | | | | | | | | | | | | | |
|---|---|---|---|---|---|---|---|---|---|---|---|---|---|---|---|---|
| gca | att | gaa | tta | tta | caa | acc | acc | cct | tta | aac | ata | gag | caa | caa | gga | 1296 |
| Ala | Ile | Glu | Leu | Leu | Gln | Thr | Thr | Pro | Leu | Asn | Ile | Glu | Gln | Gln | Gly | |
| | | | | 420 | | | | | 425 | | | | | 430 | | |

| | | | | | | | | | | | | | | | | |
|---|---|---|---|---|---|---|---|---|---|---|---|---|---|---|---|---|
| tta | gct | gat | acc | gcc | aga | aat | tgt | aca | ctg | tct | ttg | tta | gct | att | att | 1344 |
| Leu | Ala | Asp | Thr | Ala | Arg | Asn | Cys | Thr | Leu | Ser | Leu | Leu | Ala | Ile | Ile | |
| | | | 435 | | | | | 440 | | | | | 445 | | | |

| | | | | | | | | | | | | | | | | |
|---|---|---|---|---|---|---|---|---|---|---|---|---|---|---|---|---|
| aat | aat | ctg | ctg | gat | ttt | tca | cgc | atc | gag | tct | ggt | cat | ttc | aca | tta | 1392 |
| Asn | Asn | Leu | Leu | Asp | Phe | Ser | Arg | Ile | Glu | Ser | Gly | His | Phe | Thr | Leu | |
| | | 450 | | | | | 455 | | | | | 460 | | | | |

| | | | | | | | | | | | | | | | | |
|---|---|---|---|---|---|---|---|---|---|---|---|---|---|---|---|---|
| cat | atg | gaa | gaa | aca | gcg | tta | ctg | ccg | tta | ctg | gac | cag | gca | atg | caa | 1440 |
| His | Met | Glu | Glu | Thr | Ala | Leu | Leu | Pro | Leu | Leu | Asp | Gln | Ala | Met | Gln | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| acc | atc | cag | ggg | cca | gcg | caa | agc | aaa | aaa | ctg | tca | tta | cgt | act | ttt | 1488 |
| Thr | Ile | Gln | Gly | Pro | Ala | Gln | Ser | Lys | Lys | Leu | Ser | Leu | Arg | Thr | Phe | |

-continued

```
                485                 490                 495
gtc ggt caa cat gtc cct ctc tat ttt cat acc gac agt atc cgt tta    1536
Val Gly Gln His Val Pro Leu Tyr Phe His Thr Asp Ser Ile Arg Leu
        500                 505                 510 cgg caa att ttg gtt aat tta ctc ggg aac gcg gta aaa ttt acc gaa    1584
Arg Gln Ile Leu Val Asn Leu Leu Gly Asn Ala Val Lys Phe Thr Glu
        515                 520                 525 acc gga ggg ata cgt ctg acg gtc aag cgt cat gag gaa caa tta ata    1632
Thr Gly Gly Ile Arg Leu Thr Val Lys Arg His Glu Glu Gln Leu Ile
    530                 535                 540 ttt ctg gtt agc gat agc ggt aaa ggg att gaa ata cag cag cag tct    1680
Phe Leu Val Ser Asp Ser Gly Lys Gly Ile Glu Ile Gln Gln Gln Ser
545                 550                 555                 560 caa atc ttt act gct ttt tat caa gca gac aca aat tcg caa ggt aca    1728
Gln Ile Phe Thr Ala Phe Tyr Gln Ala Asp Thr Asn Ser Gln Gly Thr
                565                 570                 575 gga att gga ctg act att gcg tca agc ctg gct aaa atg atg ggc ggt    1776
Gly Ile Gly Leu Thr Ile Ala Ser Ser Leu Ala Lys Met Met Gly Gly
            580                 585                 590 aat ctg aca cta aaa agt gtc ccc ggg gtt gga acc tgt gtc tcg cta    1824
Asn Leu Thr Leu Lys Ser Val Pro Gly Val Gly Thr Cys Val Ser Leu
        595                 600                 605 gta tta ccc tta caa gaa tac cag ccg cct caa cca att aaa ggg acg    1872
Val Leu Pro Leu Gln Glu Tyr Gln Pro Pro Gln Pro Ile Lys Gly Thr
    610                 615                 620 ctg tca gcg ccg ttc tgc ctg cat cgg caa ctg gct tgc tgg gga ata    1920
Leu Ser Ala Pro Phe Cys Leu His Arg Gln Leu Ala Cys Trp Gly Ile
625                 630                 635                 640 cgc ggt gaa cca ccc cac cag caa aat gcg ctt ctc aac gca gag ctt    1968
Arg Gly Glu Pro Pro His Gln Gln Asn Ala Leu Leu Asn Ala Glu Leu
                645                 650                 655 ttg tat ttc tcc gga aaa ctc tac gac ctg gcg caa cag tta ata ttg    2016
Leu Tyr Phe Ser Gly Lys Leu Tyr Asp Leu Ala Gln Gln Leu Ile Leu
            660                 665                 670 tgt aca cca aat atg cca gta ata aat aat ttg tta cca ccc tgg cag    2064
Cys Thr Pro Asn Met Pro Val Ile Asn Asn Leu Leu Pro Pro Trp Gln
        675                 680                 685 ttg cag att ctt ttg gtt gat gat gcc gat att aat cgg gat atc atc    2112
Leu Gln Ile Leu Leu Val Asp Asp Ala Asp Ile Asn Arg Asp Ile Ile
    690                 695                 700 ggc aaa atg ctt gtc agc ctg ggc caa cac gtc act att gcc gcc agt    2160
Gly Lys Met Leu Val Ser Leu Gly Gln His Val Thr Ile Ala Ala Ser
705                 710                 715                 720 agt aac gag gct ctg act tta tca caa cag cag cga ttc gat tta gta    2208
Ser Asn Glu Ala Leu Thr Leu Ser Gln Gln Gln Arg Phe Asp Leu Val
                725                 730                 735 ctg att gac att aga atg cca gaa ata gat ggt att gaa tgt gta cga    2256
Leu Ile Asp Ile Arg Met Pro Glu Ile Asp Gly Ile Glu Cys Val Arg
            740                 745                 750 tta tgg cat gat gag ccg aat aat tta gat cct gac tgc atg ttt gtg    2304
Leu Trp His Asp Glu Pro Asn Asn Leu Asp Pro Asp Cys Met Phe Val
        755                 760                 765 gca cta tcc gct agc gta gcg aca gaa gat att cat cgt tgt aaa aaa    2352
Ala Leu Ser Ala Ser Val Ala Thr Glu Asp Ile His Arg Cys Lys Lys
    770                 775                 780 aat ggg att cat cat tac att aca aaa cca gtg aca ttg gct acc tta    2400
Asn Gly Ile His His Tyr Ile Thr Lys Pro Val Thr Leu Ala Thr Leu
785                 790                 795                 800 gct cgc tac atc agt att gcc gca gaa tac caa ctt tta cga aat ata    2448
```

```
Ala Arg Tyr Ile Ser Ile Ala Ala Glu Tyr Gln Leu Leu Arg Asn Ile
                805                 810                 815 gag cta cag gag cag gat ccg agt cgc tgc tca gcg cta ctg gcg aca    2496
Glu Leu Gln Glu Gln Asp Pro Ser Arg Cys Ser Ala Leu Leu Ala Thr
                820                 825                 830 gat gat atg gtc att aat agc aag att ttc caa tca ctg gac ctc ttg    2544
Asp Asp Met Val Ile Asn Ser Lys Ile Phe Gln Ser Leu Asp Leu Leu
                835                 840                 845 ctg gct gat att gaa aat gcc gta tcg gct gga gaa aaa atc gat cag    2592
Leu Ala Asp Ile Glu Asn Ala Val Ser Ala Gly Glu Lys Ile Asp Gln
            850                 855                 860 tta att cac aca tta aaa ggc tgt tta ggt caa ata ggg cag act gaa    2640
Leu Ile His Thr Leu Lys Gly Cys Leu Gly Gln Ile Gly Gln Thr Glu
865                 870                 875                 880 ttg gta tgc tat gtc ata gac att gag aat cgc gta aaa atg ggg aaa    2688
Leu Val Cys Tyr Val Ile Asp Ile Glu Asn Arg Val Lys Met Gly Lys
                885                 890                 895 atc atc gcg ctg gag gaa cta acc gac tta cgc cag aaa ata cgt atg    2736
Ile Ile Ala Leu Glu Glu Leu Thr Asp Leu Arg Gln Lys Ile Arg Met
                900                 905                 910 atc ttc aaa aac tac acc att act taa                                2763
Ile Phe Lys Asn Tyr Thr Ile Thr
                915                 920

<210> SEQ ID NO 35
<211> LENGTH: 920
<212> TYPE: PRT
<213> ORGANISM: Salmonella

<400> SEQUENCE: 35

Met Asn Leu Leu Asn Leu Lys Asn Thr Leu Gln Thr Ser Leu Val Ile
1               5                   10                  15

Arg Leu Thr Phe Leu Phe Leu Leu Thr Thr Ile Ile Ile Trp Leu Leu
                20                  25                  30

Ser Val Leu Thr Ala Ala Tyr Ile Ser Met Val Gln Lys Arg Gln His
            35                  40                  45

Ile Ile Glu Asp Leu Ser Val Leu Ser Glu Met Asn Ile Val Leu Ser
        50                  55                  60

Asn Gln Arg Phe Glu Glu Ala Glu Arg Asp Ala Lys Asn Leu Met Tyr
65                  70                  75                  80

Gln Cys Ser Leu Ala Thr Glu Ile His His Asn Asp Ile Phe Pro Glu
                85                  90                  95

Val Ser Arg His Leu Ser Val Gly Pro Ser Asn Cys Thr Pro Thr Leu
            100                 105                 110

Asn Gly Glu Lys His Arg Leu Phe Leu Gln Ser Ser Asp Ile Asp Glu
        115                 120                 125

Asn Ser Phe Arg Arg Asp Ser Phe Ile Leu Asn His Lys Asn Glu Ile
    130                 135                 140

Ser Leu Leu Ser Thr Asp Asn Pro Ser Asp Tyr Ser Thr Leu Gln Pro
145                 150                 155                 160

Leu Thr Arg Lys Ser Phe Pro Leu Tyr Pro Thr His Ala Gly Phe Tyr
                165                 170                 175

Trp Ser Glu Pro Glu Tyr Ile Asn Gly Lys Gly Trp His Ala Ser Val
            180                 185                 190

Ala Val Ala Asp Gln Gln Gly Val Phe Phe Glu Val Thr Val Lys Leu
        195                 200                 205

Pro Asp Leu Ile Thr Lys Ser His Leu Pro Leu Asp Asp Ser Ile Arg
```

-continued

```
            210                 215                 220
Val Trp Leu Asp Gln Asn Asn His Leu Leu Pro Phe Ser Tyr Ile Pro
225                 230                 235                 240

Gln Lys Ile Arg Thr Gln Leu Glu Asn Val Thr Leu His Asp Gly Trp
                245                 250                 255

Gln Gln Ile Pro Gly Phe Leu Ile Leu Arg Thr Thr Leu His Gly Pro
                260                 265                 270

Gly Trp Ser Leu Val Thr Leu Tyr Pro Tyr Gly Asn Leu His Asn Arg
                275                 280                 285

Ile Leu Lys Ile Ile Leu Gln Gln Ile Pro Phe Thr Leu Thr Ala Leu
                290                 295                 300

Val Leu Met Thr Ser Ala Phe Cys Trp Leu Leu His Arg Ser Leu Ala
305                 310                 315                 320

Lys Pro Leu Trp Arg Phe Val Asp Val Ile Asn Lys Thr Ala Thr Ala
                325                 330                 335

Pro Leu Ser Thr Arg Leu Pro Ala Gln Arg Leu Asp Glu Leu Asp Ser
                340                 345                 350

Ile Ala Gly Ala Phe Asn Gln Leu Leu Asp Thr Leu Gln Val Gln Tyr
                355                 360                 365

Asp Asn Leu Glu Asn Lys Val Ala Glu Arg Thr Gln Ala Leu Asn Glu
370                 375                 380

Ala Lys Lys Arg Ala Glu Arg Ala Asn Lys Arg Lys Ser Ile His Leu
385                 390                 395                 400

Thr Val Ile Ser His Glu Leu Arg Thr Pro Met Asn Gly Val Leu Gly
                405                 410                 415

Ala Ile Glu Leu Leu Gln Thr Thr Pro Leu Asn Ile Glu Gln Gln Gly
                420                 425                 430

Leu Ala Asp Thr Ala Arg Asn Cys Thr Leu Ser Leu Leu Ala Ile Ile
                435                 440                 445

Asn Asn Leu Leu Asp Phe Ser Arg Ile Glu Ser Gly His Phe Thr Leu
                450                 455                 460

His Met Glu Glu Thr Ala Leu Leu Pro Leu Leu Asp Gln Ala Met Gln
465                 470                 475                 480

Thr Ile Gln Gly Pro Ala Gln Ser Lys Lys Leu Ser Leu Arg Thr Phe
                485                 490                 495

Val Gly Gln His Val Pro Leu Tyr Phe His Thr Asp Ser Ile Arg Leu
                500                 505                 510

Arg Gln Ile Leu Val Asn Leu Leu Gly Asn Ala Val Lys Phe Thr Glu
                515                 520                 525

Thr Gly Gly Ile Arg Leu Thr Val Lys Arg His Glu Glu Gln Leu Ile
                530                 535                 540

Phe Leu Val Ser Asp Ser Gly Lys Gly Ile Glu Ile Gln Gln Gln Ser
545                 550                 555                 560

Gln Ile Phe Thr Ala Phe Tyr Gln Ala Asp Thr Asn Ser Gln Gly Thr
                565                 570                 575

Gly Ile Gly Leu Thr Ile Ala Ser Ser Leu Ala Lys Met Met Gly Gly
                580                 585                 590

Asn Leu Thr Leu Lys Ser Val Pro Gly Val Gly Thr Cys Val Ser Leu
                595                 600                 605

Val Leu Pro Leu Gln Glu Tyr Gln Pro Pro Gln Pro Ile Lys Gly Thr
                610                 615                 620

Leu Ser Ala Pro Phe Cys Leu His Arg Gln Leu Ala Cys Trp Gly Ile
625                 630                 635                 640
```

-continued

```
Arg Gly Glu Pro Pro His Gln Gln Asn Ala Leu Leu Asn Ala Glu Leu
                645                 650                 655

Leu Tyr Phe Ser Gly Lys Leu Tyr Asp Leu Ala Gln Gln Leu Ile Leu
            660                 665                 670

Cys Thr Pro Asn Met Pro Val Ile Asn Asn Leu Leu Pro Pro Trp Gln
        675                 680                 685

Leu Gln Ile Leu Leu Val Asp Asp Ala Asp Ile Asn Arg Asp Ile Ile
    690                 695                 700

Gly Lys Met Leu Val Ser Leu Gly Gln His Val Thr Ile Ala Ala Ser
705                 710                 715                 720

Ser Asn Glu Ala Leu Thr Leu Ser Gln Gln Gln Arg Phe Asp Leu Val
                725                 730                 735

Leu Ile Asp Ile Arg Met Pro Glu Ile Asp Gly Ile Glu Cys Val Arg
            740                 745                 750

Leu Trp His Asp Glu Pro Asn Asn Leu Asp Pro Asp Cys Met Phe Val
        755                 760                 765

Ala Leu Ser Ala Ser Val Ala Thr Glu Asp Ile His Arg Cys Lys Lys
    770                 775                 780

Asn Gly Ile His His Tyr Ile Thr Lys Pro Val Thr Leu Ala Thr Leu
785                 790                 795                 800

Ala Arg Tyr Ile Ser Ile Ala Ala Glu Tyr Gln Leu Leu Arg Asn Ile
                805                 810                 815

Glu Leu Gln Glu Gln Asp Pro Ser Arg Cys Ser Ala Leu Leu Ala Thr
            820                 825                 830

Asp Asp Met Val Ile Asn Ser Lys Ile Phe Gln Ser Leu Asp Leu Leu
        835                 840                 845

Leu Ala Asp Ile Glu Asn Ala Val Ser Ala Gly Glu Lys Ile Asp Gln
    850                 855                 860

Leu Ile His Thr Leu Lys Gly Cys Leu Gly Gln Ile Gly Gln Thr Glu
865                 870                 875                 880

Leu Val Cys Tyr Val Ile Asp Ile Glu Asn Arg Val Lys Met Gly Lys
                885                 890                 895

Ile Ile Ala Leu Glu Glu Leu Thr Asp Leu Arg Gln Lys Ile Arg Met
            900                 905                 910

Ile Phe Lys Asn Tyr Thr Ile Thr
        915                 920

<210> SEQ ID NO 36
<211> LENGTH: 639
<212> TYPE: DNA
<213> ORGANISM: Salmonella
<220> FEATURE:
<221> NAME/KEY: CDS
<222> LOCATION: (1)..(636)

<400> SEQUENCE: 36 atg aaa gaa tat aag atc tta tta gta gac gat cat gaa atc atc att      48
Met Lys Glu Tyr Lys Ile Leu Leu Val Asp Asp His Glu Ile Ile Ile
1               5                   10                  15 aac ggc att atg aat gcc tta tta ccc tgg cct cat ttt aaa att gta      96
Asn Gly Ile Met Asn Ala Leu Leu Pro Trp Pro His Phe Lys Ile Val
                20                  25                  30 gag cat gtt aaa aat ggt ctt gag gtt tat aat gcc tgt tgt gca tac     144
Glu His Val Lys Asn Gly Leu Glu Val Tyr Asn Ala Cys Cys Ala Tyr
            35                  40                  45 gag cct gac ata ctt atc ctt gat ctt agt cta cct ggc atc aat ggc     192
```

```
Glu Pro Asp Ile Leu Ile Leu Asp Leu Ser Leu Pro Gly Ile Asn Gly
     50                  55                  60 ctg gat atc att cct caa tta cat cag cgt tgg cca gca atg aat att      240
Leu Asp Ile Ile Pro Gln Leu His Gln Arg Trp Pro Ala Met Asn Ile
 65                  70                  75                  80 ctg gtt tac aca gca tac caa caa gag tat atg acc att aaa act tta      288
Leu Val Tyr Thr Ala Tyr Gln Gln Glu Tyr Met Thr Ile Lys Thr Leu
                 85                  90                  95 gcc gca ggt gct aat ggc tat gtt tta aaa agc agt agt cag caa gtt      336
Ala Ala Gly Ala Asn Gly Tyr Val Leu Lys Ser Ser Ser Gln Gln Val
             100                 105                 110 ctg tta gcg gca ttg caa aca gta gca gta aac aag cgt tac att gac      384
Leu Leu Ala Ala Leu Gln Thr Val Ala Val Asn Lys Arg Tyr Ile Asp
             115                 120                 125 cca acg ttg aat cgg gaa gct atc ctg gct gaa tta aac gct gac acg      432
Pro Thr Leu Asn Arg Glu Ala Ile Leu Ala Glu Leu Asn Ala Asp Thr
 130                 135                 140 acc aat cat caa ctg ctt act ttg cgc gag cgt cag gtt ctt aaa ctt      480
Thr Asn His Gln Leu Leu Thr Leu Arg Glu Arg Gln Val Leu Lys Leu
 145                 150                 155                 160 att gac gag ggg tat acc aat cat ggg atc agc gaa aag cta cat atc      528
Ile Asp Glu Gly Tyr Thr Asn His Gly Ile Ser Glu Lys Leu His Ile
                 165                 170                 175 agt ata aaa acc gtc gaa aca cac cgg atg aat atg atg aga aag cta      576
Ser Ile Lys Thr Val Glu Thr His Arg Met Asn Met Met Arg Lys Leu
             180                 185                 190 cag gtt cat aaa gtg aca gag tta ctt aac tgt gcc cga aga atg agg      624
Gln Val His Lys Val Thr Glu Leu Leu Asn Cys Ala Arg Arg Met Arg
             195                 200                 205 tta ata gag tat taa                                                  639
Leu Ile Glu Tyr
 210

<210> SEQ ID NO 37
<211> LENGTH: 212
<212> TYPE: PRT
<213> ORGANISM: Salmonella

<400> SEQUENCE: 37

Met Lys Glu Tyr Lys Ile Leu Leu Val Asp Asp His Glu Ile Ile Ile
 1               5                  10                  15

Asn Gly Ile Met Asn Ala Leu Leu Pro Trp Pro His Phe Lys Ile Val
             20                  25                  30

Glu His Val Lys Asn Gly Leu Glu Val Tyr Asn Ala Cys Cys Ala Tyr
         35                  40                  45

Glu Pro Asp Ile Leu Ile Leu Asp Leu Ser Leu Pro Gly Ile Asn Gly
     50                  55                  60

Leu Asp Ile Ile Pro Gln Leu His Gln Arg Trp Pro Ala Met Asn Ile
 65                  70                  75                  80

Leu Val Tyr Thr Ala Tyr Gln Gln Glu Tyr Met Thr Ile Lys Thr Leu
                 85                  90                  95

Ala Ala Gly Ala Asn Gly Tyr Val Leu Lys Ser Ser Ser Gln Gln Val
             100                 105                 110

Leu Leu Ala Ala Leu Gln Thr Val Ala Val Asn Lys Arg Tyr Ile Asp
             115                 120                 125

Pro Thr Leu Asn Arg Glu Ala Ile Leu Ala Glu Leu Asn Ala Asp Thr
 130                 135                 140

Thr Asn His Gln Leu Leu Thr Leu Arg Glu Arg Gln Val Leu Lys Leu
```

```
                145                 150                 155                 160
Ile Asp Glu Gly Tyr Thr Asn His Gly Ile Ser Glu Lys Leu His Ile
                    165                 170                 175
Ser Ile Lys Thr Val Glu Thr His Arg Met Asn Met Met Arg Lys Leu
            180                 185                 190
Gln Val His Lys Val Thr Glu Leu Leu Asn Cys Ala Arg Arg Met Arg
        195                 200                 205
Leu Ile Glu Tyr
    210

<210> SEQ ID NO 38
<211> LENGTH: 388
<212> TYPE: DNA
<213> ORGANISM: Salmonella

<400> SEQUENCE: 38
gcttccctcc agttgcctgt tgcaaaatct ttggcacttg atcactatcg cagtacatat      60
agtttcatca gaagattaat cgatggtgtt atcattagga agataaattt cttcatatat     120
aacccagtcg atgactacaa ttactttta ataagatggc gatgtaaaaa catcgtaaca      180
gtttatttaa taataatttt ttcaaattgt aagtttttat gtcaatgctg aaaatgtaat     240
tgtgaattta tcggaaaatc cgaatgatag aatcgcctgt gacaaggtat atgtagacag     300
catcctgata ttgtacaaga agagatagtc gaaataaatg tgaatcaggc ttttacgga     360 tgtggttgtg agcgaatttg atagaaac                                        388

<210> SEQ ID NO 39
<211> LENGTH: 262
<212> TYPE: DNA
<213> ORGANISM: Salmonella

<400> SEQUENCE: 39 taaaatatc ttagagccta tcccaccagg cgttaattgg cgcagccagt ttggacacgg       60
atagcgcgca aaaccgcag cgtacacgta gtacgtgagg tttgactcgc tacgctcgcc     120
cttcgggccg ccgctagcgg cgttcaaaac gctaacgcgt tttggcgagc actgcccagg     180
ttcaaaatgg caagtaaaat agcctaatgg gataggctct tagttagcac gttaattatc     240
tatcgtgtat atggagggga at                                              262

<210> SEQ ID NO 40
<211> LENGTH: 192
<212> TYPE: PRT
<213> ORGANISM: EPEC
<300> PUBLICATION INFORMATION:
<303> JOURNAL: Mol. Microbiol.
<304> VOLUME: 28
<306> PAGES: 1-4
<307> DATE: 1998

<400> SEQUENCE: 40

Met Asp Thr Ser Thr Thr Ala Ser Val Ala Ser Ala Asn Ala Ser Thr
1               5                   10                  15

Ser Thr Ser Met Ala Tyr Asp Leu Gly Ser Met Ser Lys Asp Asp Val
            20                  25                  30

Ile Asp Leu Phe Asn Lys Leu Gly Val Phe Gln Ala Ala Ile Leu Met
        35                  40                  45

Phe Ala Tyr Met Tyr Gln Ala Gln Ser Asp Leu Ser Ile Ala Lys Phe
    50                  55                  60
```

```
Ala Asp Met Asn Glu Ala Ser Lys Glu Ser Thr Thr Ala Gln Lys Met
 65                  70                  75                  80

Ala Asn Leu Val Asp Ala Lys Ile Ala Asp Val Gln Ser Ser Ser Asp
                 85                  90                  95

Lys Asn Ala Lys Ala Gln Leu Pro Asp Glu Val Ile Ser Tyr Ile Asn
            100                 105                 110

Asp Pro Arg Asn Asp Ile Thr Ile Ser Gly Ile Asp Asn Ile Asn Ala
            115                 120                 125

Gln Leu Gly Ala Gly Asp Leu Gln Thr Val Lys Ala Ala Ile Ser Ala
            130                 135                 140

Lys Ala Asn Asn Leu Thr Thr Thr Val Asn Asn Ser Gln Leu Glu Ile
145                 150                 155                 160

Gln Gln Met Ser Asn Thr Leu Asn Leu Leu Thr Ser Ala Arg Ser Asp
                165                 170                 175

Met Gln Ser Leu Gln Tyr Arg Thr Ile Ser Gly Ile Ser Leu Gly Lys
            180                 185                 190

<210> SEQ ID NO 41
<211> LENGTH: 380
<212> TYPE: PRT
<213> ORGANISM: EPEC
<300> PUBLICATION INFORMATION:
<303> JOURNAL: Mol. Microbiol.
<304> VOLUME: 28
<306> PAGES: 1-4
<307> DATE: 1998

<400> SEQUENCE: 41

Met Leu Asn Val Asn Asn Asp Ile Gln Ser Val Arg Ser Gly Ala Ser
  1               5                  10                  15

Ala Ala Thr Ala Thr Ser Gly Ile Asn Gln Ser Glu Val Thr Ser Ala
                 20                  25                  30

Leu Asp Leu Gln Leu Val Lys Ser Thr Ala Pro Ser Ala Ser Trp Thr
             35                  40                  45

Glu Ser Thr Ala Leu Ala Thr Pro Pro Ala Gly His Ser Leu Val Thr
 50                  55                  60

Pro Ser Ala Ala Glu Asp Val Leu Ser Lys Leu Phe Gly Gly Ile Ser
 65                  70                  75                  80

Gly Glu Val Thr Ser Arg Thr Glu Gly Thr Pro Gln Arg Ser Thr
                 85                  90                  95

Gln Asn Ala Ser Ser Gly Tyr Pro Tyr Leu Ser Gln Val Asn Asn Val
            100                 105                 110

Asp Pro Gln Ala Met Met Met Ala Thr Leu Leu Ser Leu Asp Ala
            115                 120                 125

Ser Ala Gln Arg Val Ala Ser Met Lys Asn Ser Asn Glu Ile Tyr Ala
130                 135                 140

Asp Gly Gln Asn Lys Ala Leu Asp Asn Lys Thr Leu Glu Phe Lys Lys
145                 150                 155                 160

Gln Leu Glu Glu Gln Gln Lys Ala Glu Lys Ala Gln Lys Ser Lys
                165                 170                 175

Ile Val Gly Gln Val Phe Gly Trp Leu Gly Val Ala Ala Thr Ala Ile
            180                 185                 190

Ala Ala Ile Phe Asn Pro Ala Leu Trp Ala Val Ala Ile Ser Ala
            195                 200                 205

Thr Ala Met Ala Leu Gln Thr Ala Val Asp Val Met Gly Asp Asp Ala
210                 215                 220
```

-continued

```
Pro Gln Ala Leu Lys Thr Ala Ala Gln Ala Phe Gly Gly Leu Ser Leu
225                 230                 235                 240

Ala Ala Gly Ile Leu Thr Ala Gly Ile Gly Gly Val Ser Ser Leu Ile
                245                 250                 255

Ser Lys Val Gly Asp Val Ala Asn Lys Val Gly Ser Asn Ile Val Lys
            260                 265                 270

Val Val Thr Thr Leu Ala Asp Thr Phe Val Asp Asn Val Ala Ser Lys
        275                 280                 285

Ile Ser Ala Val Ala Asn Gly Leu Thr Thr Ser Ser Arg Ser Ile Gly
    290                 295                 300

Thr Thr Val Leu Asn Asn Asp Ala Ala Tyr Tyr Asn Val Leu Ser Gln
305                 310                 315                 320

Val Ser Ala Phe Ala Val Glu Asn Leu Thr Arg Gln Ser Glu Tyr Leu
                325                 330                 335

Ser Gln Ser Ala Lys Ala Glu Leu Glu Lys Ala Thr Leu Glu Leu Gln
            340                 345                 350

Asn Gln Ala Asn Tyr Ile Gln Ser Ala Ser Gln Leu Met Ser Asp Ser
        355                 360                 365

Ala Arg Val Asn Ile Arg Ile Val Ser Gly Arg Val
    370                 375                 380

<210> SEQ ID NO 42
<211> LENGTH: 401
<212> TYPE: PRT
<213> ORGANISM: Yersinia enterocolitica
<300> PUBLICATION INFORMATION:
<301> AUTHORS: Hakansson, S.
       Schesser, K.
       Persson, C.
       Galyov, E. E.
       Rosqvist, R.
       Homble, F.
       Wolf Watz, H.
<303> JOURNAL: EMBO J.
<304> VOLUME: 15
<306> PAGES: 5812-5823
<307> DATE: 1996

<400> SEQUENCE: 42

Met Ser Ala Leu Ile Thr His Asp Arg Ser Thr Pro Val Thr Gly Ser
1               5                   10                  15

Leu Val Pro Tyr Ile Glu Thr Pro Ala Pro Ala Pro Leu Gln Thr Gln
                20                  25                  30

Gln Val Ala Gly Glu Leu Lys Asp Lys Asn Gly Val Ser Ser Ser Gln
            35                  40                  45

Gly Val Gln Leu Pro Ala Pro Leu Ala Val Val Ala Ser Gln Val Thr
        50                  55                  60

Glu Gly Gln Gln Gln Glu Ile Thr Lys Leu Leu Glu Ser Val Thr Arg
65                  70                  75                  80

Gly Thr Ala Gly Ser Gln Leu Ile Ser Asn Tyr Val Ser Val Leu Thr
                85                  90                  95

Asn Phe Thr Leu Ala Ser Pro Asp Thr Phe Glu Ile Glu Leu Gly Lys
                100                 105                 110

Leu Val Ser Asn Leu Glu Glu Val Arg Lys Asp Ile Lys Ile Ala Asp
            115                 120                 125

Ile Gln Arg Leu His Glu Gln Asn Met Lys Lys Ile Glu Glu Asn Gln
        130                 135                 140

Glu Lys Ile Lys Glu Thr Glu Glu Asn Ala Lys Gln Val Lys Lys Ser
145                 150                 155                 160
```

-continued

```
Gly Met Ala Ser Lys Ile Phe Gly Trp Leu Ile Ala Ile Ala Ser Val
                165                 170                 175
Val Ile Gly Ala Ile Met Val Ala Ser Gly Val Gly Ala Val Ala Gly
            180                 185                 190
Ala Met Met Ile Ala Ser Gly Val Ile Gly Met Ala Asn Met Ala Val
        195                 200                 205
Lys Gln Ala Ala Glu Asp Gly Leu Ile Ser Gln Glu Ala Met Gln Val
    210                 215                 220
Leu Gly Pro Ile Leu Thr Ala Ile Glu Val Ala Leu Thr Val Val Ser
225                 230                 235                 240
Thr Val Met Thr Phe Gly Gly Ser Ala Leu Lys Cys Leu Ala Asp Ile
                245                 250                 255
Gly Ala Lys Leu Gly Ala Asn Thr Ala Ser Leu Ala Ala Lys Gly Ala
            260                 265                 270
Glu Phe Ser Ala Lys Val Ala Gln Ile Ser Thr Gly Ile Ser Asn Thr
        275                 280                 285
Val Gly Ser Ala Val Thr Lys Leu Gly Gly Ser Phe Gly Ser Leu Thr
    290                 295                 300
Met Ser His Val Ile Arg Thr Gly Ser Gln Ala Thr Gln Val Ala Val
305                 310                 315                 320
Gly Val Gly Ser Gly Ile Thr Gln Thr Ile Asn Asn Lys Lys Gln Ala
                325                 330                 335
Asp Leu Gln His Asn Asn Ala Asp Leu Ala Leu Asn Lys Ala Asp Met
            340                 345                 350
Ala Ala Leu Gln Ser Ile Ile Asp Arg Leu Lys Glu Glu Leu Ser His
        355                 360                 365
Leu Ser Glu Ser His Arg Gln Val Met Glu Leu Ile Phe Gln Met Ile
    370                 375                 380
Asn Ala Lys Gly Asp Met Leu His Asn Leu Ala Gly Arg Pro His Thr
385                 390                 395                 400
Val
```

```
<210> SEQ ID NO 43
<211> LENGTH: 390
<212> TYPE: PRT
<213> ORGANISM: Pseudomonas aeruginosa
<300> PUBLICATION INFORMATION:
<301> AUTHORS: Hauser, A. R.
       Fleiszig, S.
       Kang, P. J.
       Mostov, K.
       Engel, J. N.
<303> JOURNAL: Infect. Immun.
<304> VOLUME: 66
<306> PAGES: 1413-1420
<307> DATE: 1998

<400> SEQUENCE: 43

Met Asn Pro Ile Thr Leu Glu Arg Ala Gly Leu Pro Tyr Gly Val Ala
 1               5                  10                  15
Asp Ala Gly Asp Ile Pro Ala Leu Gly Arg Pro Val Ala Arg Asp Val
            20                  25                  30
Glu Ser Leu Arg Val Glu Arg Leu Ala Ala Pro Ala Ala Ala Ser Ala
        35                  40                  45
Ser Gly Thr Gly Val Ala Leu Thr Pro Pro Ser Ala Ala Ser Gln Gln
    50                  55                  60
Arg Leu Glu Val Ala Asn Arg Ala Glu Ile Ala Ser Leu Val Gln Ala
```

```
                65                  70                  75                  80
    Val Gly Glu Asp Ala Gly Leu Ala Arg Gln Val Val Leu Ala Gly Ala
                    85                  90                  95

Ser Thr Leu Leu Ser Ala Gly Leu Met Ser Pro Gln Ala Phe Glu Ile
                    100                 105                 110

Glu Leu Ala Lys Ile Thr Gly Glu Val Glu Asn Gln Lys Lys Leu
                    115                 120                 125

Lys Leu Thr Glu Ile Glu Gln Ala Arg Lys Gln Asn Leu Gln Lys Met
                    130                 135                 140

Glu Asp Asn Gln Gln Lys Ile Arg Glu Ser Glu Ala Ala Lys Glu
    145                 150                 155                 160

Ala Gln Lys Ser Gly Leu Ala Ala Lys Ile Phe Gly Trp Ile Ser Ala
                    165                 170                 175

Ile Ala Ser Ile Ile Val Gly Ala Ile Met Val Ala Thr Gly Val Gly
                    180                 185                 190

Ala Ala Ala Gly Ala Leu Met Ile Ala Gly Gly Val Met Gly Val Val
                    195                 200                 205

Ser Gln Ser Val Gln Gln Ala Ala Ala Asp Gly Leu Ile Ser Lys Glu
                    210                 215                 220

Val Met Glu Lys Leu Gly Pro Ala Leu Met Gly Ile Glu Ile Ala Val
    225                 230                 235                 240

Ala Leu Leu Ala Ala Val Val Ser Phe Gly Ser Ala Val Gly Gly
                    245                 250                 255

Leu Ala Lys Leu Gly Ala Lys Ile Gly Gly Lys Ala Ala Glu Met Thr
                    260                 265                 270

Ala Ser Leu Ala Ser Lys Val Ala Asn Leu Gly Gly Lys Phe Gly Ser
                    275                 280                 285

Leu Ala Gly Gln Ser Leu Ser His Ser Leu Lys Leu Gly Val Gln Val
                    290                 295                 300

Ser Asp Leu Thr Leu Asp Val Ala Asn Gly Ala Ala Gln Ala Thr His
    305                 310                 315                 320

Ser Gly Phe Gln Ala Lys Ala Ala Asn Arg Gln Ala Asp Val Gln Glu
                    325                 330                 335

Ser Arg Ala Asp Leu Thr Thr Leu Gln Gly Val Ile Glu Arg Leu Lys
                    340                 345                 350

Glu Glu Leu Ser Arg Met Leu Glu Ala Phe Gln Glu Ile Met Glu Arg
                    355                 360                 365

Ile Phe Ala Met Leu Gln Ala Lys Gly Glu Thr Leu His Asn Leu Ser
                    370                 375                 380

Ser Arg Pro Ala Ala Ile
    385                 390

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 44
tttttacgtg aagcggggtg                                              20

<210> SEQ ID NO 45
<211> LENGTH: 22
<212> TYPE: DNA
<213> ORGANISM: Artificial Sequence
```

```
<220> FEATURE:
<223> OTHER INFORMATION: Description of Artificial Sequence: Primer

<400> SEQUENCE: 45
ggcattagcg gatgtctgac tg                                            22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 46
caccaggaac cattttctct gg                                            22

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 47
cagcgatgac gatattcgac aag                                           23

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 48
gaaatcccgc agaaatg                                                  17

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 49
aaggcgataa tataaac                                                  17

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 50
agagatgtat tagatac                                                  17

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 51
gcaataagag tatcaac                                                  17
```

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 52
gctaagcttc ggctcaaatt gtttggaaaa c                           31

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 53
gctaagctta gagatgtatt agatacc                                27

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 54
attggatccg caagcgtcca gaa                                    23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 55
tatggatcct cagattaagc gcg                                    23

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 56
atagaattcg gagggagatg gagtggaag                              29

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 57
atagaattcg aagataaagc gattgccgac                             30

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 58
gaaggatcca ctccatctcc ctc                                      23

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 59
gaaggatcca tttgctctat ttcttgc                                  27

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 60
atgggatccg agattcgcca gaatgcgcaa                               30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 61
atgggatcca ctggcataaa cggtttccgg                               30

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 62
attggatcct gacgtaaatc attatca                                  27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 63
attggatcct taagcaataa gtgaatc                                  27

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 64
aaggaattca acaggcaact ggagg                                    25

<210> SEQ ID NO 65

```
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 65
ctgccctcgc gaaaattaag ataata                                          26

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 66
cttaattttc gcgaggg                                                    17

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 67
ggacgcccct ggttaata                                                   18

<210> SEQ ID NO 68
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 68
ggtctgcagg atttttcacg catcgcgtc                                       29

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 69
ggtctgcaga accattgata tataagctgc                                      30

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 70
gctgtcgact tgtagtgagt gagcaag                                         27

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 71
```

```
ggatctagat tttagctcct gtcagaaag                                            29

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 72
ggatctagat ctgaggataa aaatatgg                                             28

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 73
gctgagctct gccgctgacg gaatatg                                              27
```